(12) United States Patent
Makings et al.

(10) Patent No.: US 8,642,609 B2
(45) Date of Patent: Feb. 4, 2014

(54) MODULATORS OF ATP-BINDING CASSETTE TRANSPORTERS

(75) Inventors: Lewis R. Makings, Encinitas, CA (US); Ashavini K. Singh, San Diego, CA (US); Mark T. Miller, San Diego, CA (US); Sarah S. Hadida Ruah, La Jolla, CA (US); Peter D. J. Grootenhuis, San Diego, CA (US); Matthew Hamilton, Wallingford, PA (US); Anna Ruth Hazlewood, San Diego, CA (US); Liming Huang, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 2215 days.

(21) Appl. No.: 10/862,909

(22) Filed: Jun. 7, 2004

(65) Prior Publication Data
US 2005/0059687 A1 Mar. 17, 2005

Related U.S. Application Data

(60) Provisional application No. 60/476,698, filed on Jun. 6, 2003, provisional application No. 60/500,132, filed on Sep. 4, 2003, provisional application No. 60/520,181, filed on Nov. 14, 2003.

(51) Int. Cl.
*A01N 43/54* (2006.01)
*A61K 31/517* (2006.01)
*C07D 239/72* (2006.01)
*C07D 401/00* (2006.01)

(52) U.S. Cl.
USPC .................. 514/266.2; 544/283; 544/284

(58) Field of Classification Search
USPC ................ 544/284, 287, 292, 283; 514/266.2
See application file for complete search history.

(56) References Cited

U.S. PATENT DOCUMENTS

| | | | |
|---|---|---|---|
| 3,127,401 A * | 3/1964 | Lawes et. al. | 544/283 |
| 3,624,084 A | 11/1971 | Mathieu | |
| 3,984,555 A | 10/1976 | Amschler et al. | |
| 5,674,868 A * | 10/1997 | Van Daele et al. | 514/266.22 |
| 6,127,360 A * | 10/2000 | Timmerman et al. | 514/211.05 |
| 6,291,481 B1 * | 9/2001 | Bosmans et al. | 514/320 |
| 6,479,499 B1 | 11/2002 | Kuo et al. | |
| 6,559,153 B2 * | 5/2003 | Becker et al. | 514/266.22 |
| 6,632,810 B2 * | 10/2003 | Kodama et al. | 514/218 |
| 2003/0144350 A1 * | 7/2003 | Stevenson et al. | 514/485 |

FOREIGN PATENT DOCUMENTS

| | | |
|---|---|---|
| WO | WO 97/20823 | 6/1997 |
| WO | WO 00/64424 | 11/2000 |
| WO | WO 01/21598 | 3/2001 |
| WO | WO 02/48117 | 6/2002 |
| WO | WO 03/020280 | 3/2003 |
| WO | WO 03/039460 | 5/2003 |
| WO | WO 03/059884 | 7/2003 |
| WO | WO 03/076418 | 9/2003 |
| WO | WO 03/084544 | 10/2003 |
| WO | WO 2004/024162 | 3/2004 |

OTHER PUBLICATIONS

Hori, M. et. al., "Effects of a 2-Substituent . . . ", Chem. Pharm. Bull. (1993), vol. 41, No. 6, pp. 1114-1117.*
Database Chemcats, Chemical Abstracts Service, XP-002298958, "ComGenex Product List", Jun. 23, 2003.
Database Chemcats, Chemical Abstracts Service, XP-002298957, "ComGenex Product List", Jun. 23, 2003.

* cited by examiner

*Primary Examiner* — Paul V. Ward
(74) *Attorney, Agent, or Firm* — Nancy K. Brennan

(57) ABSTRACT

The present invention relates to modulators of ATP-Binding Cassette ("ABC") transporters or fragments thereof, including Cystic Fibrosis Transmembrane Conductance Regulator ("CFTR"), compositions thereof, and methods therewith. The present invention also relates to methods of treating ABC transporter mediated diseases using such modulators.

21 Claims, No Drawings

MODULATORS OF ATP-BINDING CASSETTE TRANSPORTERS

CROSS-REFERENCE TO RELATED APPLICATIONS

The present application claims priority under 35 U.S.C. §119 to U.S. Provisional Application Nos. 60/476,698 filed Jun. 6, 2003, entitled "Modulators of ATP-Binding Cassette Transporters"; 60/500,132, filed Sep. 4, 2003, entitled "Modulators of ATP-Binding Cassette Transporters"; and 60/520,181, filed Nov. 14, 2003, entitled "Modulators of ATP-Binding Cassette Transporters", and the entire contents of each of these applications is hereby incorporated by reference.

TECHNICAL FIELD OF THE INVENTION

The present invention relates to modulators of ATP-Binding Cassette ("ABC") transporters or fragments thereof, including Cystic Fibrosis Transmembrane Conductance Regulator ("CFTR"), compositions thereof, and methods therewith. The present invention also relates to methods of treating ABC transporter mediated diseases using such modulators.

BACKGROUND OF THE INVENTION

ABC transporters are a family of membrane transporter proteins that regulate the transport of a wide variety of pharmacological agents, potentially toxic drugs, and xenobiotics, as well as anions. ABC transporters are homologous membrane proteins that bind and use cellular adenosine triphosphate (ATP) for their specific activities. Some of these transporters were discovered as multidrug resistance proteins (like the MDR1-P glycoprotein, or the multidrug resistance protein, MRP1), defending malignant cancer cells against chemotherapeutic agents. To date, 48 ABC Transporters have been identified and grouped into 7 families based on their sequence identity and function.

ABC transporters regulate a variety of important physiological roles within the body and provide defense against harmful environmental compounds. Because of this, they represent important potential drug targets for the treatment of diseases associated with defects in the transporter, prevention of drug transport out of the target cell, and intervention in other diseases in which modulation of ABC transporter activity may be beneficial.

One member of the ABC transporter family commonly associated with disease is the cAMP/ATP-mediated anion channel, CFTR. CFTR is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeate of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in Cystic Fibrosis ("CF"), the most common fatal genetic disease in humans. Cystic Fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, >1000 disease causing mutations in the CF gene have been identified (http://www.genet.sickkids.on.ca/cftr/). The most prevalent mutation is a deletion of phenylalanine at position 508 of the CFTR amino acid sequence, and is commonly referred to as $\Delta$F508-CFTR. This mutation occurs in approximately 70% of the cases of cystic fibrosis and is associated with a severe disease.

The deletion of residue 508 in $\Delta$F508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of $\Delta$F508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to $\Delta$F508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and $Cl^-$ channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

In addition to Cystic Fibrosis, modulation of CFTR activity may be beneficial for other diseases not directly caused by mutations in CFTR, such as secretory diseases and other protein folding diseases mediated by CFTR. These include, but are not limited to, chronic obstructive pulmonary disease (COPD), dry eye disease, and Sjögren's Syndrome. COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as Cystic Fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease, for which treatment options are limited. Modulators of CFTR activity may hydrate the various organs afflicted by the disease and help to elevate the associated symptoms.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. Infact, this cellular phenomenon of defective ER processing of ABC transporters by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)]. The diseases associated with the first class of ER malfunction are Cystic fibrosis (due to misfolded ΔF508-CFTR as discussed above), Hereditary emphysema (due to a1-antitrypsin; non Piz variants), Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses (due to Lysosomal processing enzymes), Sandhof/Tay-Sachs (due to β-Hexosaminidase), Crigler-Najjar type II (due to UDP-glucuronyl-sialyc-transferase), Polyendocrinopathy/Hyperinsulemia, Diabetes mellitus (due to Insulin receptor), Laron dwarfism (due to Growth hormone receptor), Myleoperoxidase deficiency, Primary hypoparathyroidism (due to Preproparathyroid hormone), Melanoma (due to Tyrosinase). The diseases associated with the latter class of ER malfunction are Glycanosis CDG type 1, Hereditary emphysema (due to α1-Antitrypsin (PiZ variant), Congenital hyperthyroidism, Osteogenesis imperfecta (due to Type I, II, IV procollagen), Hereditary hypofibrinogenemia (due to Fibrinogen), ACT deficiency (due to α1-Antichymotrypsin), Diabetes insipidus (DI), Neurophyseal DI (due to Vasopvessin hormone/V2-receptor), Neprogenic DI (due to Aquaporin II), Charcot-Marie Tooth syndrome (due to Peripheral myelin protein 22), Perlizaeus-Merzbacher disease, neurodegenerative diseases such as Alzheimer's disease (due to βAPP and presenilins), Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease (due to lysosomal α-galactosidase A) and Straussler-Scheinker syndrome (due to Prp processing defect).

In addition to up-regulation of CFTR activity, reducing anion secretion by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Although there are numerous causes of diarrhea, the major consequences of diarrheal diseases, resulting from excessive chloride transport are common to all, and include dehydration, acidosis, impaired growth and death.

Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients of acquired immunodeficiency syndrome (AIDS) and chronic inflammatory bowel disease (IBD). 16 million travelers to developing countries from industrialized nations every year develop diarrhea, with the severity and number of cases of diarrhea varying depending on the country and area of travel.

Diarrhea in barn animals and pets such as cows, pigs and horses, sheep, goats, cats and dogs, also known as scours, is a major cause of death in these animals. Diarrhea can result from any major transition, such as weaning or physical movement, as well as in response to a variety of bacterial or viral infections and generally occurs within the first few hours of the animal's life.

The most common diarrheal causing bacteria is enterotoxogenic *E-coli* (ETEC) having the K99 pilus antigen. Common viral causes of diarrhea include rotavirus and coronavirus. Other infectious agents include *cryptosporidium, giardia lamblia*, and *salmonella*, among others.

Symptoms of rotaviral infection include excretion of watery feces, dehydration and weakness. Coronavirus causes a more severe illness in the newborn animals, and has a higher mortality rate than rotaviral infection. Often, however, a young animal may be infected with more than one virus or with a combination of viral and bacterial microorganisms at one time. This dramatically increases the severity of the disease.

Accordingly, there is a need for modulators of an ABC transporter activity, and compositions thereof, that can be used to modulate the activity of the ABC transporter in the cell membrane of a mammal.

There is a need for methods of treating ABC transporter mediated diseases using such modulators of ABC transporter activity.

There is a need for methods of modulating an ABC transporter activity in an ex vivo cell membrane of a mammal.

There is a need for modulators of CFTR activity that can be used to modulate the activity of CFTR in the cell membrane of a mammal.

There is a need for methods of treating CFTR-mediated diseases using such modulators of CFTR activity.

There is a need for methods of modulating CFTR activity in an ex vivo cell membrane of a mammal.

SUMMARY OF THE INVENTION

It has now been found that compounds of this invention, and pharmaceutically acceptable compositions thereof, are useful as modulators of ABC transporter activity. These compounds have the general formula I:

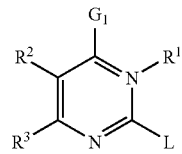

or a pharmaceutically acceptable salt thereof, wherein $G_1$, $R^1$, $R^2$, $R^3$ and L are described generally and in classes and subclasses below.

These compounds and pharmaceutically acceptable compositions are useful for treating or lessening the severity of a variety of diseases, disorders, or conditions, including, but not limited to, Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, or Straussler-Scheinker syndrome.

DETAILED DESCRIPTION OF THE INVENTION

I. General Description of Compounds of the Invention

The present invention relates to compounds of formula I useful as modulators of ABC transporter activity:

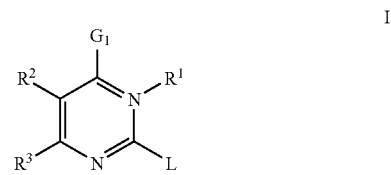

or a pharmaceutically acceptable salt thereof, wherein:

$G_1$ is =O, —$R^A$, —$OR^A$, $SR^A$, or $NR^AR^B$, wherein $R^A$ and $R^B$ are each independently V-$R^V$, or $R^A$ and $R^B$, taken together with the nitrogen atom, form an optionally substituted 3-12 membered saturated, partially unsaturated, or fully unsaturated monocyclic or bicyclic ring having 0-4 heteroatoms independently selected from nitrogen, oxygen, or sulfur, wherein V is a bond or is an optionally substituted $C_1$-$C_6$ alkylidene chain wherein up to two methylene units of V are optionally and independently replaced by —CO—, —CS—, —COCO—, —CONR'—, —CONR'NR'—, —$CO_2$—, —OCO—, —NR'$CO_2$—, —O—, —NR'CONR'—, —OCONR'—, —NR'NR', —NR'NR'CO—, —NR'CO—, —S—, —SO, —$SO_2$—, —NR'—, —$SO_2$NR'—, NR'$SO_2$—, —NR'$SO_2$NR'—, and each occurrence of $R^V$ is independently R', halogen, $NO_2$, or CN, and wherein $R^A$ and $R^B$, or any ring formed by $R^A$ and $R^B$ taken together with the nitrogen atom, are optionally and independently substituted by q occurrences of U—$R^U$, wherein q is 0-5, U is a bond or is an optionally substituted $C_1$-$C_6$ alkylidene chain wherein up to two methylene units of U are optionally and independently replaced by —CO—, —CS—, —COCO—, —CONR'—, —CONR'NR'—, —$CO_2$—, —OCO—, —NR'$CO_2$—, —O—, —NR'CONR'—, —OCONR'—, —NR'NR', —NR'NR'CO—, —NR'CO—, —S—, —SO, —$SO_2$—, —NR'—, —$SO_2$NR'—, —NR'$SO_2$—, —NR'$SO_2$NR'—, and each occurrence of $R^U$ is independently R', halogen, $NO_2$, or CN, $R^1$ is absent or is Y—$R^Y$;

Y is a bond or is an optionally substituted $C_1$-$C_6$ alkylidene chain wherein up to two methylene units of Y are optionally and independently replaced by —CO—, —CONR—, —O—, —NRCO—, —S—, —$SO_2$—, —NR—, —$SO_2$NR—, or —NR$SO_2$—, and each occurrence of $R^Y$ is independently R', OR', SR', N(R')$_2$, halogen, $NO_2$, or CN, provided that when $R^1$ is present, it is always bonded to the nitrogen atom through a carbon atom;

each occurrence of R is independently selected from hydrogen or an optionally substituted $C_{1-8}$ aliphatic group; and each occurrence of R' is independently selected from hydrogen or an optionally substituted group selected from a $C_1$-$C_8$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R, or two occurrences of R, are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;

$R^2$ and $R^3$ are each independently halogen or -T-$R^Z$, or $R^2$ and $R^3$, taken together, form an optionally substituted 5- or 6-membered monocyclic aryl ring having 0-5 heteroatoms independently selected from nitrogen, oxygen, or sulfur or a 5-, 6-, or 7-membered saturated or partially unsaturated monocyclic ring having 0-3 heteroatoms independently selected from nitrogen, oxygen, or sulfur, wherein any ring formed by $R^2$ and $R^3$ taken together is optionally substituted at one or more carbon atoms with x independent occurrences of Q-$R^X$, wherein x is 0-5;

T is a bond or is an optionally substituted $C_1$-$C_6$ alkylidene chain wherein up to two methylene units of T are optionally and independently replaced by —CO—, —CS—, —COCO—, —CONR—, —CONRNR—, —$CO_2$—, —OCO—, —$NRCO_2$—, —O—, —NRCONR—, —OCONR—, —NRNR, —NRNRCO—, —NRCO—, —S—, —SO, —$SO_2$—, —NR—, —$SO_2$NR—, —$NRSO_2$—, —$NRSO_2$NR—, and each occurrence of $R^Z$ is independently R', halogen, $NO_2$, or CN;

Q is a bond or is an optionally substituted $C_1$-$C_6$ alkylidene chain wherein up to two methylene units of Q are optionally and independently replaced by —CO—, —CS—, —COCO—, —CONR—, —CONRNR—, —$CO_2$—, —OCO—, —$NRCO_2$—, —O—, —NRCONR—, —OCONR—, —NRNR, —NRNRCO—, —NRCO—, —S—, —SO, —$SO_2$—, —NR—, —$SO_2$NR—, —$NRSO_2$—, —$NRSO_2$NR—, and each occurrence of $R^X$ is independently R', halogen, $NO_2$, or CN;

L is $G^2$-B-$G^3$-$Ar^1$,
 wherein $G^2$ is absent, an optionally substituted $C_1$-$C_6$ alkylidene chain, or a $C_3$-$C_6$ spirocycloalkylidene ring, wherein one or two methylene units in said alkylidene are optionally and independently replaced with —CO—, —CS—, —SO—, —$SO_2$, —NR'—, N($SO_2$R')—, N(COR')—, —O—, or —S—, and wherein one or two hydrogen atoms of one or more methylene units are optionally substituted with R';
 $G^3$ is absent or an optionally substituted $C_1$-$C_6$ alkylidene chain, wherein one or two methylene units are optionally and independently replaced with —CO—, —CS—, —SO—, —$SO_2$—, —NR'—, N($SO_2$R')—, N(COR')—, —O—, or —S—, and wherein one or two hydrogen atoms of one or more methylene units are optionally substituted with R';

B is absent or is an optionally substituted $C_{6-10}$ aryl, a heteroaryl ring having 5-10 ring atoms, a cycloalkyl or heterocyclyl ring having 3-10 ring atoms, or a $C_1$-$C_6$ alkylidene chain, wherein one or two methylene units in the alkylidene chain are optionally replaced with —CO—, —CS—, —SO—, —$SO_2$—, —NR'—, —N($SO_2$R'), —N(COR')—, —O—, or —S—, and wherein one or two hydrogen atoms of one or more methylene units are optionally substituted with R'; and $Ar^1$ is absent or is a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein $Ar^1$ is optionally substituted with m independent occurrences of $WR^W$, wherein m is 0-5 and W is a bond or is an optionally substituted $C_1$-$C_6$ alkylidene chain wherein up to two methylene units of W are optionally and independently replaced by —CO—, —CS—, —COCO—, —CONR—, —CONRNR—, —$CO_2$—, —OCO—, —$NRCO_2$—, —O—, —NRCONR—, —OCONR—, —NRNR, —NRNRCO—, —NRCO—, —S—, —SO, —$SO_2$—, —NR—, —$SO_2$NR—, —$NRSO_2$—, —$NRSO_2$NR—, and each occurrence of $R^W$ is independently R', halogen, $NO_2$, or CN;

provided that $G^2$, B, $G^3$, and $Ar^1$ are not simultaneously absent.

In certain other embodiments, for compounds of general formula I, none of $G^2$, B, $G^3$, or $Ar^1$ is absent and thus compounds of formula I are provided:

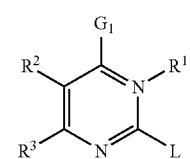

I or a pharmaceutically acceptable salt thereof, wherein:
 $G_1$ is =O, —$R^A$, —$OR^A$, $SR^A$, or $NR^AR^B$, wherein $R^A$ and $R^B$ are each independently V—$R^V$, or $R^A$ and $R^B$, taken together with the nitrogen atom, form an optionally substituted 3-12 membered saturated, partially unsaturated, or fully unsaturated monocyclic or bicyclic ring having 0-4 heteroatoms independently selected from nitrogen, oxygen, or sulfur, wherein V is a bond or is an optionally substituted $C_1$-$C_6$ alkylidene chain wherein up to two methylene units of V are optionally and independently replaced by —CO—, —CS—, —COCO—, —CONR'—, —CONR'NR'—, —$CO_2$—, —OCO—, —NR'$CO_2$—, —O—, —NR'CONR'—, —OCONR'—, —NR'NR', —NR'NR'CO—, —NR'CO—, —S—, —SO, —$SO_2$—, —NR'—, —$SO_2$NR'—, NR'$SO_2$—, —NR'$SO_2$NR'—, and each occurrence of $R^V$ is independently R', halogen, $NO_2$, or CN, and wherein $R^A$ and $R^B$, or any ring formed by $R^A$ and $R^B$ taken together with the nitrogen atom, are optionally and independently substituted by q occurrences of U—$R^U$, wherein q is 0-5, U is a bond or is an optionally substituted $C_1$-$C_6$ alkylidene chain wherein up to two methylene units of U are optionally and independently replaced by —CO—, —CS—, —COCO—, —CONR'—, —CONR'NR'—, —CO$_2$—, —OCO—, —NR'CO$_2$—, —O—, —NR'CONR'—, —OCONR'—, —NR'NR', —NR'NR'CO—, —NR'CO—, —S—, —SO, —SO$_2$—, —NR'—, —SO$_2$NR'—, —NR'SO$_2$—, —NR'SO$_2$NR'—, and each occurrence of $R^U$ is independently R', halogen, NO$_2$, or CN;

$R^1$ is absent or is Y—$R^Y$; wherein Y is a bond or is an optionally substituted $C_1$-$C_6$ alkylidene chain wherein up to two methylene units of Y are optionally and independently replaced by —CO—, —CONR—, —O—, —NRCO—, —S—, —SO$_2$—, —NR—, —SO$_2$NR—, or —NRSO$_2$—, and each occurrence of $R^Y$ is independently R', OR', SR', N(R')$_2$, halogen, NO$_2$, or CN, provided that when $R^1$ is present, it is always bonded to the nitrogen atom through a carbon atom;

each occurrence of R is independently selected from hydrogen or an optionally substituted $C_{1-8}$ aliphatic group; and each occurrence of R' is independently selected from hydrogen or an optionally substituted group selected from a $C_1$-$C_8$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R, or two occurrences of R, are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;

$R^2$ and $R^3$ are each independently halogen or -T-$R^Z$, or $R^2$ and $R^3$, taken together, form an optionally substituted 5- or 6-membered monocyclic aryl ring having 0-5 heteroatoms independently selected from nitrogen, oxygen, or sulfur or a 5-, 6-, or 7-membered saturated or partially unsaturated monocyclic ring having 0-3 heteroatoms independently selected from nitrogen, oxygen, or sulfur, wherein any ring formed by $R^2$ and $R^3$ taken together is optionally substituted at one or more carbon atoms with x independent occurrences of Q-$R^X$, wherein x is 0-5;

T is a bond or is an optionally substituted $C_1$-$C_6$ alkylidene chain wherein up to two methylene units of T are optionally and independently replaced by —CO—, —CS—, —COCO—, —CONR—, —CONRNR—, —CO$_2$—, —OCO—, —NRCO$_2$—, —O—, —NRCONR—, —OCONR—, —NRNR, —NRNRCO—, —NRCO—, —S—, —SO, —SO$_2$—, —NR—, —SO$_2$NR—, —NRSO$_2$—, —NRSO$_2$NR—, and each occurrence of $R^Z$ is independently R', halogen, NO$_2$, or CN;

Q is a bond or is an optionally substituted $C_1$-$C_6$ alkylidene chain wherein up to two methylene units of Q are optionally and independently replaced by —CO—, —CS—, —COCO—, —CONR—, —CONRNR—, —CO$_2$—, —OCO—, —NRCO$_2$—, —O—, —NRCONR—, —OCONR—, —NRNR, —NRNRCO—, —NRCO—, —S—, —SO, —SO$_2$—, —NR—, —SO$_2$NR—, —NRSO$_2$—, —NRSO$_2$NR—, and each occurrence of $R^X$ is independently R', halogen, NO$_2$, or CN;

L is $G^2$-$G^3$-$Ar^1$,
wherein $G^2$ is absent, an optionally substituted $C_1$-$C_6$ alkylidene chain, or a $C_3$-$C_6$ spirocycloalkylidene ring, wherein one or two methylene units in said alkylidene are optionally and independently replaced with —CO—, —CS—, —SO—, —SO$_2$—, —NR'—, N(SO$_2$R')—, N(COR')—, —O—, or —S—, and wherein one or two hydrogen atoms of one or more methylene units are optionally substituted with R';

$G^3$ is absent or an optionally substituted $C_1$-$C_6$ alkylidene chain, wherein one or two methylene units are optionally and independently replaced with —CO—, —CS—, —SO—, —SO$_2$—, —NR'—, N(SO$_2$R')—, N(COR')—, —O—, or —S—, and wherein one or two hydrogen atoms of one or more methylene units are optionally substituted with R';

B is absent or is an optionally substituted $C_6$-10 aryl, a heteroaryl ring having 5-10 ring atoms, a cycloalkyl or heterocyclyl ring having 3-10 ring atoms, or a $C_1$-$C_6$ alkylidene chain, wherein one or two methylene units in the alkylidene chain are optionally replaced with —CO—, —CS—, —SO—, —SO$_2$—, —NR'—, —N(SO$_2$R'), —N(COR')—, —O, or —S—, and wherein one or two hydrogen atoms of one or more methylene units are optionally substituted with R'; and $Ar^1$ is absent or is a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein $Ar^1$ is optionally substituted with m independent occurrences of $WR^W$, wherein m is 0-5 and W is a bond or is an optionally substituted $C_1$-$C_6$ alkylidene chain wherein up to two methylene units of W are optionally and independently replaced by —CO—, —CS—, —COCO—, —CONR—, —CONRNR—, —CO$_2$—, —OCO—, —NRCO$_2$—, —O—, —NRCONR—, —OCONR—, —NRNR, —NRNRCO—, —NRCO—, —S—, —SO, —SO$_2$—, —NR—, —SO$_2$NR—, —NRSO$_2$—, —NRSO$_2$NR—, and each occurrence of $R^W$ is independently R', halogen, SCF$_3$, NO$_2$, or CN;

provided that:
i) when B is piperazinyl, $G^1$ is =O, $G^2$ is CHMe, and $G^3$ is —CONH—, then $R^1$ is not benzyl or ethyl;
ii) when $R^2$ and $R^3$, taken together form a fused thieno ring, then $G^1$ is not NH$_2$ or optionally substituted phenyl;
iii) when $G^1$ is hydrogen, $R^2$ and $R^3$, taken together form a fused benzene ring, and x is 3, then each occurrence of Q-$R^X$ is not OMe;
iv) $G^1$, $R^2$ and $R^3$ are not each simultaneously hydrogen;
v) if $G^1$ is hydrogen, then $G^2$ is not CO; and
vi) 2H Indol-2-one, 1,3-dihydro-3,3,7-trimethyl-4-[3-[4-(2-quinazolinylmethyl)-1-piperazinyl]propoxy] and 2(1H)-Quinoline, 3,4-dihydro-8-methyl-5-[3-4-(2-quinazolinyl methyl)-1-piperazinyl]propoxy are excluded.

2. Compounds and Definitions

Compounds of this invention include those described generally above, and are further illustrated by the classes, subclasses, and species disclosed herein. As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane regulator or a mutation thereof capable of regulator activity, including, but not limited to, ΔF508 CFTR and G551D CFTR (see, e.g., http://www.genet.sickkids.on.ca/cftr/, for CFTR mutations).

The term "modulating" as used herein means increasing or decreasing by a measurable amount.

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; —R°; —OR°; —SR°; 1,2-methylene-dioxy; 1,2-ethylenedioxy; phenyl (Ph) optionally substituted with R°; —O(Ph) optionally substituted with R°; —(CH$_2$)$_{1-2}$(Ph), optionally substituted with R°; —CH═CH(Ph), optionally substituted with R°; —NO$_2$; —CN; —N(R°)$_2$; —NR°C(O)R°; —NR°C(O)N(R°)$_2$; —NR°CO$_2$R°; —NR°NR°C(O)R°; —NR°NR°C(O)

N(R°)$_2$; —NR°NR°CO$_2$R°; —C(O)C(O)R°; —C(O)CH$_2$C(O)R°; —CO$_2$R°; —C(O)R°; —C(O)N(R°)$_2$; —OC(O)N(R°)$_2$; —S(O)$_2$R°; —SO$_2$N(R°)$_2$; —S(O)R°; —NR°SO$_2$N(R°)$_2$; —NR°SO$_2$R°; —C(=S)N(R°)$_2$; —C(=NH)—N(R°)$_2$; or —(CH$_2$)$_{0-2}$NHC(O)R° wherein each independent occurrence of R° is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R°, on the same substituent or different substituents, taken together with the atom(s) to which each R° group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R° is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R* is unsubstituted.

Optional substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R$^+$ is unsubstituted.

The term "alkylidene chain" refers to a straight or branched carbon chain that may be fully saturated or have one or more units of unsaturation and has two points of attachment to the rest of the molecule. The term "spirocycloalkylidene" refers to a carbocyclic ring that may be fully saturated or have one or more units of unsaturation and has two points of attachment from the same ring carbon atom to the rest of the molecule.

As detailed above, in some embodiments, two independent occurrences of R° (or R$^+$, or any other variable similarly defined herein), are taken together together with the atom(s) to which each variable is bound to form a 3-8-membered cycloalkyl, heterocyclyl, aryl, or heteroaryl ring having 0-3 heteroatoms independently selected from nitrogen, oxygen, or sulfur. Exemplary rings that are formed when two independent occurrences of R° (or R$^+$, or any other variable similarly defined herein) are taken together with the atom(s) to which each variable is bound include, but are not limited to the following: a) two independent occurrences of R° (or R$^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of OR°

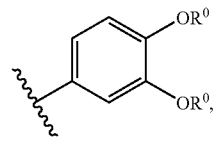

these two occurrences of R° are taken together with the oxygen atoms to which they are bound to form a fused 6-membered oxygen containing ring:

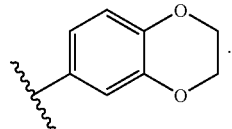 [SMILES: *c1ccc2c(c1)OCCO2]

It will be appreciated that a variety of other rings can be formed when two independent occurrences of R° (or R$^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C— or $^{14}$C-enriched carbon are within the scope of this invention. Such compounds are useful, for example, as analytical tools or probes in biological assays.

3. Description of Exemplary Compounds

As described generally above, for compounds of the invention, G$_1$ is =O, R$^A$, —OR$^A$, SR$^A$, or NR$^A$R$^B$. As depicted for compounds of structural formula I, the bond between the nitrogen atom and C-G$^1$ can be a single or double bond (as represented by the dotted line), depending upon the G$^1$ substituent. For example, when G$^1$ is =O, the bond between the nitrogen atom and the carbon atom of C-G$^1$ is a single bond, and thus R$^1$ will be present. Additionally, when G$^1$ is —R$^A$, —OR$^A$, SR$^A$, or NR$^A$R$^B$, the bond between the nitrogen atom and the carbon atom of C-G$^1$ is a double bond, and thus R$^1$ will be absent. Accordingly, the present invention provides compounds having any one of the following general structures I-A, I-B, I-C, I-D and I-E, as depicted below.

I-A
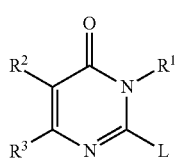

I-B
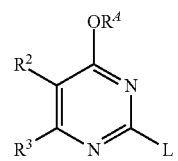

I-C
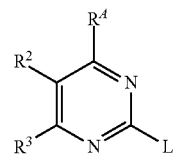

I-D
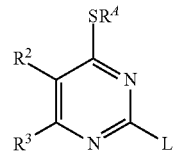

I-E
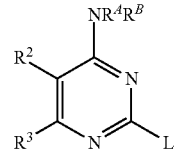

In some embodiments, compounds of the invention have the structure of general formula I-A. In other embodiments, compounds of the invention have the structure of general formula I-B. In yet other embodiments, compounds of the invention have the structure of general formula I-E. Or, compounds of the invention have the structure of general formula IC. Or, compounds of the invention have the structure of general formula ID. In some embodiments, R$^A$ is H in compounds of formula IC. In other embodiments, R$^A$ is an optionally substituted C$_1$-C$_6$ aliphatic. Or, compounds of the invention have the structure of general formula IE.

As described generally above, R$^A$ and R$^B$ are each independently V—R$^V$, or R$^A$ and R$^B$, taken together with the nitrogen atom, form an optionally substituted 3-12 membered saturated, partially unsaturated, or fully unsaturated monocyclic or bicyclic ring having 0-4 heteroatoms independently selected from nitrogen, oxygen, or sulfur, wherein V is a bond or is an optionally substituted C$_1$-C$_6$ alkylidene chain wherein up to two methylene units of V are optionally and independently replaced by —CO—, —CS—, —COCO—, —CONR'—, —CONR'NR'—, —CO$_2$—, —OCO—, —NR'CO$_2$—, —O—, —NR'CONR'—, —OCONR'—, —NR'NR—, —NR'NR'CO—, —NR'CO—, —S—, —SO, —SO$_2$—, —NR'—, —SO$_2$NR'—, NR'SO$_2$—, —NR'SO$_2$NR'—, and each occurrence of R$^V$ is independently R', halogen, NO$_2$, or CN. As also described above, R$^A$ and R$^B$, or any ring formed by R$^A$ and R$^B$ taken together with the nitrogen atom, are optionally and independently substituted by q occurrences of U—R$^U$, wherein q is 0-5, U is a bond or is an optionally substituted C$_1$-C$_6$ alkylidene chain wherein up to two methylene units of U are optionally and independently replaced by —CO—, —CS—, —COCO—, —CONR'—, —CONR'NR'—, —CO$_2$—, —OCO—, —NR'CO$_2$—, —O—, —NR'CONR'—, —OCONR'—, —NR'NR', —NR'NR'CO—, —NR'CO—, —S—, —SO, —SO$_2$—, —NR'—, —SO$_2$NR'—, —NR'SO$_2$—, —NR'SO$_2$NR'—, and each occurrence of R$^U$ is independently R', halogen, NO$_2$, or CN.

In some embodiments R$^A$ and R$^B$ are each independently hydrogen, an optionally substituted C$_1$-C$_8$alkyl group, or V—R$^V$, where V is as defined generally above, and R$^V$ is an optionally substituted 3-12 membered saturated, partially unsaturated, or fully unsaturated monocyclic or bicyclic ring having 0-4 heteroatoms independently selected from nitrogen, oxygen, or sulfur. In other embodiments, R$^A$ and R$^B$, taken together with the nitrogen atom, form an optionally substituted 5-, 6-, or 7-membered heterocyclyl ring. In other embodiments, R$^A$ and R$^B$ are each independently hydrogen; an optionally substituted group selected from methyl, ethyl, propyl, isopropyl, butyl, tert-butyl, or pentyl; an optionally substituted ring selected from:

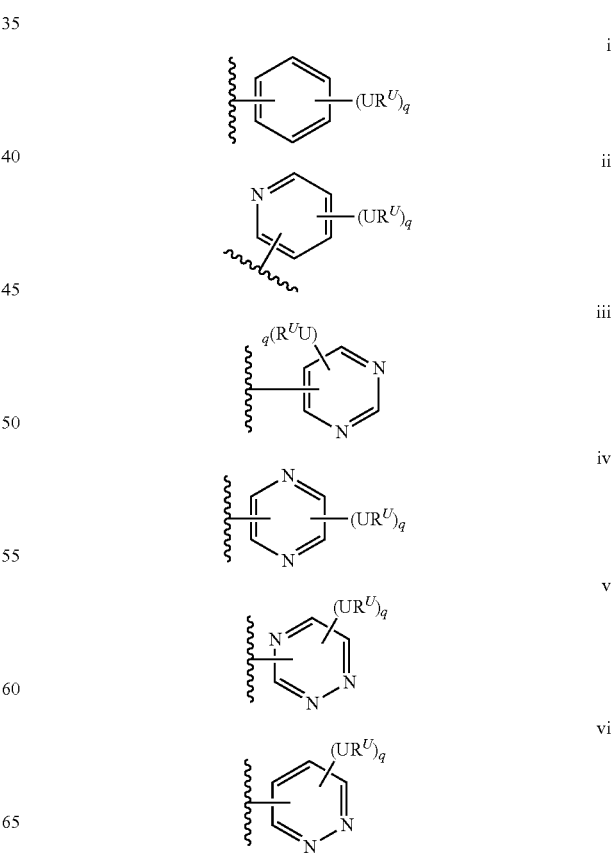

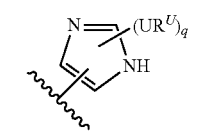 vii
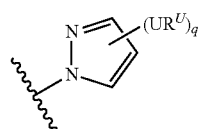 viii
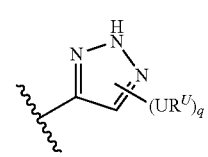 ix
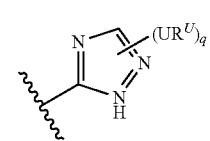 x
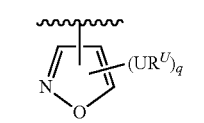 xi
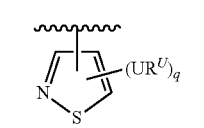 xii
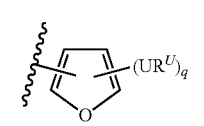 xiii
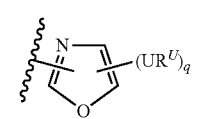 xiv
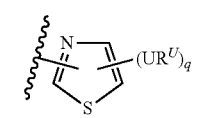 xv
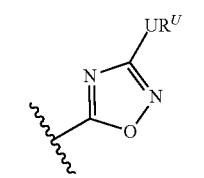 xvi
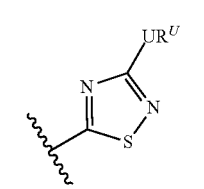 xvii
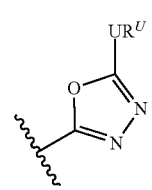 xviii
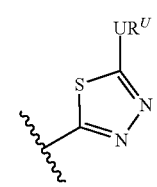 xix
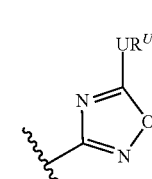 xx
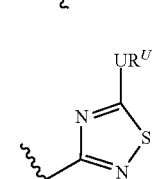 xxi
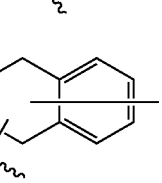 xxii
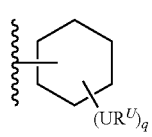 xxiii
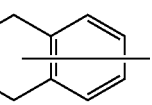 xxiv
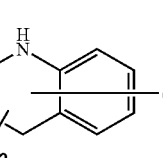 xxv
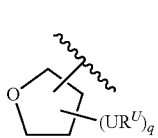 xxvi
xxvii

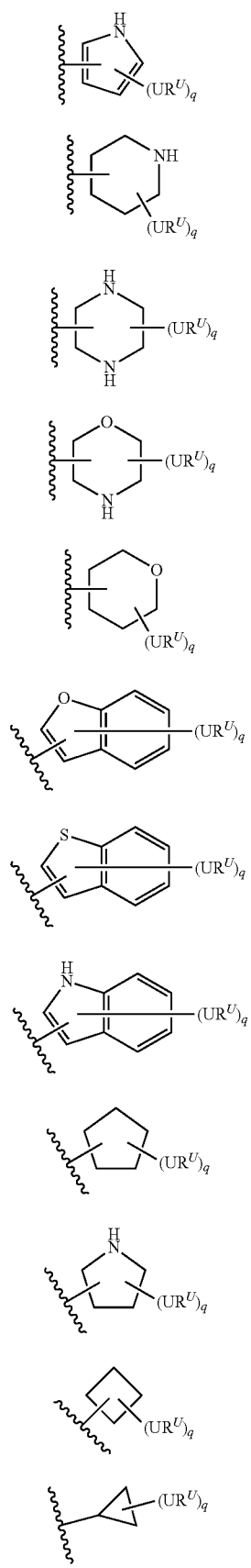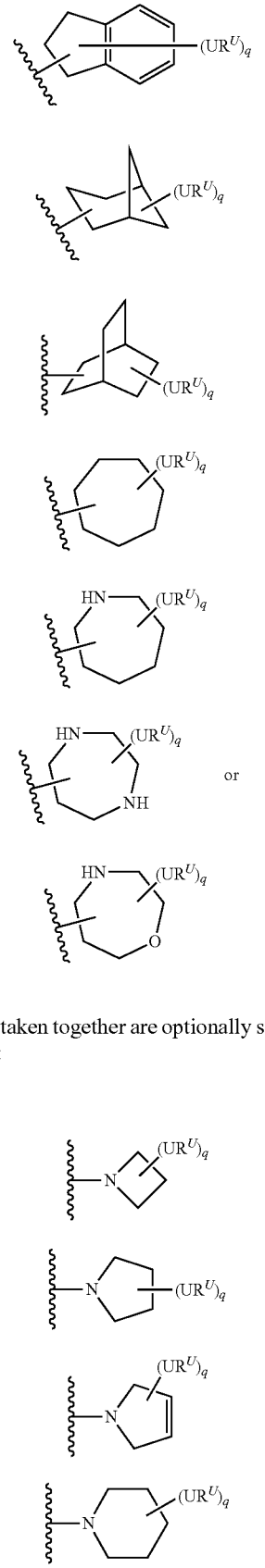
or $R^A$ and $R^B$, taken together are optionally substituted group selected from:

-continued e 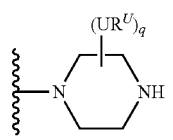

f 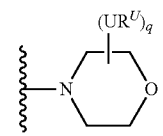

g 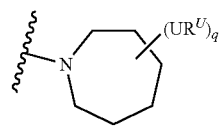

h 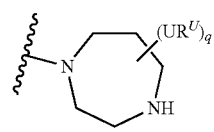

i 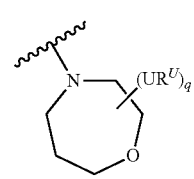

j 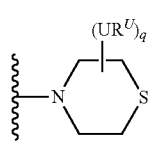

k 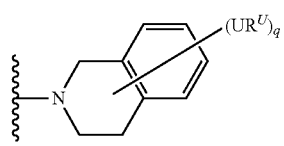

l 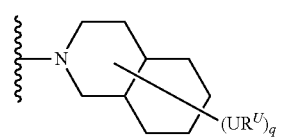

m 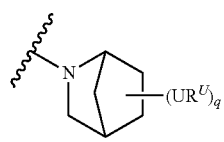

n 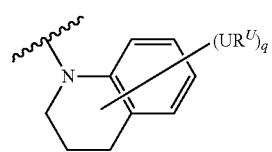

or o 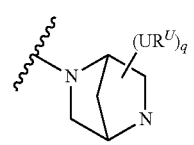

In some embodiments, $OR^A$ is selected from methoxy, ethoxy, t-butoxy, n-propyloxy, isopropyloxy[1,3]dioxolan-4-ylmethoxy, pyrrolidin-1-ylethoxy, 2-(N,N-dimethyl)ethoxy, cyclobutyloxy, cyclopentyloxy, cyclohexyloxy, 4-methxyl-cyclohexyloxy, 3,4-dimethylcyclohexyloxy, pyridinyloxy, 1-pyran-4-yloxy, 5-Methyl-[1,3]dioxan-5-ylmethoxy or bicyclo[3.1.1]hept-2-yloxy.

In some embodiments, $NR^AR^B$ is selected from methylamino, dimethylamino, diethylamino, ethylamino, cyclopentylamino, cyclohexylamino, benzylamino, benzylmethylamino, piperdinyl, 2-methylpiperidin-1-yl, 3-methylpiperidin-1-yl, 3-hydroxymethylpiperidin-1-yl, 4-hydroxymethylpiperidin-1-yl, 4-methylpiperidin-1-yl, 4-propylpiperidin-1-yl, 4-benzylpiperidin-1-yl, 4-(ethylcarboethoxy)piperidin-1-yl, 3,6-dihydro-2H-pyridin-1-yl, 3,5-dimethylpiperidin-1-yl, 4-acylpiperazin-1-yl, 4-methylpiperazin-1-yl, 4-phenylpiperazin-1-yl, 4-morpholinyl, 4-thiomorpholinyl, 1-pyrrolidinyl, 2-methylpyrrolidinyl, 3,4-dihydropyrrol-1-yl, isothiazolidin-2-yl, 1-azepinyl, 1,4-dioxa-8-aza-spiro[4.5]decan-8-yl, N-methyl, N-(1,4-dioxolan-5-yl)methylamino, decahydroisoquinolin-2-yl, 1,2,3,4-tetrahydroquinolin-1-yl, 2-aza-bicyclo[2.2.1]heptan-2-yl, or anilinyl;

In some embodiments, $Ar^1$ is selected from:

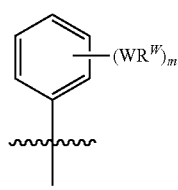 b-i

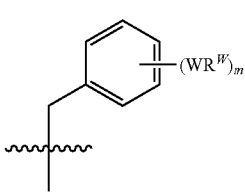 b-ii

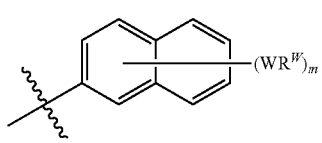 b-iii

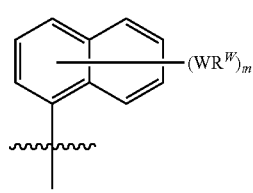 b-iv

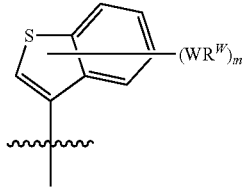 b-v

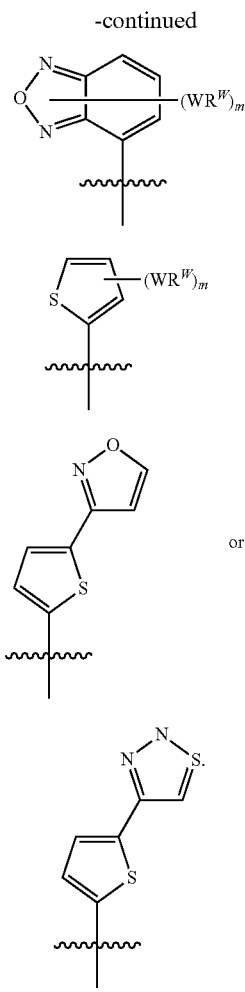

b-vi b-vii b-viii or b-ix

In some embodiments, q is 0, 1, 2, or 3, and each occurrence of U—$R^U$ is independently hydrogen, R', —CH$_2$R', halogen, CN, NO$_2$, —N(R')$_2$, —CH$_2$N(R')$_2$, —OR', —CH$_2$OR', —SR', —CH$_2$SR', —COOR', —NR'COR', —NR'COOR', —CON(R')$_2$, —SO$_2$N(R')$_2$, —CONR'(CH$_2$)$_2$N(R')$_2$, —CONR(CH$_2$)$_3$N(R')$_2$, —CONR'(CH$_2$)$_4$N(R')$_2$, —O(CH$_2$)$_2$OR', —O(CH$_2$)$_3$OR', O(CH$_2$)$_4$OR', —O(CH$_2$)$_2$N(R')$_2$, —O(CH$_2$)$_3$N(R')$_2$, —O(CH$_2$)$_4$N(R')$_2$, —NR'CH(CH$_2$OH)R', —NR'CH(CH$_2$CH$_2$OH)R', —NR'(CH$_2$)R', —NR'(CH$_2$)$_2$R', —NR'(CH$_2$)$_3$R', —NR'(CH$_2$)$_4$R', —NR'(CH$_2$)N(R')$_2$, —NR'(CH$_2$)$_2$N(R')$_2$, —NR'(CH$_2$)$_3$N(R')$_2$, —NR'(CH$_2$)$_4$N(R')$_2$, —NR'(CH$_2$)OR', —NR'(CH$_2$)$_2$OR', —NR'(CH$_2$)$_3$OR', or —NR'(CH$_2$)$_4$OR'. In still other embodiments, q is 1, 2, or 3 and each occurrence of U—$R^U$ is independently F, Cl, Br, CN, —OH, —NH$_2$, —CH$_2$OH, —C$_1$-C$_6$alkyl, —O(C$_1$-C$_6$alkyl), —CH$_2$O(C$_1$-C$_6$alkyl), —CO(C$_1$-C$_6$alkyl), —COO(C$_1$-C$_6$alkyl), —NHSO$_2$(C$_1$-C$_6$alkyl), —SO$_2$NH$_2$, —CONH$_2$, —CON(C$_1$-C$_6$alkyl), —SO$_2$(C$_1$-C$_6$alkyl), —SO$_2$phenyl, phenyl, benzyl, —N(C$_1$-C$_6$alkyl)$_2$, or —S(C$_1$-C$_6$alkyl), wherein each of the foregoing phenyl, benzyl, and C$_1$-C$_6$alkyl groups is independently and optionally substituted, and wherein each of the foregoing C$_1$-C$_6$alkyl groups is linear, branched, or cyclic.

As also described generally above, $R^1$ is absent or is Y—$R^Y$; wherein Y is a bond or is an optionally substituted C$_1$-C$_6$ alkylidene chain wherein up to two methylene units of Y are optionally and independently replaced by —CO—, —CONR—, —O—, —NRCO—, —S—, —SO$_2$—, —NR—, —SO$_2$NR—, or —NRSO$_2$—, and each occurrence of $R^Y$ is independently R', OR', SR', N(R')$_2$, halogen, NO$_2$, or CN, provided that when $R^1$ is present, it is always bonded to the nitrogen atom through a carbon atom. In certain embodiments, when $R^1$ is present, $R^1$ is Y—$R^Y$, wherein Y is an optionally substituted C$_1$-C$_4$alkylidene chain, wherein one or two non-adjacent methylene units of Y are optionally and independently replaced by —CO—, —CONR—, —O—, —NRCO—, —S—, —SO$_2$—, —NR—, —SO$_2$NR—, or —NRSO$_2$—, and each occurrence of $R^Y$ is independently R', OR', SR', N(R')$_2$, halogen, NO$_2$, or CN. In other embodiments, $R^1$ is optionally substituted C$_1$-C$_4$alkyl. In still other embodiments, $R^1$ is —CH$_3$, —CH$_2$CH$_3$, —CH$_2$CH$_2$CH$_3$, —CH$_2$CH$_2$CH$_2$CH$_3$, —(CH$_2$)$_2$OR', —(CH$_2$)$_3$OR', —(CH$_2$)$_2$N(R')$_2$, —(CH$_2$)$_3$N(R')$_2$, —(CH$_2$)$_2$NRCOR', or —(CH$_2$)$_3$NRCOR'.

As described generally for compounds of formula (I), $R^2$ and $R^3$ are each independently -T-$R^Z$, or $R^2$ and $R^3$, taken together, form an optionally substituted 5- or 6-membered monocyclic aryl ring having 0-5 heteroatoms independently selected from nitrogen, oxygen, or sulfur or a 5-, 6-, or 7-membered saturated or partially unsaturated monocyclic ring having 0-3 heteroatoms independently selected from nitrogen, oxygen, or sulfur, wherein any ring formed by $R^2$ and $R^3$ taken together is optionally substituted at one or more carbon atoms or one or more substitutable nitrogen atoms with x independent occurrences of Q-$R^X$, wherein x is 0-5.

In certain embodiments, $R^2$ and $R^3$ are each independently -T-$R^Z$. In some embodiments, $R^2$ and $R^3$ are each independently hydrogen, halogen, or an optionally substituted group selected from C$_{1-6}$alkyl, aryl, aryl(C$_{1-6}$)alkyl, —N(R')$_2$, —CH$_2$N(R')$_2$, OR', —CH$_2$OR', SR', —CH$_2$SR', COOR', —NRCOR', —(CH$_2$)$_2$N(R')$_2$, —(CH$_2$)$_2$OR', —(CH$_2$)$_2$SR', —COR', —CON(R')$_2$, SO$_2$R', or —SO$_2$N(R')$_2$. In other embodiments, $R^2$ and $R^3$ are each independently H, Cl, Br, F, CF$_3$, Me, Et, —COOH, NH$_2$, —N(CH$_3$)$_2$, —N(Et)$_2$, —N(iPr)$_2$, —O(CH$_2$)$_2$OCH$_3$, —CO(C$_1$-C$_4$alkyl), —CONH$_2$, —COOCH$_3$, —OH, —CH$_2$OH, —NHCOCH$_3$, —SO$_2$(C$_1$-C$_4$alkyl), —SO$_2$NH$_2$, —SO$_2$N(CH$_3$)$_2$, or an optionally substituted group selected from C$_{1-4}$alkoxy, phenyl, phenyloxy, benzyl, or benzyloxy.

In still other embodiments $R^2$ and $R^3$ taken together form a ring selected from:

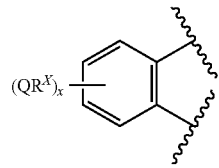

o

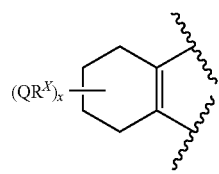

p

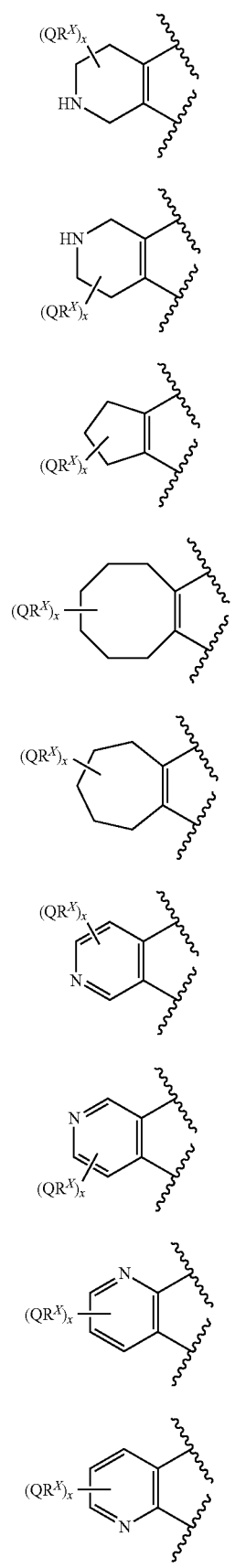
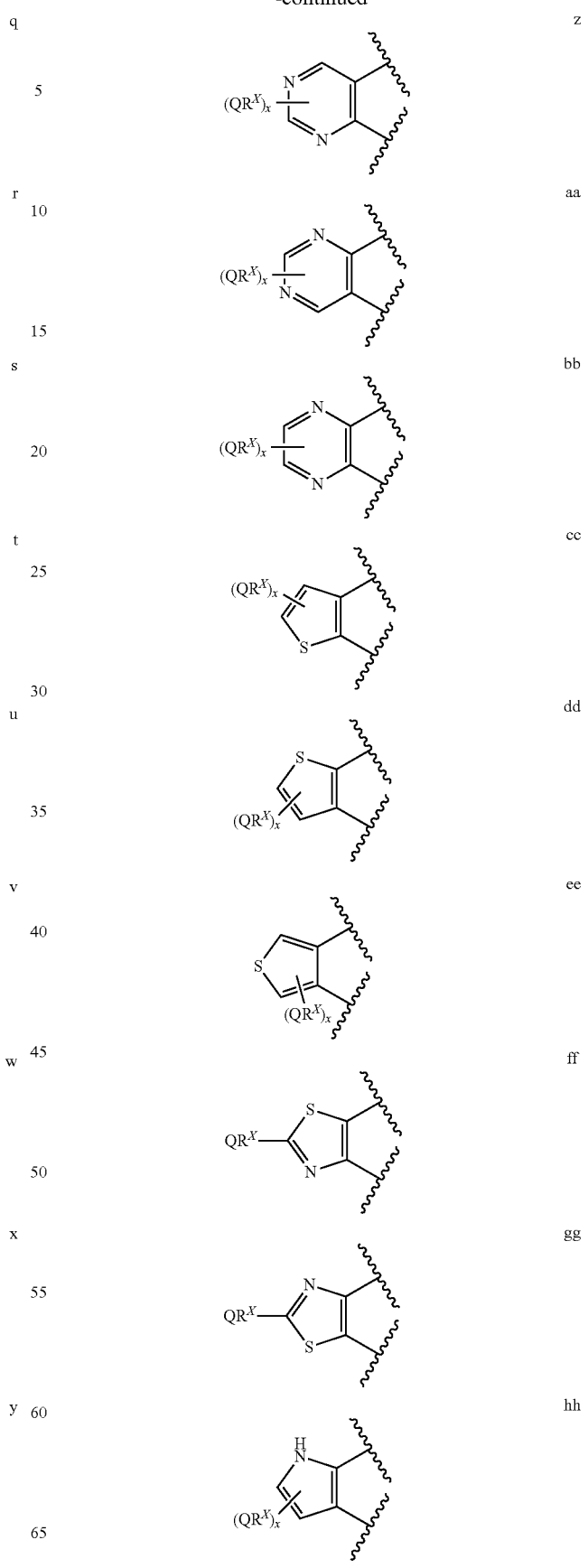

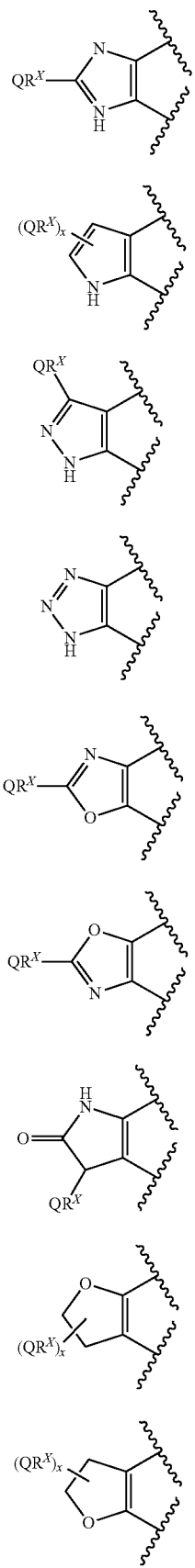
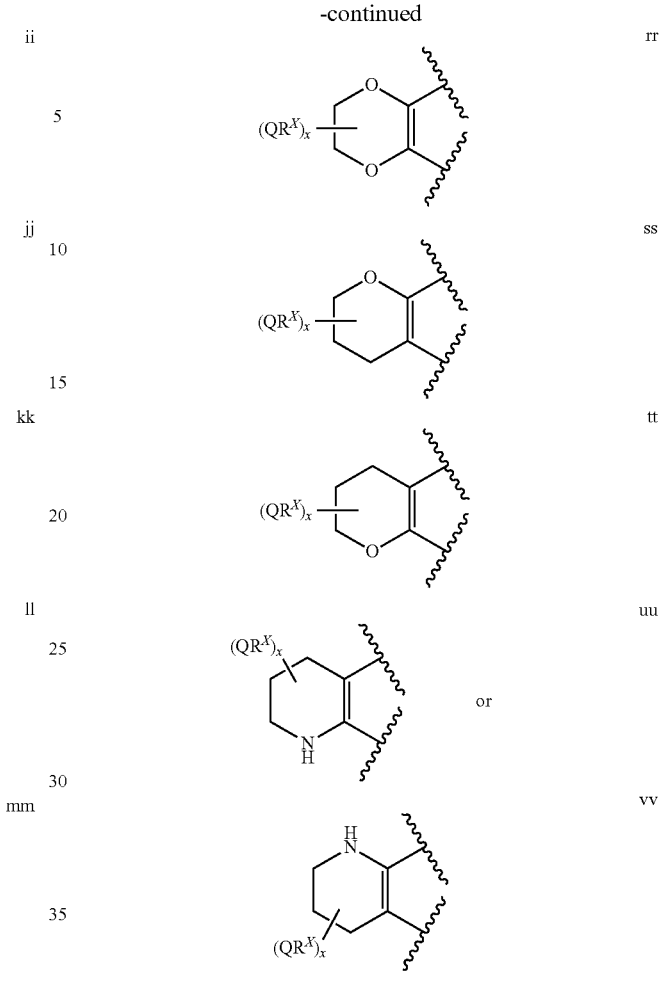

In some embodiments, R² and R³ are taken together to form ring o or ring bb.

It will also be appreciated that one or more hydrogen atoms on any substitutable nitrogen or carbon atom may optionally be substituted with one or more independent occurrences of Q-R$^X$. In some embodiments, R² and R³ are taken together to form a phenyl, halophenyl, amidophenyl, cyanophenyl, methylsulfonylphenyl, tetrazolylphenyl, methoxyphenyl, dimethoxyphenyl, or methylcarboxamidophenyl;

As described generally above, rings formed by R² and R³ taken together are optionally substituted with x occurrences of Q-R$^X$, wherein x is 0-5. In certain embodiments, x is 0-4, and each occurrence of Q-R$^X$, when present, is independently halogen, CN, NO₂, or an optionally substituted group selected from $C_{1-4}$alkyl, aryl, aralkyl, heteroaryl, a cycloalkyl or heterocycloalkyl group having 3-10 atoms, —N(R')₂, —CH₂N(R')₂, —OR', —CH₂OR', —SR', —SO₂R', —CH₂SR', —COOR', —NRCOR', —CON(R')₂, or —S(O)₂N(R')₂. In other embodiments, each occurrence of Q-R$^X$, when present, is Cl, Br, F, CF₃, methyl, ethyl, propyl, butyl, CN, —COOH, —N(CH₃)₂, —N(Et)₂, —N(iPr)₂, —O(CH₂)₂OCH₃, —CONH₂, —COOCH₃, —OH, —OCH₃, —OCH₂CH₃, —OCH₂CH₂CH₃, —OCH₂CH₂CH₂CH₃, —CH₂OH, —NHCOCH₃, —SO₂NH₂, or an optionally substituted group selected from piperidinyl, piperizinyl, morpholino, phenyl, phenyloxy, benzyl, benzyloxy, pyridyl, pyrimidinyl, pyridazinyl, thiophene, furan, thiazole, oxazole, thiadiazole, oxadiazole, pyrazole, or pyrrole. In other embodiments, x is 2. In still other embodiments, x is 1. In yet other embodiments, x is 0.

As described generally above, $G^2$ and $G^3$ are each independently absent or an optionally substituted $C_1$-$C_6$ alkylidene chain, wherein one or two methylene units are optionally and independently replaced with CO, CS, SO, $SO_2$, NR', $N(SO_2R')$—, $N(COR')$—, O, or S, and wherein one or two hydrogen atoms of one or more methylene units are optionally substituted with R'.

In some embodiments, $G^2$ is a $C_1$-$C_3$ alkylidene chain wherein one or two methylene units are optionally and independently replaced by —NR'—, —$N(SO_2R')$—, $N(COR')$—, —O—, —S—, —CO—, —CS, or —$SO_2$—, and wherein any hydrogen atom in the $C_1$-$C_3$ alkylidene chain is optionally and independently substituted with R'. In other embodiments, $G^2$ is —$(C(R')_2)_{1-3}$—, —NR'—, —$N(SO_2R')$—, $N(COR')$—, —$C(R')_2NR'$—, or —$NR'C(R')_2$—. In still other embodiments $G^2$ is —CHR', wherein R' is hydrogen, or optionally substituted $C_1$-$C_4$ alkyl. In yet other embodiments, $G^2$ is selected from $CH_2$, $CH(CH_3)$, $CH(CH_2$—$CH_3)$, $CH(CH_2CH_2CH_3)$, or $C(CH_3)_2$. In yet other embodiments, $G^2$ is $CH(CH_3)$.

In some embodiments, $G^2$ is absent. In yet other embodiments, $G^2$ is a $C_3$-$C_6$ spirocycloalkylidene ring. In such a ring, one or two methylene units in said alkylidene are optionally and independently replaced with —CO—, —CS—, —SO—, —$SO_2$—, —NR'—, $N(SO_2R')$—, $N(COR')$—, —O—, or —S—, and wherein one or two hydrogen atoms of one or more methylene units are optionally substituted with R'. In yet other embodiments, $G^2$ is spirocycloalkyl, spirocyclopentyl, or spirocyclohexyl.

In some embodiments, $G^2$ is a $C_3$-$C_6$ spirocycloalkylidene ring, wherein any hydrogen atom in the ring is optionally and independently substituted with R'. In certain embodiment, $G^2$ is selected from spirocyclopropyl, spirocyclopentyl, or spirocyclohexyl. In yet other embodiments, $G^2$ is spirocyclopropyl.

In some embodiments, $G^3$ is an optionally substituted $C_1$-$C_3$ alkylidene chain wherein one or two methylene units are optionally and independently replaced by —NR'—, —O—, —S—, —CO—, —CS—, or —$SO_2$—, and wherein any hydrogen atom in the $C_1$-$C_3$ alkylidene chain is optionally and independently substituted with R'. In other embodiments, $G^3$ is —$(C(R')_2)_{1-3}$—, —NR'—, —CO—, —$SO_2$—, or —CONR—. In yet other embodiments, $G^3$ is —CO—, —$SO_2$—, —$SO_2$—$CH_2$—, or —CONH—.

In certain embodiments, B is an optionally substituted group selected from $C_{6-10}$ aryl, a heteroaryl ring having 5-10 ring atoms, a cycloalkyl or heterocyclyl ring having 3-10 ring atoms, or is an optionally substituted $C_1$-$C_6$ alkylidene chain, wherein one or two methylene units are optionally and independently replaced with —CO—, —CS—, —SO—, —$SO_2$—, —NR'—, —$N(SO_2R')$, —$N(COR')$—, —O, or —S—, and wherein one or two hydrogen atoms of one or more methylene units are optionally substituted with R'.

In some embodiments, B is —$NR'C(R')_2NR'$—, —$NR'(C(R')_2)_2NR'$—, —$NR'(C(R')_2)_3NR'$—, —$NR'(C(R')_2)_4NR'$—, or is an optionally substituted 5-, 6- or 7-membered saturated, partially unsaturated or fully unsaturated ring having the structure

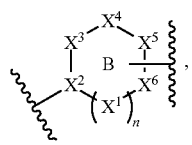

wherein n is 0, 1, or 2; $X^2$ and $X^5$ are each independently CR' or N; and each occurrence of $X^1$, when present, and $X^3$, $X^4$ and $X^6$ are each independently, as valency and stability permit, $C(R')_2$, —O—, —NR—, S, C=O, or C=S. In still other embodiments, at least one of $X^1$, $X^2$, $X^3$, $X^4$, $X^5$ or $X^6$ is a nitrogen atom. In yet other embodiments, at least one of $X^2$ or $X^5$ is a nitrogen atom. In still other embodiments, at least one of $X^2$ or $X^5$ is a nitrogen atom, and each occurrence of $X^1$, when present, and $X^3$, $X^4$, and $X^6$ are each independently $C(R')_2$. In yet other embodiments, $X^2$ is nitrogen, $X^5$ is CR', and and each occurrence of $X^1$, when present, and $X^3$, $X^4$, and $X^6$ are each independently $C(R')_2$. In still other embodiments, $X^2$ is CR', $X^5$ is N, and $X^3$, $X^4$, and $X^6$ are each independently $C(R')_2$. In yet other embodiments, $X^2$ and $X^5$ are each N, and $X^3$, $X^4$, and $X^6$ are each independently $C(R')_2$.

In some embodiments, B is selected from:

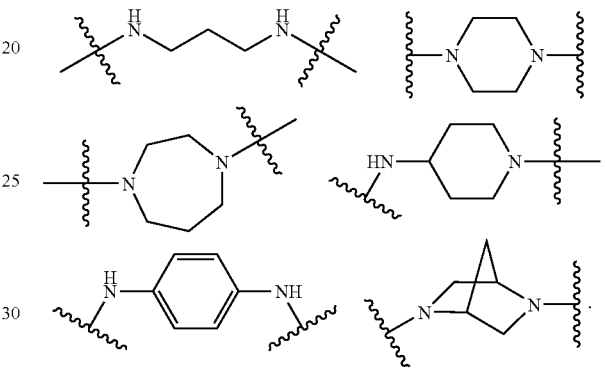

In some embodiments, R' is R.

In yet other embodiments, $R^2$ and $R^3$, taken together form an optionally substituted phenyl group and compounds have the formula II:

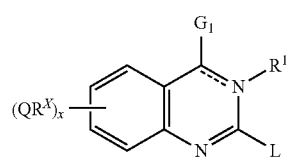

II

In yet other embodiments for compounds of general formula II, $G_1$ is =O, —$R^A$, —$OR^A$, $SR^A$, or $NR^AR^B$, and compounds of formula II-A, II-B, II-C, II-D, and II-E are provided as depicted generally below.

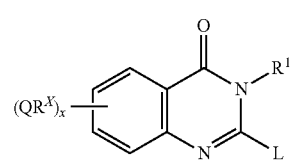

II-A

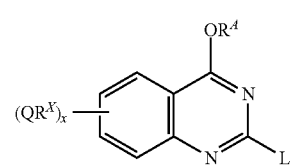

II-B

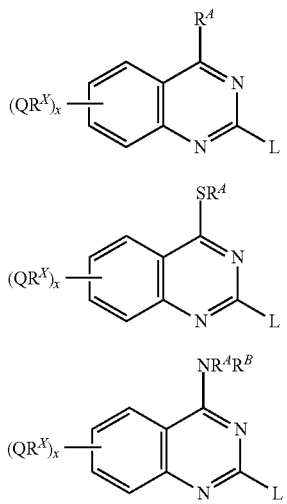

As described generally above, rings formed by $R^2$ and $R^3$ taken together are optionally substituted with x occurrences of $Q\text{-}R^X$, wherein x is 0-5. In certain embodiments, x is 0-4, and each occurrence of $Q\text{-}R^X$, when present, is independently halogen, CN, $NO_2$, or an optionally substituted group selected from $C_{1-4}$alkyl, aryl, aralkyl, heteroaryl, a cycloalkyl or heterocycloalkyl group having 3-10 atoms, —N(R')$_2$, —CH$_2$N(R')$_2$, —OR', —CH$_2$OR', —SR', —SO$_2$R', —CH$_2$SR', —COOR', —NRCOR', —CON(R')$_2$, or —S(O)$_2$N(R—)$_2$. In other embodiments, each occurrence of $Q\text{-}R^X$, when present, is Cl, Br, F, $CF_3$, methyl, ethyl, propyl, butyl, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —OCH$_2$CH$_2$CH$_3$, —OCH$_2$CH$_2$CH$_2$CH$_3$, —CH$_2$OH, —NHCOCH$_3$, —SO$_2$NH$_2$, or an optionally substituted group selected from piperidinyl, piperizinyl, morpholino, phenyl, phenyloxy, benzyl, benzyloxy, pyridyl, pyrimidinyl, pyridazinyl, thiophene, furan, thiazole, oxazole, thiadiazole, oxadiazole, pyrazole, or pyrrole. In other embodiments, x is 2. In still other embodiments, x is 1. In yet other embodiments, x is 0.

As described generally above, $G^2$ and $G^3$ are each independently absent or an optionally substituted $C_1\text{-}C_6$ alkylidene chain, wherein one or two methylene units are optionally and independently replaced with CO, CS, SO, $SO_2$, NR', N(SO$_2$R')—, N(COR')—, O, or S, and wherein one or two hydrogen atoms of one or more methylene units are optionally substituted with R'.

In some embodiments, $G^2$ is a $C_1\text{-}C_3$alkylidene chain wherein one or two methylene units are optionally and independently replaced by —NR'—, —N(SO$_2$R')—, N(COR')—, —O—, —S—, —CO—, —CS, or —SO$_2$—, and wherein any hydrogen atom in the $C_1\text{-}C_3$alkylidene chain is optionally and independently substituted with R'. In other embodiments, $G^2$ is —(C(R')$_2$)$_{1-3}$—, —NR'—, —N(SO$_2$R')—, N(COR')—, —C(R')$_2$NR'—, or —NR'C(R')$_2$—. In still other embodiments $G^2$ is —CHR', wherein R' is hydrogen, or optionally substituted $C_1\text{-}C_4$alkyl.

In some embodiments, $G^3$ is an optionally substituted $C_1\text{-}C_3$alkylidene chain wherein one or two methylene units are optionally and independently replaced by —NR'—, —O—, —S—, —CO—, —CS—, or —SO$_2$—, and wherein any hydrogen atom in the $C_1\text{-}C_3$alkylidene chain is optionally and independently substituted with R'. In other embodiments, $G^3$ is —(C(R')$_2$)$_{1-3}$—, —NR'—, —CO—, —SO$_2$—, or —CONR—.

As described generally above, B is absent or is an optionally substituted group selected from $C_{6-10}$ aryl, a heteroaryl ring having 5-10 ring atoms, a cycloalkyl or heterocyclyl ring having 3-10 ring atoms, or is an optionally substituted $C_1\text{-}C_6$ alkylidene chain, wherein one or two methylene units are optionally and independently replaced with —CO—, —CS—, —SO—, —SO$_2$—, —NR'—, —N(SO$_2$R'), —N(COR')—, —O, or —S—, and wherein one or two hydrogen atoms of one or more methylene units are optionally substituted with R'.

In some embodiments, B is —NR'C(R')$_2$NR'—, —NR'(C(R')$_2$)$_2$NR'—, —NR'(C(R')$_2$)$_3$NR'—, —NR'(C(R')$_2$)$_4$NR'—, or is an optionally substituted 5-, 6- or 7-membered saturated, partially unsaturated or fully unsaturated ring having the structure

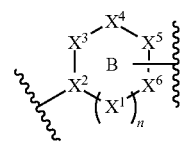

wherein n is 0, 1, or 2; $X^2$ and $X^5$ are each independently CR' or N; and each occurrence of $X^1$, when present, and $X^3$, $X^4$ and $X^6$ are each independently, as valency and stability permit, C(R')$_2$, —O—, —NR—, S, C=O, or C=S. In still other embodiments, at least one of $X^1$, $X^2$, $X^3$, $X^4$, $X^5$ or $X^6$ is a nitrogen atom. In yet other embodiments, at least one of $X^2$ or $X^5$ is a nitrogen atom. In still other embodiments, at least one of $X^2$ or $X^5$ is a nitrogen atom, and each occurrence of $X^1$, when present, and $X^3$, $X^4$, and $X^6$ are each independently C(R')$_2$. In yet other embodiments, $X^2$ is nitrogen, $X^5$ is CR', and and each occurrence of $X^1$, when present, and $X^3$, $X^4$, and $X^6$ are each independently C(R')$_2$. In still other embodiments, $X^2$ is CR', $X^5$ is N, and $X^3$, $X^4$, and $X^6$ are each independently C(R')$_2$. In yet other embodiments, $X^2$ and $X^5$ are each N, and $X^3$, $X^4$, and $X^6$ are each independently C(R')$_2$.

In still other embodiments, B is an optionally substituted 5-, 6- or 7-membered saturated, partially unsaturated or fully unsaturated ring having the structure

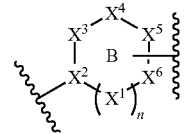

and compounds have the structure of formula III:

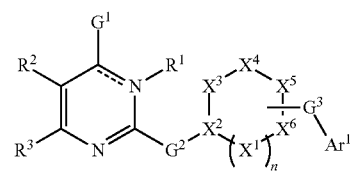

wherein $G^1$, $R^1$, $R^2$, $R^3$, $G^2$, $G^3$, and $Ar^1$ are as described generally above and in classes and subclasses herein; n is 0, 1, or 2; $X^2$ and $X^5$ are each independently CR' or N; and each occurrence of $X^1$, when present, and $X^3$, $X^4$ and $X^6$ are each independently, as valency and stability permit, $C(R')_2$, —O—, —NR—, S, C=O, or C=S.

In some embodiments, for compounds of formula III, at least one of $X^1$, $X^2$, $X^3$, $X^4$, $X^5$ or $X^6$ is a nitrogen atom. In yet other embodiments, at least one of $X^2$ or $X^5$ is a nitrogen atom. In still other embodiments, at least one of $X^2$ or $X^5$ is a nitrogen atom and each occurrence of $X^1$, when present, and $X^3$, $X^4$, and $X^6$ are each independently $C(R')_2$. In yet other embodiments, $X^2$ is nitrogen, $X^5$ is CR', and and each occurrence of $X^1$, when present, and $X^3$, $X^4$, and $X^6$ are each independently $C(R')_2$. In still other embodiments, $X^2$ is CR', $X^5$ is N, and $X^3$, $X^4$, and $X^6$ are each independently $C(R')_2$. In yet other embodiments, $X^2$ and $X^5$ are each N, and $X^3$, $X^4$, and $X^6$ are each independently $C(R')_2$.

In other embodiments, for compounds of general formula III described directly above, $G_1$ is =O, —$OR^A$, $SR^A$, or $NR^AR^B$, and compounds having the following general structures III-A, III-B, III-C, III-D, and III-E, are provided as depicted generally below.

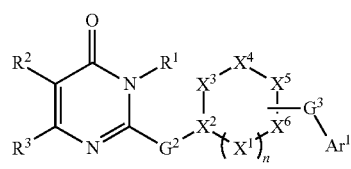

III-A

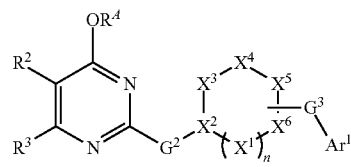

III-B

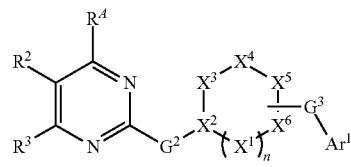

III-C

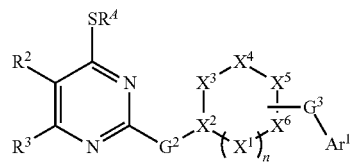

III-D

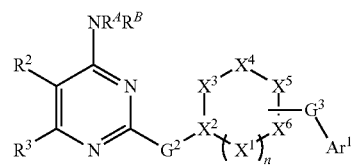

III-E

In still other embodiments, for compounds of general formula III described directly above, $G_1$ is =O, —$R^A$, —$OR^A$, $SR^A$, or $NR^AR^B$, and $G^3$ is bonded to $X^5$ and compounds having formulae IV-A, IV-B, IV-C, IV-D, and IV-E, are provided as depicted generally below.

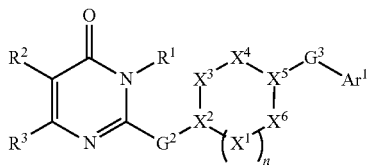

IV-A

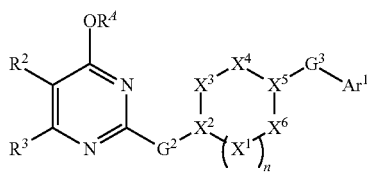

IV-B

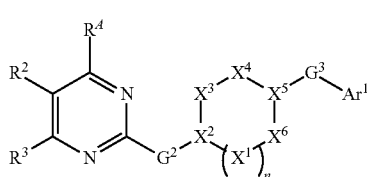

IV-C

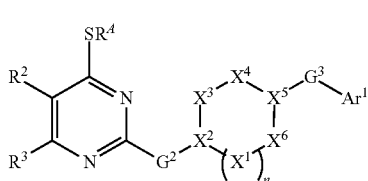

IV-D

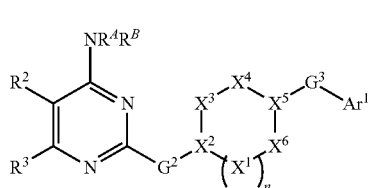

IV-E

In yet other embodiments, for compounds of general formula III described directly above, $R^2$ and $R^3$, taken together form an optionally substituted phenyl group, $G_1$ is =O, —$R^A$, —$OR^A$, $SR^A$, or $NR^AR^B$, and $G^3$ is bonded to $X^5$ and compounds having formulae V-A, V-B, V-C, V-D, and V-E, are provided as depicted generally below.

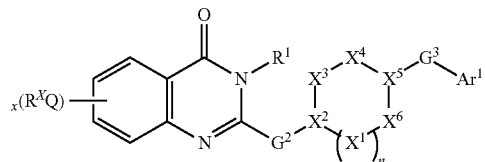

V-A

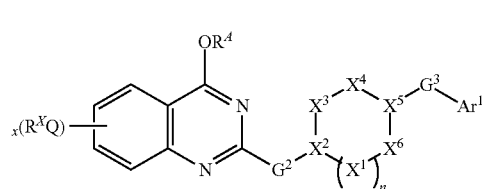

V-B

-continued

V-C
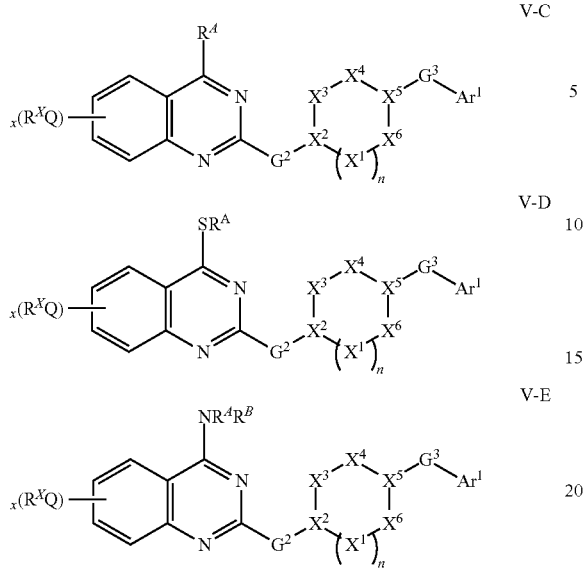

V-D

V-E

In general, as described above, Ar$^1$ is absent or is a 3-7 membered saturated, partially unsaturated, or fully unsaturated monocyclic ring having 0-3 heteroatoms independently selected from nitrogen, oxygen, or sulfur, or an 8-10 membered saturated, partially unsaturated, or fully unsaturated bicyclic ring system having 0-5 heteroatoms independently selected from nitrogen, oxygen, or sulfur; wherein Ar$^1$ is optionally substituted with m independent occurrences of —W—R$^W$, wherein m is 0-5 and W is a bond or is an optionally substituted C$_1$-C$_6$ alkylidene chain wherein up to two methylene units of W are optionally and independently replaced by —CO—, —CS—, —COCO—, —CONR—, —CONRNR—, —CO$_2$—, —OCO—, —NRCO$_2$—, —O—, —NRCONR—, —OCONR—, —NRNR, —NRNRCO—, —NRCO—, —S—, —SO, —SO$_2$—, —NR—, —SO$_2$NR—, —NRSO$_2$—, —NRSO$_2$NR—, and each occurrence of R$^W$ is independently R', halogen, NO$_2$, or CN.

In some embodiments, Ar$^1$ is selected from:

a-i
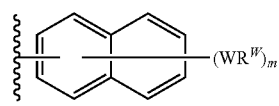

a-ii
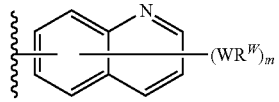

a-iii
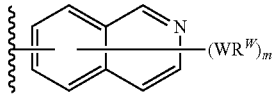

a-iv
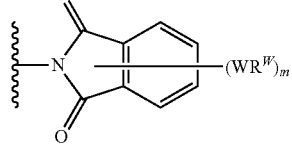

a-v
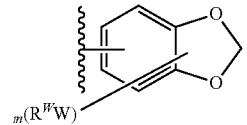

a-vi
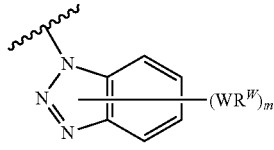

a-vii a-viii a-ix a-x
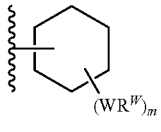

a-xi
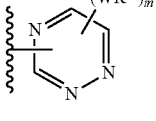

a-xii
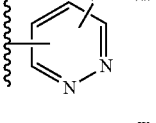

a-xiii
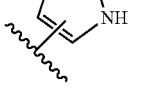

a-xiv
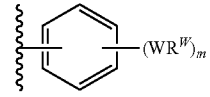

a-xv
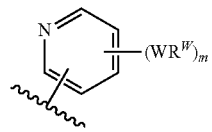

a-xvi
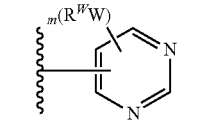

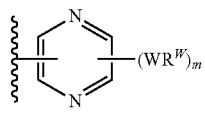

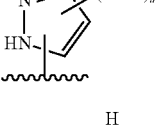

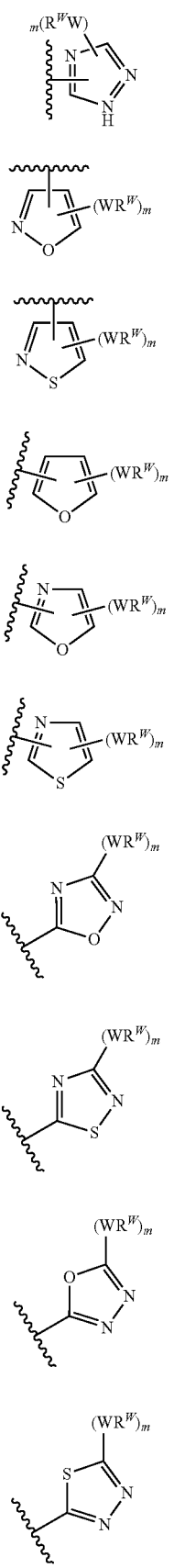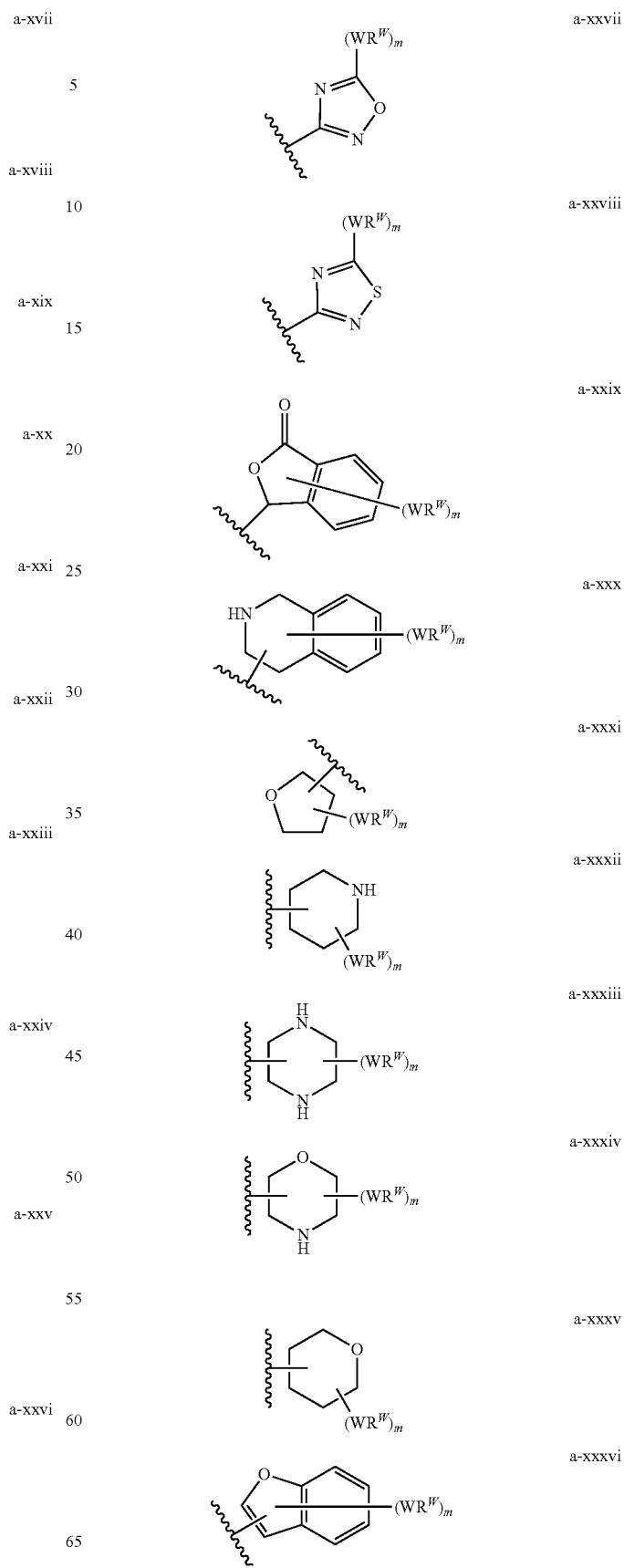

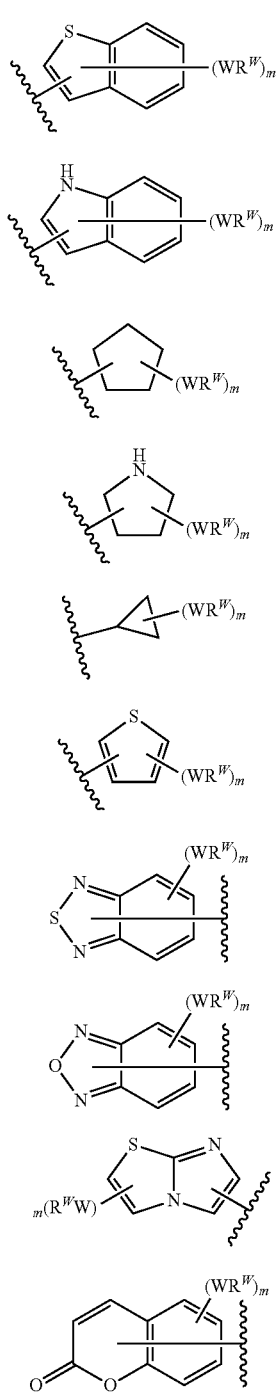

wherein m is 0, 1, 2, 3, 4 or 5, and wherein any Ar$^1$ is bonded to G$^3$ through any substitutable nitrogen or carbon atom, and wherein one or more hydrogen atoms on any substitutable nitrogen or carbon atom is substituted with one or more independent occurrences of W—R$^W$. In some embodiments, Ar$^1$ is an optionally substituted group selected from a-i, a-ii, a-v, a-vi, a-vii, a-xx, a-xLii, a-xLiii, a-xLiv, a-xLv, or a-xLvi. In other embodiments, Ar$^1$ is an optionally substituted phenyl group (a-i).

In other embodiments, W is a bond or is an optionally substituted C$_{1-6}$ alkylidene chain wherein one or two non-adjacent methylene units are optionally and independently replaced by O, NR, S, SO$_2$, or COO, CO, and R$^W$ is R' or halogen. In still other embodiments, each occurrence of WR$^W$ is independently —C$_{1-3}$alkyl, —O(C$_{1-3}$alkyl), —CF$_3$, —OCF$_3$, —SCF$_3$, —F, —Cl, —Br, or —COOR', —COR', —O(CH$_2$)$_2$N(R)(R'), —O(CH$_2$)N(R)(R'), —CON(R)(R'), —(CH$_2$)$_2$OR', —(CH$_2$)OR', optionally substituted phenyl, —N(R)(R'), —(CH$_2$)$_2$N(R)(R'), or —(CH$_2$)N(R)(R').

In addition to these subsets already described herein, in certain embodiments, for compounds of formula V described directly above:

R$^A$ and R$^B$ are each independently hydrogen, an optionally substituted group selected from C$_1$-C$_7$alkyl, C$_3$-C$_7$ cycloalkyl, or C$_3$-C$_7$ heterocyclyl, or R$^A$ and R$^B$, taken together, form an optionally substituted 5-, 6-, or 7-membered heterocyclyl ring;

R$^1$ is —CH$_3$, —CH$_2$CH$_3$, —CH$_2$CH$_2$CH$_3$, —CH$_2$CH$_2$CH$_2$CH$_3$, —(CH$_2$)$_2$OR', —(CH$_2$)$_3$OR', —(CH$_2$)$_2$N(R')$_2$, —(CH$_2$)$_3$N(R')$_2$, —(CH$_2$)$_2$NRCOR', or —(CH$_2$)$_3$NRCOR'.

x is 0, 1, or 2, and each occurrence of -Q-R$^X$, when present, is Cl, Br, F, CF$_3$, methyl, ethyl, propyl, butyl, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —OCH$_2$CH$_2$CH$_3$, —OCH$_2$CH$_2$CH$_2$CH$_3$, —CH$_2$OH, —NHCOCH$_3$, —SO$_2$NH$_2$, or an optionally substituted group selected from piperidinyl, piperizinyl, morpholino, phenyl, phenyloxy, benzyl, benzyloxy, pyridyl, pyrimidinyl, pyridazinyl, thiophene, furan, thiazole, oxazole, thiadiazole, oxadiazole, pyrazole, or pyrrole;

n is 1 and X$^1$, X$^3$, X$^4$, and X$^6$ are each CHR;

G$^2$ is —(C(R')$_2$)$_{1-3}$—, —NR'—, —C(R')$_2$NR'—, or —NR'C(R')$_2$—;

G$^3$ is —(C(R')$_2$)$_{1-3}$—, —NR'—, —CO—, —SO$_2$—, or —(C=O)NR'—;

Ar$^1$ is selected from one of rings a-i through a-xLvi; and each occurrence of WR$^W$ is independently —C$_{1-3}$alkyl, —O(C$_{1-3}$alkyl), —CF$_3$, —OCF$_3$, —SCF$_3$, —F, —Cl, —Br, or —COOR', —COR', —O(CH$_2$)$_2$N(R)(R'), —O(CH$_2$)N(R)(R'), —C(O)N(R)(R'), —(CH$_2$)$_2$OR', —(CH$_2$)OR', optionally substituted phenyl, —N(R)(R'), —(CH$_2$)$_2$N(R)(R'), or —(CH$_2$)N(R)(R').

In other embodiments for compounds described directly above, G$^2$ is CH(C$_{1-3}$alkyl) or spirocyclopropyl; G$^3$ is —CO—, —SO$_2$—, or —CONR—; and Ar$^1$ is phenyl optionally substituted with —WR$^W$.

Some embodiments of compounds of formula V-A have one or any combination of the following features:

(i) R$^1$ is H, —CH$_3$, —CH$_2$CH$_3$, —CH$_2$CH$_2$CH$_3$, —CH$_2$CH$_2$OCH$_3$;

(ii) x is 0 or x is 1, and QR$^X$ is halo, —CONH$_2$, CN, SO$_2$Me, tetrazolyl, methoxy, dimethoxy, or CO$_2$Me;

(iii) G$^2$ is —CH$_2$—, —CH(CH$_3$)—, —C(CH$_3$)$_2$—, —CH(CH$_2$CH$_3$)—, or —CH(CH$_2$CH$_2$CH$_3$)—;

(iv) B is 1,4-piperazinyl;

(v) G$^3$ is —SO$_2$—, —C(O)—, or —C(O)NH—; and (vi) Ar$^1$ is selected from an optionally substituted ring selected from:

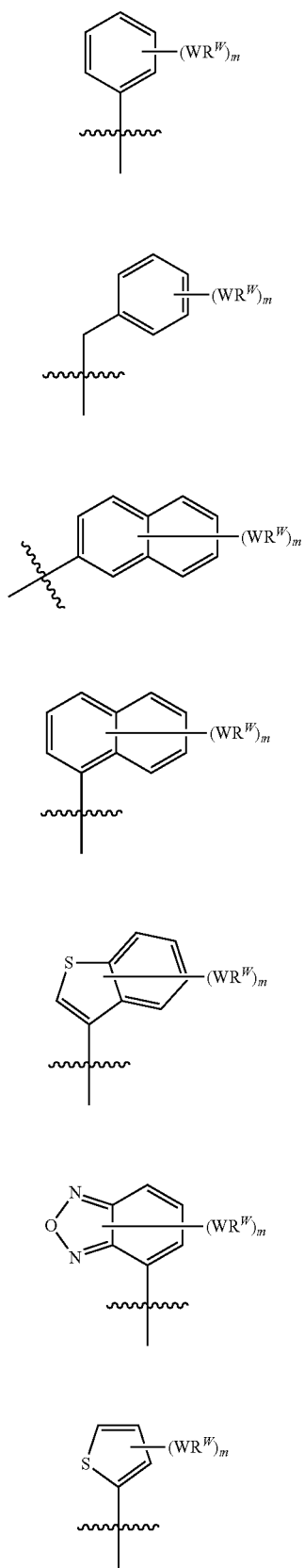

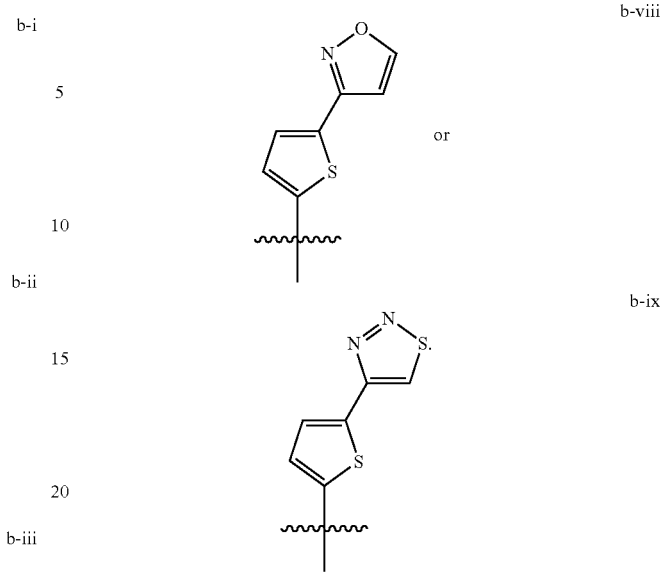

Some embodiments of compounds of formula V-B have one or any combination of the following features:

(i) —OR$^A$ is methoxy, ethoxy, t-butoxy, n-propyloxy, iso-propyloxy[1,3]dioxolan-4-ylmethoxy, pyrrolidin-1-ylethoxy, 2-(N,N-dimethyl)ethoxy, cyclobutyloxy, cyclopentyloxy, cyclohexyloxy, 4-methxylcyclohexyloxy, 3,4-dimethylcyclohexyloxy, pyridinyloxy, 1-pyran-4-yloxy, 5-Methyl-[1,3]dioxan-5-ylmethoxy or bicyclo[3.1.1]hept-2-yloxy;

(ii) x is 0, or x is 1 and QR$^X$ is halo;

(iii) G$^2$ is —CH$_2$—, —CH(CH$_3$)—, or —C(CH$_3$)$_2$—

(iv) B is 1,4-piperazinyl;

(v) G$^3$ is —SO$_2$—;

(vi) Ar$^1$ is an optionally substituted phenyl ring.

Some embodiments of compounds of formula V-E have one or any combination of the following features:

(i) —NR$^A$R$^B$ is methylamino, dimethylamino, diethylamino, ethylamino, cyclopentylamino, cyclohexylamino, benzylamino, benzylmethylamino, piperdinyl, 2-methylpiperidin-1-yl, 3-methylpiperidin-1-yl, 3-hydroxymethylpiperidin-1-yl, 4-hydroxymethylpiperidin-1-yl, 4-methylpiperidin-1-yl, 4-propylpiperidin-1-yl, 4-benzylpiperidin-1-yl, 4-(ethylcarboethoxy)piperidin-1-yl, 3,6-dihydro-2H-pyridin-1-yl, 3,5-dimethylpiperidin-1-yl, 4-acylpiperazin-1-yl, 4-methylpiperazin-1-yl, 4-phenylpiperazin-1-yl, 4-morpholinyl, 4-thiomorpholinyl, 1-pyrrolidinyl, 2-methylpyrrolidinyl, 3,4-dihydropyrrol-1-yl, isothiazolidin-2-yl, 1-azepinyl, 1,4-dioxa-8-aza-spiro[4.5]decan-8-yl, N-methyl, N-(1,4-dioxalan-5-yl)methylamino, decahydroisoquinolin-2-yl, 1,2,3,4-tetrahydroquinolin-1-yl, 2-aza-bicyclo[2.2.1]heptan-2-yl, or anilinyl;

(iii) x is 0 or QR$^X$ is halo;

(iv) G$^2$ is —CH(CH$_3$)—, —CH(CH$_2$CH$_3$)—, —CH(CH$_2$CH$_2$CH$_3$)— or spirocyclopropyl;

(v) B is 1,4-piperazinyl;

(vi) G$^3$ is —SO$_2$—;

(vii) Ar$^1$ is an optionally substituted phenyl ring.

Representative compounds of formula I are set forth below in Table 1.

TABLE 1
| Cmpd No. | Structure |
|---|---|
| 1 | 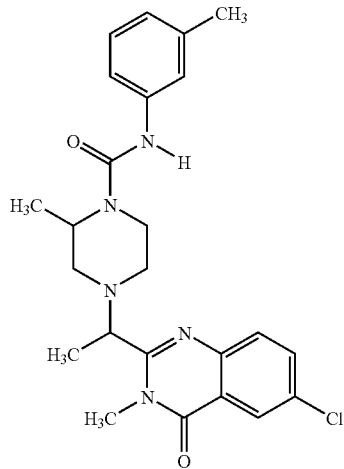 [SMILES: Cc1cccc(NC(=O)N2CCN(C(C)c3nc4ccc(Cl)cc4c(=O)n3C)CC2C)c1] |
| 2 | 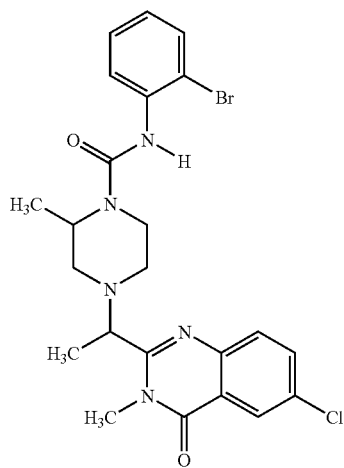 [SMILES: CC(c1nc2ccc(Cl)cc2c(=O)n1C)N1CCN(C(=O)Nc2ccccc2Br)C(C)C1] |
| 3 | 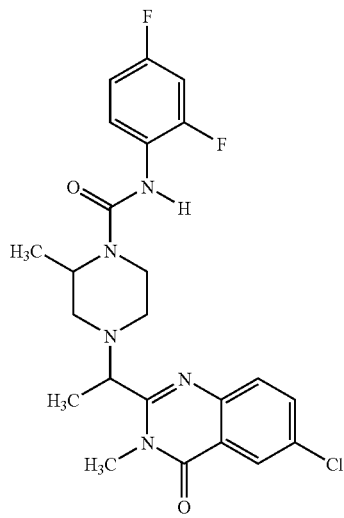 [SMILES: CC(c1nc2ccc(Cl)cc2c(=O)n1C)N1CCN(C(=O)Nc2ccc(F)cc2F)C(C)C1] |

TABLE 1-continued
| Cmpd No. | Structure |
|---|---|
| 4 | 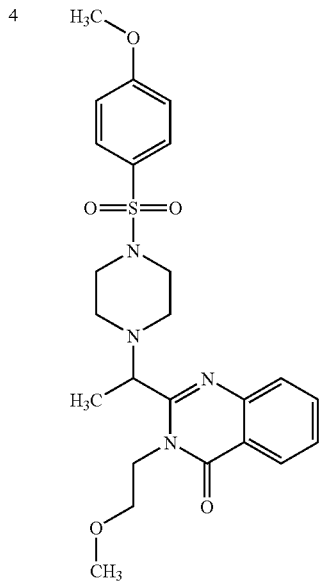 |
| 5 | 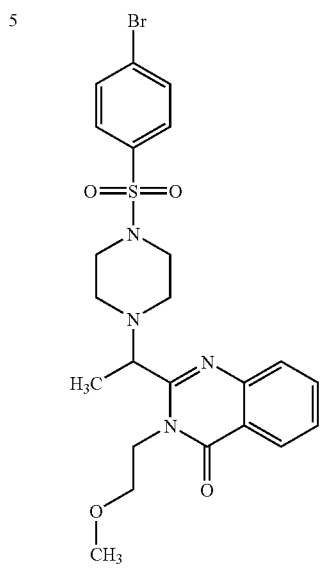 |

TABLE 1-continued
| Cmpd No. | Structure |
|---|---|
| 6 | 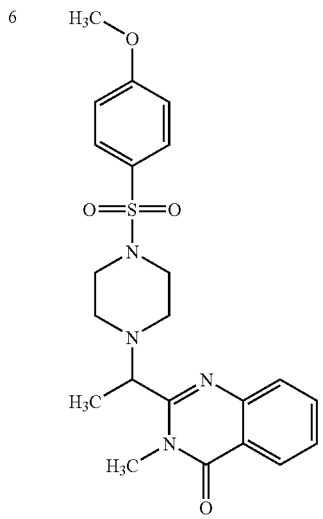 |
| 7 | 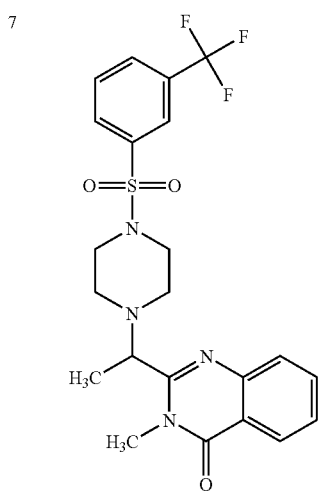 |
| 8 | 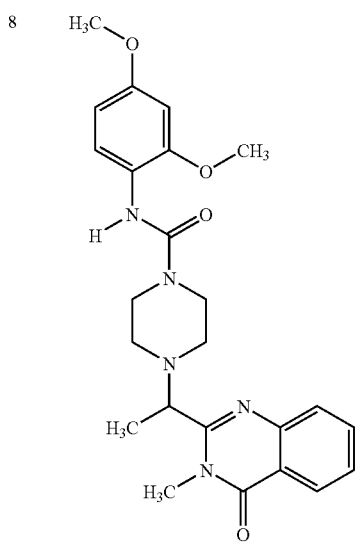 |

TABLE 1-continued
| Cmpd No. | Structure |
|---|---|
| 9 | 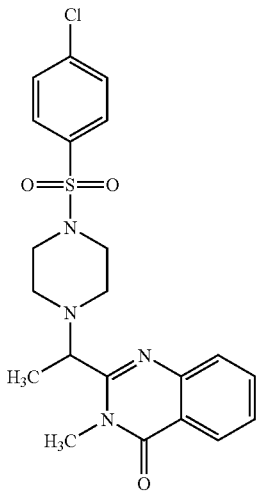 [SMILES: CC(c1nc2ccccc2c(=O)n1C)N1CCN(S(=O)(=O)c2ccc(Cl)cc2)CC1] |
| 10 | 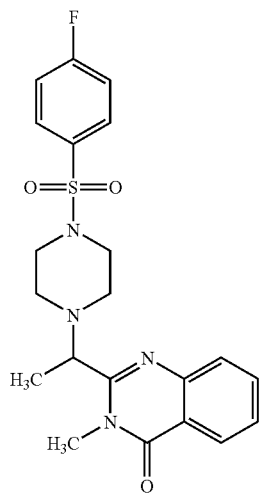 [SMILES: CC(c1nc2ccccc2c(=O)n1C)N1CCN(S(=O)(=O)c2ccc(F)cc2)CC1] |
| 11 | 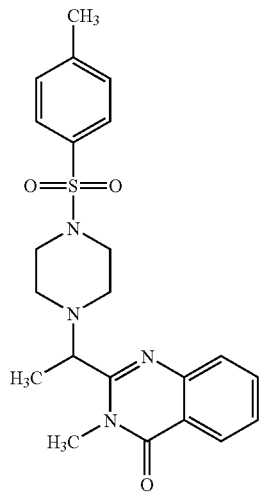 [SMILES: Cc1ccc(S(=O)(=O)N2CCN(C(C)c3nc4ccccc4c(=O)n3C)CC2)cc1] |

TABLE 1-continued
| Cmpd No. | Structure |
| --- | --- |
| 12 | 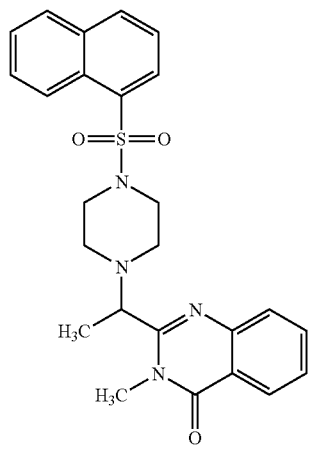 [SMILES: CC(c1nc2ccccc2c(=O)n1C)N1CCN(S(=O)(=O)c2cccc3ccccc23)CC1] |
| 13 | 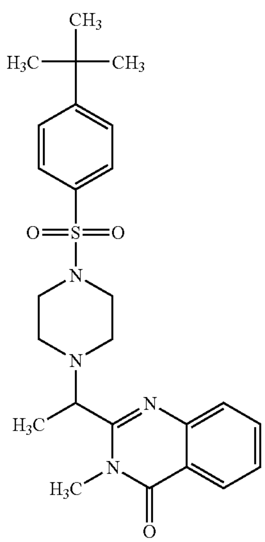 [SMILES: CC(c1nc2ccccc2c(=O)n1C)N1CCN(S(=O)(=O)c2ccc(C(C)(C)C)cc2)CC1] |
| 14 | 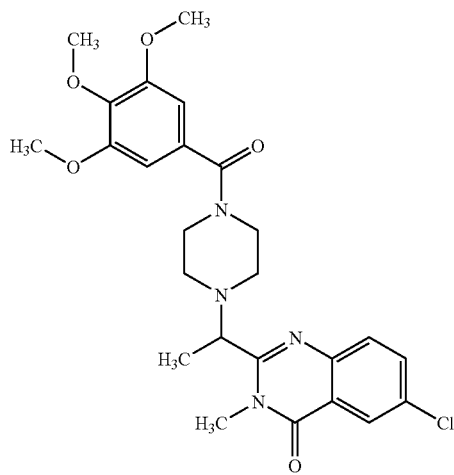 [SMILES: COc1cc(C(=O)N2CCN(C(C)c3nc4ccc(Cl)cc4c(=O)n3C)CC2)cc(OC)c1OC] |

TABLE 1-continued
| Cmpd No. | Structure |
| --- | --- |
| 15 | 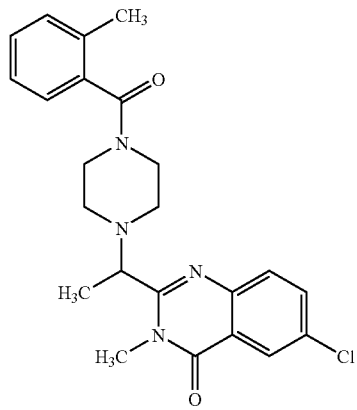 |
| 16 | 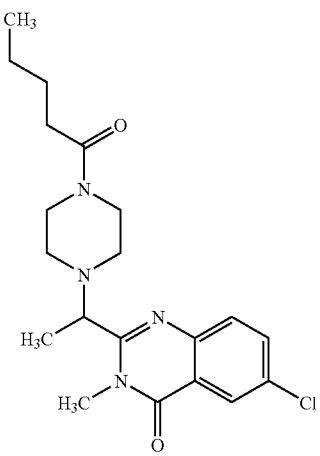 [SMILES: CCCCC(=O)N1CCN(C(C)c2nc3ccc(Cl)cc3c(=O)n2C)CC1] |
| 17 | 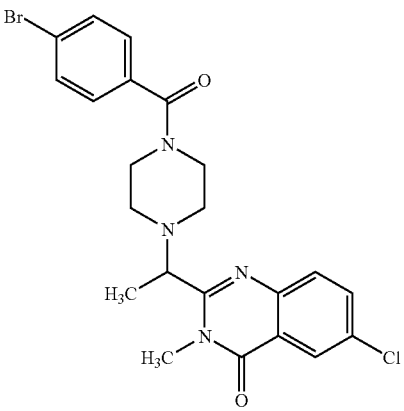 [SMILES: CC(c1nc2ccc(Cl)cc2c(=O)n1C)N1CCN(C(=O)c2ccc(Br)cc2)CC1] |

TABLE 1-continued

| Cmpd No. | Structure |
|---|---|
| 18 | 4-chlorophenyl carbamoyl piperazine linked via N to CH(CH₃) at 2-position of 3-methyl-6-chloro-quinazolin-4(3H)-one |
| 19 | 4-(phenylsulfonyl)piperazine linked via N to CH(CH₃) at 2-position of 3-propyl-quinazolin-4(3H)-one |
| 20 | 4-((4-chloro-3-nitrophenyl)sulfonyl)piperazine linked via N to CH(CH₃) at 2-position of 3-propyl-quinazolin-4(3H)-one |

TABLE 1-continued
| Cmpd No. | Structure |
|---|---|
| 21 | 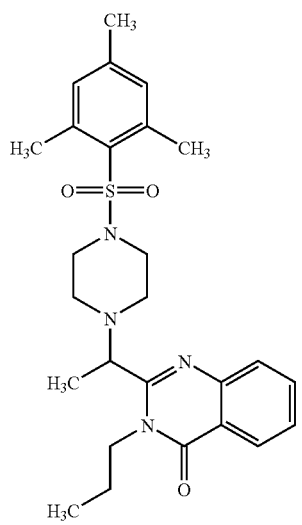 [SMILES: CCCn1c(C(C)N2CCN(S(=O)(=O)c3c(C)cc(C)cc3C)CC2)nc2ccccc2c1=O] |
| 22 | 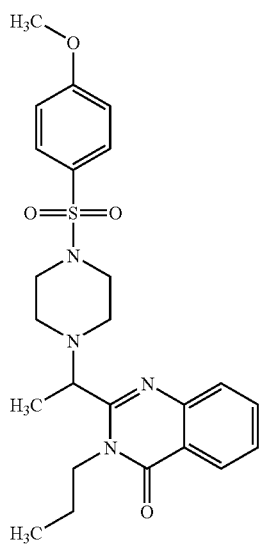 [SMILES: CCCn1c(C(C)N2CCN(S(=O)(=O)c3ccc(OC)cc3)CC2)nc2ccccc2c1=O] |
| 23 | 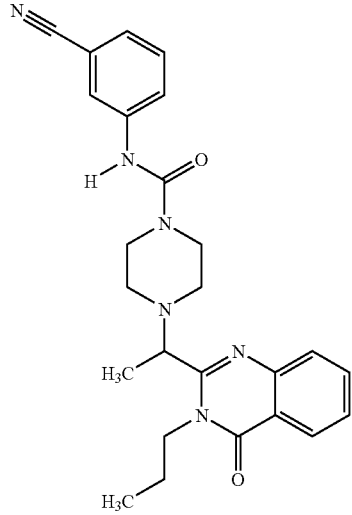 [SMILES: CCCn1c(C(C)N2CCN(C(=O)Nc3cccc(C#N)c3)CC2)nc2ccccc2c1=O] |

TABLE 1-continued
| Cmpd No. | Structure |
|---|---|
| 24 | 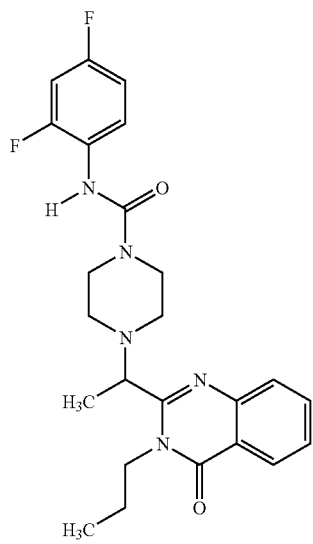 [SMILES: CCCn1c(C(C)N2CCN(C(=O)Nc3ccc(F)cc3F)CC2)nc2ccccc2c1=O] |
| 25 | 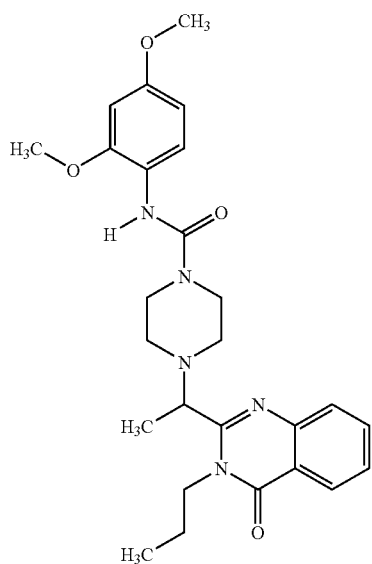 [SMILES: CCCn1c(C(C)N2CCN(C(=O)Nc3ccc(OC)cc3OC)CC2)nc2ccccc2c1=O] |
| 26 | 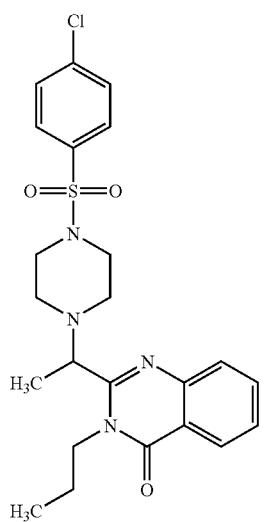 |

TABLE 1-continued
| Cmpd No. | Structure |
|---|---|
| 27 | 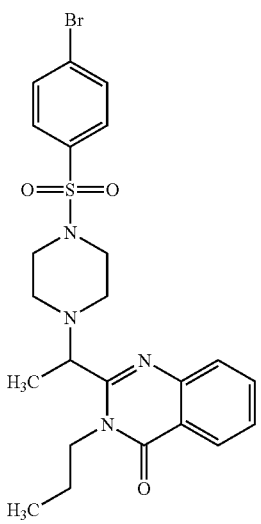 [SMILES: CCCn1c(C(C)N2CCN(S(=O)(=O)c3ccc(Br)cc3)CC2)nc2ccccc2c1=O] |
| 28 | 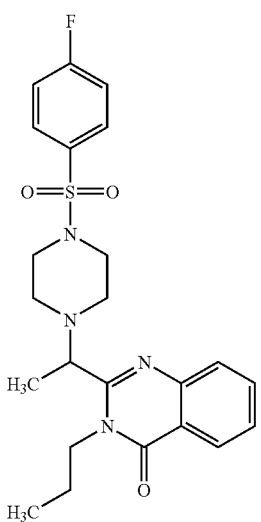 |
| 29 | 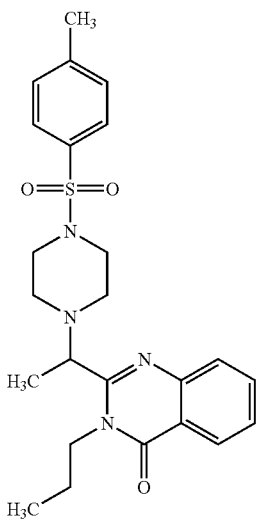 |

TABLE 1-continued
| Cmpd No. | Structure |
| --- | --- |
| 30 | 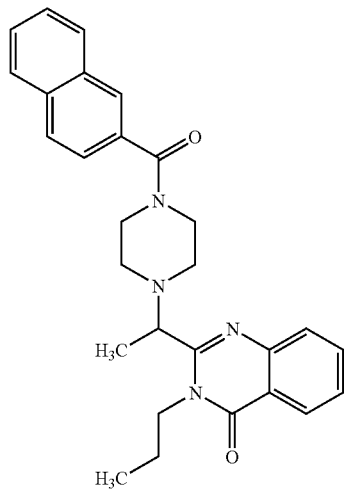 [SMILES: CCCn1c(C(C)N2CCN(C(=O)c3ccc4ccccc4c3)CC2)nc2ccccc2c1=O] |
| 31 | 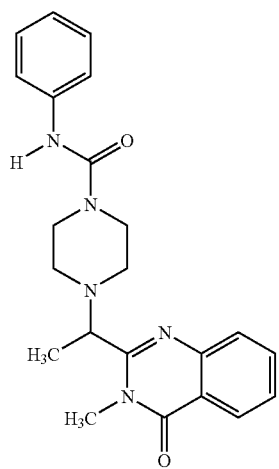 [SMILES: CC(c1nc2ccccc2c(=O)n1C)N1CCN(C(=O)Nc2ccccc2)CC1] |
| 32 | 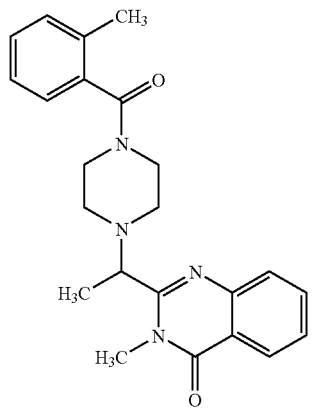 [SMILES: Cc1ccccc1C(=O)N1CCN(C(C)c2nc3ccccc3c(=O)n2C)CC1] |

TABLE 1-continued
| Cmpd No. | Structure |
|---|---|
| 33 | 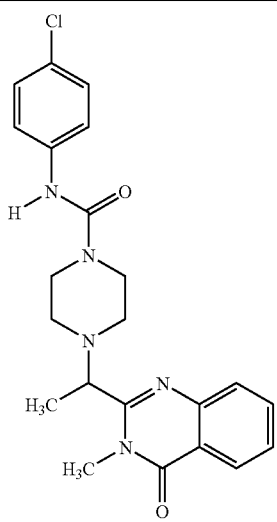 |
| 34 | 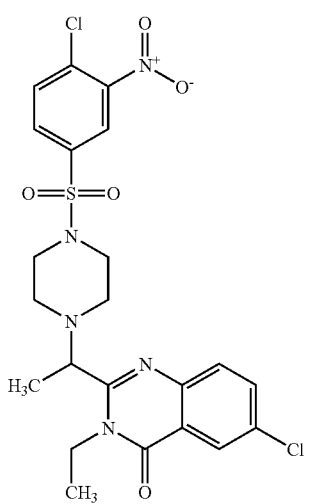 [SMILES: CCn1c(C(C)N2CCN(S(=O)(=O)c3ccc(Cl)c([N+](=O)[O-])c3)CC2)nc2ccc(Cl)cc2c1=O] |
| 35 | 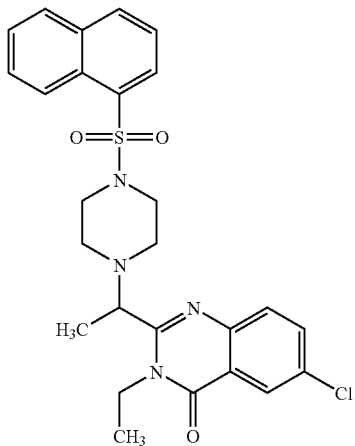 [SMILES: CCn1c(C(C)N2CCN(S(=O)(=O)c3cccc4ccccc34)CC2)nc2ccc(Cl)cc2c1=O] |

TABLE 1-continued
| Cmpd No. | Structure |
|---|---|
| 36 | 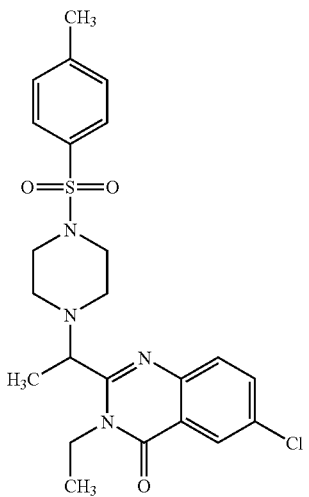 [SMILES: CCn1c(C(C)N2CCN(S(=O)(=O)c3ccc(C)cc3)CC2)nc2ccc(Cl)cc2c1=O] |
| 37 | 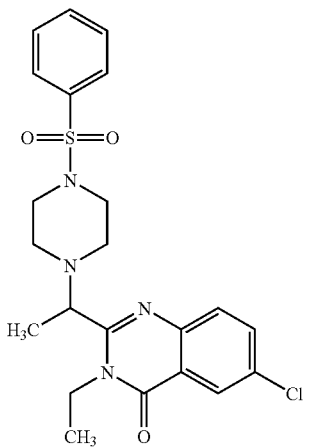 [SMILES: CCn1c(C(C)N2CCN(S(=O)(=O)c3ccccc3)CC2)nc2ccc(Cl)cc2c1=O] |
| 38 | 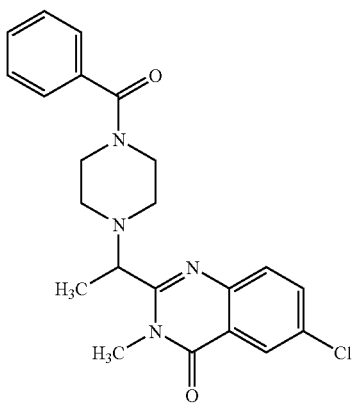 [SMILES: CC(c1nc2ccc(Cl)cc2c(=O)n1C)N1CCN(C(=O)c2ccccc2)CC1] |

TABLE 1-continued
| Cmpd No. | Structure |
|---|---|
| 39 | 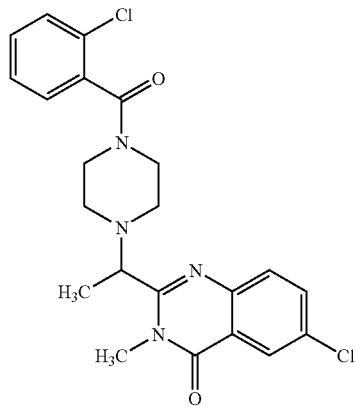 [SMILES: CC(c1nc2ccc(Cl)cc2c(=O)n1C)N1CCN(C(=O)c2ccccc2Cl)CC1] |
| 40 | 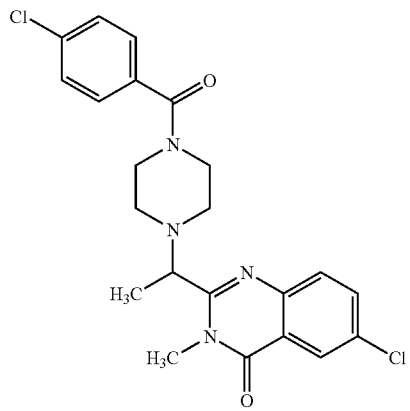 [SMILES: CC(c1nc2ccc(Cl)cc2c(=O)n1C)N1CCN(C(=O)c2ccc(Cl)cc2)CC1] |
| 41 | 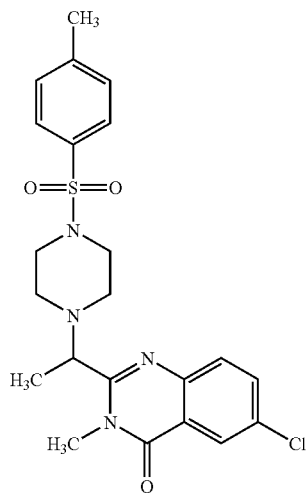 [SMILES: Cc1ccc(S(=O)(=O)N2CCN(C(C)c3nc4ccc(Cl)cc4c(=O)n3C)CC2)cc1] |

TABLE 1-continued
| Cmpd No. | Structure |
|---|---|
| 42 | 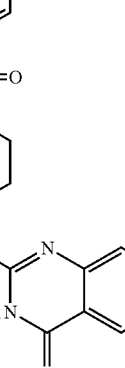 |
| 43 | 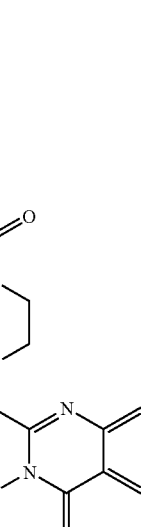 |
| 44 | 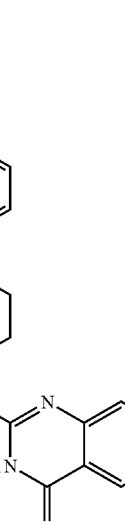 |

TABLE 1-continued
| Cmpd No. | Structure |
|---|---|
| 45 | 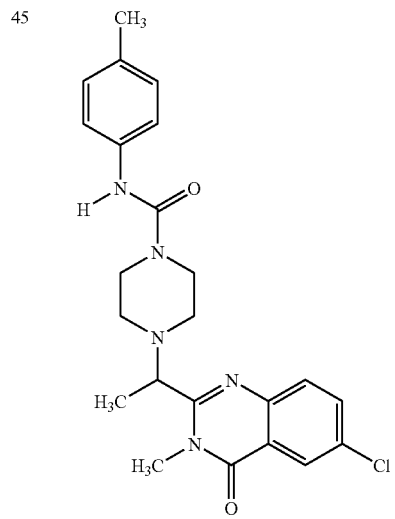 |
| 46 | 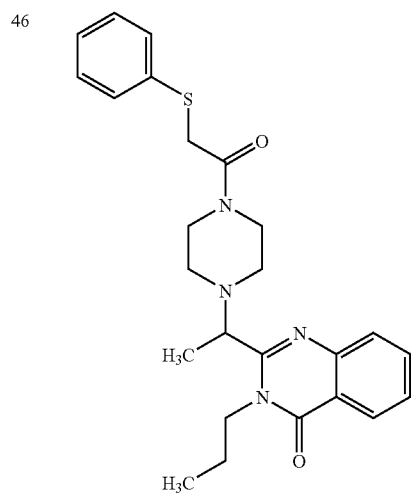 |
| 47 | 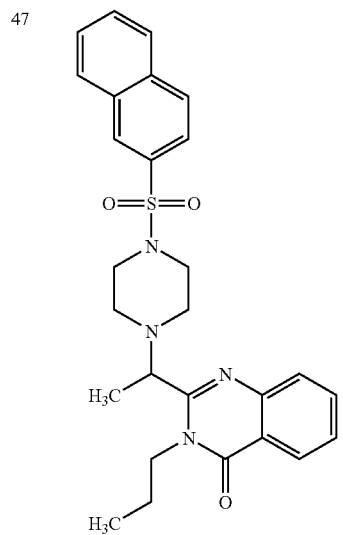 |

TABLE 1-continued
| Cmpd No. | Structure |
|---|---|
| 48 | 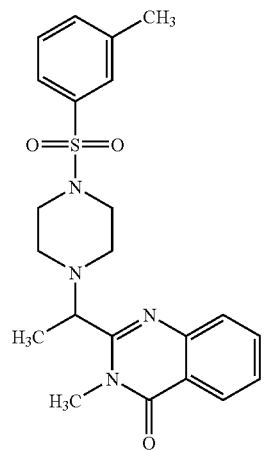 [SMILES: Cc1cccc(S(=O)(=O)N2CCN(C(C)c3nc4ccccc4c(=O)n3C)CC2)c1] |
| 49 | 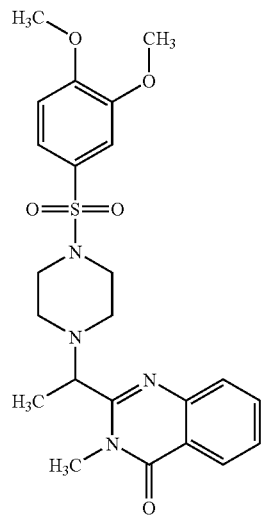 [SMILES: COc1ccc(S(=O)(=O)N2CCN(C(C)c3nc4ccccc4c(=O)n3C)CC2)cc1OC] |
| 50 | 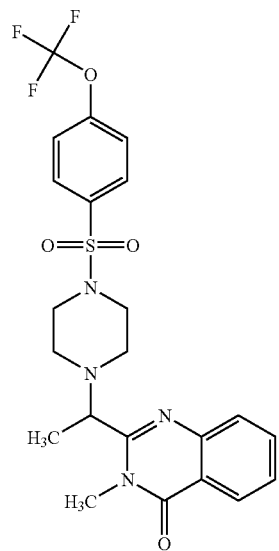 [SMILES: CC(c1nc2ccccc2c(=O)n1C)N1CCN(S(=O)(=O)c2ccc(OC(F)(F)F)cc2)CC1] |

TABLE 1-continued
| Cmpd No. | Structure |
|---|---|
| 51 | 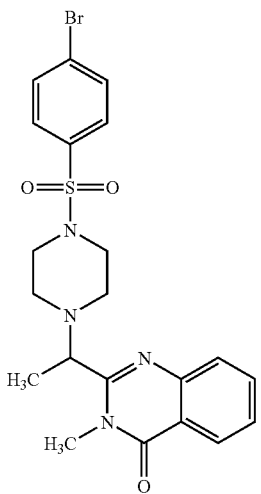 [SMILES: CC(c1nc2ccccc2c(=O)n1C)N1CCN(S(=O)(=O)c2ccc(Br)cc2)CC1] |
| 52 | 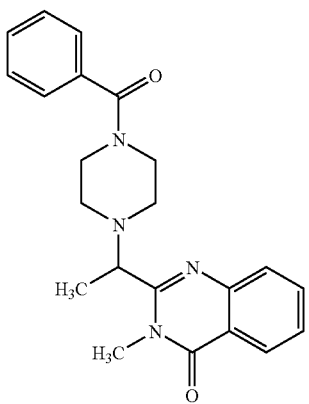 [SMILES: CC(c1nc2ccccc2c(=O)n1C)N1CCN(C(=O)c2ccccc2)CC1] |
| 53 | 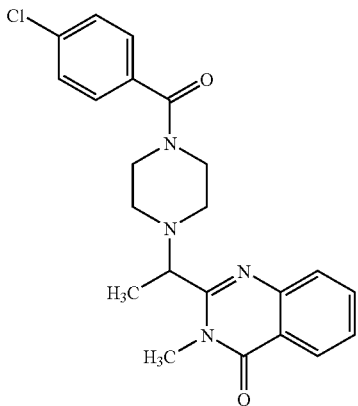 [SMILES: CC(c1nc2ccccc2c(=O)n1C)N1CCN(C(=O)c2ccc(Cl)cc2)CC1] |

TABLE 1-continued
| Cmpd No. | Structure |
|---|---|
| 54 | 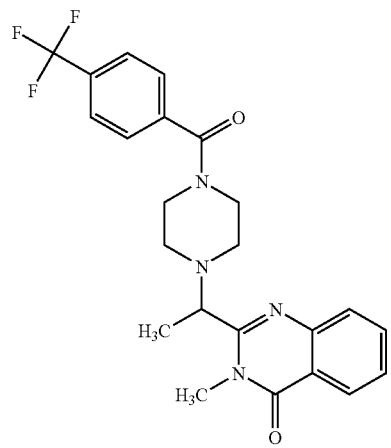 [SMILES: CC(c1nc2ccccc2c(=O)n1C)N1CCN(C(=O)c2ccc(C(F)(F)F)cc2)CC1] |
| 55 | 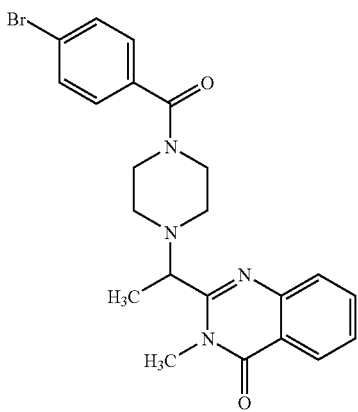 |
| 56 | 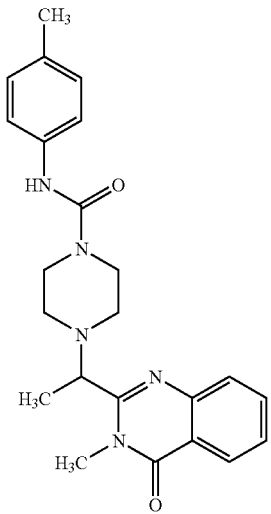 [SMILES: Cc1ccc(NC(=O)N2CCN(C(C)c3nc4ccccc4c(=O)n3C)CC2)cc1] |

TABLE 1-continued
| Cmpd No. | Structure |
|---|---|
| 57 | 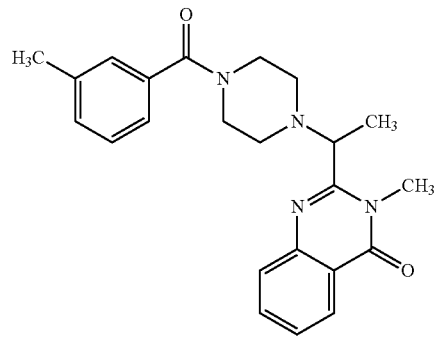 [SMILES: Cc1cccc(C(=O)N2CCN(C(C)c3nc4ccccc4c(=O)n3C)CC2)c1] |
| 58 | 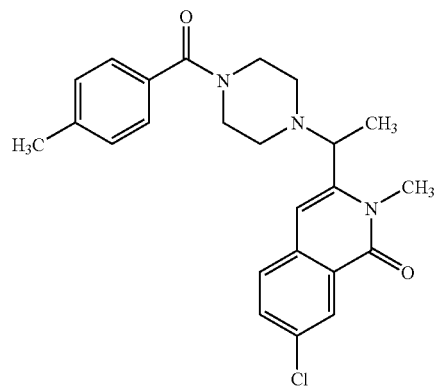 [SMILES: Cc1ccc(C(=O)N2CCN(C(C)c3cc4ccc(Cl)cc4c(=O)n3C)CC2)cc1] |
| 59 | 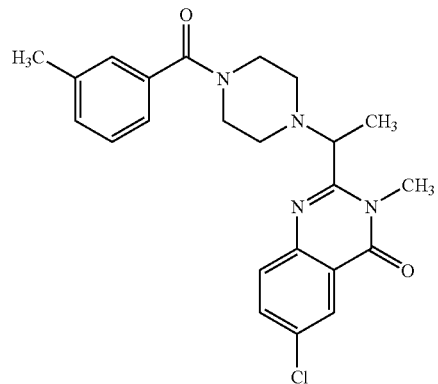 [SMILES: Cc1cccc(C(=O)N2CCN(C(C)c3nc4ccc(Cl)cc4c(=O)n3C)CC2)c1] |
| 60 | 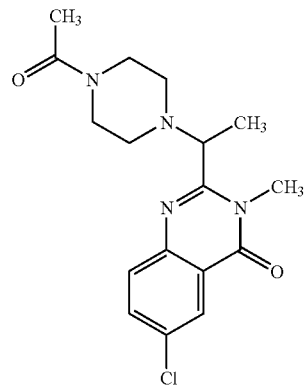 [SMILES: CC(=O)N1CCN(C(C)c2nc3ccc(Cl)cc3c(=O)n2C)CC1] |

TABLE 1-continued
| Cmpd No. | Structure |
|---|---|
| 61 | 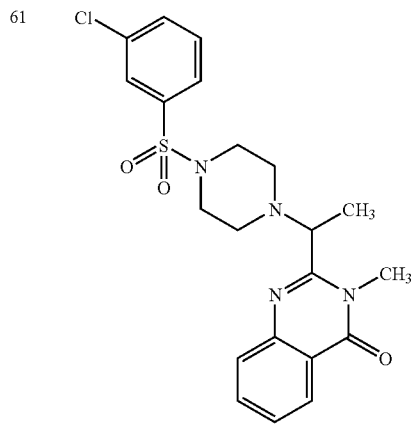 |
| 62 | 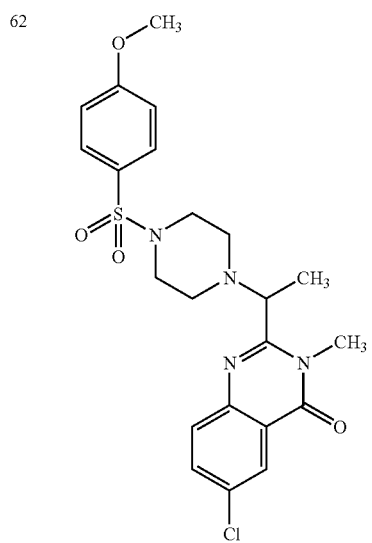 |
| 63 | 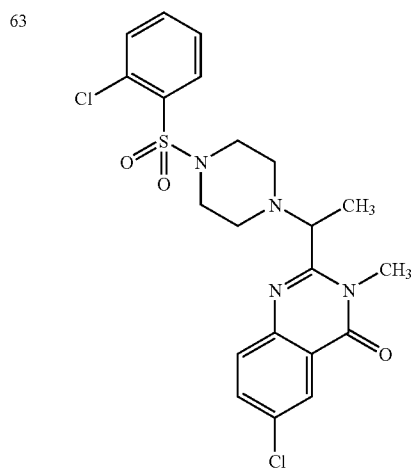 |

TABLE 1-continued
| Cmpd No. | Structure |
|---|---|
| 64 | 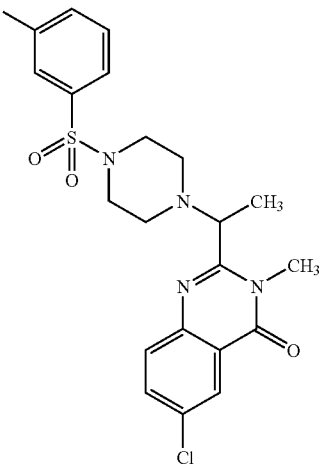 |
| 65 | 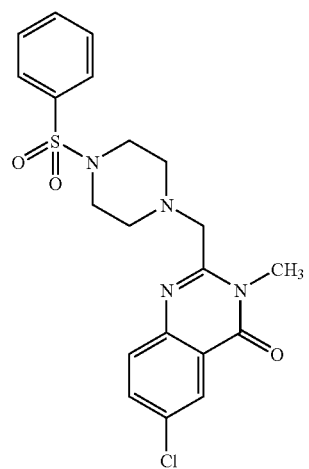 [SMILES: Cn1c(CN2CCN(S(=O)(=O)c3ccccc3)CC2)nc2ccc(Cl)cc2c1=O] |
| 66 | 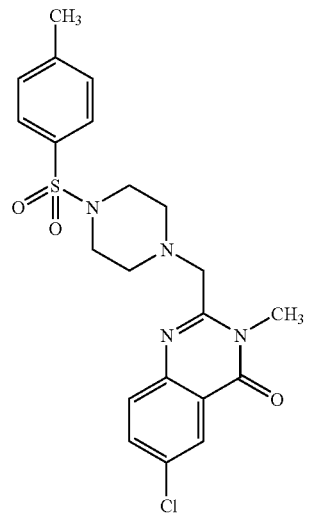 [SMILES: Cc1ccc(S(=O)(=O)N2CCN(Cc3nc4ccc(Cl)cc4c(=O)n3C)CC2)cc1] |

TABLE 1-continued
| Cmpd No. | Structure |
|---|---|
| 67 | 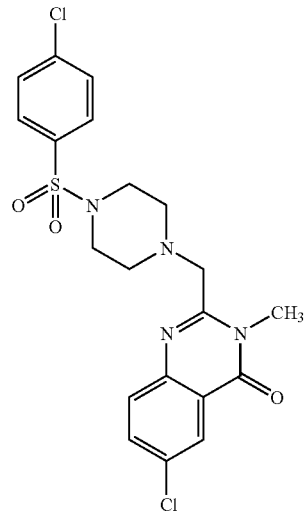 [SMILES: Cn1c(CN2CCN(S(=O)(=O)c3ccc(Cl)cc3)CC2)nc2ccc(Cl)cc2c1=O] |
| 68 | 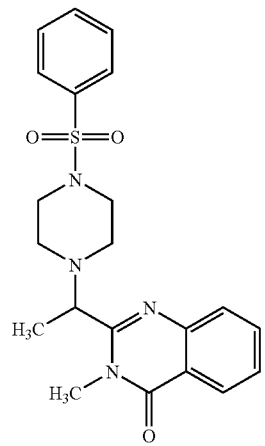 [SMILES: CC(c1nc2ccccc2c(=O)n1C)N1CCN(S(=O)(=O)c2ccccc2)CC1] |
| 69 | 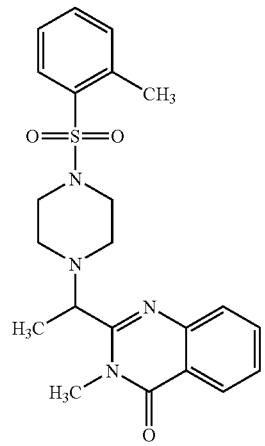 [SMILES: Cc1ccccc1S(=O)(=O)N1CCN(C(C)c2nc3ccccc3c(=O)n2C)CC1] |

TABLE 1-continued
| Cmpd No. | Structure |
|---|---|
| 70 | 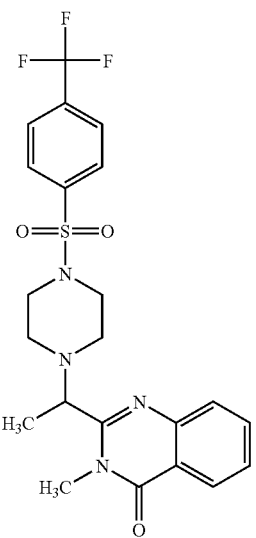 [SMILES: CC(c1nc2ccccc2c(=O)n1C)N1CCN(S(=O)(=O)c2ccc(C(F)(F)F)cc2)CC1] |
| 71 | 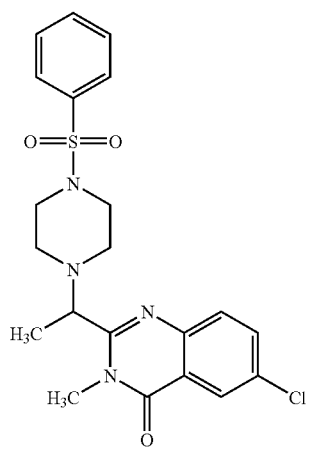 [SMILES: CC(c1nc2ccc(Cl)cc2c(=O)n1C)N1CCN(S(=O)(=O)c2ccccc2)CC1] |
| 72 | 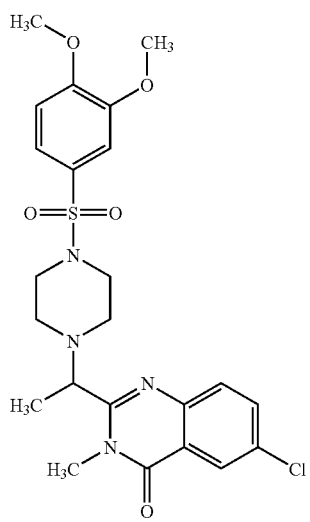 [SMILES: COc1ccc(S(=O)(=O)N2CCN(C(C)c3nc4ccc(Cl)cc4c(=O)n3C)CC2)cc1OC] |

TABLE 1-continued
| Cmpd No. | Structure |
|---|---|
| 73 | 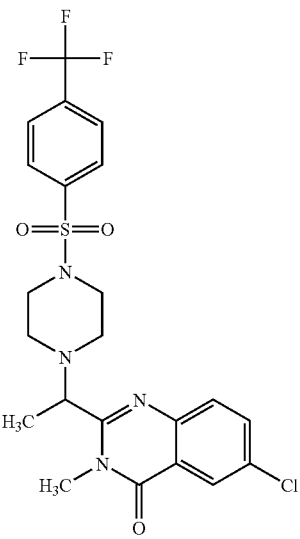 [SMILES: CC(c1nc2ccc(Cl)cc2c(=O)n1C)N1CCN(S(=O)(=O)c2ccc(C(F)(F)F)cc2)CC1] |
| 74 | 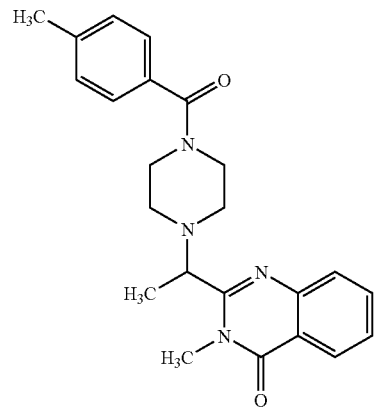 [SMILES: Cc1ccc(C(=O)N2CCN(C(C)c3nc4ccccc4c(=O)n3C)CC2)cc1] |
| 75 | 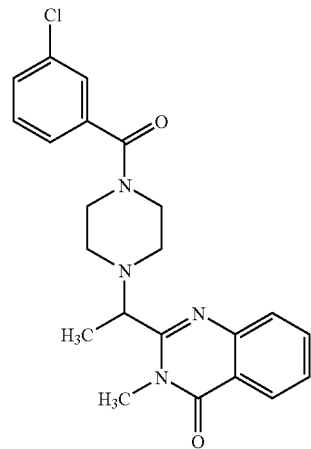 [SMILES: CC(c1nc2ccccc2c(=O)n1C)N1CCN(C(=O)c2cccc(Cl)c2)CC1] |

TABLE 1-continued
| Cmpd No. | Structure |
|---|---|
| 76 | 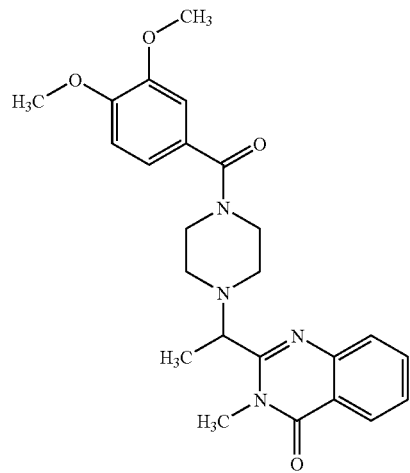 [SMILES: COc1ccc(C(=O)N2CCN(C(C)c3nc4ccccc4c(=O)n3C)CC2)cc1OC] |
| 77 | 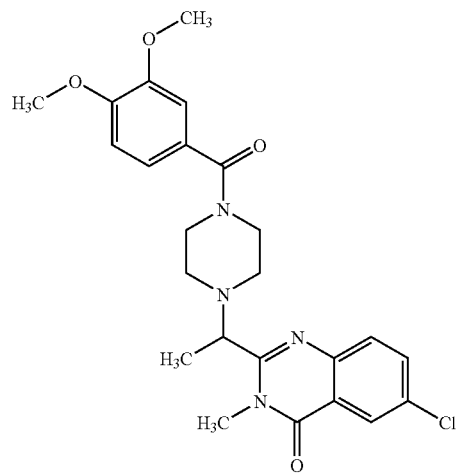 [SMILES: COc1ccc(C(=O)N2CCN(C(C)c3nc4ccc(Cl)cc4c(=O)n3C)CC2)cc1OC] |
| 78 | 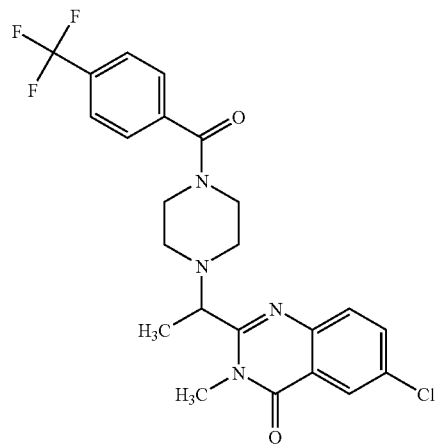 [SMILES: CC(c1nc2ccc(Cl)cc2c(=O)n1C)N1CCN(C(=O)c2ccc(C(F)(F)F)cc2)CC1] |

TABLE 1-continued
| Cmpd No. | Structure |
|---|---|
| 79 | 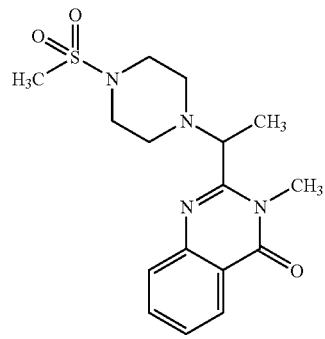 |
| 80 | 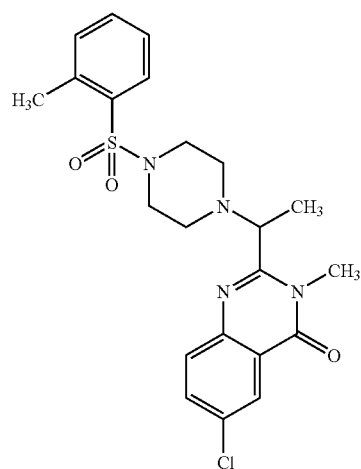 |
| 81 | 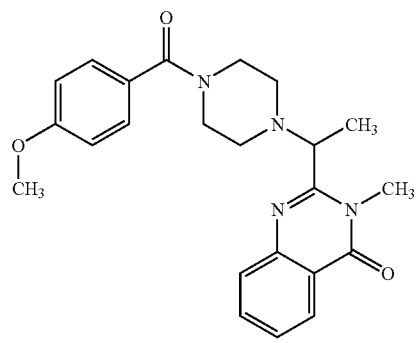 [SMILES: COc1ccc(C(=O)N2CCN(C(C)c3nc4ccccc4c(=O)n3C)CC2)cc1] |
| 82 | 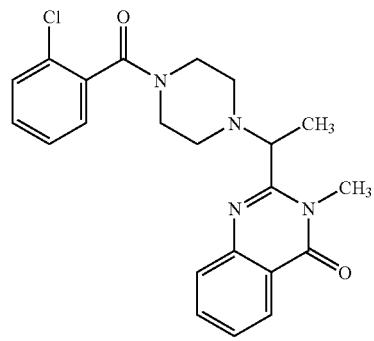 [SMILES: CC(c1nc2ccccc2c(=O)n1C)N1CCN(C(=O)c2ccccc2Cl)CC1] |

TABLE 1-continued
| Cmpd No. | Structure |
|---|---|
| 83 | 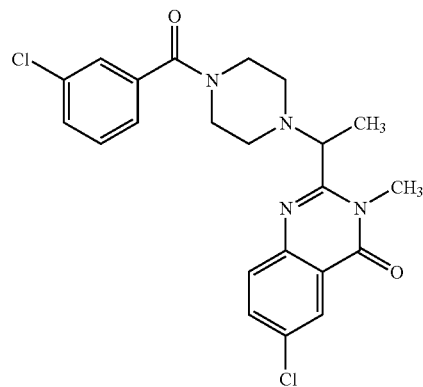 [SMILES: CC(c1nc2ccc(Cl)cc2c(=O)n1C)N1CCN(C(=O)c2cccc(Cl)c2)CC1] |
| 84 | 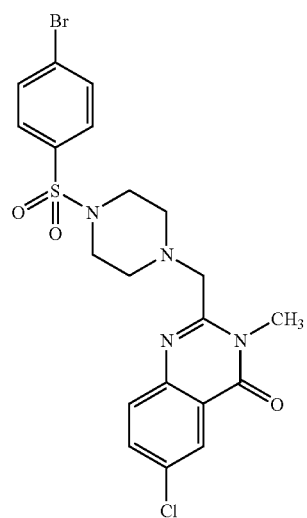 |
| 85 | 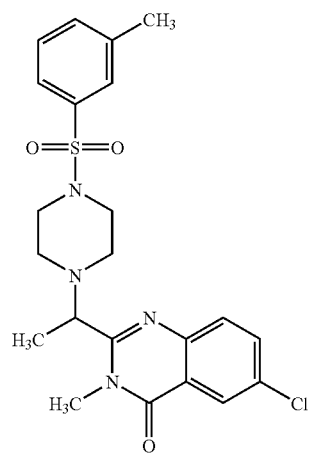 [SMILES: Cc1cccc(S(=O)(=O)N2CCN(C(C)c3nc4ccc(Cl)cc4c(=O)n3C)CC2)c1] |

TABLE 1-continued
| Cmpd No. | Structure |
|---|---|
| 86 | 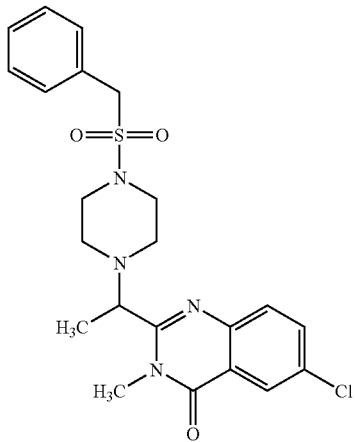 [SMILES: CC(c1nc2ccc(Cl)cc2c(=O)n1C)N1CCN(S(=O)(=O)Cc2ccccc2)CC1] |
| 87 | 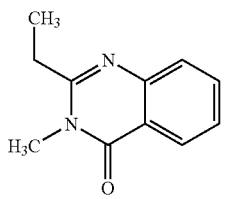 |
| 88 | 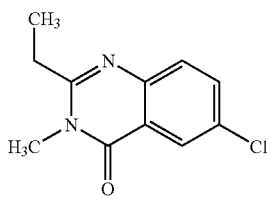 |
| 89 | 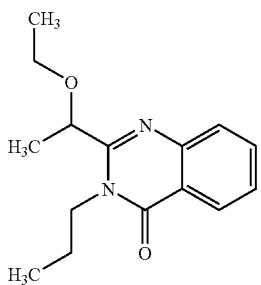 [SMILES: CCCn1c(C(C)OCC)nc2ccccc2c1=O] |
| 90 | 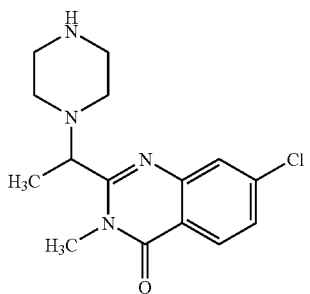 [SMILES: CC(c1nc2cc(Cl)ccc2c(=O)n1C)N1CCNCC1] |

TABLE 1-continued
| Cmpd No. | Structure |
|---|---|
| 91 | 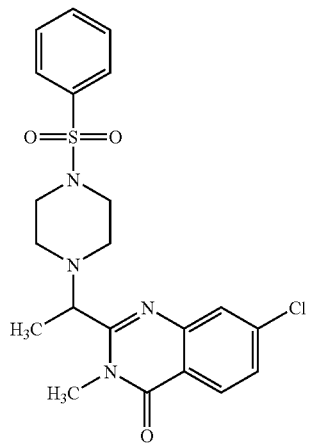 [SMILES: CC(c1nc2cc(Cl)ccc2c(=O)n1C)N1CCN(S(=O)(=O)c2ccccc2)CC1] |
| 92 | 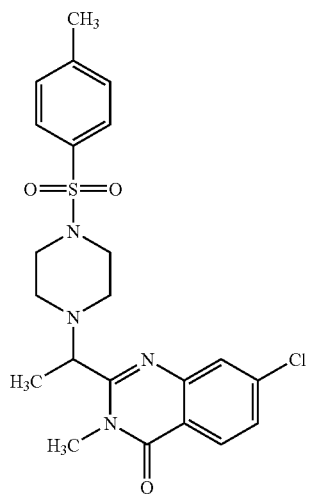 [SMILES: Cc1ccc(S(=O)(=O)N2CCN(C(C)c3nc4cc(Cl)ccc4c(=O)n3C)CC2)cc1] |
| 93 | 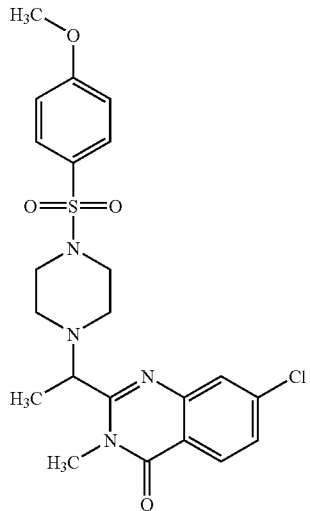 [SMILES: COc1ccc(S(=O)(=O)N2CCN(C(C)c3nc4cc(Cl)ccc4c(=O)n3C)CC2)cc1] |

TABLE 1-continued
| Cmpd No. | Structure |
|---|---|
| 94 | 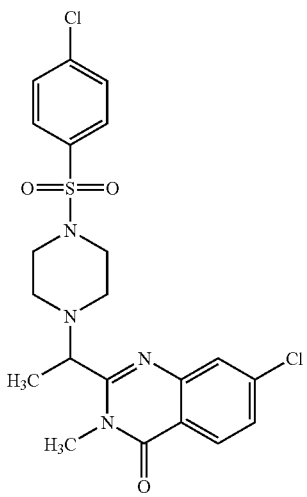 |
| 95 | 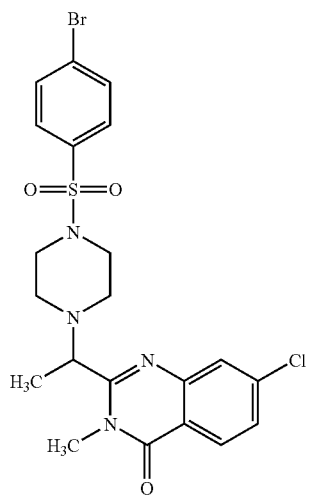 [SMILES: CC(c1nc2cc(Cl)ccc2c(=O)n1C)N1CCN(S(=O)(=O)c2ccc(Cl)cc2)CC1] |
| 96 | 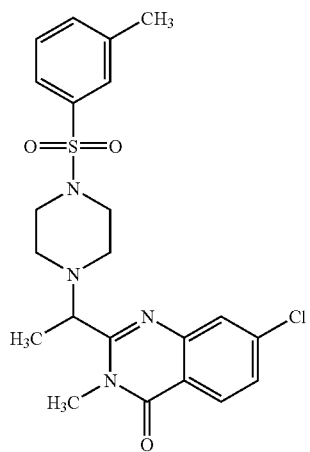 [SMILES: Cc1cccc(S(=O)(=O)N2CCN(C(C)c3nc4cc(Cl)ccc4c(=O)n3C)CC2)c1] |

TABLE 1-continued
| Cmpd No. | Structure |
|---|---|
| 97 | 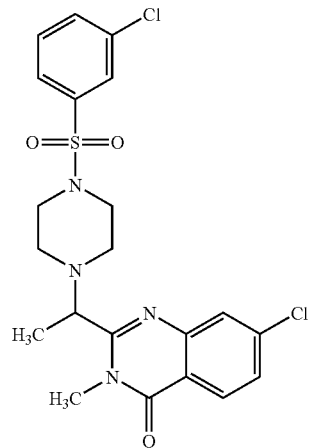 [SMILES: CC(c1nc2cc(Cl)ccc2c(=O)n1C)N1CCN(S(=O)(=O)c2cccc(Cl)c2)CC1] |
| 98 | 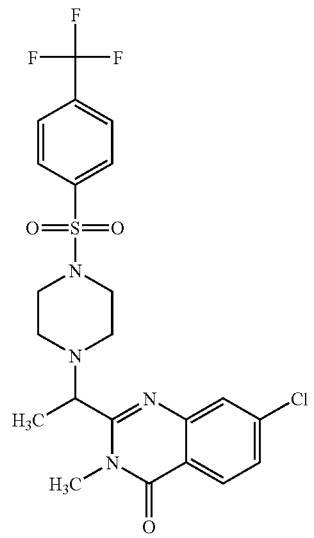 [SMILES: CC(c1nc2cc(Cl)ccc2c(=O)n1C)N1CCN(S(=O)(=O)c2ccc(C(F)(F)F)cc2)CC1] |
| 99 | 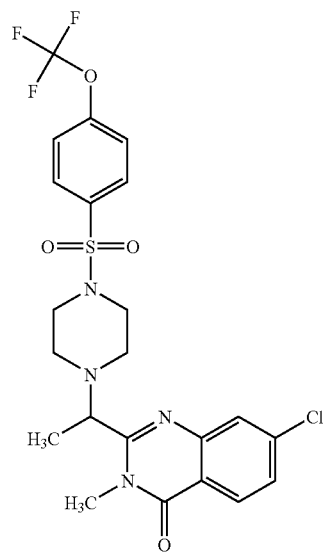 [SMILES: CC(c1nc2cc(Cl)ccc2c(=O)n1C)N1CCN(S(=O)(=O)c2ccc(OC(F)(F)F)cc2)CC1] |

TABLE 1-continued
| Cmpd No. | Structure |
|---|---|
| 100 | 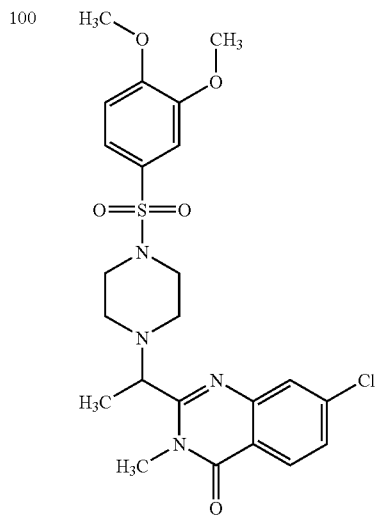 |
| 101 | 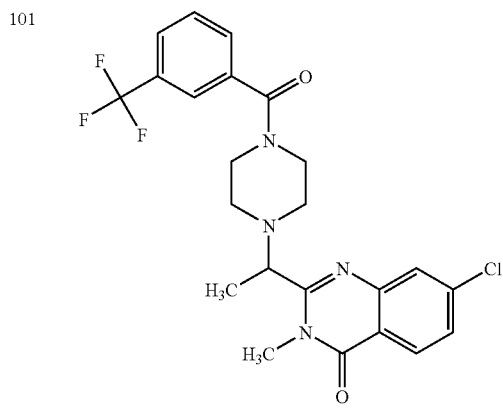 |
| 102 | 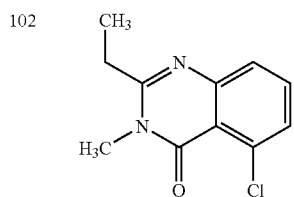 |
| 103 | 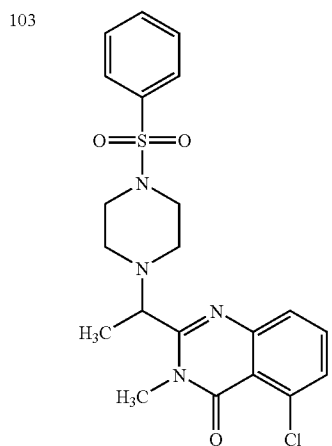 |

TABLE 1-continued
| Cmpd No. | Structure |
|---|---|
| 104 | 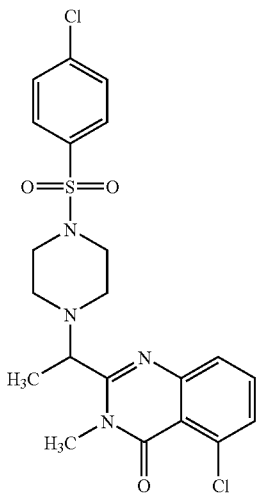 |
| 105 | 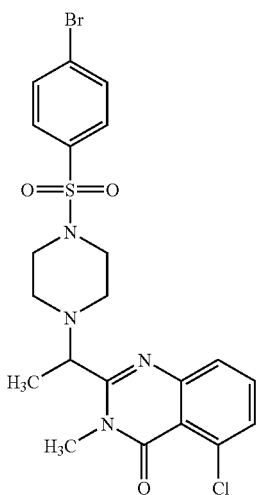 [SMILES: CC(c1nc2cccc(Cl)c2c(=O)n1C)N1CCN(S(=O)(=O)c2ccc(Br)cc2)CC1] |
| 106 | 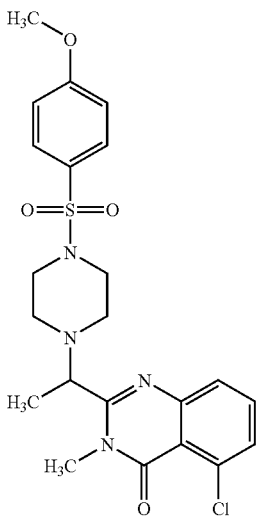 [SMILES: COc1ccc(S(=O)(=O)N2CCN(C(C)c3nc4cccc(Cl)c4c(=O)n3C)CC2)cc1] |

TABLE 1-continued
| Cmpd No. | Structure |
|---|---|
| 107 | 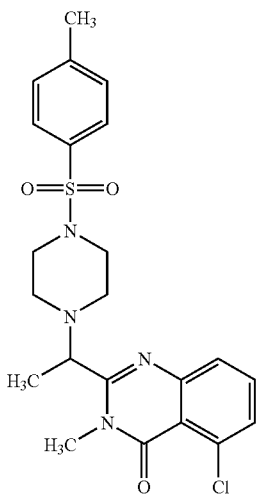 |
| 108 | 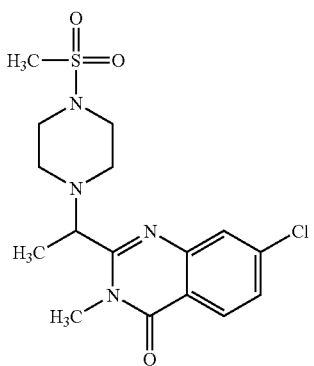 [SMILES: CC(c1nc2cc(Cl)ccc2c(=O)n1C)N1CCN(S(C)(=O)=O)CC1] |
| 109 | 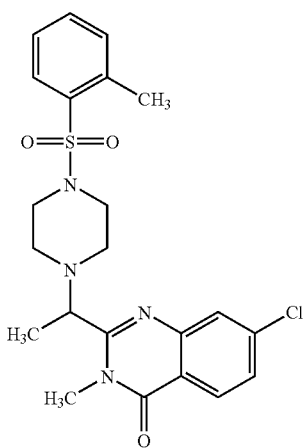 [SMILES: Cc1ccccc1S(=O)(=O)N1CCN(C(C)c2nc3cc(Cl)ccc3c(=O)n2C)CC1] |

TABLE 1-continued
| Cmpd No. | Structure |
|---|---|
| 110 | 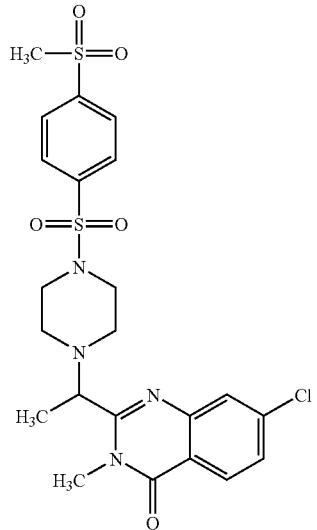 [SMILES: CC(c1nc2cc(Cl)ccc2c(=O)n1C)N1CCN(S(=O)(=O)c2ccc(S(C)(=O)=O)cc2)CC1] |
| 111 | 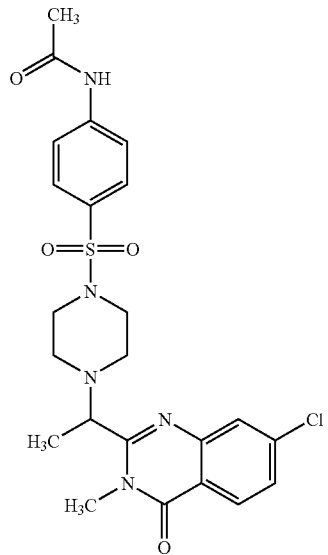 [SMILES: CC(=O)Nc1ccc(S(=O)(=O)N2CCN(C(C)c3nc4cc(Cl)ccc4c(=O)n3C)CC2)cc1] |
| 112 | 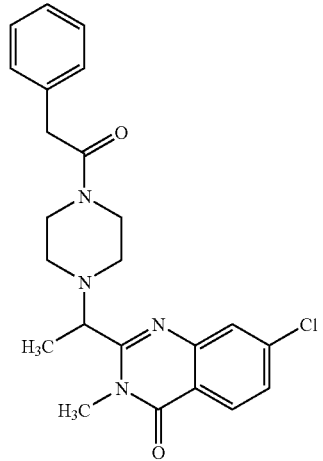 [SMILES: CC(c1nc2cc(Cl)ccc2c(=O)n1C)N1CCN(C(=O)Cc2ccccc2)CC1] |

TABLE 1-continued
| Cmpd No. | Structure |
|---|---|
| 113 | 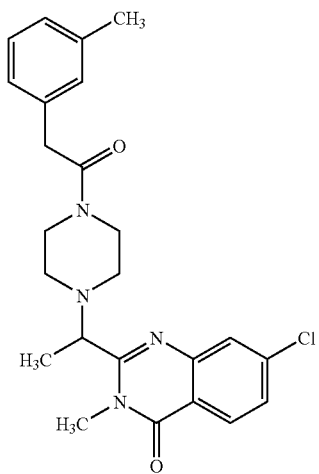 [SMILES: Cc1cccc(CC(=O)N2CCN(C(C)c3nc4cc(Cl)ccc4c(=O)n3C)CC2)c1] |
| 114 | 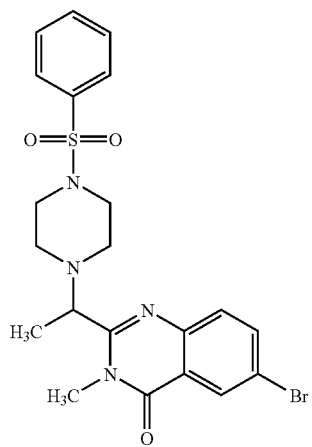 [SMILES: CC(c1nc2ccc(Br)cc2c(=O)n1C)N1CCN(S(=O)(=O)c2ccccc2)CC1] |
| 115 | 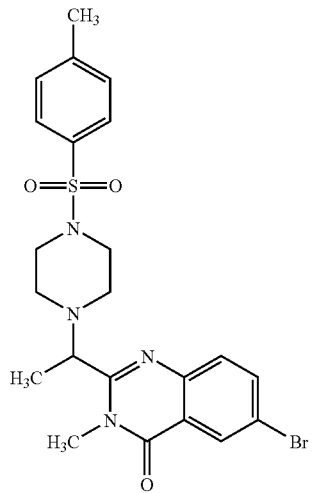 [SMILES: CC(c1nc2ccc(Br)cc2c(=O)n1C)N1CCN(S(=O)(=O)c2ccc(Cl)cc2)CC1] |

117
118
TABLE 1-continued
| Cmpd No. | Structure |
|---|---|
| 116 | 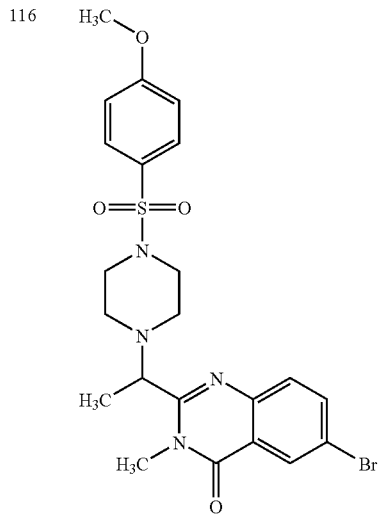 |
| 117 | 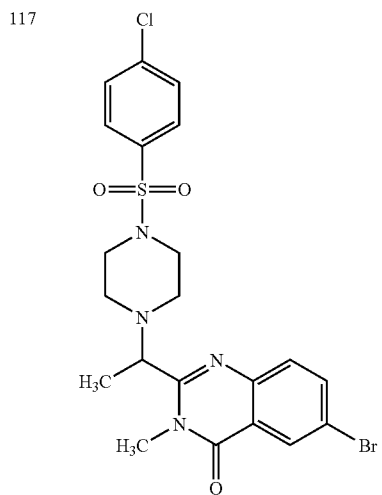 |
| 118 | 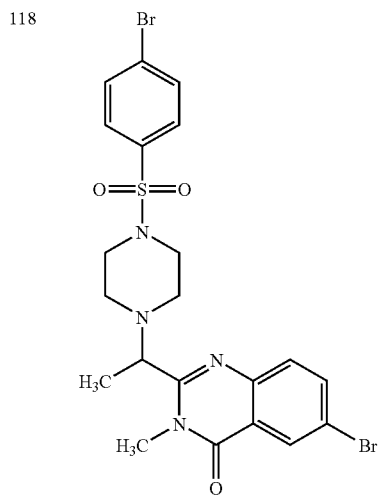 |

TABLE 1-continued
| Cmpd No. | Structure |
|---|---|
| 119 | 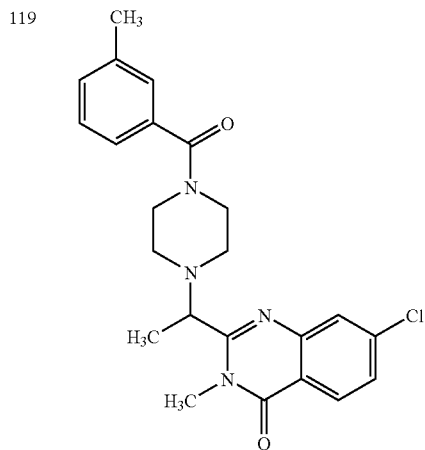 |
| 120 | 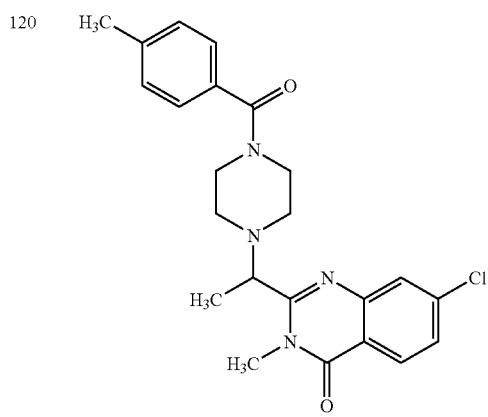 |
| 121 | 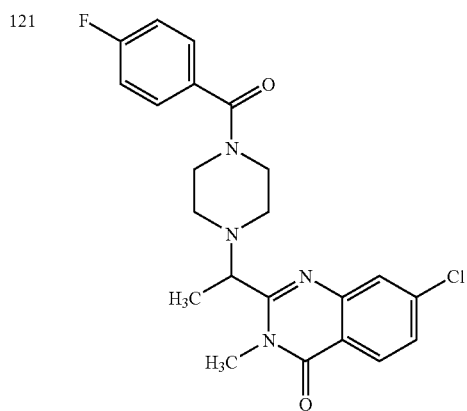 |

TABLE 1-continued
| Cmpd No. | Structure |
| --- | --- |
| 122 | 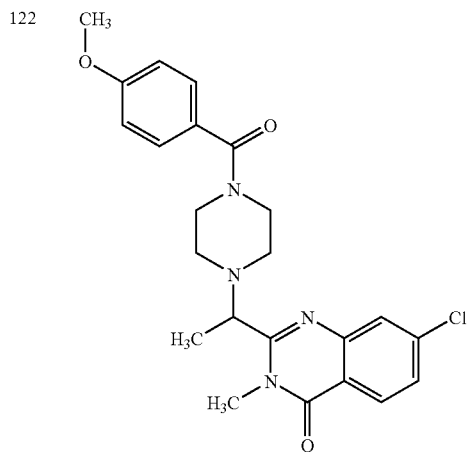 |
| 123 | 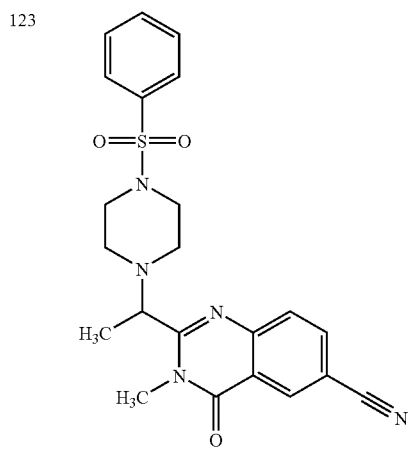 |
| 124 | 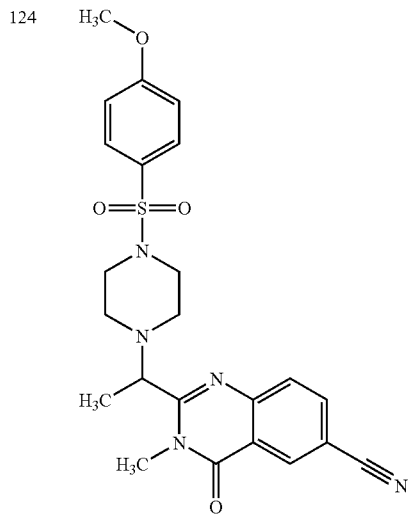 |

TABLE 1-continued
| Cmpd No. | Structure |
|---|---|
| 125 | 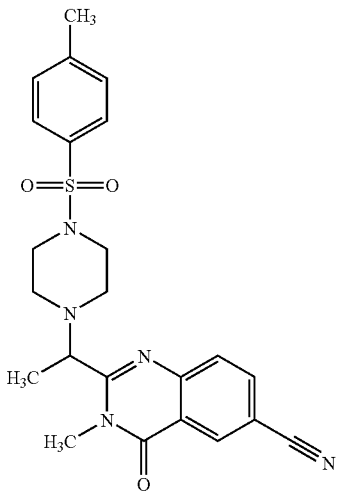 [SMILES: Cc1ccc(S(=O)(=O)N2CCN(C(C)c3nc4ccc(C#N)cc4c(=O)n3C)CC2)cc1] |
| 126 | 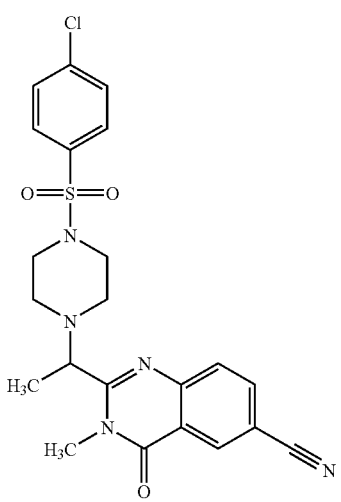 [SMILES: CC(c1nc2ccc(C#N)cc2c(=O)n1C)N1CCN(S(=O)(=O)c2ccc(Cl)cc2)CC1] |
| 127 | 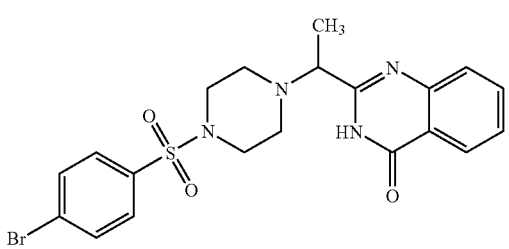 [SMILES: CC(c1nc2ccccc2c(=O)[nH]1)N1CCN(S(=O)(=O)c2ccc(Br)cc2)CC1] |
| 128 | 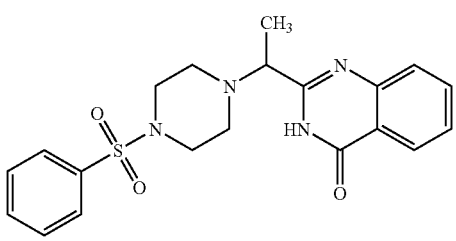 [SMILES: CC(c1nc2ccccc2c(=O)[nH]1)N1CCN(S(=O)(=O)c2ccccc2)CC1] |

TABLE 1-continued
| Cmpd No. | Structure |
|---|---|
| 129 | 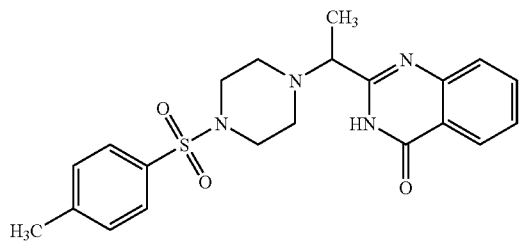 [SMILES: Cc1ccc(S(=O)(=O)N2CCN(C(C)c3nc4ccccc4c(=O)[nH]3)CC2)cc1] |
| 130 | 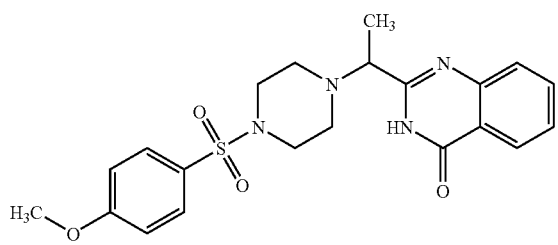 [SMILES: COc1ccc(S(=O)(=O)N2CCN(C(C)c3nc4ccccc4c(=O)[nH]3)CC2)cc1] |
| 131 | 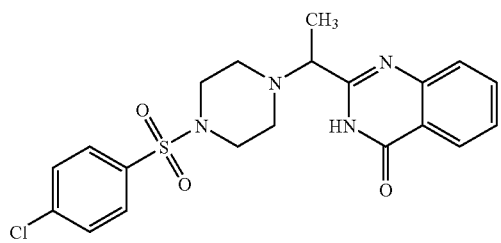 [SMILES: CC(c1nc2ccccc2c(=O)[nH]1)N1CCN(S(=O)(=O)c2ccc(Cl)cc2)CC1] |
| 132 | 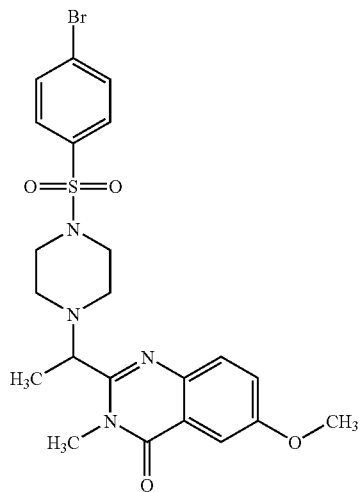 [SMILES: COc1ccc2nc(C(C)N3CCN(S(=O)(=O)c4ccc(Br)cc4)CC3)n(C)c(=O)c2c1] |

TABLE 1-continued
| Cmpd No. | Structure |
|---|---|
| 133 | 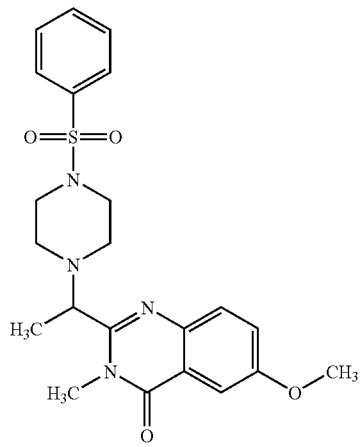 [SMILES: COc1ccc2nc(C(C)N3CCN(S(=O)(=O)c4ccccc4)CC3)n(C)c(=O)c2c1] |
| 134 | 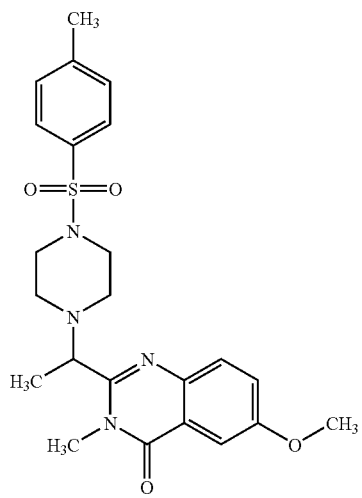 [SMILES: COc1ccc2nc(C(C)N3CCN(S(=O)(=O)c4ccc(C)cc4)CC3)n(C)c(=O)c2c1] |
| 135 | 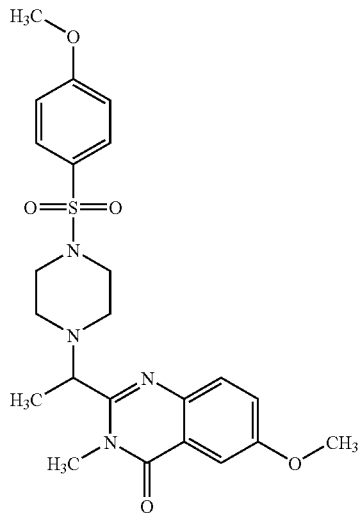 [SMILES: COc1ccc(S(=O)(=O)N2CCN(C(C)c3nc4ccc(OC)cc4c(=O)n3C)CC2)cc1] |

TABLE 1-continued
| Cmpd No. | Structure |
| --- | --- |
| 136 | 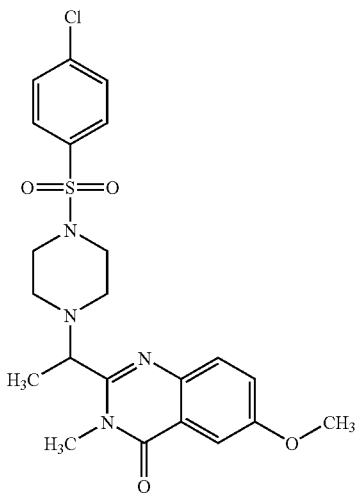 [SMILES: COc1ccc2nc(C(C)N3CCN(S(=O)(=O)c4ccc(Cl)cc4)CC3)n(C)c(=O)c2c1] |
| 137 | 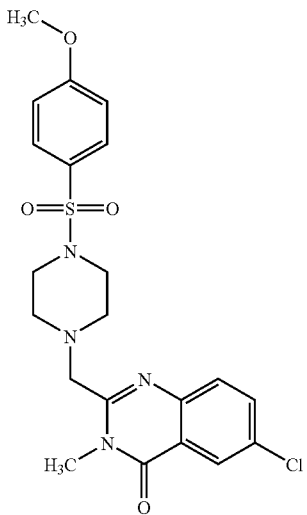 [SMILES: COc1ccc(S(=O)(=O)N2CCN(Cc3nc4ccc(Cl)cc4c(=O)n3C)CC2)cc1] |
| 138 | 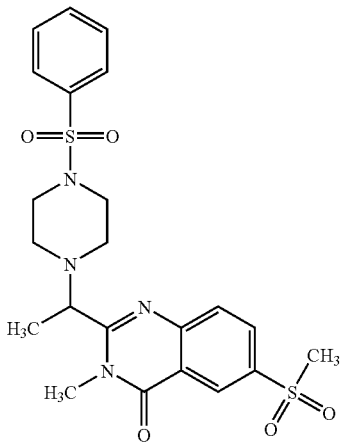 [SMILES: CC(c1nc2ccc(S(C)(=O)=O)cc2c(=O)n1C)N1CCN(S(=O)(=O)c2ccccc2)CC1] |

TABLE 1-continued
| Cmpd No. | Structure |
|---|---|
| 139 | 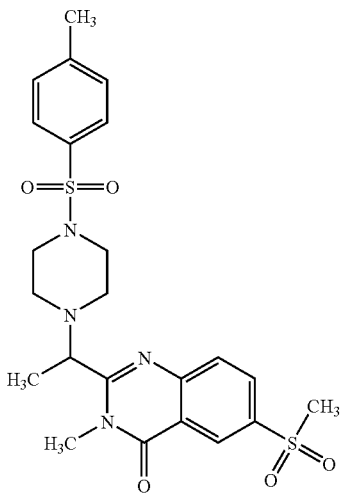 [SMILES: Cc1ccc(S(=O)(=O)N2CCN(C(C)c3nc4ccc(S(C)(=O)=O)cc4c(=O)n3C)CC2)cc1] |
| 140 | 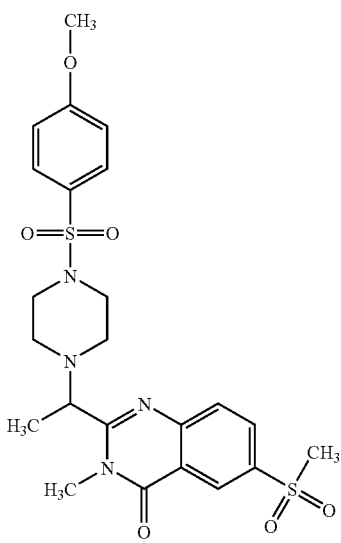 [SMILES: COc1ccc(S(=O)(=O)N2CCN(C(C)c3nc4ccc(S(C)(=O)=O)cc4c(=O)n3C)CC2)cc1] |
| 141 | 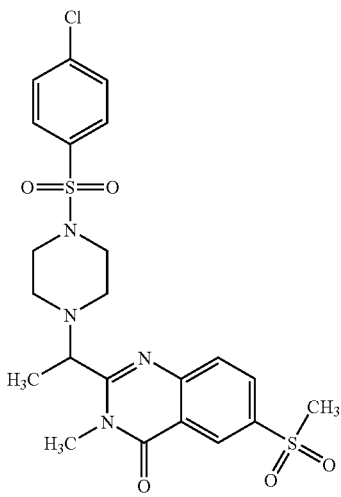 [SMILES: CC(c1nc2ccc(S(C)(=O)=O)cc2c(=O)n1C)N1CCN(S(=O)(=O)c2ccc(Cl)cc2)CC1] |

TABLE 1-continued
| Cmpd No. | Structure |
|---|---|
| 142 | 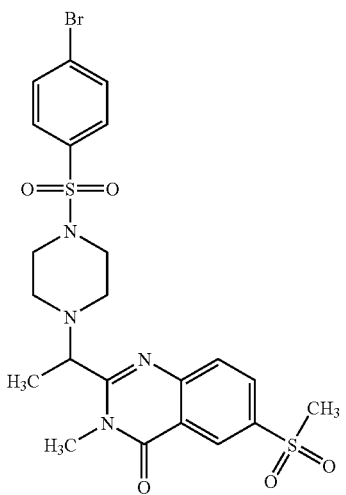 [SMILES: CC(c1nc2ccc(S(C)(=O)=O)cc2c(=O)n1C)N1CCN(S(=O)(=O)c2ccc(Br)cc2)CC1] |
| 143 | 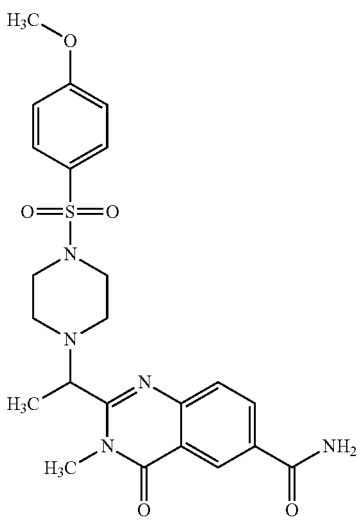 [SMILES: COc1ccc(S(=O)(=O)N2CCN(C(C)c3nc4ccc(C(N)=O)cc4c(=O)n3C)CC2)cc1] |
| 144 | 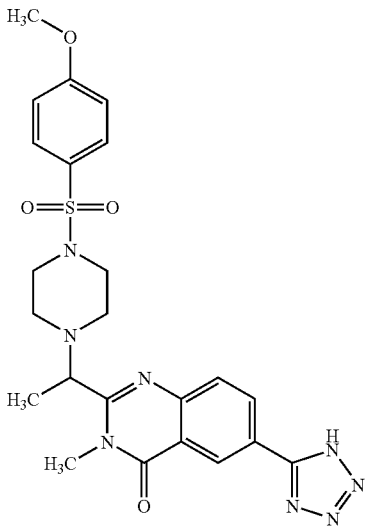 [SMILES: COc1ccc(S(=O)(=O)N2CCN(C(C)c3nc4ccc(-c5nnn[nH]5)cc4c(=O)n3C)CC2)cc1] |

TABLE 1-continued
| Cmpd No. | Structure |
|---|---|
| 145 | 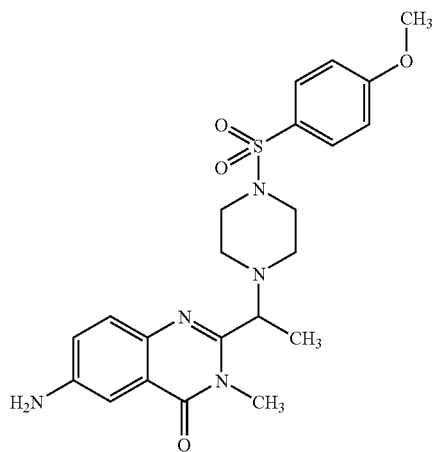 [SMILES: COc1ccc(S(=O)(=O)N2CCN(C(C)c3nc4ccc(N)cc4c(=O)n3C)CC2)cc1] |
| 146 | 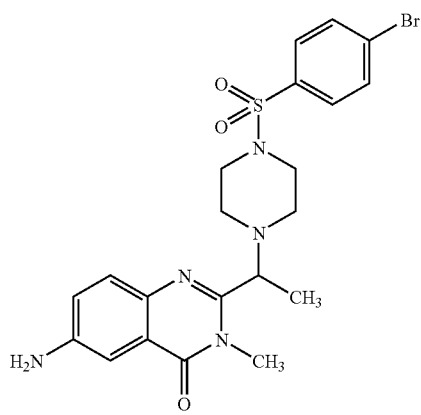 [SMILES: CC(c1nc2ccc(N)cc2c(=O)n1C)N1CCN(S(=O)(=O)c2ccc(Br)cc2)CC1] |
| 147 | 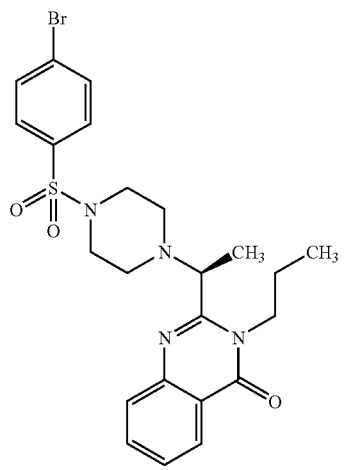 [SMILES: CCCn1c([C@H](C)N2CCN(S(=O)(=O)c3ccc(Br)cc3)CC2)nc2ccccc2c1=O] |

TABLE 1-continued
| Cmpd No. | Structure |
|---|---|
| 148 | 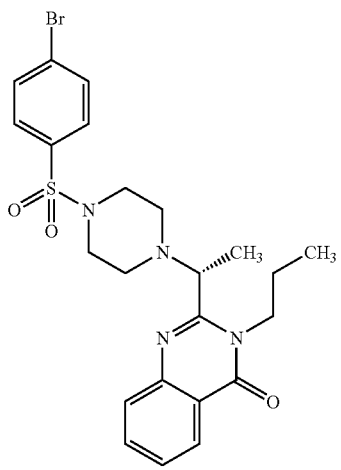 [SMILES: CCCn1c([C@@H](C)N2CCN(S(=O)(=O)c3ccc(Br)cc3)CC2)nc2ccccc2c1=O] |
| 149 | 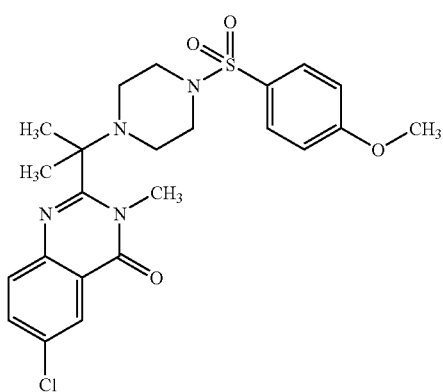 [SMILES: COc1ccc(S(=O)(=O)N2CCN(C(C)(C)c3nc4ccc(Cl)cc4c(=O)n3C)CC2)cc1] |
| 150 | 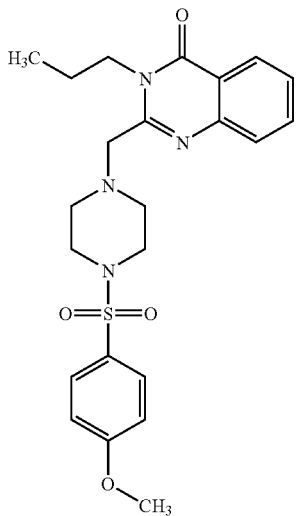 [SMILES: CCCn1c(CN2CCN(S(=O)(=O)c3ccc(OC)cc3)CC2)nc2ccccc2c1=O] |

TABLE 1-continued
| Cmpd No. | Structure |
|---|---|
| 151 | 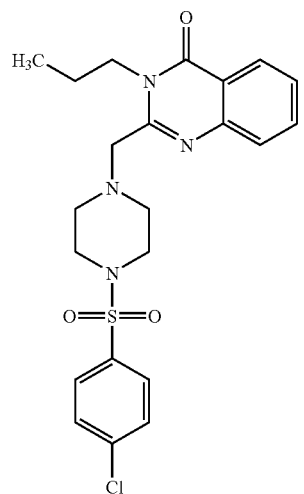 [SMILES: CCCn1c(CN2CCN(S(=O)(=O)c3ccc(Cl)cc3)CC2)nc2ccccc2c1=O] |
| 152 | 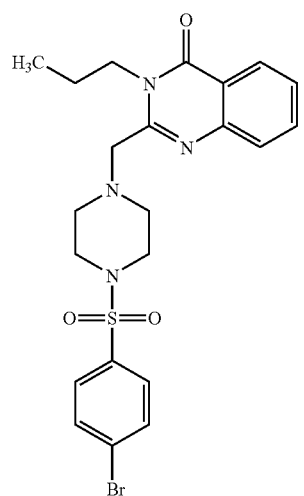 |
| 153 | 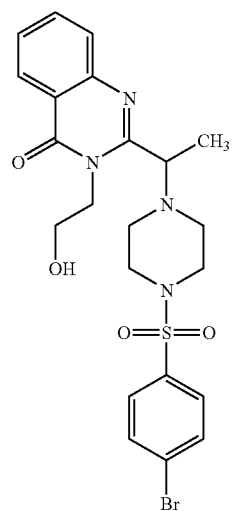 [SMILES: CC(c1nc2ccccc2c(=O)n1CCO)N1CCN(S(=O)(=O)c2ccc(Br)cc2)CC1] |

TABLE 1-continued
| Cmpd No. | Structure |
|---|---|
| 154 | 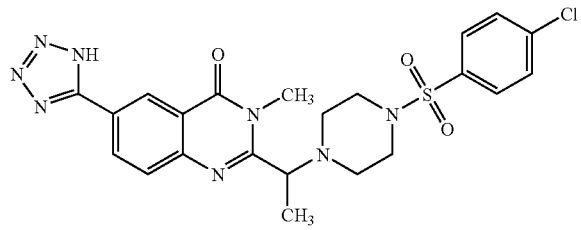 [SMILES: CC(c1nc2ccc(-c3nnn[nH]3)cc2c(=O)n1C)N1CCN(S(=O)(=O)c2ccc(Cl)cc2)CC1] |
| 155 | 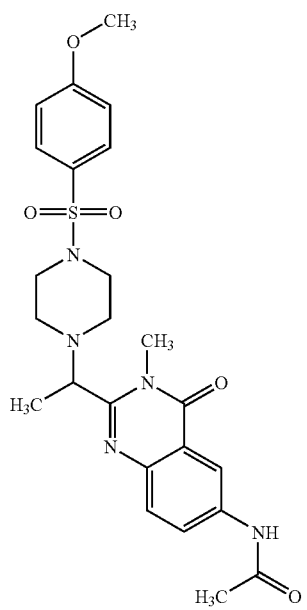 [SMILES: COc1ccc(S(=O)(=O)N2CCN(C(C)c3nc4ccc(NC(C)=O)cc4c(=O)n3C)CC2)cc1] |
| 156 | 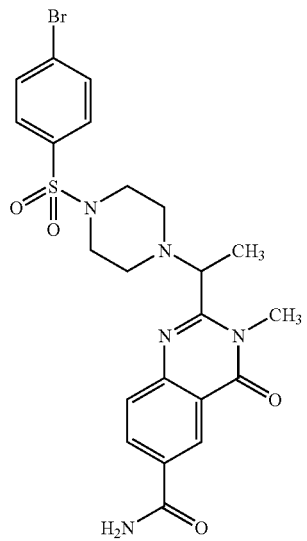 |

TABLE 1-continued
| Cmpd No. | Structure |
|---|---|
| 157 | 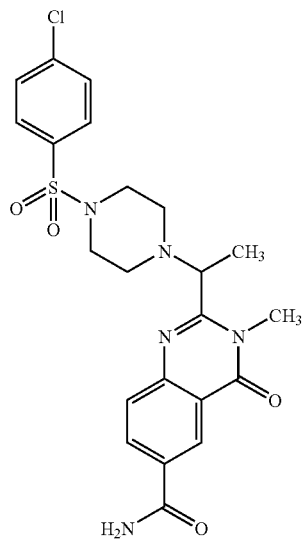 [SMILES: CC(c1nc2ccc(C(N)=O)cc2c(=O)n1C)N1CCN(S(=O)(=O)c2ccc(Cl)cc2)CC1] |
| 158 | 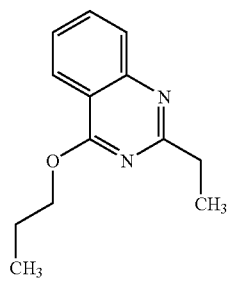 [SMILES: CCCOc1nc(CC)nc2ccccc12] |
| 159 | 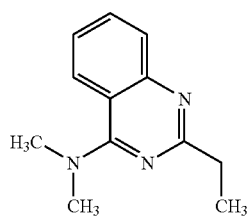 |
| 160 | 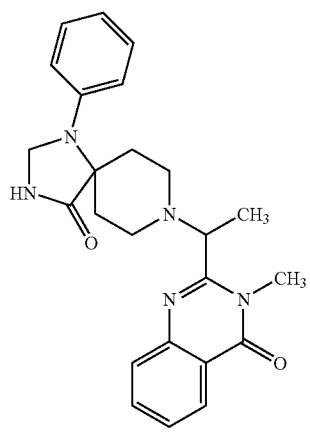 [SMILES: CC(c1nc2ccccc2c(=O)n1C)N1CCC2(CC1)C(=O)NCN2c1ccccc1] |

TABLE 1-continued
| Cmpd No. | Structure |
|---|---|
| 161 | 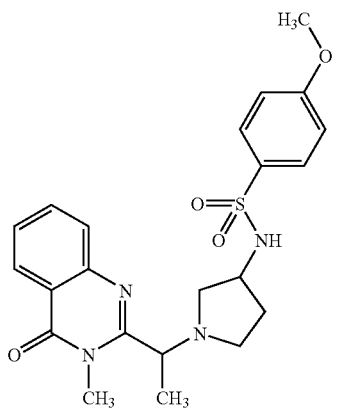 [SMILES: COc1ccc(S(=O)(=O)NC2CCN(C(C)c3nc4ccccc4c(=O)n3C)C2)cc1] |
| 162 | 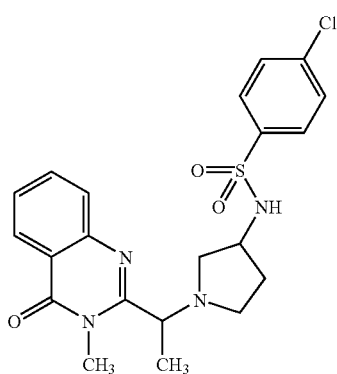 [SMILES: CC(c1nc2ccccc2c(=O)n1C)N1CCC(NS(=O)(=O)c2ccc(Cl)cc2)C1] |
| 163 | 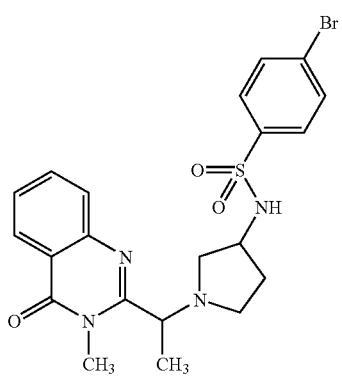 [SMILES: CC(c1nc2ccccc2c(=O)n1C)N1CCC(NS(=O)(=O)c2ccc(Br)cc2)C1] |
| 164 | 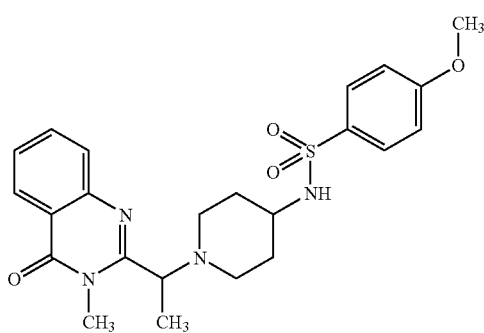 [SMILES: COc1ccc(S(=O)(=O)NC2CCN(C(C)c3nc4ccccc4c(=O)n3C)CC2)cc1] |

TABLE 1-continued
| Cmpd No. | Structure |
|---|---|
| 165 | 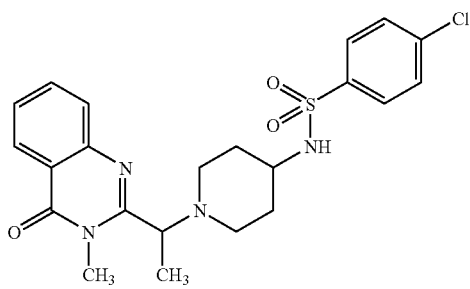 [SMILES: CC(c1nc2ccccc2c(=O)n1C)N1CCC(NS(=O)(=O)c2ccc(Cl)cc2)CC1] |
| 166 | 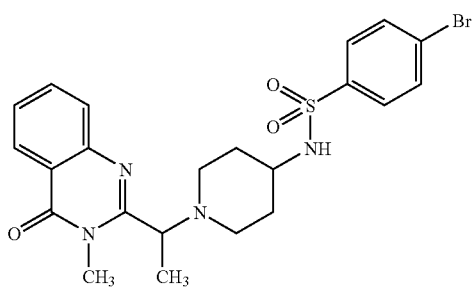 |
| 167 | 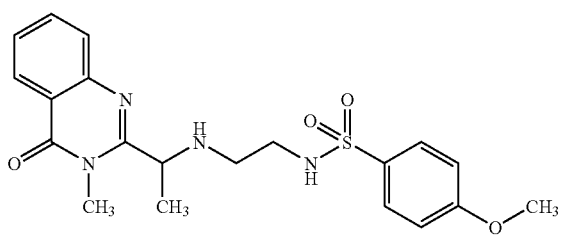 [SMILES: COc1ccc(S(=O)(=O)NCCNC(C)c2nc3ccccc3c(=O)n2C)cc1] |
| 168 | 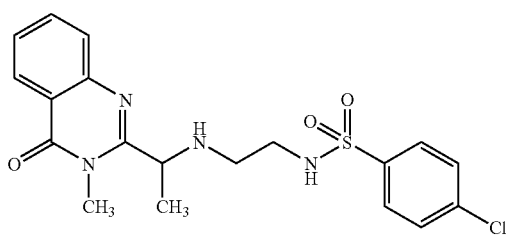 [SMILES: CC(NCCNS(=O)(=O)c1ccc(Cl)cc1)c1nc2ccccc2c(=O)n1C] |
| 169 | 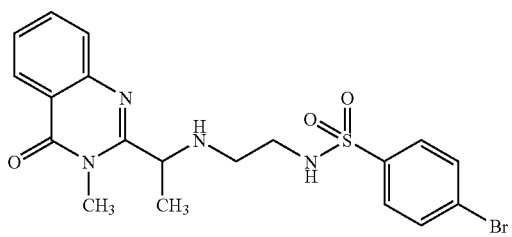 [SMILES: CC(NCCNS(=O)(=O)c1ccc(Br)cc1)c1nc2ccccc2c(=O)n1C] |
| 170 | 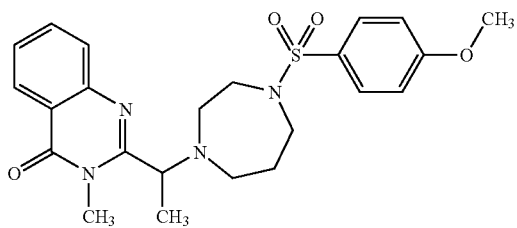 [SMILES: COc1ccc(S(=O)(=O)N2CCCN(C(C)c3nc4ccccc4c(=O)n3C)CC2)cc1] |

TABLE 1-continued
| Cmpd No. | Structure |
|---|---|
| 171 | 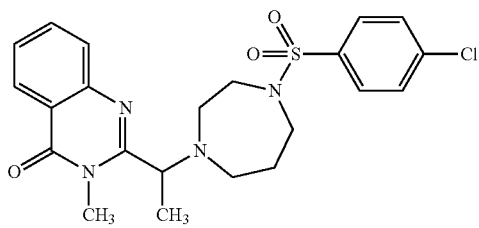 |
| 172 | 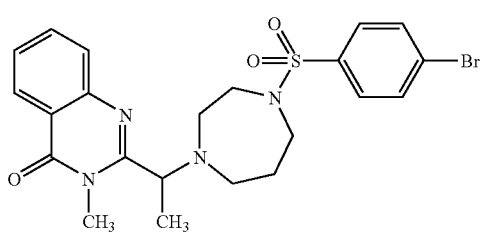 [SMILES: CC(c1nc2ccccc2c(=O)n1C)N1CCCN(S(=O)(=O)c2ccc(Cl)cc2)CC1] |
| 173 | 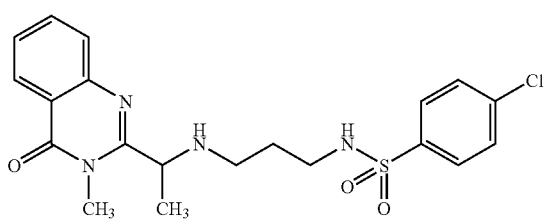 [SMILES: CC(NCCCNS(=O)(=O)c1ccc(Cl)cc1)c1nc2ccccc2c(=O)n1C] |
| 174 | 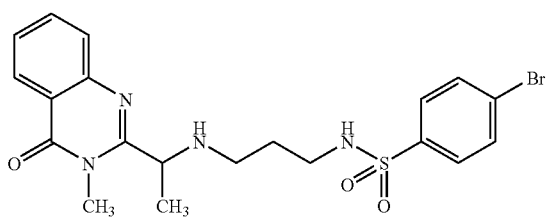 [SMILES: CC(NCCCNS(=O)(=O)c1ccc(Br)cc1)c1nc2ccccc2c(=O)n1C] |
| 175 | 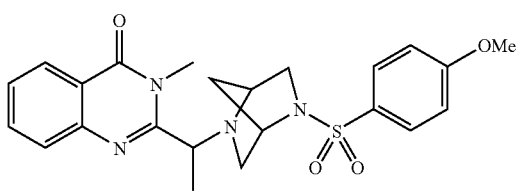 [SMILES: COc1ccc(S(=O)(=O)N2CC3CC2CN3C(C)c2nc3ccccc3c(=O)n2C)cc1] |
| 176 | 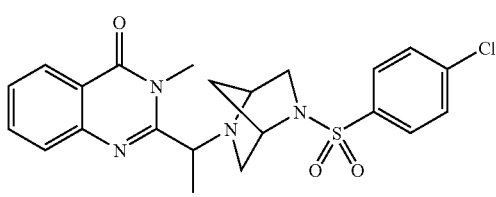 [SMILES: CC(c1nc2ccccc2c(=O)n1C)N1CC2CC1CN2S(=O)(=O)c1ccc(Cl)cc1] |
| 177 | 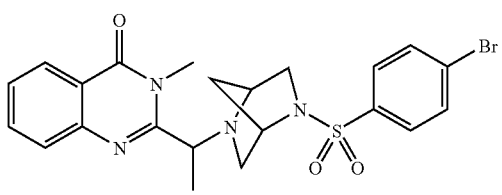 [SMILES: CC(c1nc2ccccc2c(=O)n1C)N1CC2CC1CN2S(=O)(=O)c1ccc(Br)cc1] |

TABLE 1-continued
| Cmpd No. | Structure |
|---|---|
| 178 | 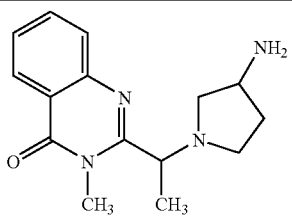 |
| 179 | 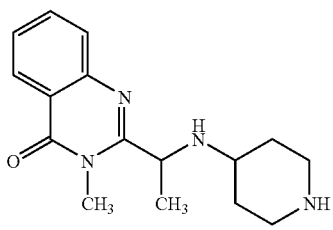 [SMILES: CC(NC1CCNCC1)c1nc2ccccc2c(=O)n1C] |
| 180 | 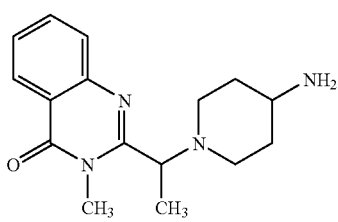 [SMILES: CC(c1nc2ccccc2c(=O)n1C)N1CCC(N)CC1] |
| 181 | 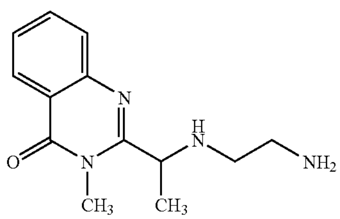 [SMILES: CC(NCCN)c1nc2ccccc2c(=O)n1C] |
| 182 | 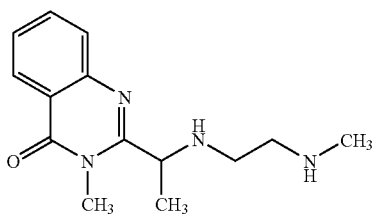 [SMILES: CNCCNC(C)c1nc2ccccc2c(=O)n1C] |
| 183 | 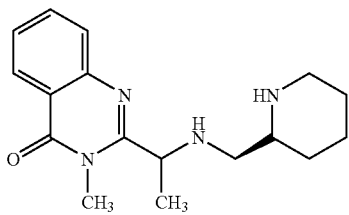 |
| 184 | 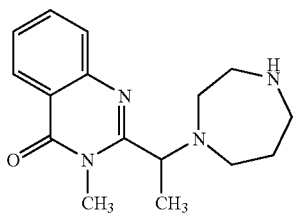 [SMILES: CC(c1nc2ccccc2c(=O)n1C)N1CCCNCC1] |

TABLE 1-continued
| Cmpd No. | Structure |
|---|---|
| 185 | 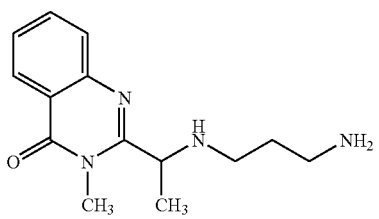 [SMILES: CC(NCCCN)c1nc2ccccc2c(=O)n1C] |
| 186 | 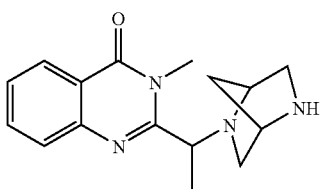 [SMILES: CC(c1nc2ccccc2c(=O)n1C)N1CC2CC1CN2] |
| 187 | 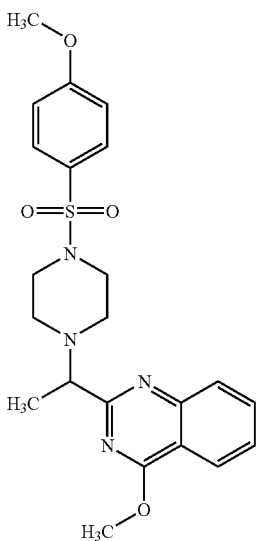 [SMILES: COc1ccc(S(=O)(=O)N2CCN(C(C)c3nc(OC)c4ccccc4n3)CC2)cc1] |
| 188 | 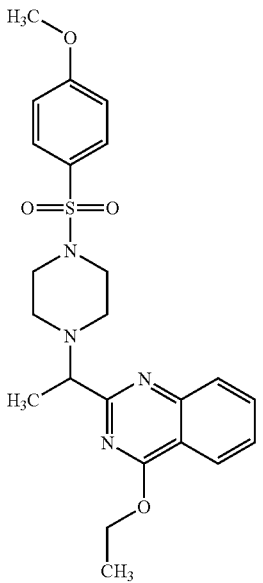 [SMILES: CCOc1nc(C(C)N2CCN(S(=O)(=O)c3ccc(OC)cc3)CC2)nc2ccccc12] |

TABLE 1-continued
| Cmpd No. | Structure |
|---|---|
| 189 | 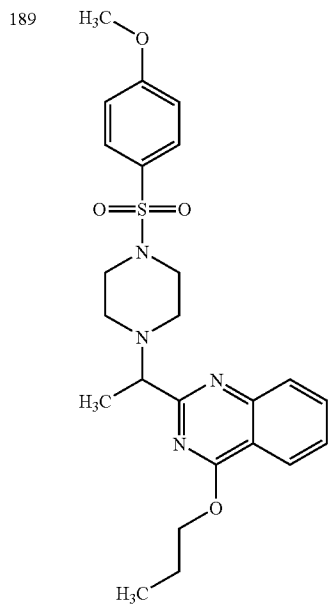 |
| 190 | 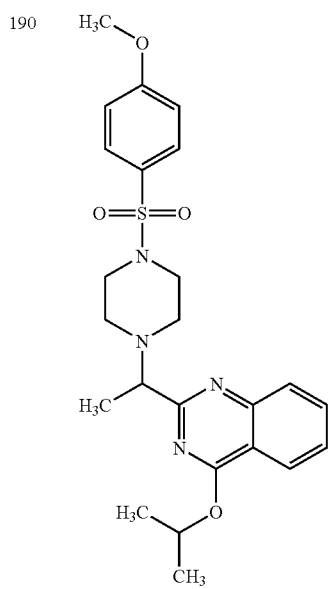 |

TABLE 1-continued
| Cmpd No. | Structure |
|---|---|
| 191 | 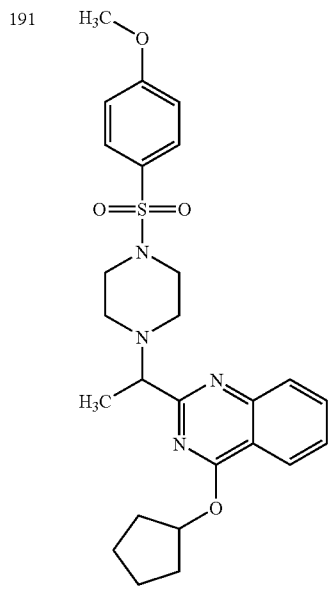 |
| 192 | 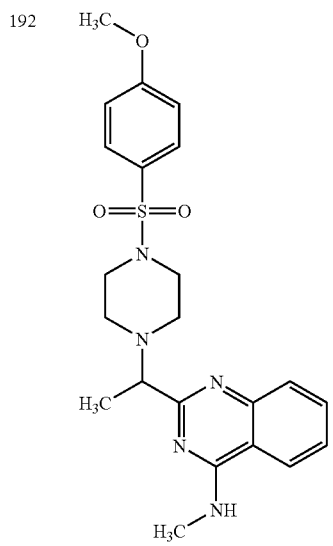 |

TABLE 1-continued
| Cmpd No. | Structure |
|---|---|
| 193 | 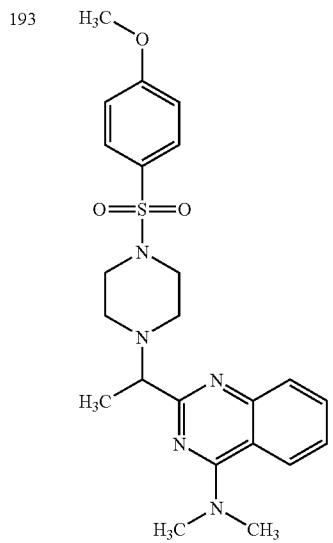 |
| 194 | 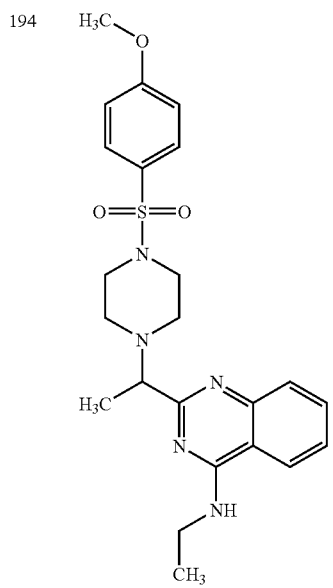 |

TABLE 1-continued
| Cmpd No. | Structure |
|---|---|
| 195 | 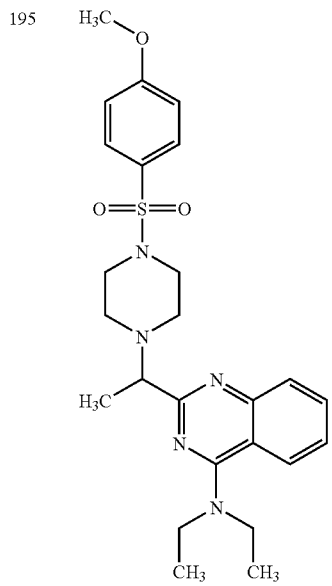 |
| 196 | 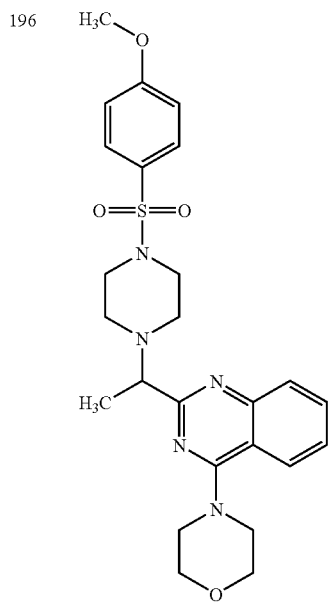 |
| 197 | 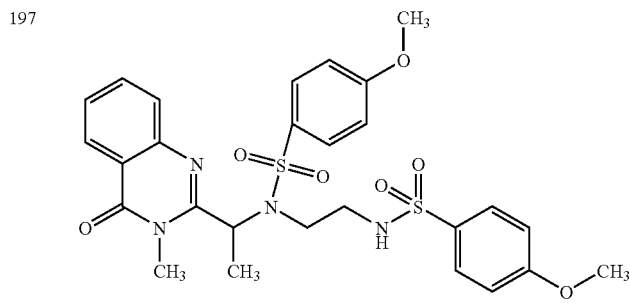 |

TABLE 1-continued
| Cmpd No. | Structure |
|---|---|
| 198 | 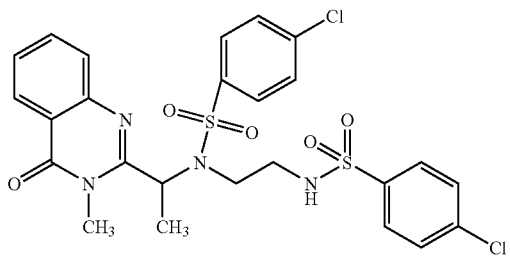 [SMILES: CC(c1nc2ccccc2c(=O)n1C)N(CCNS(=O)(=O)c1ccc(Cl)cc1)S(=O)(=O)c1ccc(Cl)cc1] |
| 199 | 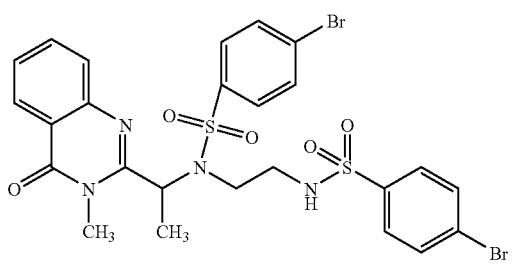 [SMILES: CC(c1nc2ccccc2c(=O)n1C)N(CCNS(=O)(=O)c1ccc(Br)cc1)S(=O)(=O)c1ccc(Br)cc1] |
| 200 | 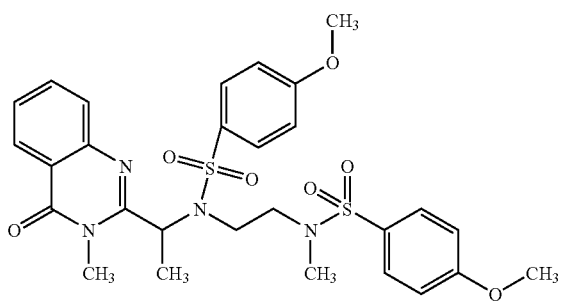 [SMILES: COc1ccc(S(=O)(=O)N(C)CCN(C(C)c2nc3ccccc3c(=O)n2C)S(=O)(=O)c2ccc(OC)cc2)cc1] |
| 201 | 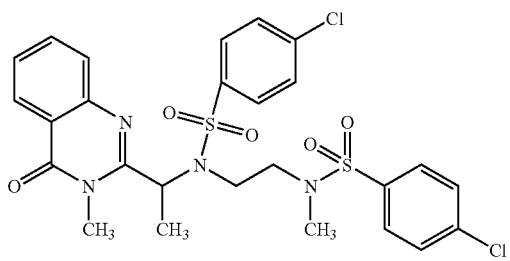 [SMILES: CC(c1nc2ccccc2c(=O)n1C)N(CCN(C)S(=O)(=O)c1ccc(Cl)cc1)S(=O)(=O)c1ccc(Cl)cc1] |
| 202 | 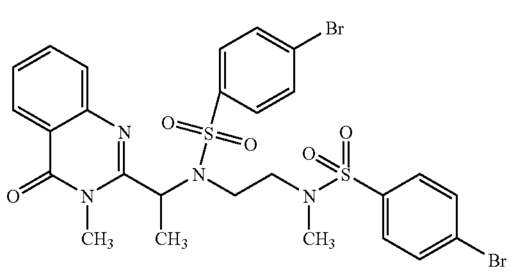 [SMILES: CC(c1nc2ccccc2c(=O)n1C)N(CCN(C)S(=O)(=O)c1ccc(Br)cc1)S(=O)(=O)c1ccc(Br)cc1] |

TABLE 1-continued
| Cmpd No. | Structure |
|---|---|
| 203 | 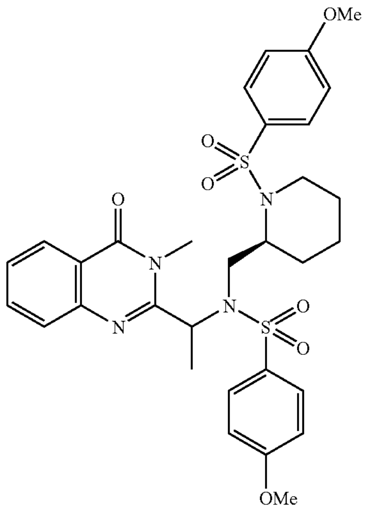 [SMILES: COc1ccc(S(=O)(=O)N(C[C@@H]2CCCCN2S(=O)(=O)c2ccc(OC)cc2)C(C)c2nc3ccccc3c(=O)n2C)cc1] |
| 204 | 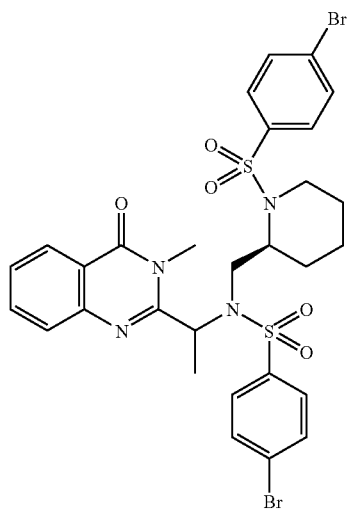 [SMILES: CC(c1nc2ccccc2c(=O)n1C)N(C[C@@H]1CCCCN1S(=O)(=O)c1ccc(Br)cc1)S(=O)(=O)c1ccc(Br)cc1] |
| 205 | 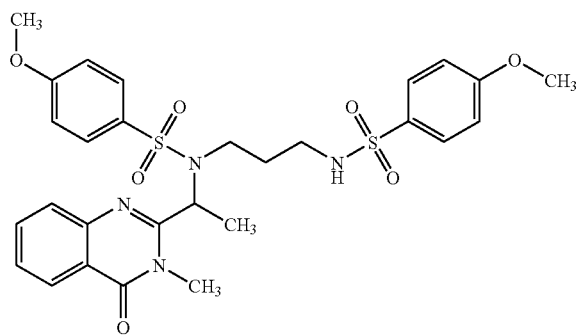 [SMILES: COc1ccc(S(=O)(=O)NCCCN(C(C)c2nc3ccccc3c(=O)n2C)S(=O)(=O)c2ccc(OC)cc2)cc1] |

TABLE 1-continued
| Cmpd No. | Structure |
|---|---|
| 206 | 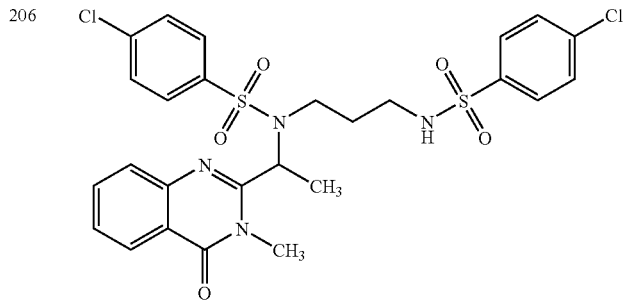 |
| 207 | 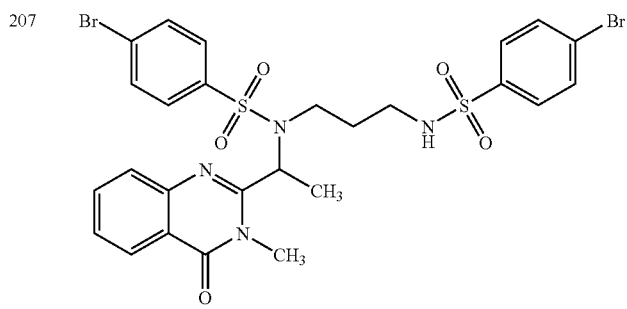 |
| 208 | 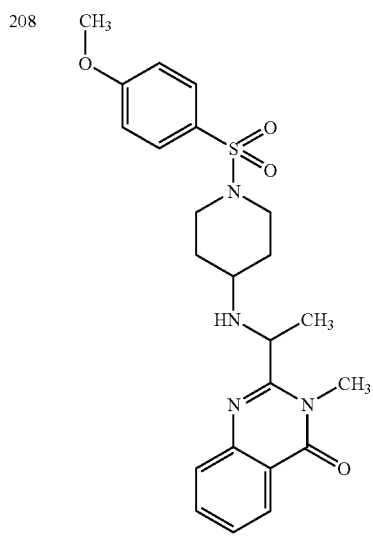 |

TABLE 1-continued
| Cmpd No. | Structure |
|---|---|
| 209 | 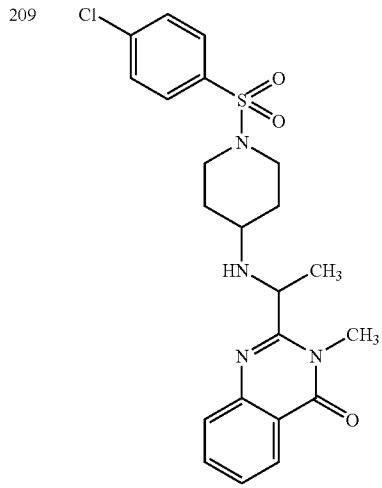 |
| 210 | 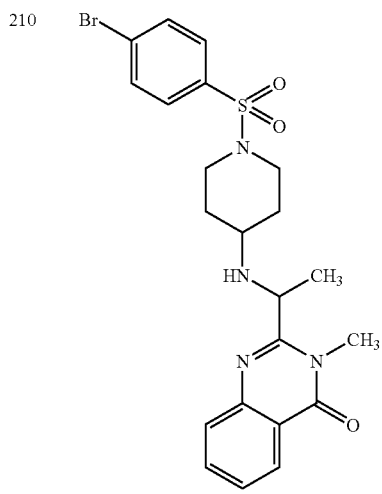 |
| 211 | 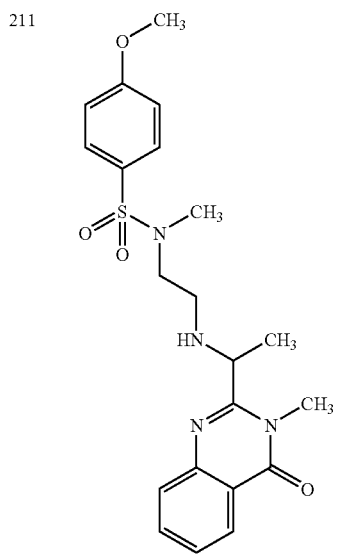 |

TABLE 1-continued
| Cmpd No. | Structure |
|---|---|
| 212 | 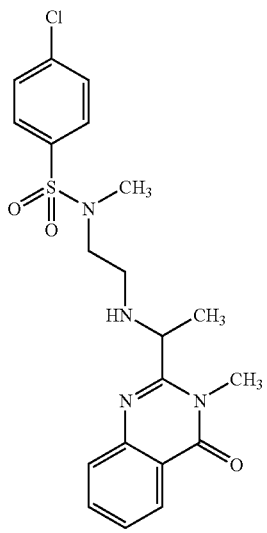 [SMILES: CC(NCCN(C)S(=O)(=O)c1ccc(Cl)cc1)c1nc2ccccc2c(=O)n1C] |
| 213 | 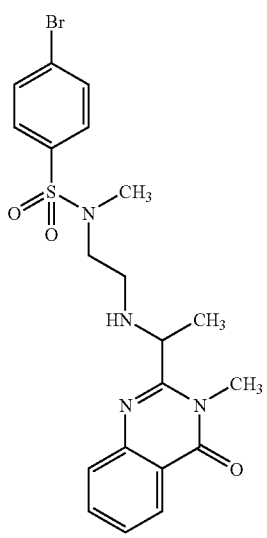 [SMILES: CC(NCCN(C)S(=O)(=O)c1ccc(Br)cc1)c1nc2ccccc2c(=O)n1C] |
| 214 | 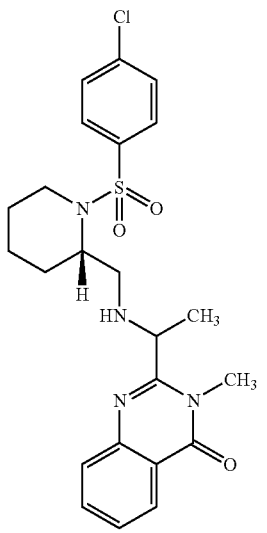 [SMILES: CC(NC[C@@H]1CCCCN1S(=O)(=O)c1ccc(Cl)cc1)c1nc2ccccc2c(=O)n1C] |

US 8,642,609 B2
173
TABLE 1-continued
| Cmpd No. | Structure |
|---|---|
| 215 | 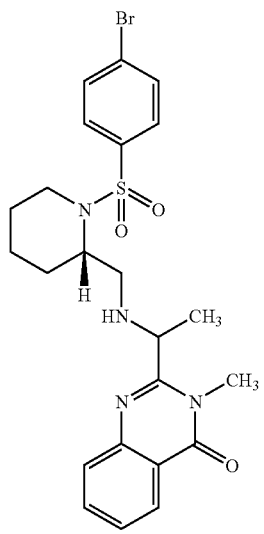 [SMILES: CC(NC[C@@H]1CCCCN1S(=O)(=O)c1ccc(Br)cc1)c1nc2ccccc2c(=O)n1C] |
| 216 | 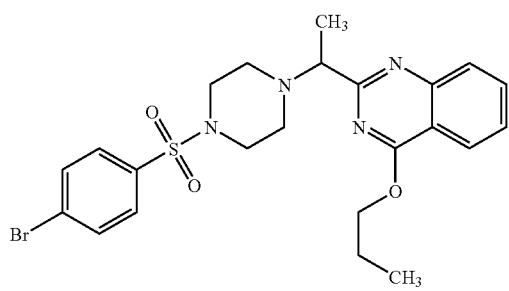 [SMILES: CCCOc1nc(C(C)N2CCN(S(=O)(=O)c3ccc(Br)cc3)CC2)nc2ccccc12] |
| 217 | 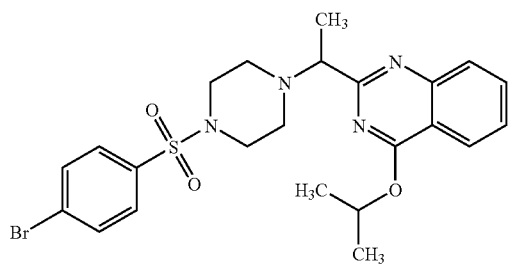 [SMILES: CC(C)Oc1nc(C(C)N2CCN(S(=O)(=O)c3ccc(Br)cc3)CC2)nc2ccccc12] |
| 218 | 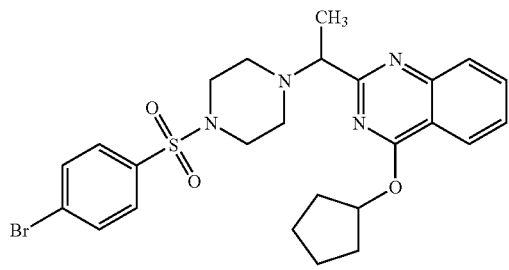 [SMILES: CC(c1nc(OC2CCCC2)c2ccccc2n1)N1CCN(S(=O)(=O)c2ccc(Br)cc2)CC1] |
| 219 | 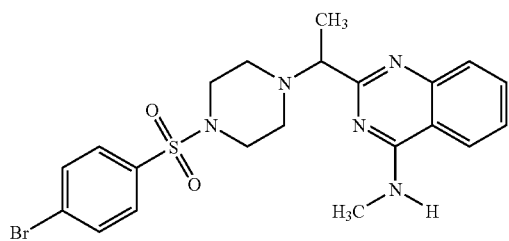 [SMILES: CNc1nc(C(C)N2CCN(S(=O)(=O)c3ccc(Br)cc3)CC2)nc2ccccc12] |
174

TABLE 1-continued
| Cmpd No. | Structure |
|---|---|
| 220 | 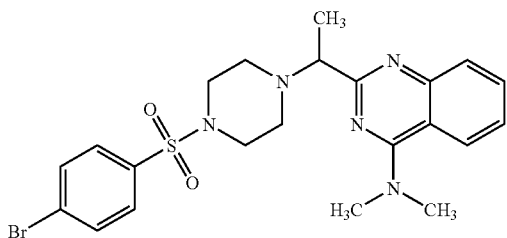 [SMILES: CC(c1nc(N(C)C)c2ccccc2n1)N1CCN(S(=O)(=O)c2ccc(Br)cc2)CC1] |
| 221 | 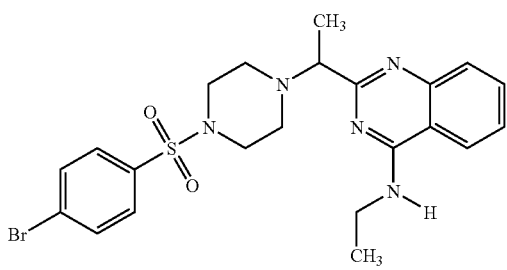 [SMILES: CCNc1nc(C(C)N2CCN(S(=O)(=O)c3ccc(Br)cc3)CC2)nc2ccccc12] |
| 222 | 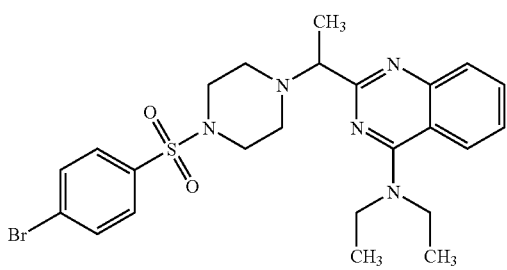 [SMILES: CCN(CC)c1nc(C(C)N2CCN(S(=O)(=O)c3ccc(Br)cc3)CC2)nc2ccccc12] |
| 223 | 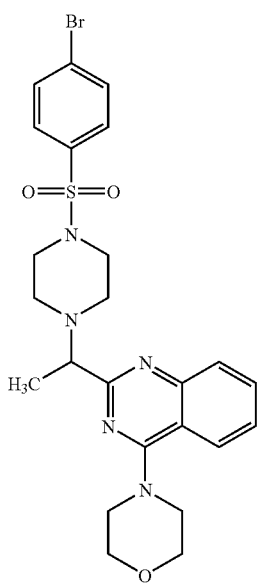 |

TABLE 1-continued

| Cmpd No. | Structure |
|---|---|
| 224 | 4-methoxyphenylsulfonyl-pyrrolidin-3-ylamino-ethyl-3-methyl-quinazolin-4(3H)-one |
| 225 | 4-chlorophenylsulfonyl-pyrrolidin-3-ylamino-ethyl-3-methyl-quinazolin-4(3H)-one |
| 226 | 4-bromophenylsulfonyl-pyrrolidin-3-ylamino-ethyl-3-methyl-quinazolin-4(3H)-one |
| 227 | 4-bromophenylsulfonyl-piperazinyl-ethyl-4-methoxyquinazoline |

TABLE 1-continued
| Cmpd No. | Structure |
|---|---|
| 228 | 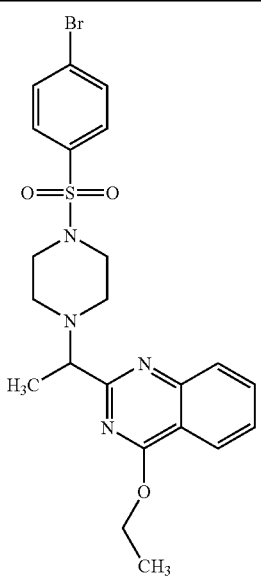 |
| 229 | 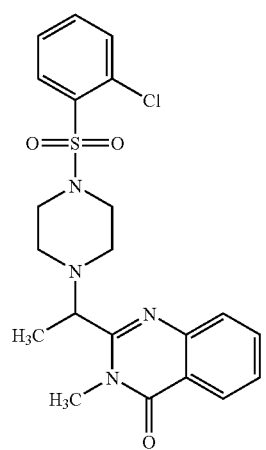 |
| 230 | 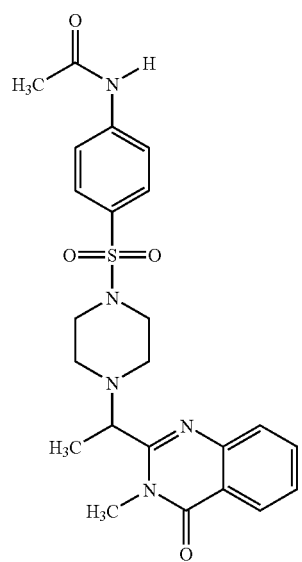 [SMILES: CC(=O)Nc1ccc(S(=O)(=O)N2CCN(C(C)c3nc4ccccc4c(=O)n3C)CC2)cc1] |

TABLE 1-continued
| Cmpd No. | Structure |
|---|---|
| 231 | 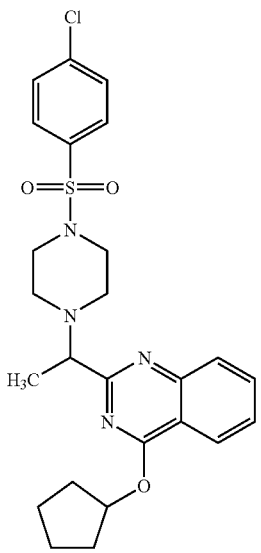 [SMILES: CC(c1nc(OC2CCCC2)c2ccccc2n1)N1CCN(S(=O)(=O)c2ccc(Cl)cc2)CC1] |
| 232 | 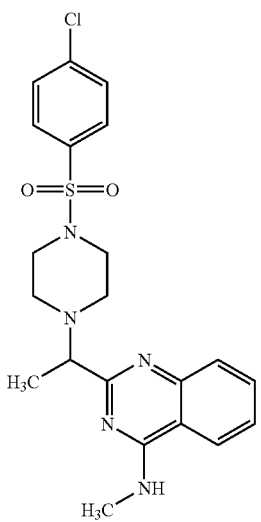 [SMILES: CNc1nc(C(C)N2CCN(S(=O)(=O)c3ccc(Cl)cc3)CC2)nc2ccccc12] |
| 233 | 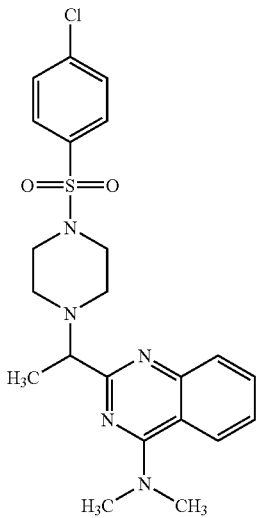 [SMILES: CC(c1nc(N(C)C)c2ccccc2n1)N1CCN(S(=O)(=O)c2ccc(Cl)cc2)CC1] |

TABLE 1-continued
| Cmpd No. | Structure |
|---|---|
| 234 | 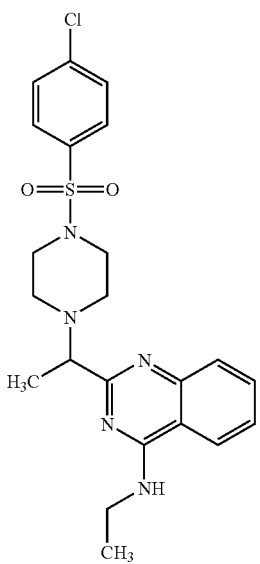 [SMILES: CCNc1nc(C(C)N2CCN(S(=O)(=O)c3ccc(Cl)cc3)CC2)nc2ccccc12] |
| 235 | 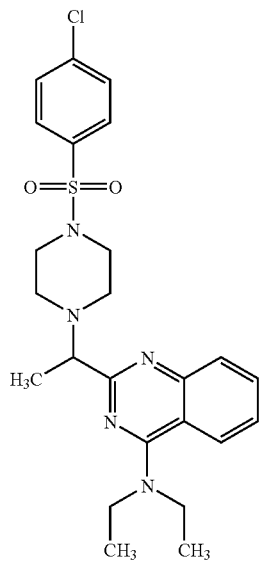 [SMILES: CCN(CC)c1nc(C(C)N2CCN(S(=O)(=O)c3ccc(Cl)cc3)CC2)nc2ccccc12] |

TABLE 1-continued
| Cmpd No. | Structure |
|---|---|
| 236 | 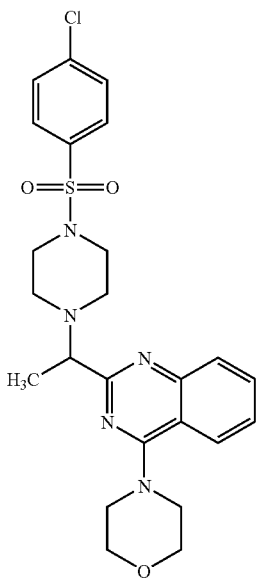 |
| 237 | 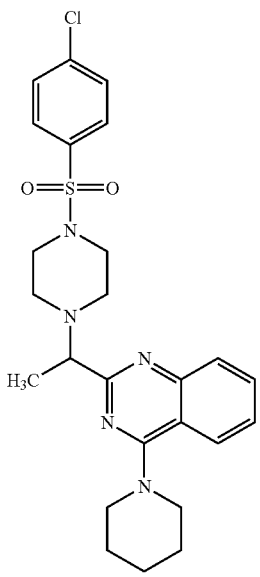 [SMILES: CC(c1nc(N2CCCCC2)c2ccccc2n1)N1CCN(S(=O)(=O)c2ccc(Cl)cc2)CC1] |

TABLE 1-continued
| Cmpd No. | Structure |
|---|---|
| 238 | 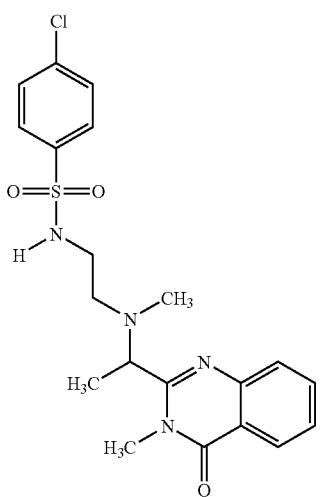 [SMILES: CC(c1nc2ccccc2c(=O)n1C)N(C)CCNS(=O)(=O)c1ccc(Cl)cc1] |
| 239 | 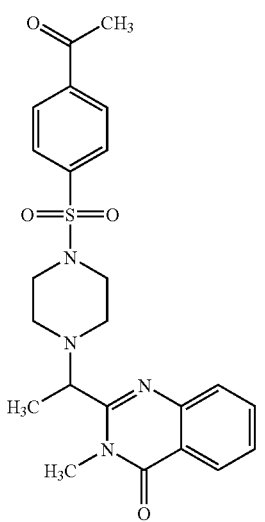 [SMILES: CC(=O)c1ccc(S(=O)(=O)N2CCN(C(C)c3nc4ccccc4c(=O)n3C)CC2)cc1] |
| 240 | 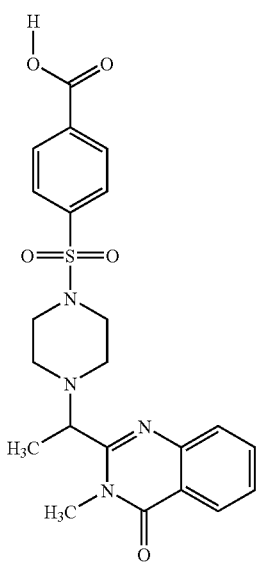 [SMILES: CC(c1nc2ccccc2c(=O)n1C)N1CCN(S(=O)(=O)c2ccc(C(=O)O)cc2)CC1] |

TABLE 1-continued

| Cmpd No. | Structure |
|---|---|
| 241 | (3,4-dichlorophenyl)sulfonyl-piperazine linked to 1-(3-methyl-4-oxo-3,4-dihydroquinazolin-2-yl)ethyl |
| 242 | biphenyl-4-sulfonyl-piperazine linked to 1-(3-methyl-4-oxo-3,4-dihydroquinazolin-2-yl)ethyl |
| 243 | 2-acetamido-4-methylthiazol-5-sulfonyl-piperazine linked to 1-(3-methyl-4-oxo-3,4-dihydroquinazolin-2-yl)ethyl |

TABLE 1-continued
| Cmpd No. | Structure |
|---|---|
| 244 | 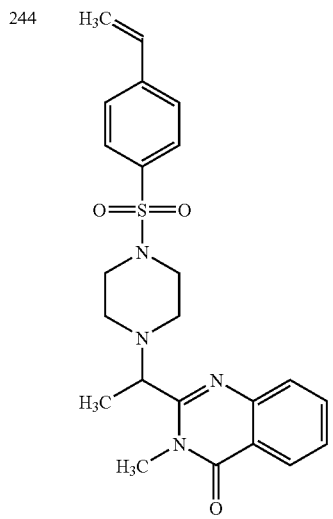 |
| 245 | 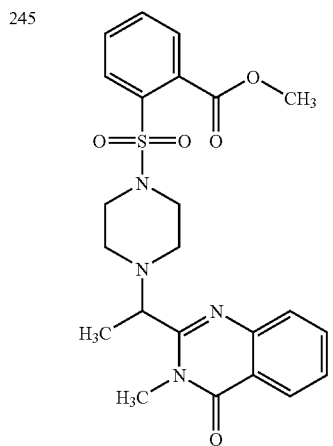 |
| 246 | 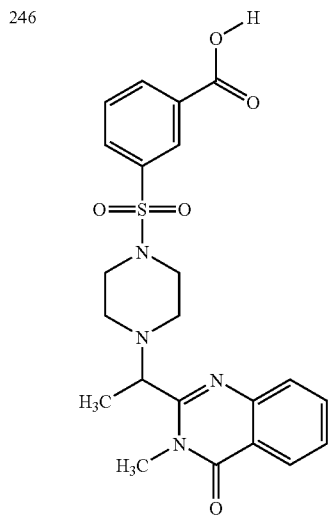 |

TABLE 1-continued
| Cmpd No. | Structure |
|---|---|
| 247 | 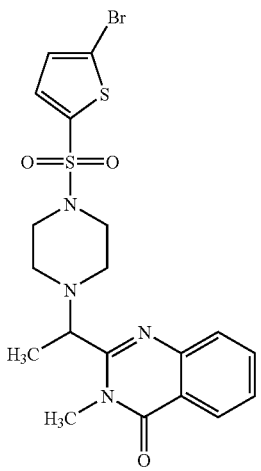 |
| 248 | 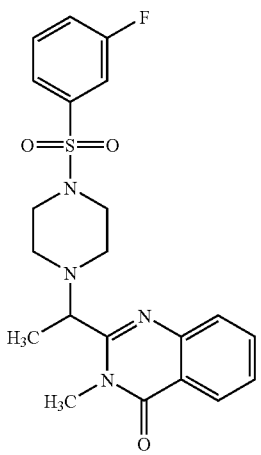 [SMILES: CC(c1nc2ccccc2c(=O)n1C)N1CCN(S(=O)(=O)c2cccc(F)c2)CC1] |
| 249 | 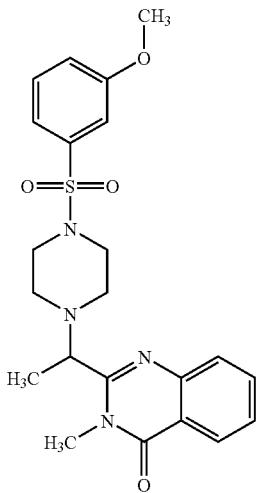 [SMILES: COc1cccc(S(=O)(=O)N2CCN(C(C)c3nc4ccccc4c(=O)n3C)CC2)c1] |

195 196
TABLE 1-continued
| Cmpd No. | Structure |
|---|---|
| 250 | 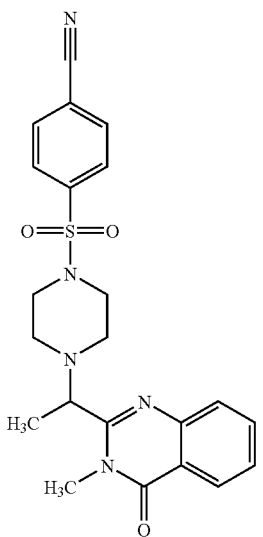 [SMILES: CC(c1nc2ccccc2c(=O)n1C)N1CCN(S(=O)(=O)c2ccc(C#N)cc2)CC1] |
| 251 | 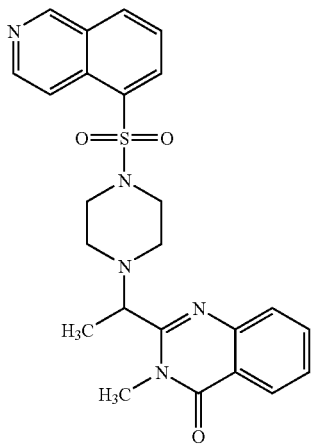 [SMILES: CC(c1nc2ccccc2c(=O)n1C)N1CCN(S(=O)(=O)c2cccc3cnccc23)CC1] |
| 252 | 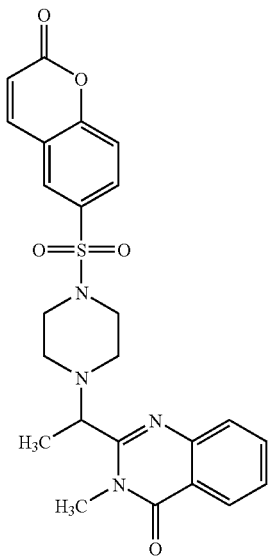 [SMILES: CC(c1nc2ccccc2c(=O)n1C)N1CCN(S(=O)(=O)c2ccc3oc(=O)ccc3c2)CC1] |

TABLE 1-continued
| Cmpd No. | Structure |
|---|---|
| 253 | 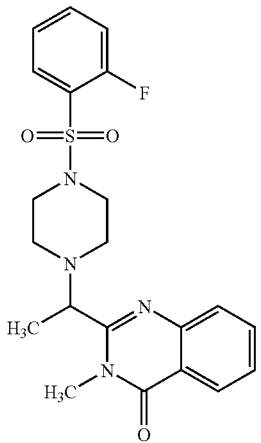 [SMILES: CC(c1nc2ccccc2c(=O)n1C)N1CCN(S(=O)(=O)c2ccccc2F)CC1] |
| 254 | 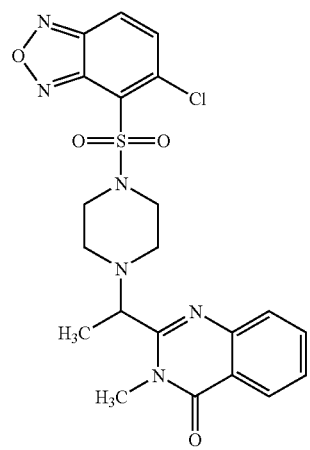 [SMILES: CC(c1nc2ccccc2c(=O)n1C)N1CCN(S(=O)(=O)c2c(Cl)ccc3nonc23)CC1] |
| 255 | 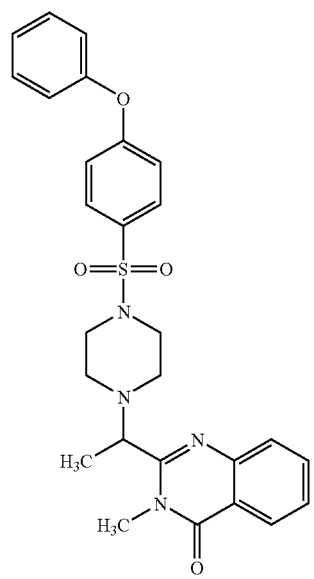 |

TABLE 1-continued
| Cmpd No. | Structure |
|---|---|
| 256 | 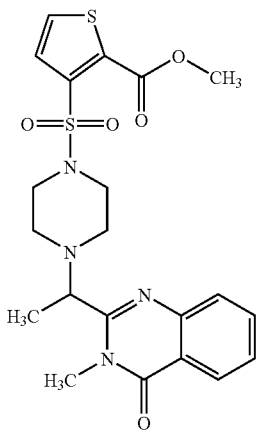 [SMILES: COC(=O)c1sccc1S(=O)(=O)N1CCN(C(C)c2nc3ccccc3c(=O)n2C)CC1] |
| 257 | 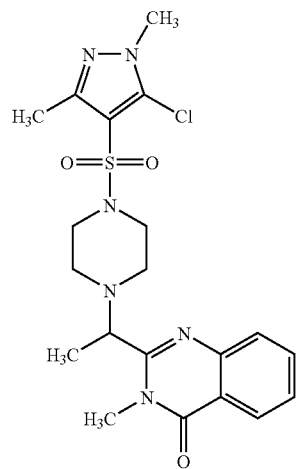 [SMILES: Cc1nn(C)c(Cl)c1S(=O)(=O)N1CCN(C(C)c2nc3ccccc3c(=O)n2C)CC1] |
| 258 | 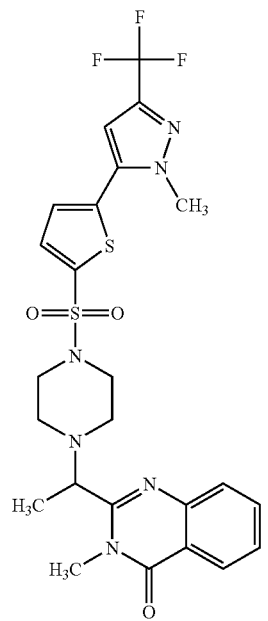 [SMILES: CC(c1nc2ccccc2c(=O)n1C)N1CCN(S(=O)(=O)c2ccc(-c3cc(C(F)(F)F)nn3C)s2)CC1] |

TABLE 1-continued
| Cmpd No. | Structure |
|---|---|
| 259 | 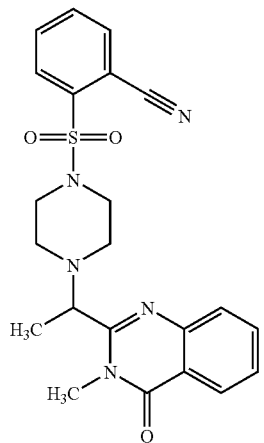 [SMILES: CC(c1nc2ccccc2c(=O)n1C)N1CCN(S(=O)(=O)c2ccccc2C#N)CC1] |
| 260 | 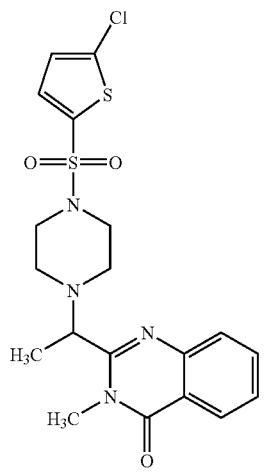 [SMILES: CC(c1nc2ccccc2c(=O)n1C)N1CCN(S(=O)(=O)c2ccc(Cl)s2)CC1] |
| 261 | 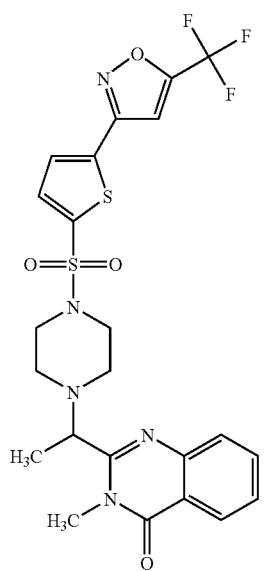 [SMILES: CC(c1nc2ccccc2c(=O)n1C)N1CCN(S(=O)(=O)c2ccc(-c3cc(C(F)(F)F)on3)s2)CC1] |

TABLE 1-continued
| Cmpd No. | Structure |
|---|---|
| 262 | 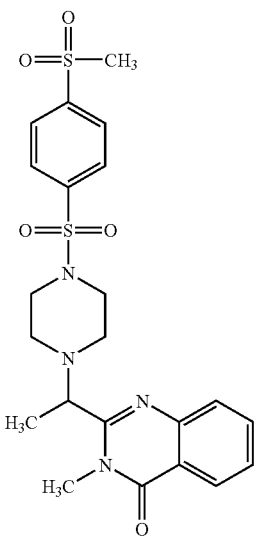 [SMILES: CC(c1nc2ccccc2c(=O)n1C)N1CCN(S(=O)(=O)c2ccc(S(C)(=O)=O)cc2)CC1] |
| 263 | 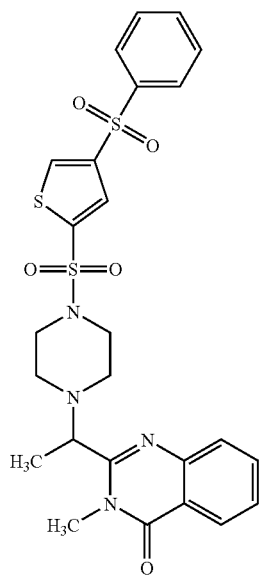 [SMILES: CC(c1nc2ccccc2c(=O)n1C)N1CCN(S(=O)(=O)c2cc(S(=O)(=O)c3ccccc3)cs2)CC1] |
| 264 | 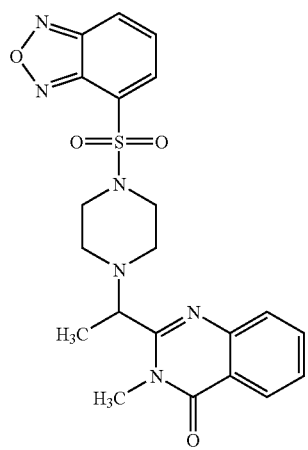 [SMILES: CC(c1nc2ccccc2c(=O)n1C)N1CCN(S(=O)(=O)c2cccc3nonc23)CC1] |

TABLE 1-continued
| Cmpd No. | Structure |
|---|---|
| 265 | 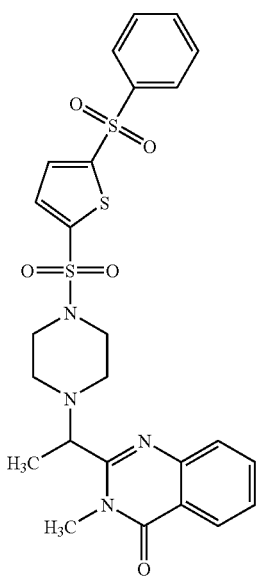 [SMILES: CC(c1nc2ccccc2c(=O)n1C)N1CCN(S(=O)(=O)c2ccc(S(=O)(=O)c3ccccc3)s2)CC1] |
| 266 | 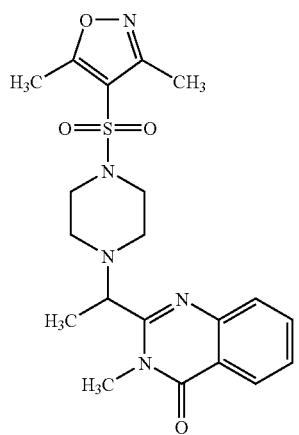 [SMILES: Cc1noc(C)c1S(=O)(=O)N1CCN(C(C)c2nc3ccccc3c(=O)n2C)CC1] |
| 267 | 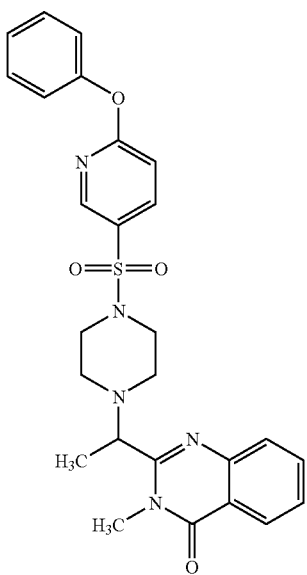 [SMILES: CC(c1nc2ccccc2c(=O)n1C)N1CCN(S(=O)(=O)c2ccc(Oc3ccccc3)nc2)CC1] |

TABLE 1-continued
| Cmpd No. | Structure |
|---|---|
| 268 | 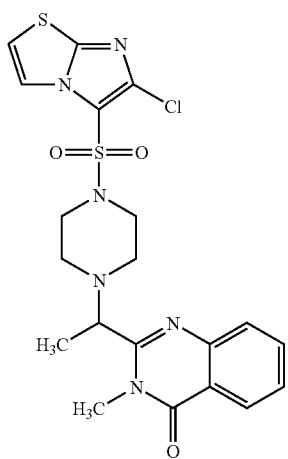 [SMILES: CC(c1nc2ccccc2c(=O)n1C)N1CCN(S(=O)(=O)c2c(Cl)nc3sccn23)CC1] |
| 269 | 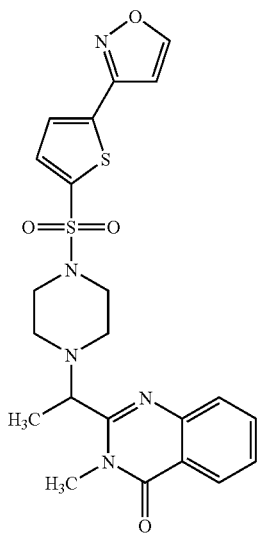 [SMILES: CC(c1nc2ccccc2c(=O)n1C)N1CCN(S(=O)(=O)c2ccc(-c3ccon3)s2)CC1] |
| 270 | 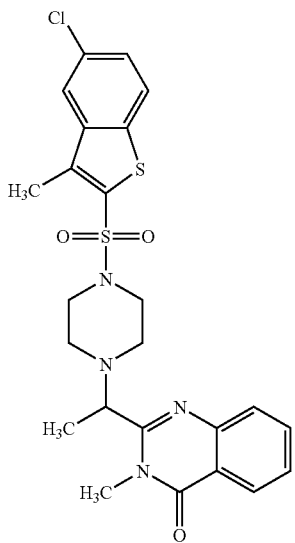 [SMILES: Cc1c(S(=O)(=O)N2CCN(C(C)c3nc4ccccc4c(=O)n3C)CC2)sc2ccc(Cl)cc12] |

TABLE 1-continued
| Cmpd No. | Structure |
|---|---|
| 271 | 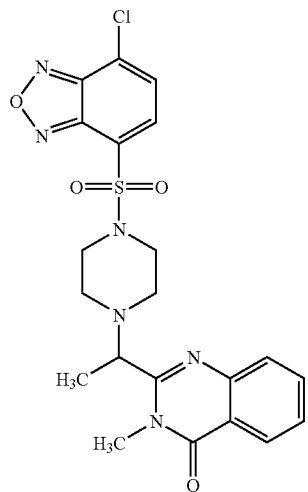 [SMILES: CC(c1nc2ccccc2c(=O)n1C)N1CCN(S(=O)(=O)c2ccc(Cl)c3nonc23)CC1] |
| 272 | 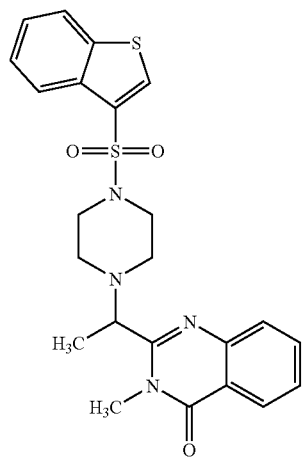 [SMILES: CC(c1nc2ccccc2c(=O)n1C)N1CCN(S(=O)(=O)c2csc3ccccc23)CC1] |
| 273 | 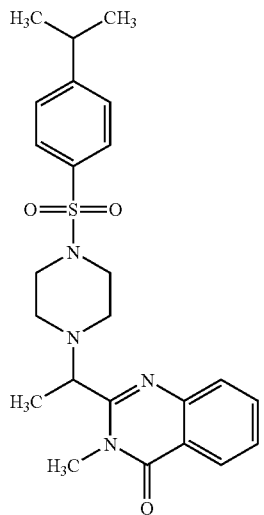 [SMILES: CC(C)c1ccc(S(=O)(=O)N2CCN(C(C)c3nc4ccccc4c(=O)n3C)CC2)cc1] |

TABLE 1-continued
| Cmpd No. | Structure |
|---|---|
| 274 | 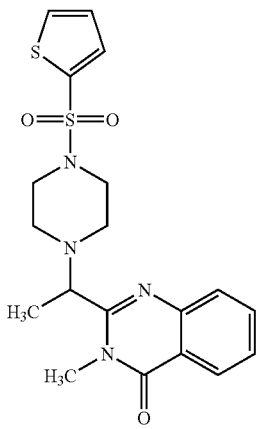 [SMILES: CC(c1nc2ccccc2c(=O)n1C)N1CCN(S(=O)(=O)c2cccs2)CC1] |
| 275 | 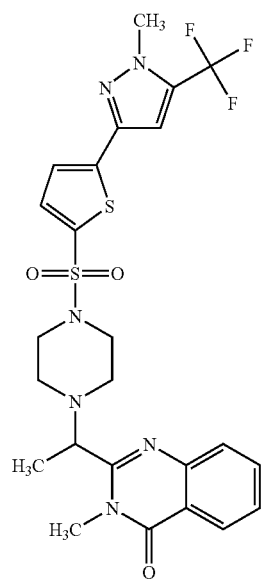 [SMILES: CC(c1nc2ccccc2c(=O)n1C)N1CCN(S(=O)(=O)c2ccc(-c3cc(C(F)(F)F)n(C)n3)s2)CC1] |
| 276 | 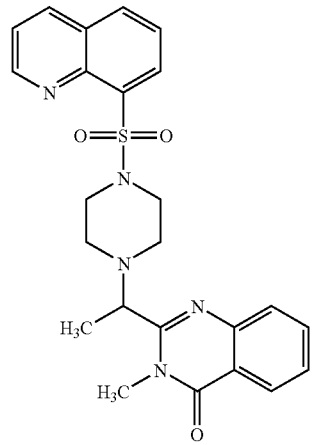 [SMILES: CC(c1nc2ccccc2c(=O)n1C)N1CCN(S(=O)(=O)c2cccc3cccnc23)CC1] |

TABLE 1-continued
| Cmpd No. | Structure |
|---|---|
| 277 | 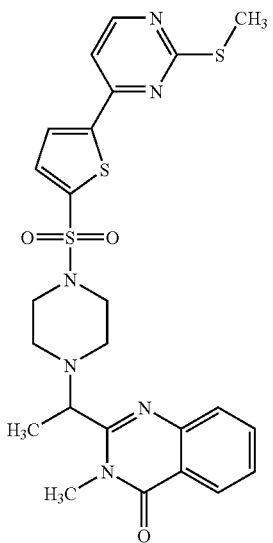 [SMILES: CSc1nccc(-c2ccc(S(=O)(=O)N3CCN(C(C)c4nc5ccccc5c(=O)n4C)CC3)s2)n1] |
| 278 | 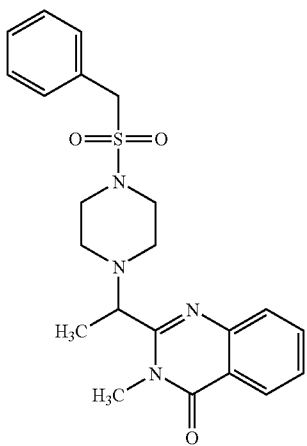 [SMILES: CC(c1nc2ccccc2c(=O)n1C)N1CCN(S(=O)(=O)Cc2ccccc2)CC1] |
| 279 | 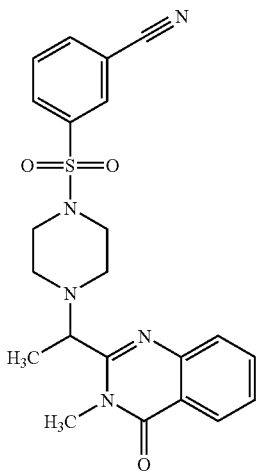 [SMILES: CC(c1nc2ccccc2c(=O)n1C)N1CCN(S(=O)(=O)c2cccc(C#N)c2)CC1] |

TABLE 1-continued

| Cmpd No. | Structure |
| --- | --- |
| 280 | (chemical structure) |
| 281 | (chemical structure) |
| 282 | (chemical structure) |

TABLE 1-continued
| Cmpd No. | Structure |
|---|---|
| 283 | 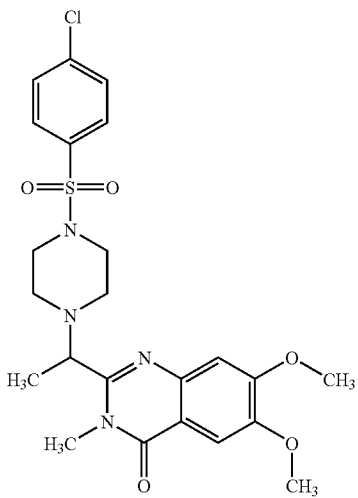 |
| 284 | 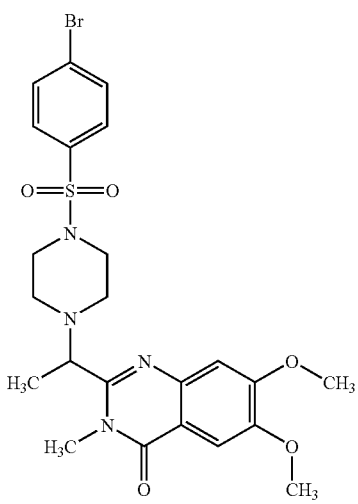 [SMILES: COc1cc2nc(C(C)N3CCN(S(=O)(=O)c4ccc(Cl)cc4)CC3)n(C)c(=O)c2cc1OC] |
| 285 | 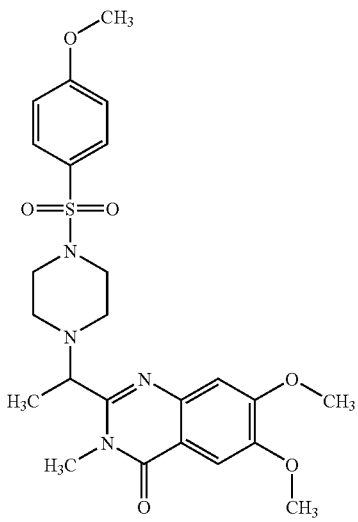 [SMILES: COc1ccc(S(=O)(=O)N2CCN(C(C)c3nc4cc(OC)c(OC)cc4c(=O)n3C)CC2)cc1] |

TABLE 1-continued
| Cmpd No. | Structure |
|---|---|
| 286 | 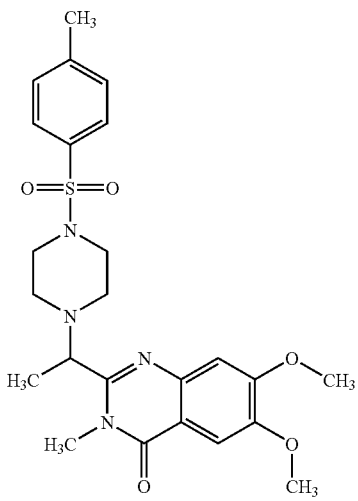 [SMILES: COc1cc2nc(C(C)N3CCN(S(=O)(=O)c4ccc(C)cc4)CC3)n(C)c(=O)c2cc1OC] |
| 287 | 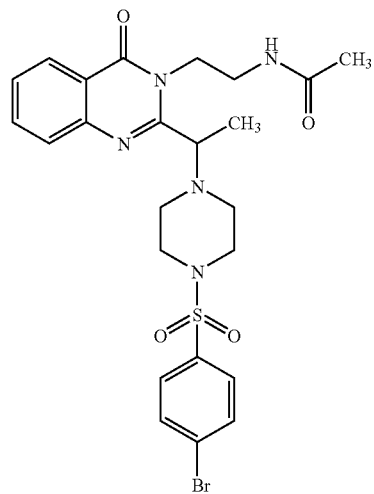 [SMILES: CC(=O)NCCn1c(C(C)N2CCN(S(=O)(=O)c3ccc(Br)cc3)CC2)nc2ccccc2c1=O] |
| 288 | 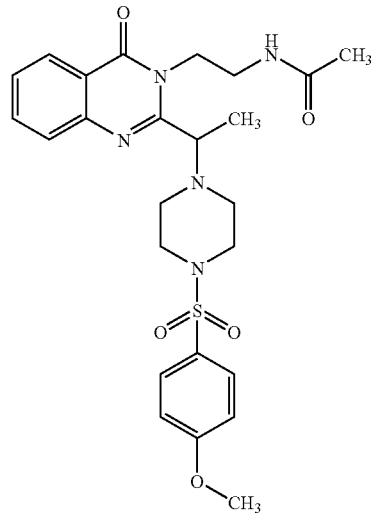 [SMILES: COc1ccc(S(=O)(=O)N2CCN(C(C)c3nc4ccccc4c(=O)n3CCNC(C)=O)CC2)cc1] |

TABLE 1-continued
| Cmpd No. | Structure |
|---|---|
| 289 | 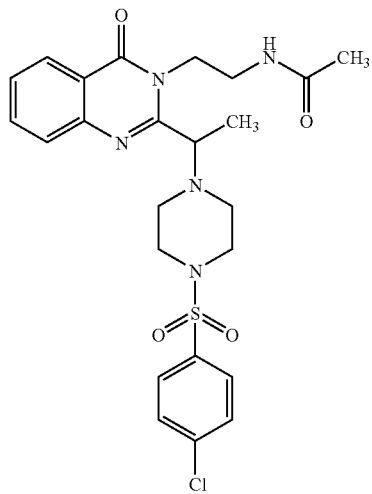 [SMILES: CC(=O)NCCn1c(C(C)N2CCN(S(=O)(=O)c3ccc(Cl)cc3)CC2)nc2ccccc2c1=O] |
| 290 | 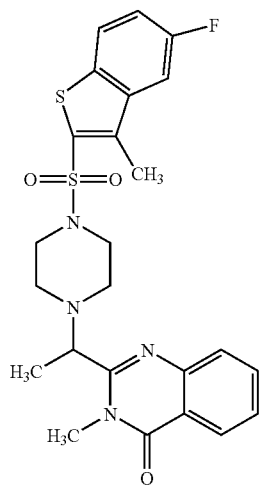 [SMILES: Cc1c(S(=O)(=O)N2CCN(C(C)c3nc4ccccc4c(=O)n3C)CC2)sc2ccc(F)cc12] |
| 291 | 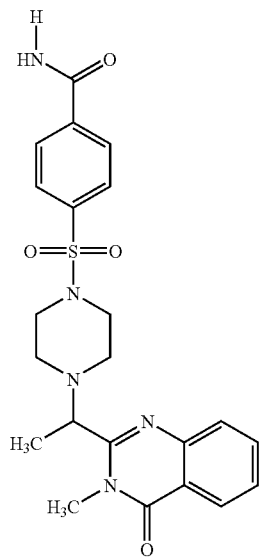 [SMILES: CC(c1nc2ccccc2c(=O)n1C)N1CCN(S(=O)(=O)c2ccc(C(N)=O)cc2)CC1] |

TABLE 1-continued
| Cmpd No. | Structure |
|---|---|
| 292 | 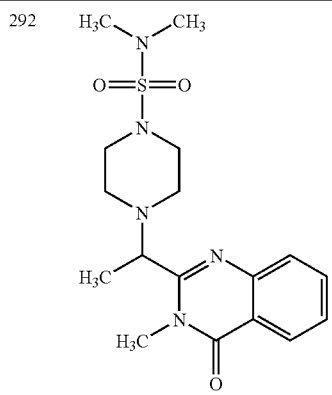 |
| 293 | 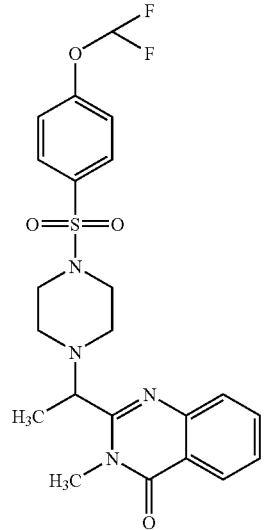 [SMILES: CC(c1nc2ccccc2c(=O)n1C)N1CCN(S(=O)(=O)c2ccc(OC(F)F)cc2)CC1] |
| 294 | 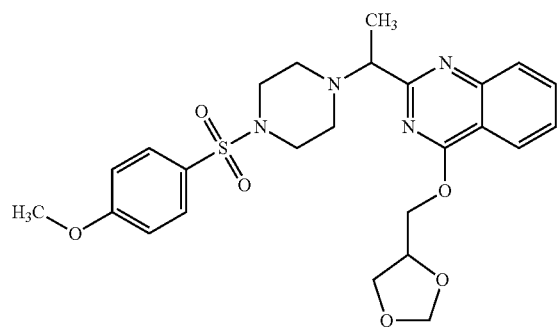 [SMILES: COc1ccc(S(=O)(=O)N2CCN(C(C)c3nc(OCC4COCO4)c4ccccc4n3)CC2)cc1] |
| 295 | 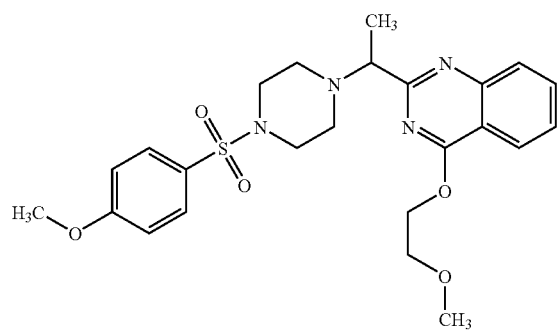 [SMILES: COCCOc1nc(C(C)N2CCN(S(=O)(=O)c3ccc(OC)cc3)CC2)nc2ccccc12] |

TABLE 1-continued
| Cmpd No. | Structure |
|---|---|
| 296 | 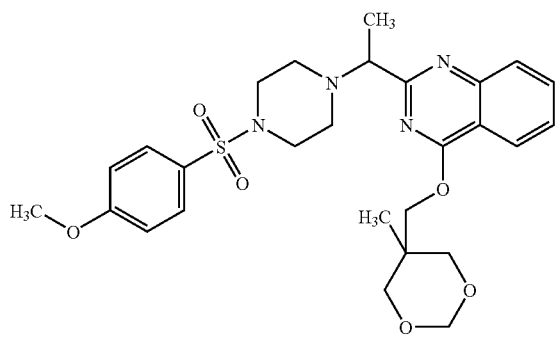 [SMILES: COc1ccc(S(=O)(=O)N2CCN(C(C)c3nc(OCC4(C)COCOC4)c4ccccc4n3)CC2)cc1] |
| 297 | 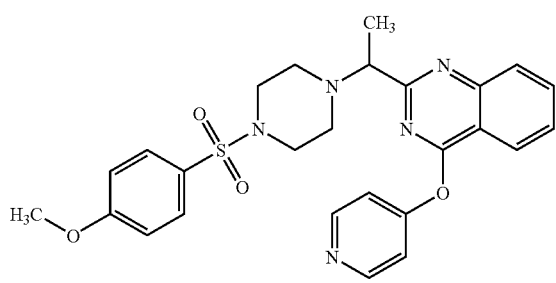 [SMILES: COc1ccc(S(=O)(=O)N2CCN(C(C)c3nc(Oc4ccncc4)c4ccccc4n3)CC2)cc1] |
| 298 | 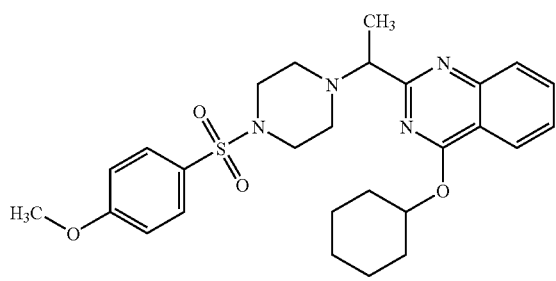 [SMILES: COc1ccc(S(=O)(=O)N2CCN(C(C)c3nc(OC4CCCCC4)c4ccccc4n3)CC2)cc1] |
| 299 | 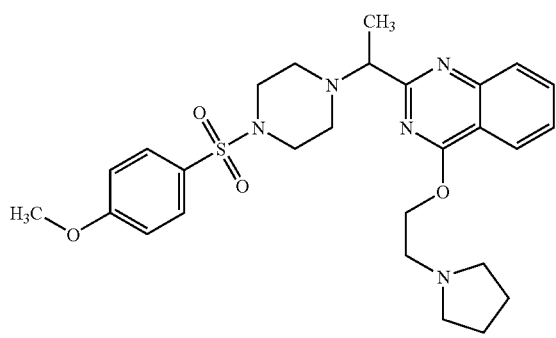 [SMILES: COc1ccc(S(=O)(=O)N2CCN(C(C)c3nc(OCCN4CCCC4)c4ccccc4n3)CC2)cc1] |
| 300 | 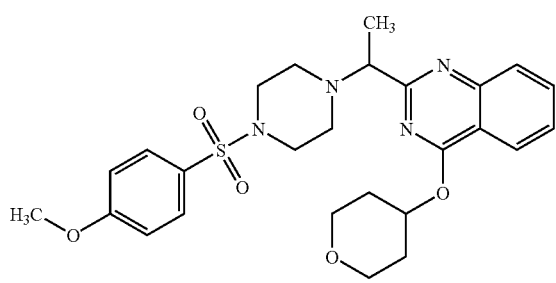 [SMILES: COc1ccc(S(=O)(=O)N2CCN(C(C)c3nc(OC4CCOCC4)c4ccccc4n3)CC2)cc1] |

TABLE 1-continued
| Cmpd No. | Structure |
|---|---|
| 301 | 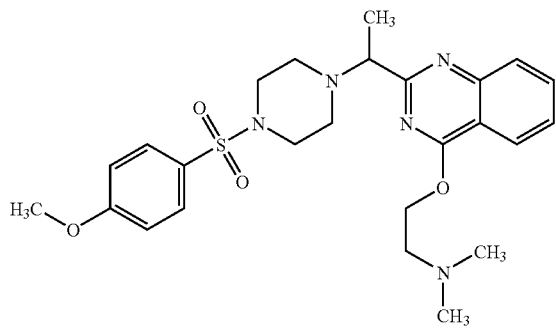 [SMILES: COc1ccc(S(=O)(=O)N2CCN(C(C)c3nc(OCCN(C)C)c4ccccc4n3)CC2)cc1] |
| 302 | 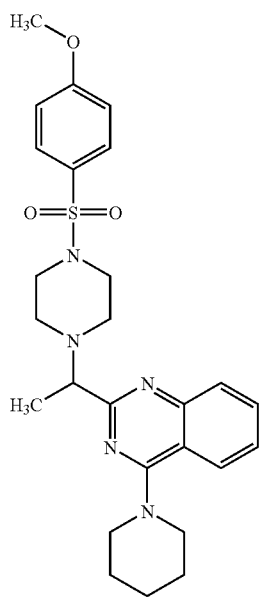 [SMILES: COc1ccc(S(=O)(=O)N2CCN(C(C)c3nc(N4CCCCC4)c4ccccc4n3)CC2)cc1] |
| 303 | 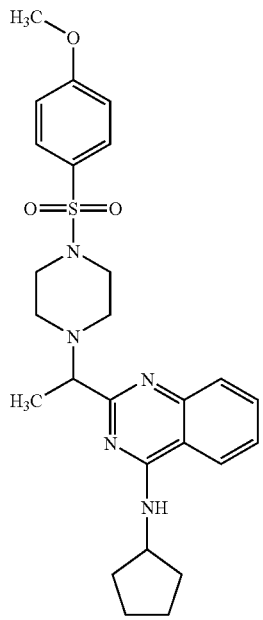 [SMILES: COc1ccc(S(=O)(=O)N2CCN(C(C)c3nc(NC4CCCC4)c4ccccc4n3)CC2)cc1] |

TABLE 1-continued
| Cmpd No. | Structure |
|---|---|
| 304 | 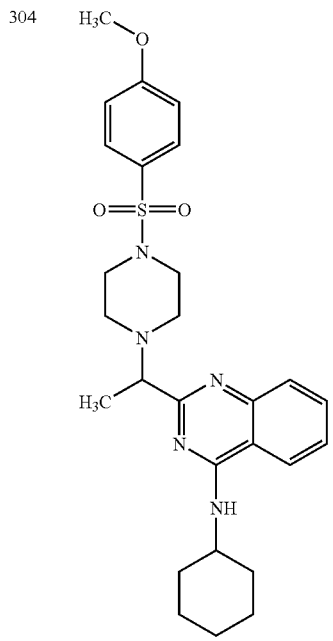 |
| 305 | 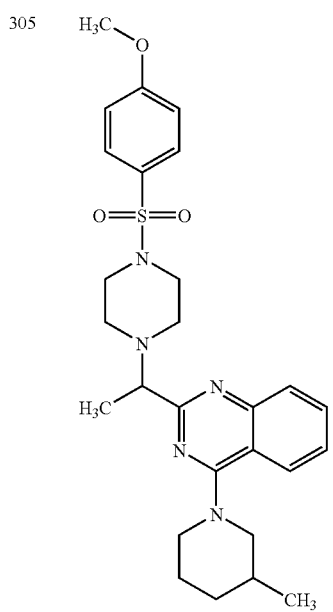 |

TABLE 1-continued
| Cmpd No. | Structure |
|---|---|
| 306 | 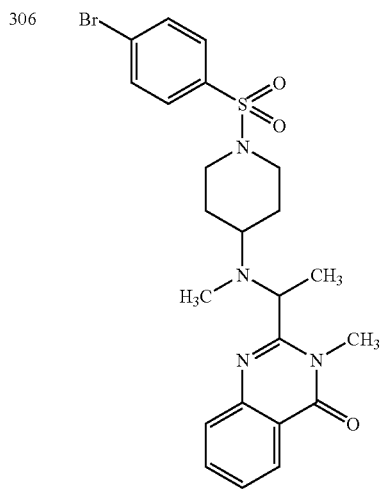 |
| 307 | 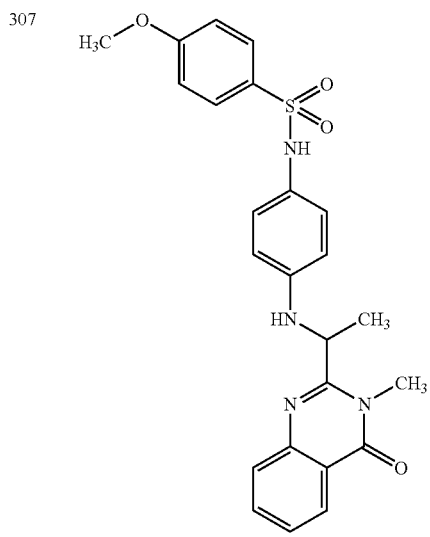 |
| 308 | 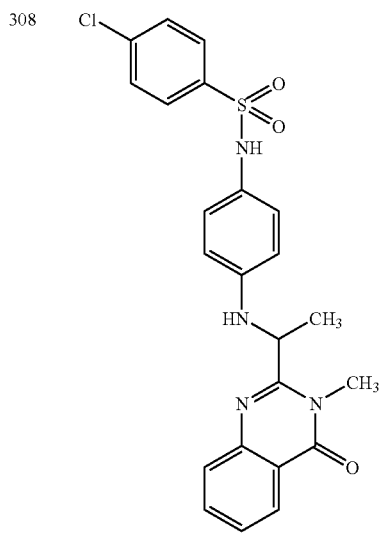 |

TABLE 1-continued
| Cmpd No. | Structure |
|---|---|
| 309 | 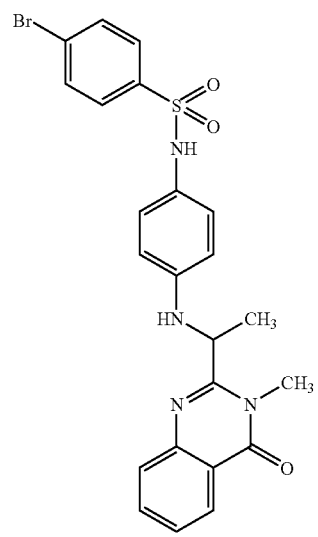 [SMILES: CC(Nc1ccc(NS(=O)(=O)c2ccc(Cl)cc2)cc1)c1nc2ccccc2c(=O)n1C] |
| 310 | 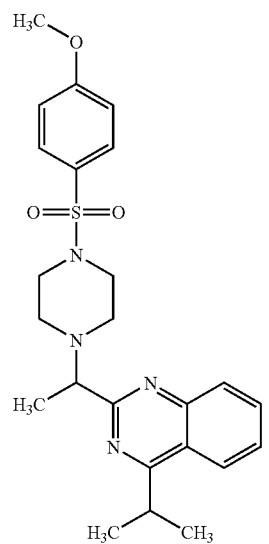 [SMILES: COc1ccc(S(=O)(=O)N2CCN(C(C)c3nc(C(C)C)c4ccccc4n3)CC2)cc1] |

TABLE 1-continued
| Cmpd No. | Structure |
|---|---|
| 311 | 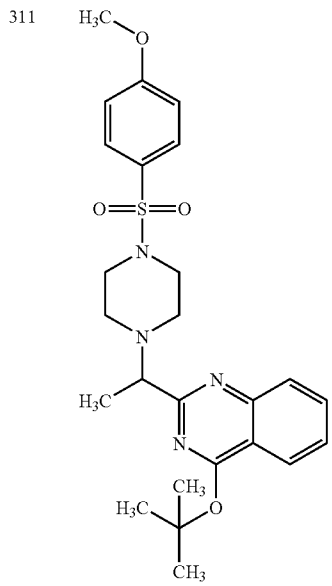 |
| 312 | 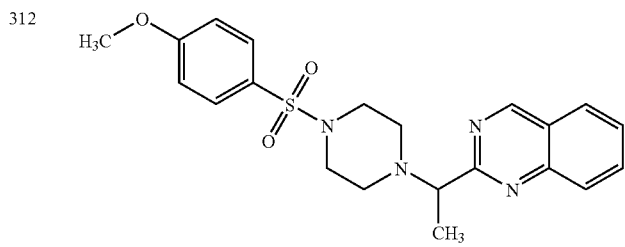 |
| 313 | 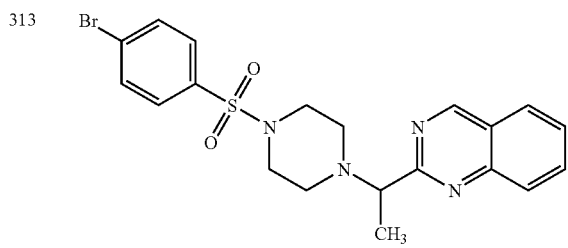 |
| 314 | 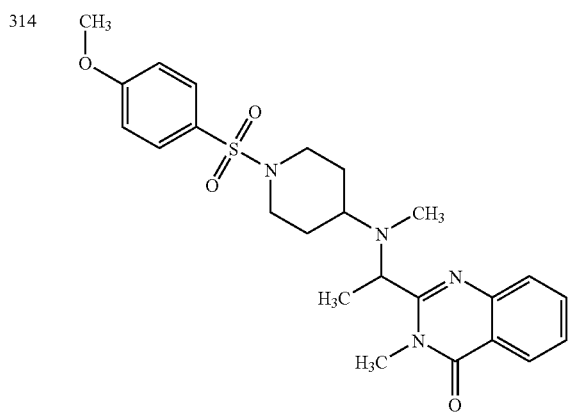 |

TABLE 1-continued
| Cmpd No. | Structure |
|---|---|
| 315 | 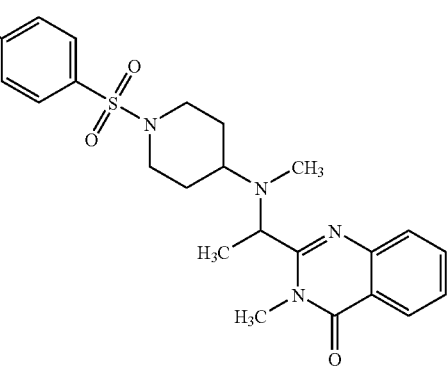 |
| 316 | 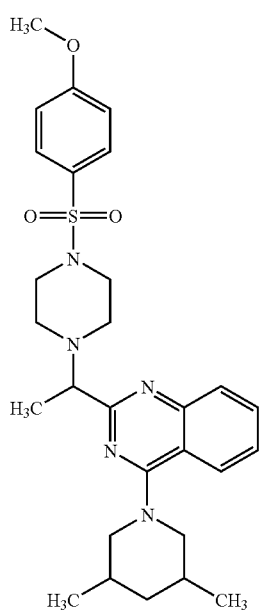 [SMILES: COc1ccc(S(=O)(=O)N2CCN(C(C)c3nc(N4CC(C)CC(C)C4)c4ccccc4n3)CC2)cc1] |
| 317 | 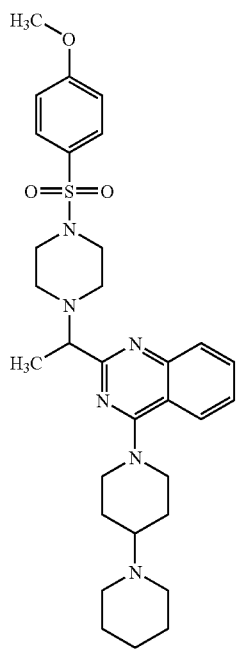 [SMILES: COc1ccc(S(=O)(=O)N2CCN(C(C)c3nc(N4CCC(N5CCCCC5)CC4)c4ccccc4n3)CC2)cc1] |

TABLE 1-continued
| Cmpd No. | Structure |
|---|---|
| 318 | 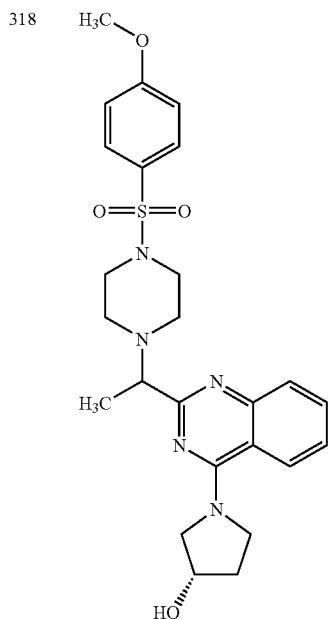 |
| 319 | 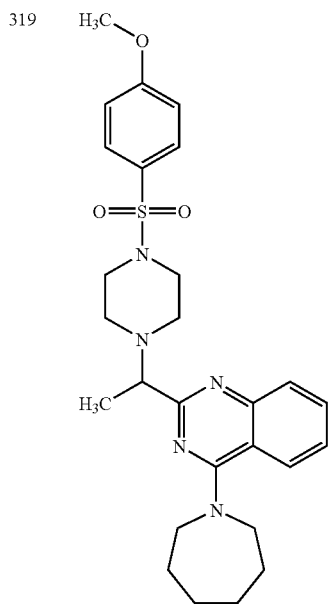 |

TABLE 1-continued
| Cmpd No. | Structure |
|---|---|
| 320 | 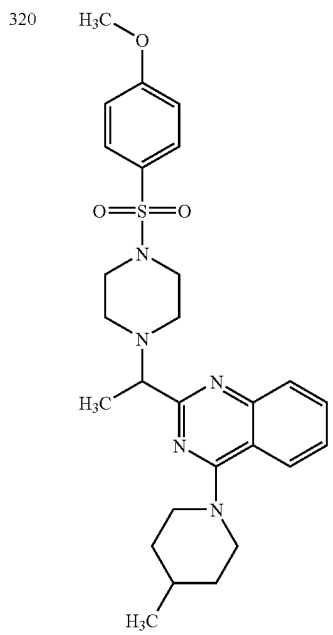 |
| 321 | 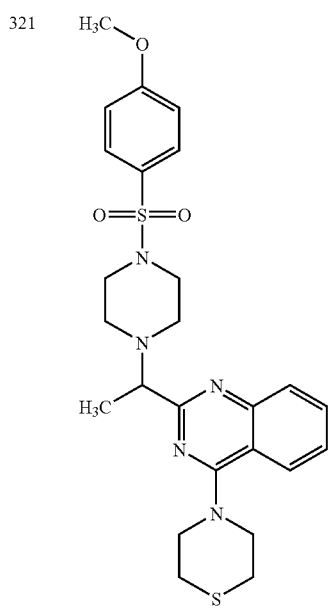 |

TABLE 1-continued
| Cmpd No. | Structure |
|---|---|
| 322 | 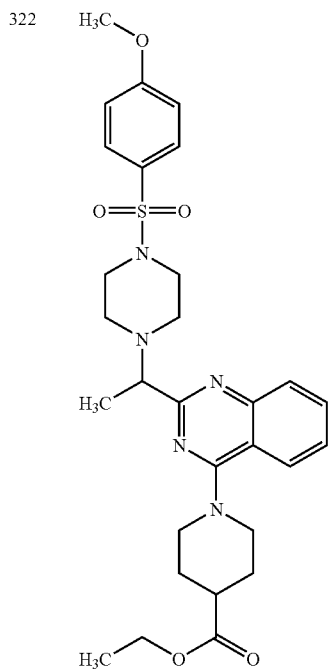 |
| 323 | 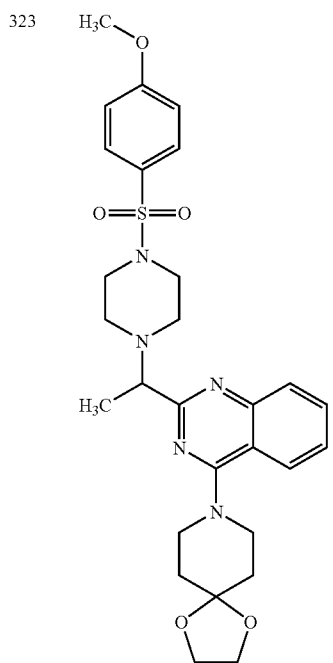 |

TABLE 1-continued
| Cmpd No. | Structure |
|---|---|
| 324 | 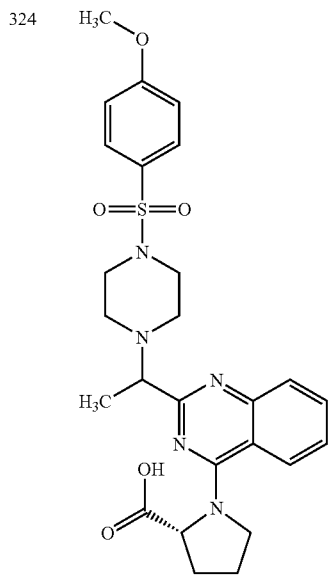 |
| 325 | 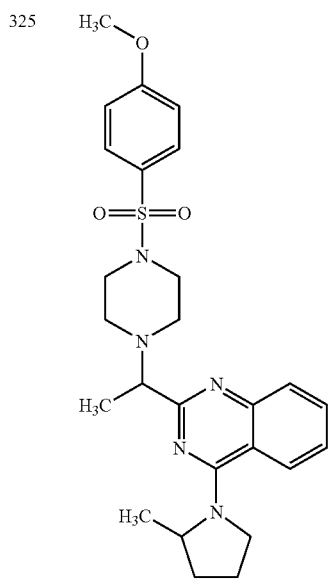 |

TABLE 1-continued
| Cmpd No. | Structure |
|---|---|
| 326 | 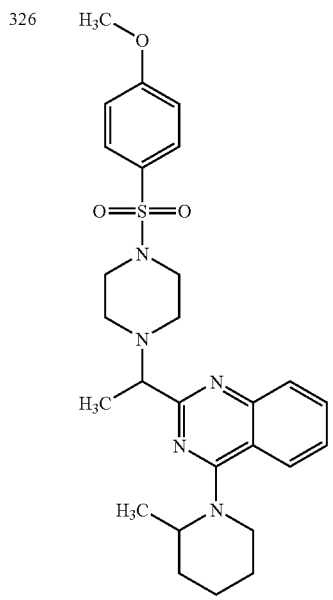 |
| 327 | 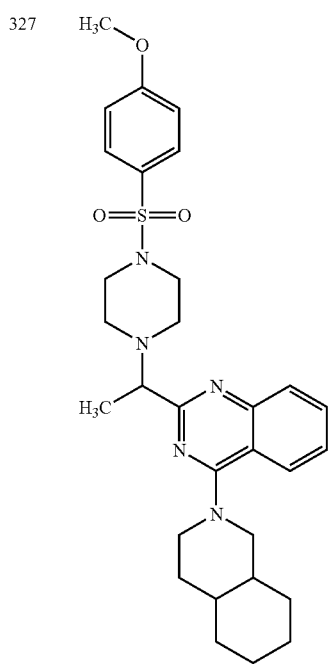 |

TABLE 1-continued
| Cmpd No. | Structure |
|---|---|
| 328 | 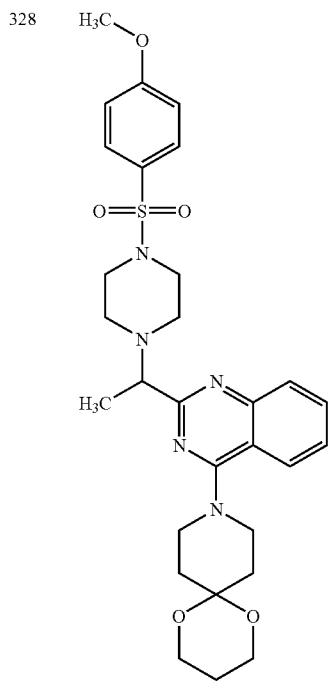 |
| 329 | 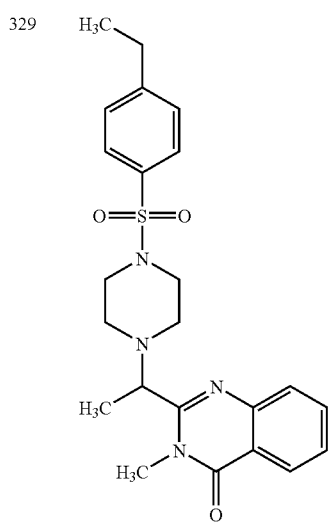 |

TABLE 1-continued
| Cmpd No. | Structure |
|---|---|
| 330 | 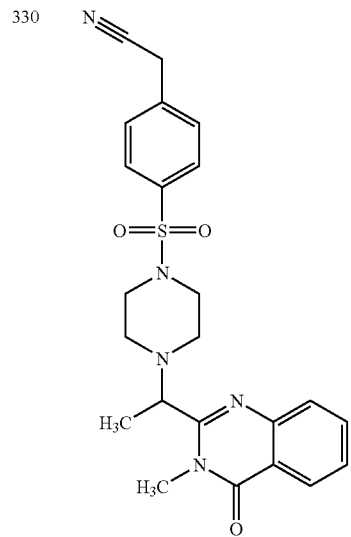 |
| 331 | 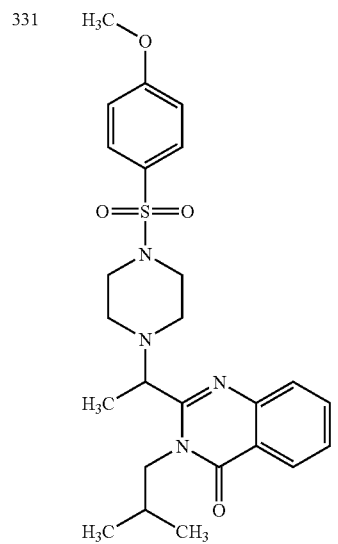 |

TABLE 1-continued
| Cmpd No. | Structure |
|---|---|
| 332 | 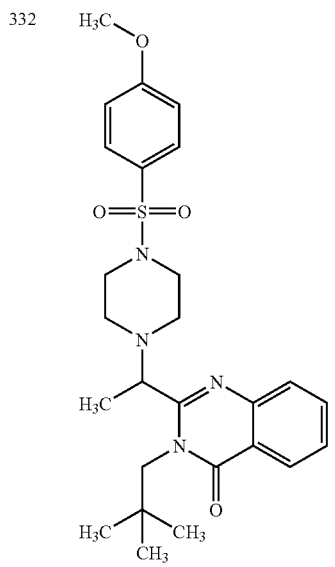 |
| 333 | 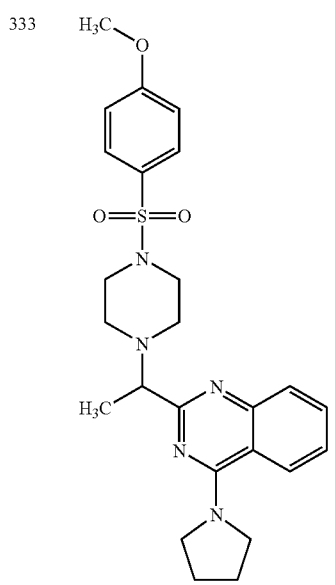 |

TABLE 1-continued
| Cmpd No. | Structure |
|---|---|
| 334 | 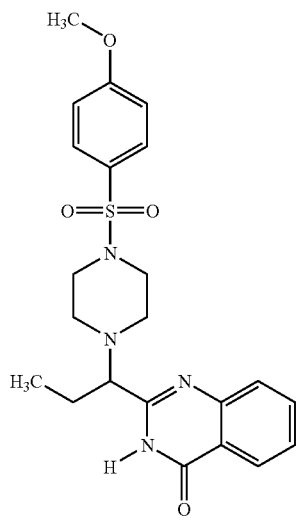 [SMILES: CCC(c1nc2ccccc2c(=O)[nH]1)N1CCN(S(=O)(=O)c2ccc(OC)cc2)CC1] |
| 335 | 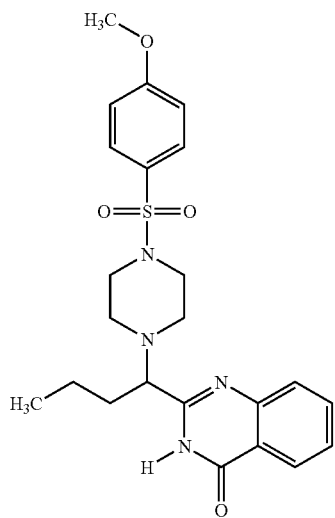 [SMILES: CCCC(c1nc2ccccc2c(=O)[nH]1)N1CCN(S(=O)(=O)c2ccc(OC)cc2)CC1] |
| 336 | 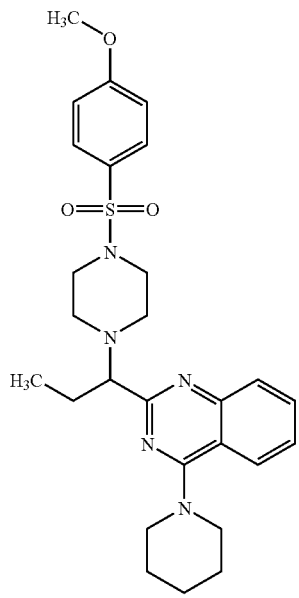 [SMILES: CCC(c1nc(N2CCCCC2)c2ccccc2n1)N1CCN(S(=O)(=O)c2ccc(OC)cc2)CC1] |

TABLE 1-continued
| Cmpd No. | Structure |
|---|---|
| 337 | 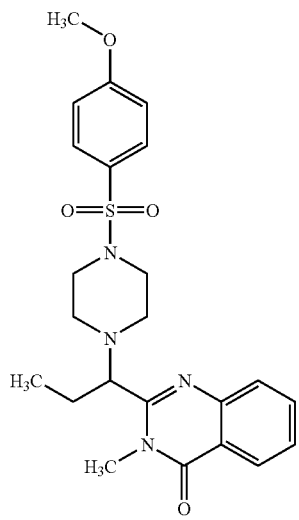 [SMILES: CCC(c1nc2ccccc2c(=O)n1C)N1CCN(S(=O)(=O)c2ccc(OC)cc2)CC1] |
| 338 | 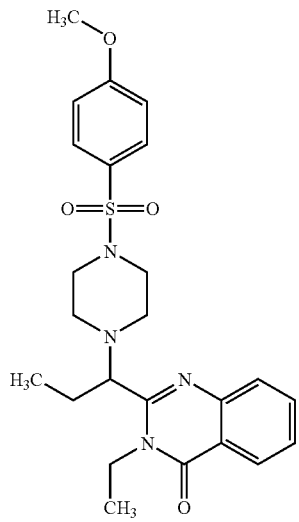 [SMILES: CCC(c1nc2ccccc2c(=O)n1CC)N1CCN(S(=O)(=O)c2ccc(OC)cc2)CC1] |

TABLE 1-continued
| Cmpd No. | Structure |
|---|---|
| 339 | 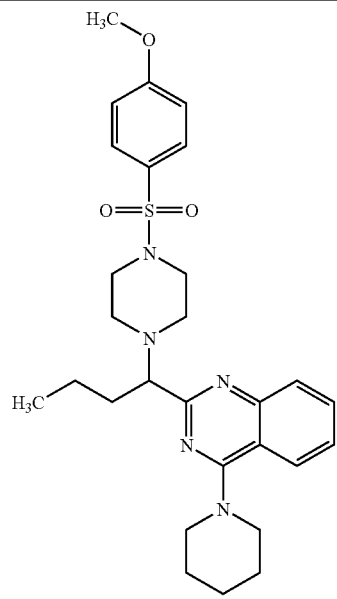 |
| 340 | 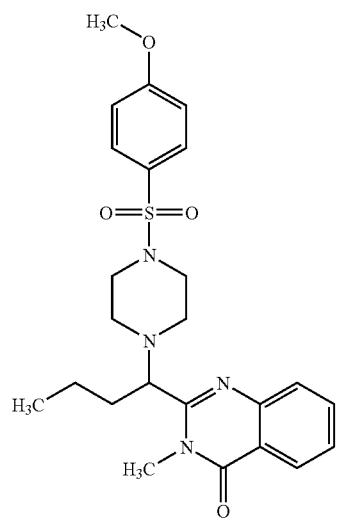 [SMILES: CCCC(c1nc2ccccc2c(=O)n1C)N1CCN(S(=O)(=O)c2ccc(OC)cc2)CC1] |
| 341 | 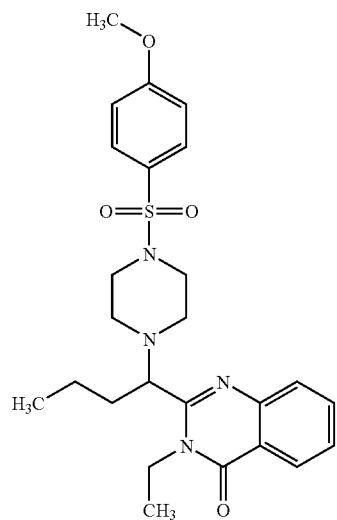 [SMILES: CCCC(c1nc2ccccc2c(=O)n1CC)N1CCN(S(=O)(=O)c2ccc(OC)cc2)CC1] |

TABLE 1-continued
| Cmpd No. | Structure |
|---|---|
| 342 | 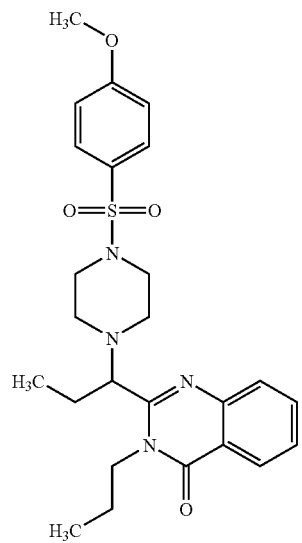 [SMILES: CCCn1c(C(CC)N2CCN(S(=O)(=O)c3ccc(OC)cc3)CC2)nc2ccccc2c1=O] |
| 343 | 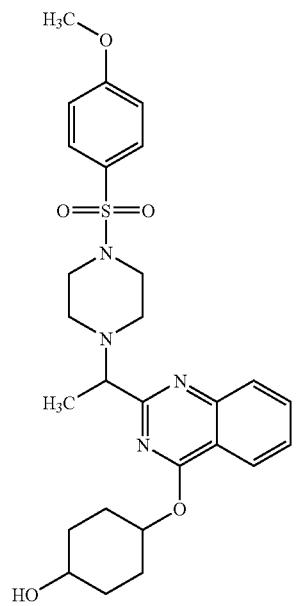 [SMILES: COc1ccc(S(=O)(=O)N2CCN(C(C)c3nc(OC4CCC(O)CC4)c4ccccc4n3)CC2)cc1] |

TABLE 1-continued
| Cmpd No. | Structure |
|---|---|
| 344 | 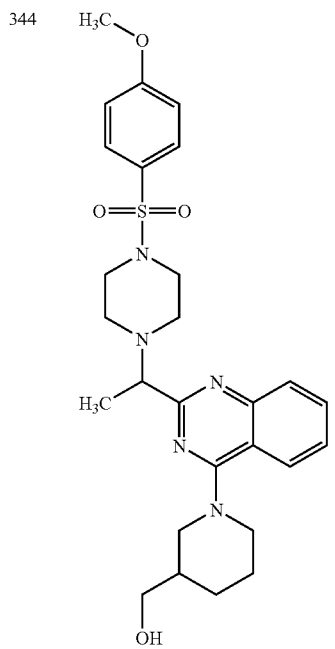 |
| 345 | 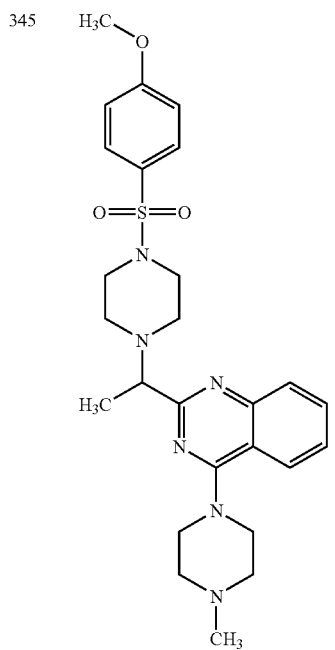 |

TABLE 1-continued
| Cmpd No. | Structure |
|---|---|
| 346 | 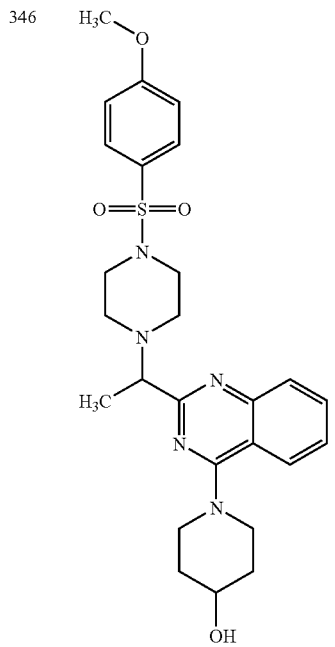 |
| 347 | 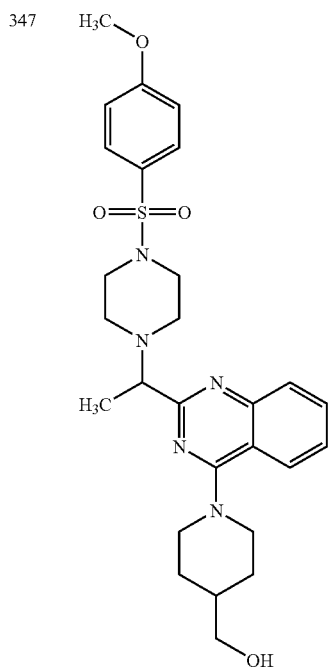 |

TABLE 1-continued
| Cmpd No. | Structure |
|---|---|
| 348 | 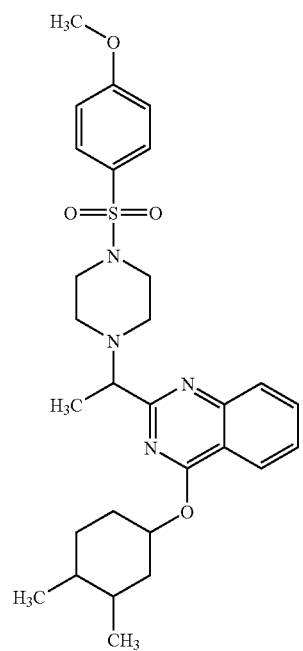 [SMILES: COc1ccc(S(=O)(=O)N2CCN(C(C)c3nc(OC4CCC(C)C(C)C4)c4ccccc4n3)CC2)cc1] |
| 349 | 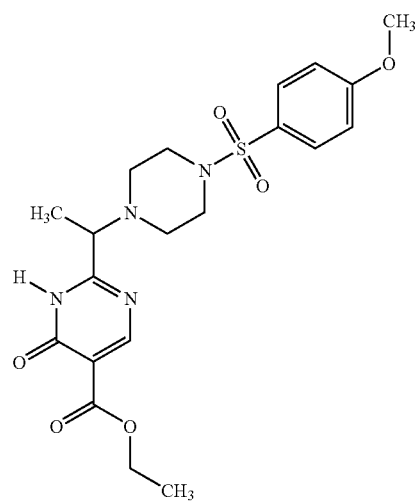 [SMILES: CCOC(=O)c1cnc(C(C)N2CCN(S(=O)(=O)c3ccc(OC)cc3)CC2)[nH]c1=O] |

TABLE 1-continued
| Cmpd No. | Structure |
|---|---|
| 350 | 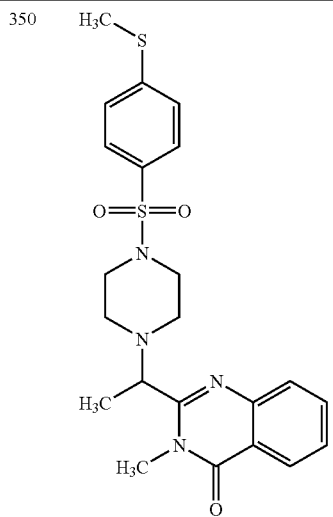 |
| 351 | 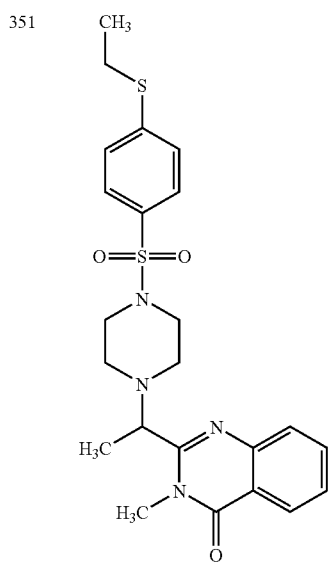 |
| 352 | 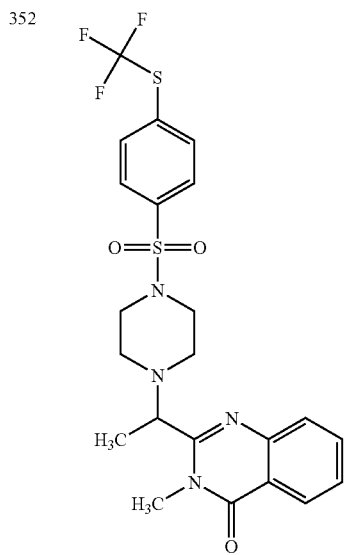 |

TABLE 1-continued
| Cmpd No. | Structure |
|---|---|
| 353 | 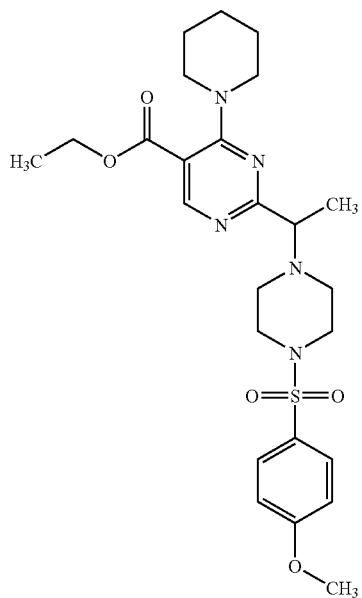 [SMILES: CCOC(=O)c1cnc(C(C)N2CCN(S(=O)(=O)c3ccc(OC)cc3)CC2)nc1N1CCCCC1] |
| 354 | 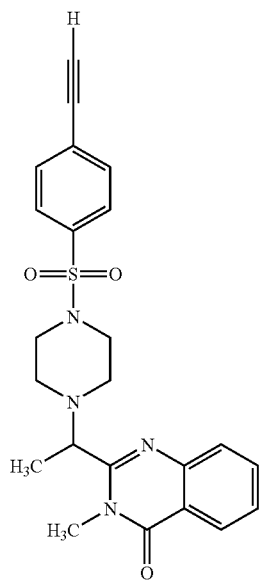 [SMILES: C#Cc1ccc(S(=O)(=O)N2CCN(C(C)c3nc4ccccc4c(=O)n3C)CC2)cc1] |

TABLE 1-continued
| Cmpd No. | Structure |
|---|---|
| 355 | 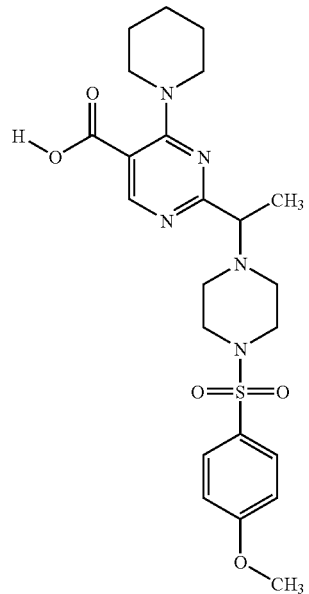 [SMILES: COc1ccc(S(=O)(=O)N2CCN(C(C)c3ncc(C(=O)O)c(N4CCCCC4)n3)CC2)cc1] |
| 356 | 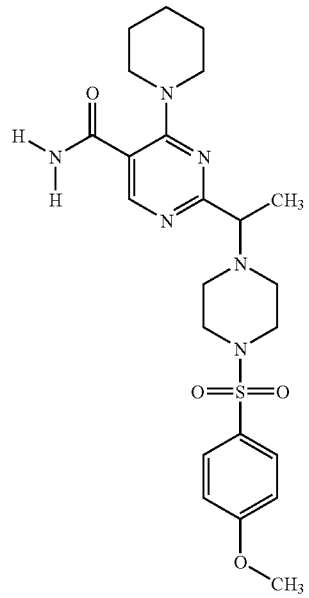 [SMILES: COc1ccc(S(=O)(=O)N2CCN(C(C)c3ncc(C(N)=O)c(N4CCCCC4)n3)CC2)cc1] |

TABLE 1-continued
| Cmpd No. | Structure |
|---|---|
| 357 | 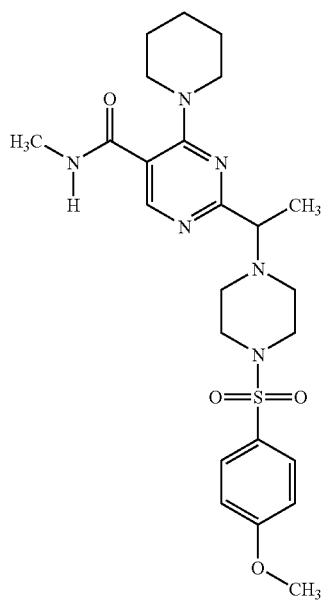 [SMILES: CNC(=O)c1cnc(C(C)N2CCN(S(=O)(=O)c3ccc(OC)cc3)CC2)nc1N1CCCCC1] |
| 358 | 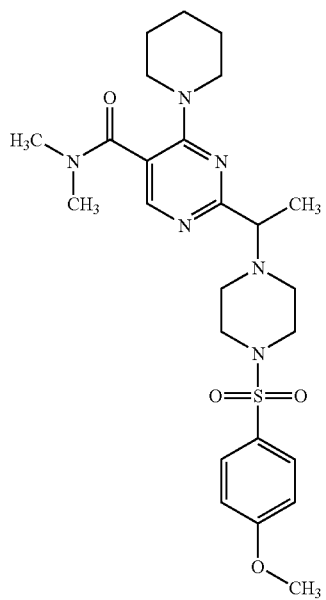 [SMILES: COc1ccc(S(=O)(=O)N2CCN(C(C)c3ncc(C(=O)N(C)C)c(N4CCCCC4)n3)CC2)cc1] |
| 359 | 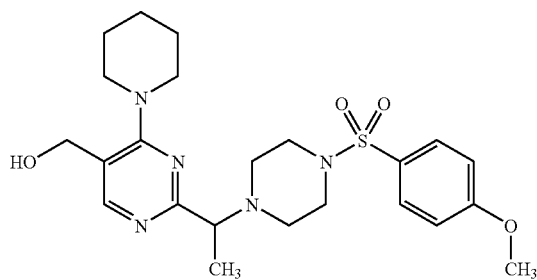 [SMILES: COc1ccc(S(=O)(=O)N2CCN(C(C)c3ncc(CO)c(N4CCCCC4)n3)CC2)cc1] |

TABLE 1-continued
| Cmpd No. | Structure |
|---|---|
| 360 | 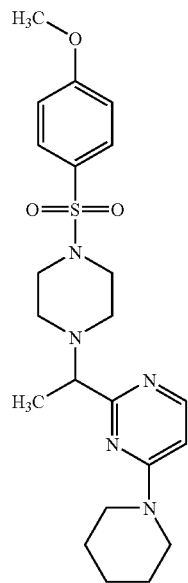 [SMILES: COc1ccc(S(=O)(=O)N2CCN(C(C)c3nccc(N4CCCCC4)n3)CC2)cc1] |
| 361 | 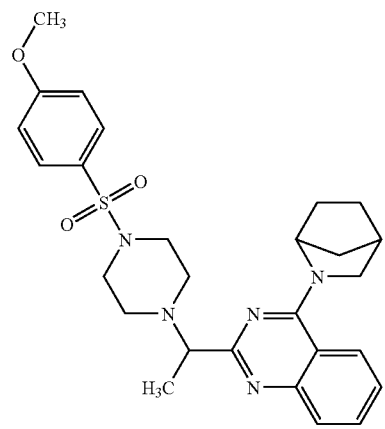 [SMILES: COc1ccc(S(=O)(=O)N2CCN(C(C)c3nc(N4CC5CCC4C5)c4ccccc4n3)CC2)cc1] |
| 362 | 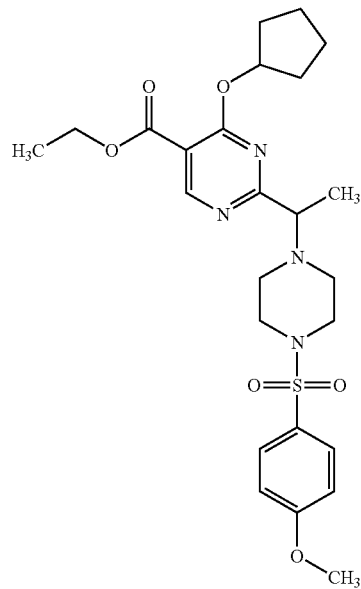 [SMILES: CCOC(=O)c1cnc(C(C)N2CCN(S(=O)(=O)c3ccc(OC)cc3)CC2)nc1OC1CCCC1] |

TABLE 1-continued
| Cmpd No. | Structure |
| --- | --- |
| 363 | 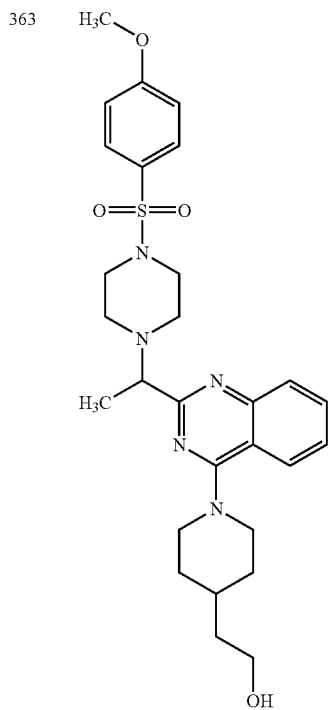 |
| 364 | 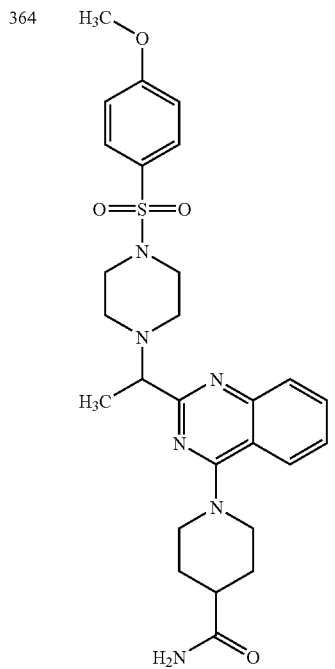 |

TABLE 1-continued
| Cmpd No. | Structure |
|---|---|
| 365 | 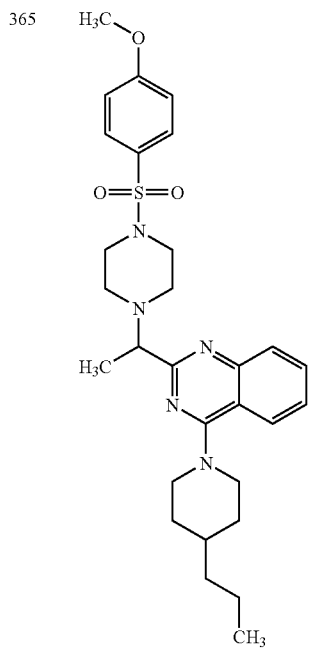 |
| 366 | 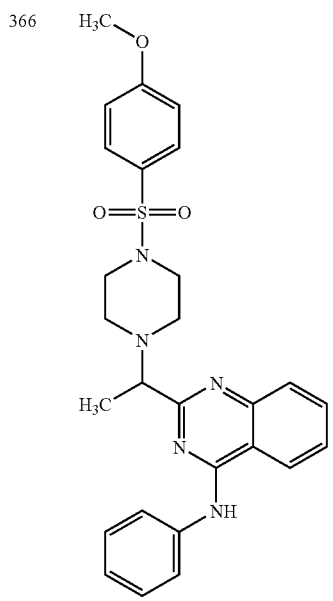 |

TABLE 1-continued
| Cmpd No. | Structure |
|---|---|
| 367 | 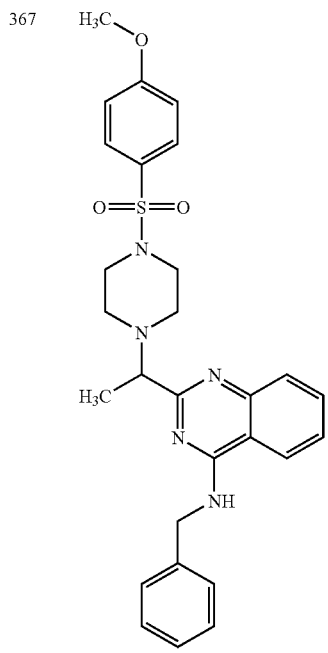 |
| 368 | 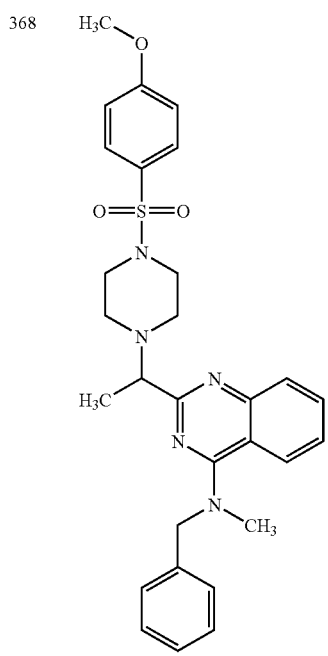 |

TABLE 1-continued
| Cmpd No. | Structure |
|---|---|
| 369 | 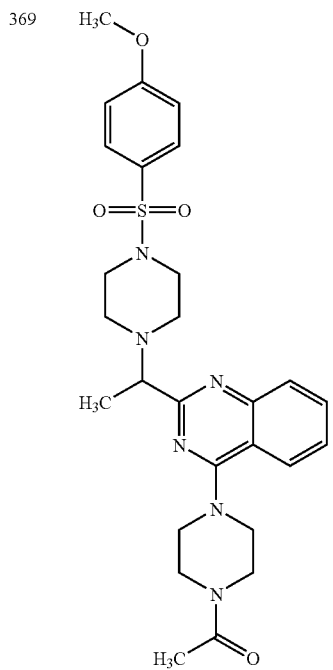 |
| 370 | 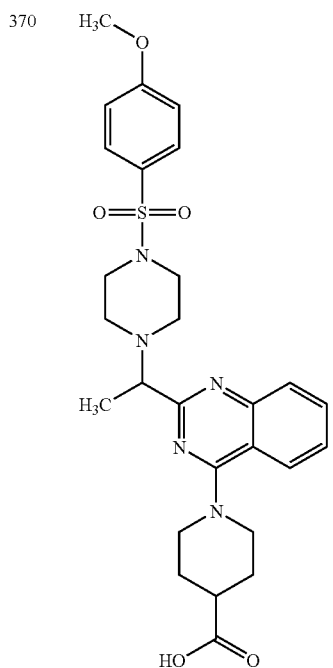 |

TABLE 1-continued
| Cmpd No. | Structure |
|---|---|
| 371 | 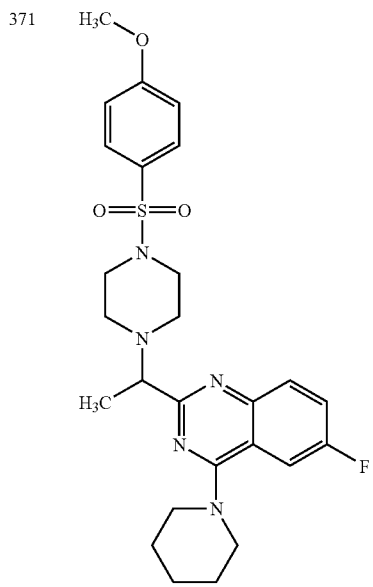 |
| 372 | 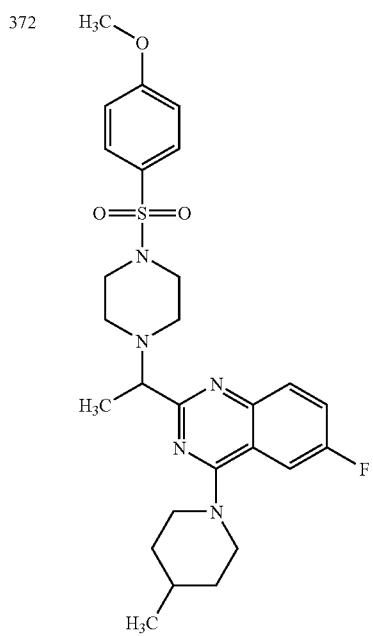 |

TABLE 1-continued
| Cmpd No. | Structure |
|---|---|
| 373 | 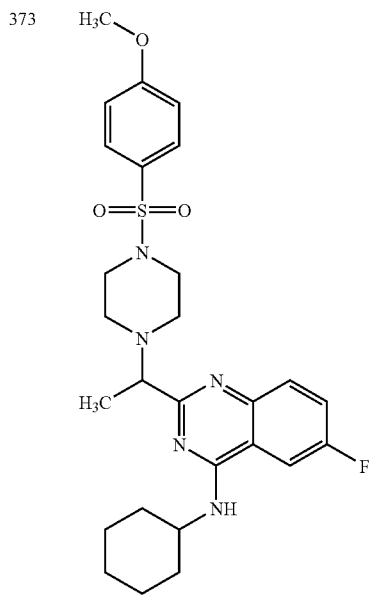 |
| 374 | 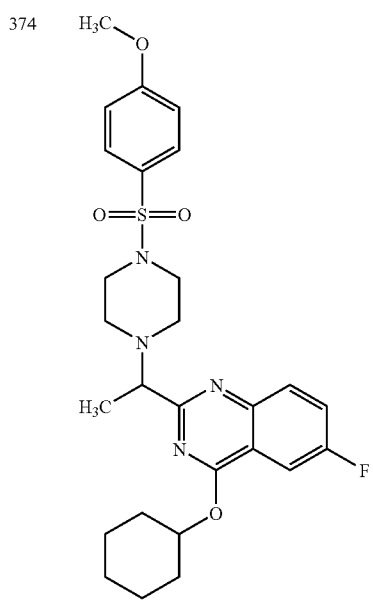 |

TABLE 1-continued
| Cmpd No. | Structure |
|---|---|
| 375 | 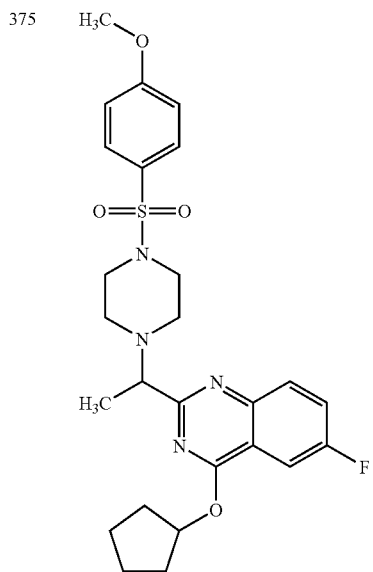 |
| 376 | 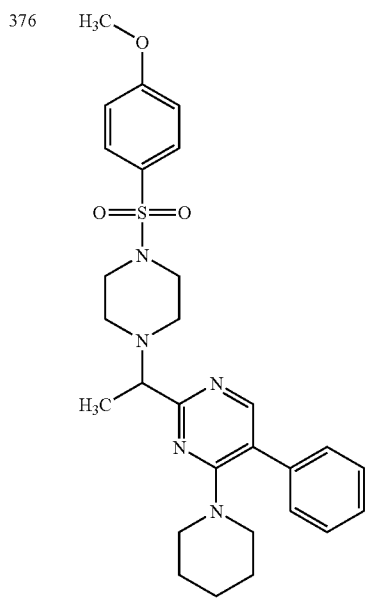 |

TABLE 1-continued
| Cmpd No. | Structure |
|---|---|
| 377 | 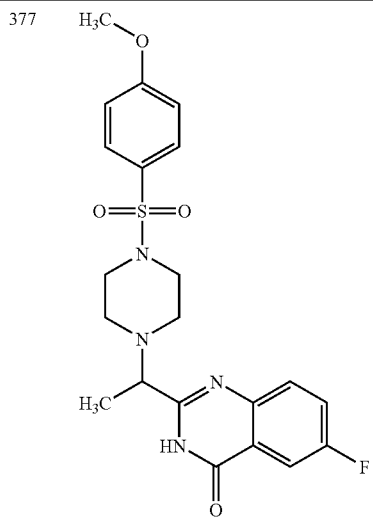 |
| 378 | 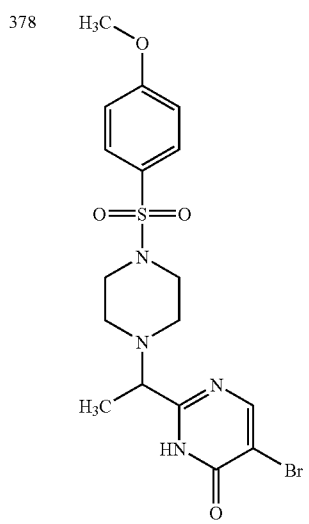 |
| 379 | 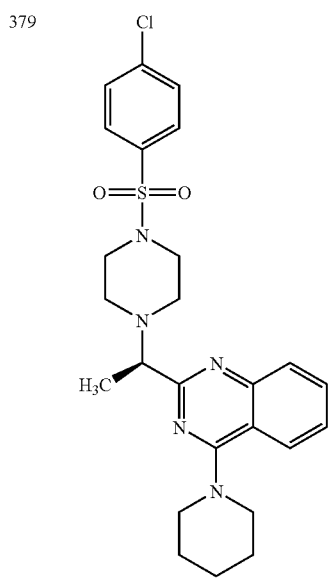 |

TABLE 1-continued
| Cmpd No. | Structure |
|---|---|
| 380 | 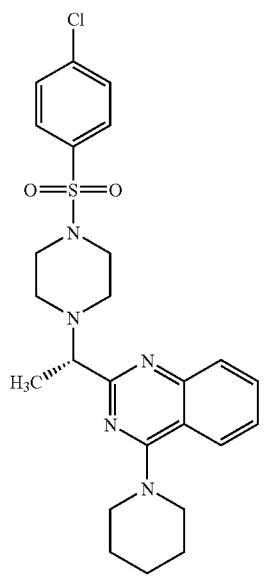 |
| 381 | 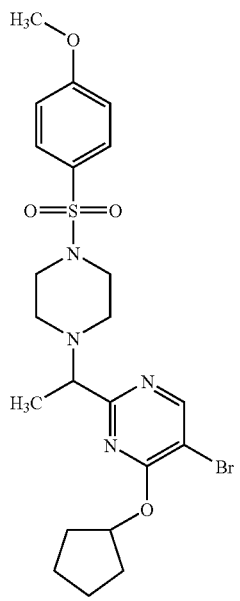 [SMILES: COc1ccc(S(=O)(=O)N2CCN(C(C)c3ncc(Br)c(OC4CCCC4)n3)CC2)cc1] |

TABLE 1-continued
| Cmpd No. | Structure |
|---|---|
| 382 | 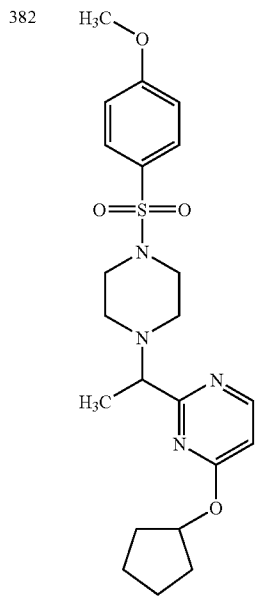 |
| 383 | 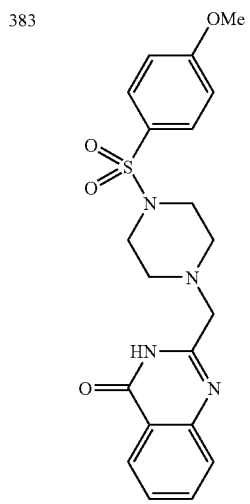 |

TABLE 1-continued
| Cmpd No. | Structure |
|---|---|
| 384 | 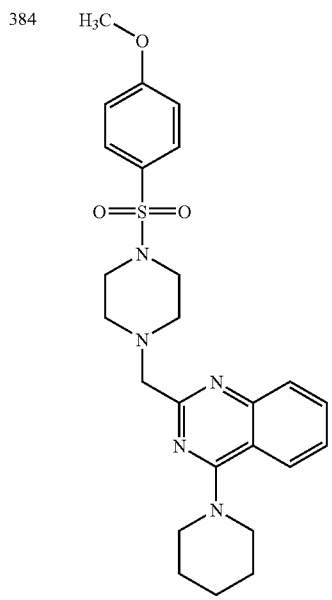 |
| 385 | 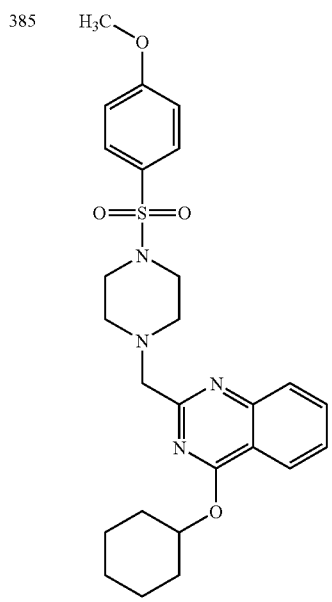 |

TABLE 1-continued
| Cmpd No. | Structure |
|---|---|
| 386 | 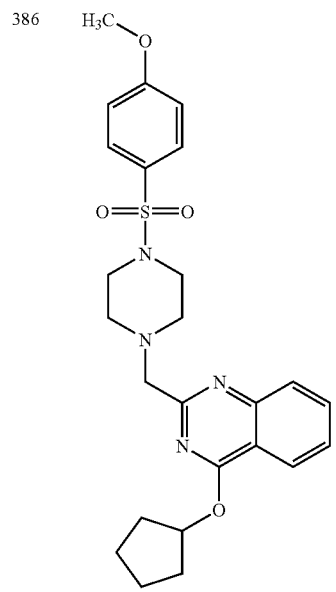 |
| 387 | 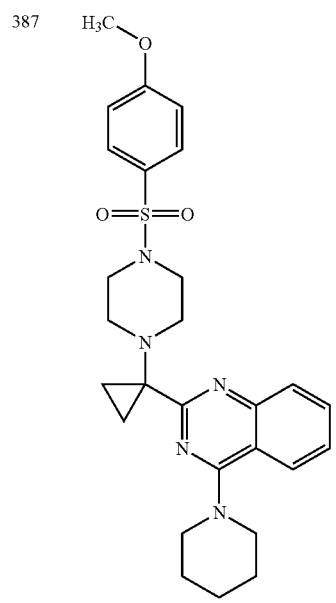 |

TABLE 1-continued
| Cmpd No. | Structure |
|---|---|
| 388 | 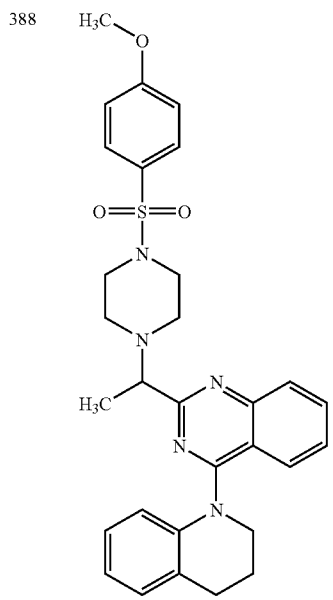 |
| 389 | 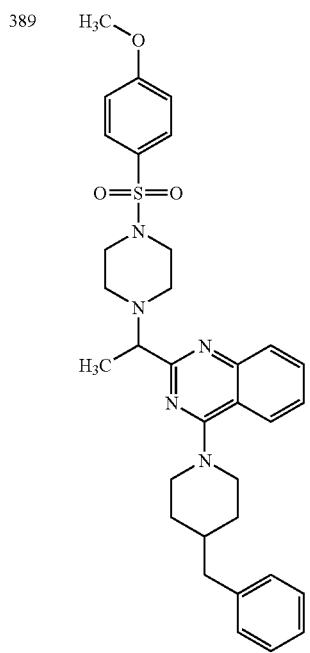 |

TABLE 1-continued
| Cmpd No. | Structure |
|---|---|
| 390 | 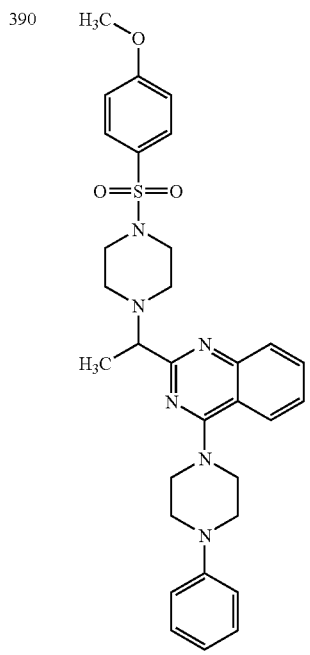 |
| 391 | 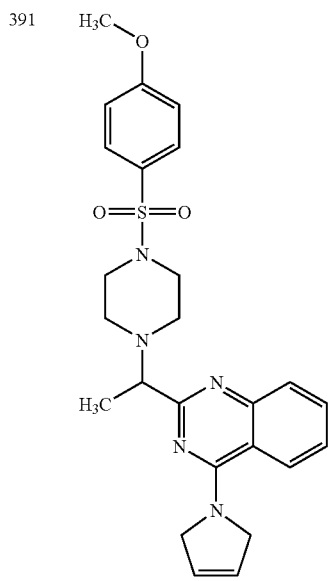 |

TABLE 1-continued
| Cmpd No. | Structure |
|---|---|
| 392 | 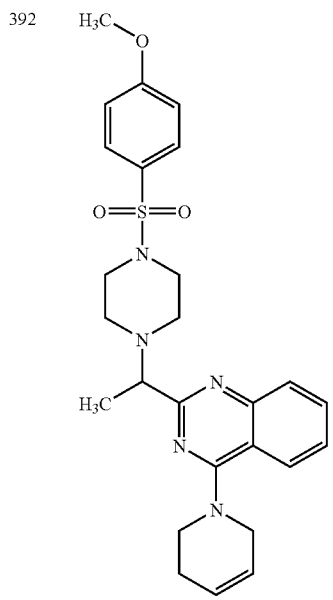 |
| 393 | 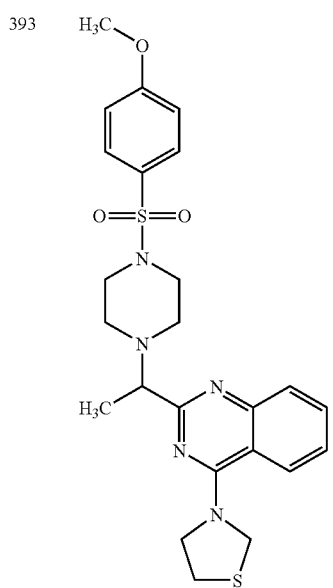 |

TABLE 1-continued
| Cmpd No. | Structure |
|---|---|
| 394 | 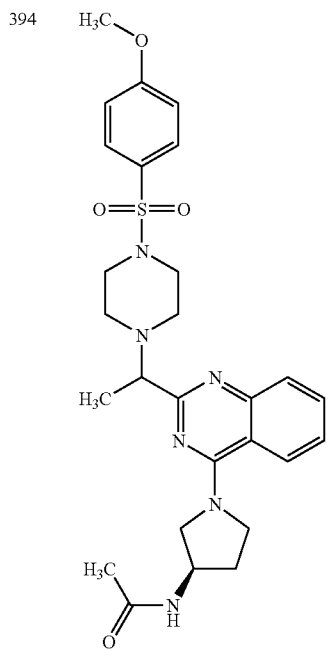 |
| 395 | 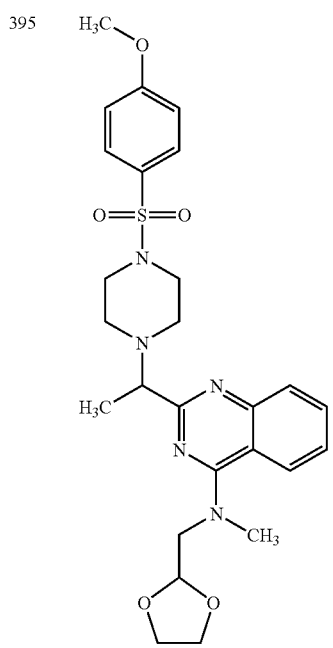 |

TABLE 1-continued
| Cmpd No. | Structure |
|---|---|
| 396 | 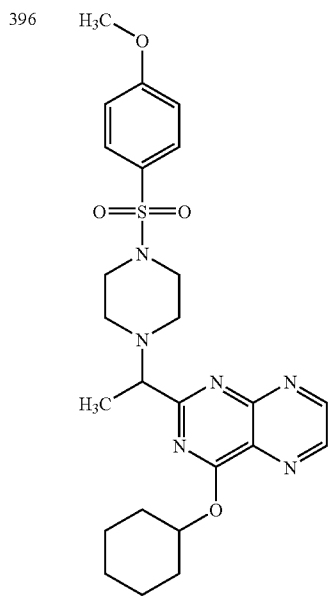 |
| 397 | 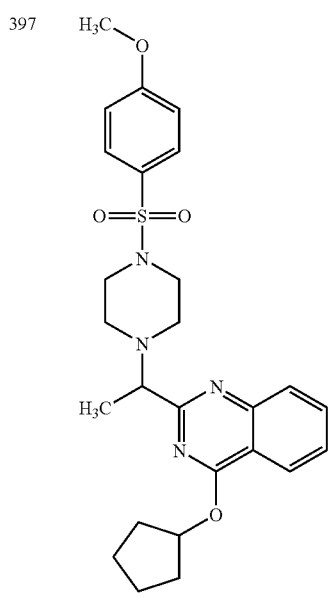 |

TABLE 1-continued
| Cmpd No. | Structure |
|---|---|
| 398 | 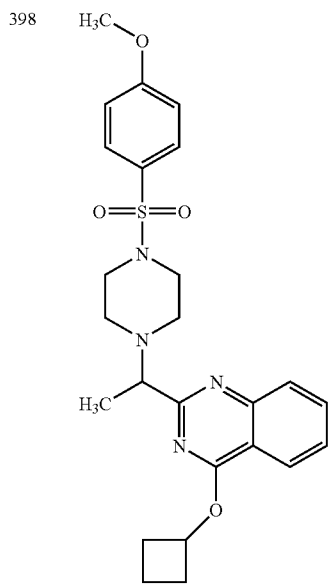 |
| 399 | 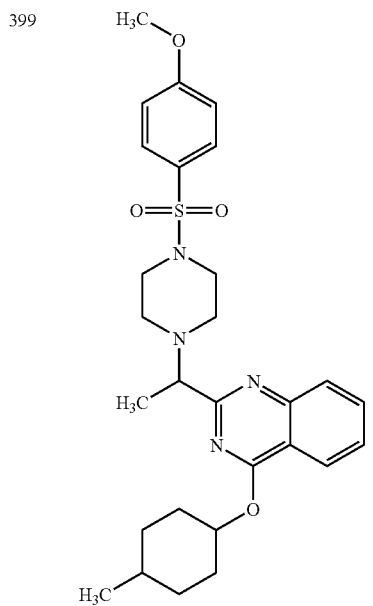 |

TABLE 1-continued
| Cmpd No. | Structure |
|---|---|
| 400 | 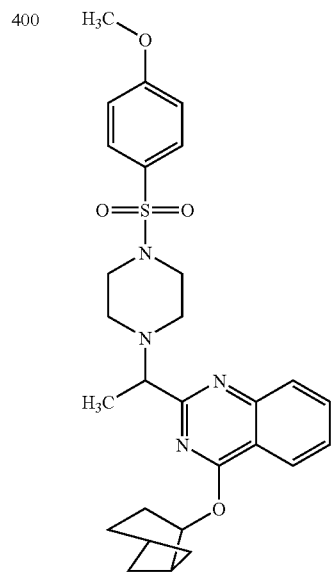 |
| 401 | 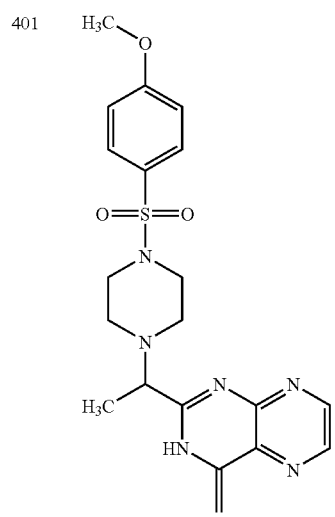 |
| 402 | 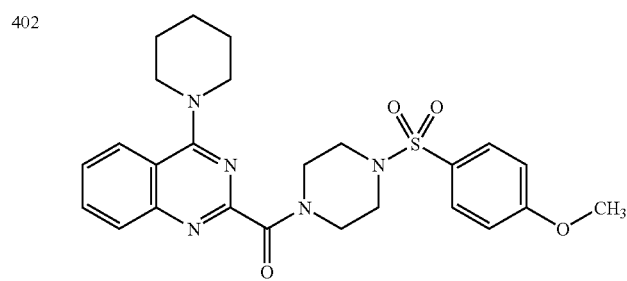 |

TABLE 1-continued

| Cmpd No. | Structure |
|---|---|
| 403 | 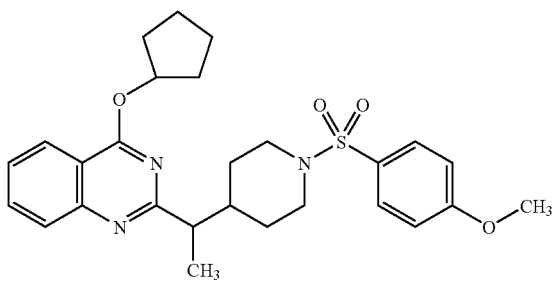 [SMILES: COc1ccc(S(=O)(=O)N2CCC(C(C)c3nc(OC4CCCC4)c4ccccc4n3)CC2)cc1] |
| 404 | 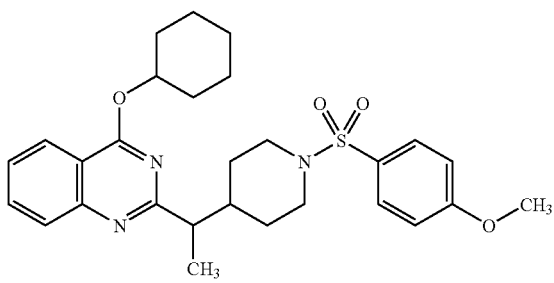 [SMILES: COc1ccc(S(=O)(=O)N2CCC(C(C)c3nc(OC4CCCCC4)c4ccccc4n3)CC2)cc1] |
| 405 | 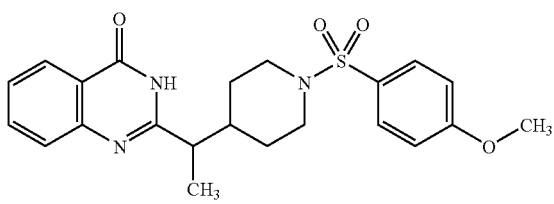 [SMILES: COc1ccc(S(=O)(=O)N2CCC(C(C)c3nc4ccccc4c(=O)[nH]3)CC2)cc1] |

4. General Synthetic Methodology:

The compounds of this invention may be prepared in general by methods known to those skilled in the art for analogous compounds, as illustrated by the general scheme below, and the preparative examples that follow.

Scheme IA, Scheme IB, and Scheme IC below depict general conditions for the synthesis of compounds of formula I where $G^2$ is —CH(CH$_3$)—, and B is piperizinyl.

Scheme IA:

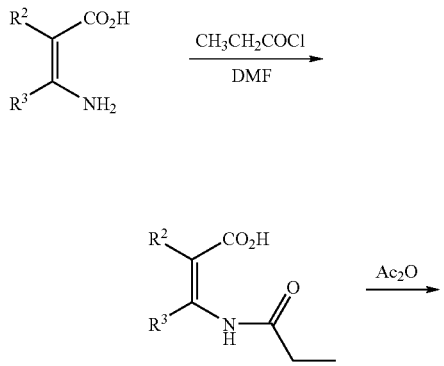

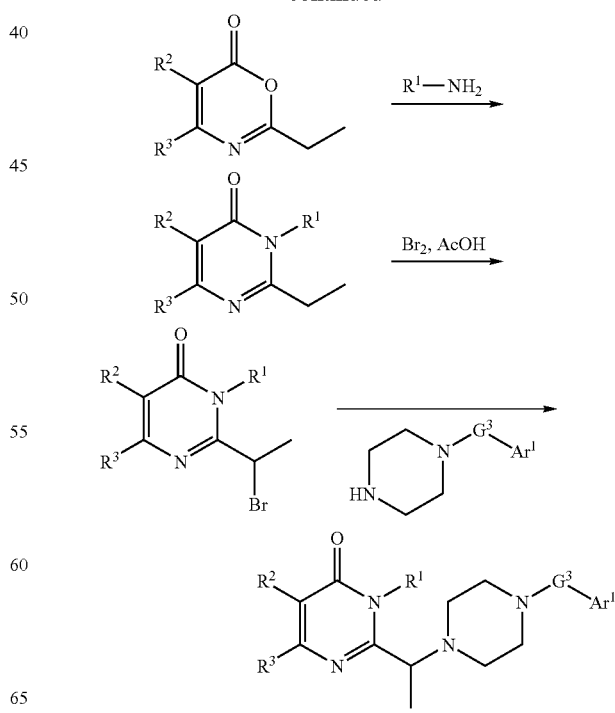

Scheme IB:

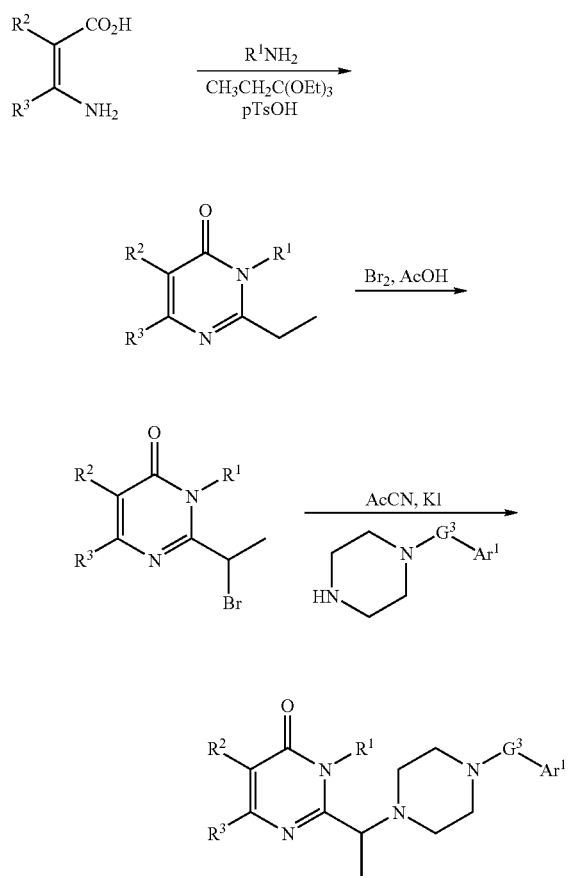

Scheme IC:

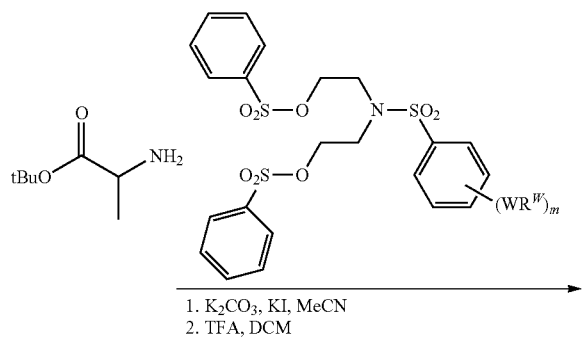

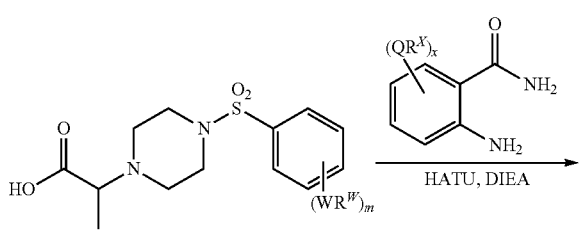

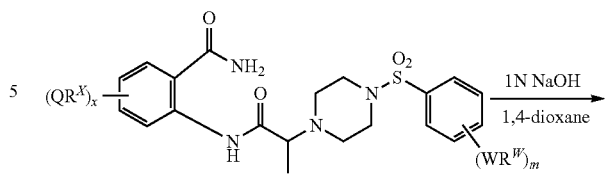

Scheme IIA below depicts conditions for the synthesis of one exemplary embodiment for compounds of formula I where $G^2$ is —CH(CH$_3$)—, $R^1$ is n-propyl, B is piperizinyl, $G^3$ is SO$_2$, and $Ar^1$ is optionally substituted phenyl.

Scheme IIA:

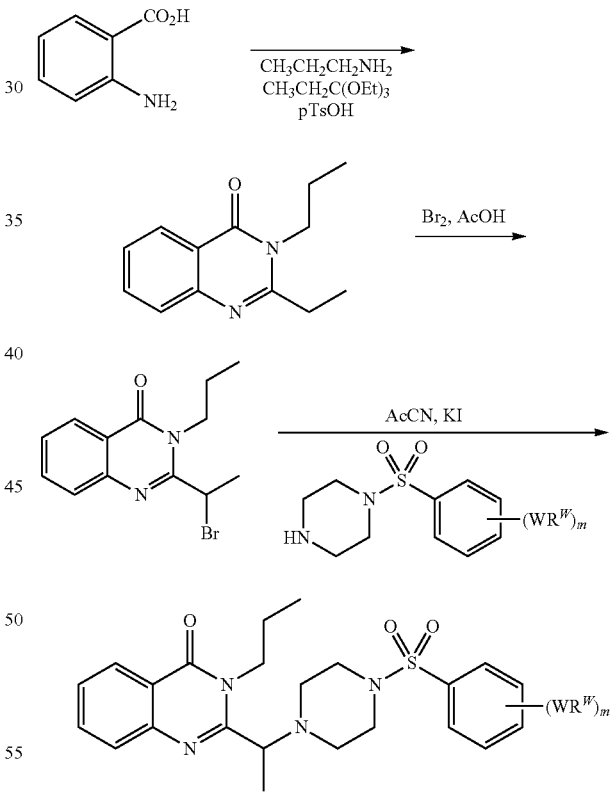

Scheme IIB below depicts conditions for the synthesis of one exemplary embodiment for compounds of formula I wherein (a) $G^1$ is =O, $G^2$ is —CH(CH$_3$)—, $R^1$ is H, B is piperizinyl, $G^3$ is SO$_2$, and $Ar^1$ is 4-methoxyphenyl; (b) $G^1$ is N-piperidinyl, $G^2$ is —CH(CH$_3$)—, B is piperizinyl, $G^3$ is SO$_2$, and $Ar^1$ is 4-methoxyphenyl; and (c) $G^1$ is cyclopentyloxy, $G^2$ is —CH(CH$_3$)—, B is piperizinyl, $G^3$ is SO$_2$, and $Ar^1$ is 4-methoxyphenyl.

Scheme IIB:
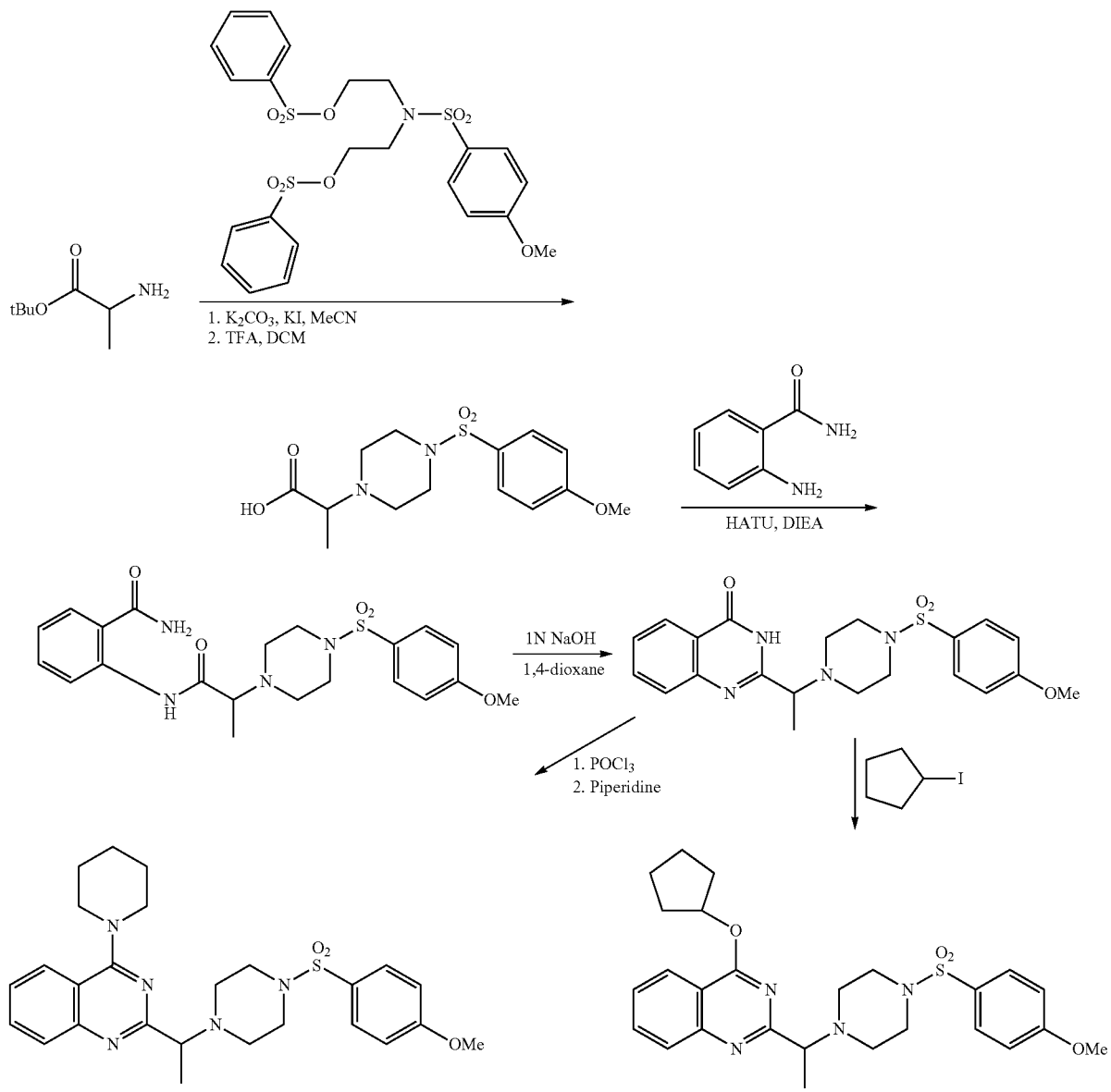
Scheme III below depicts conditions for the synthesis of one exemplary embodiment for compounds of formula I where $Q^2$ is —CH(CH$_3$)—, $R^1$ is methyl, B is a diamine linker (cyclic or linear and optionally substituted), and $Q^3$ is SO$_2$.
Scheme III:
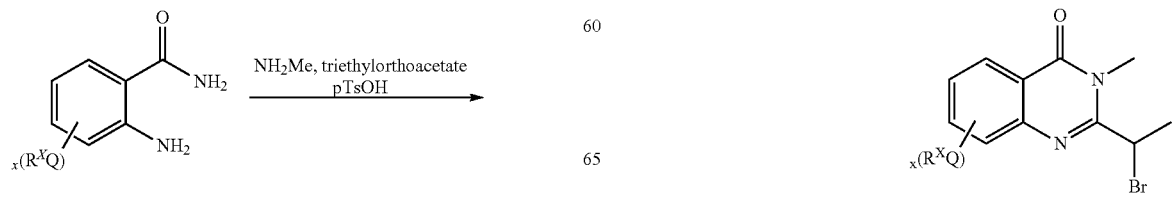
-continued
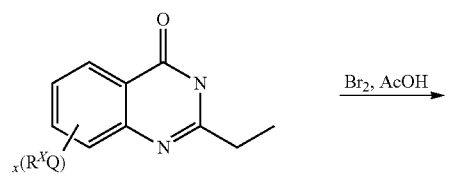

323
-continued
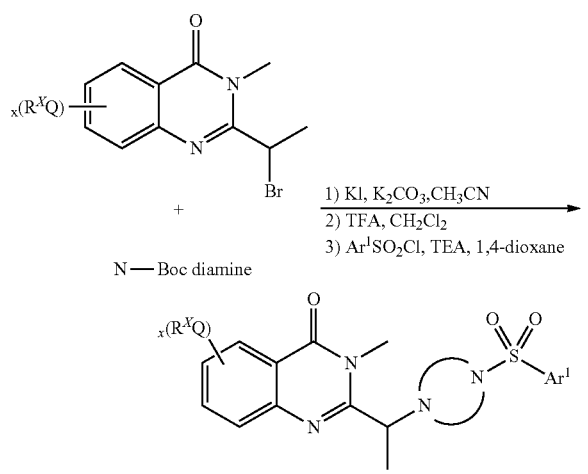
Schemes IV and V below depict conditions for the synthesis of one exemplary embodiment for compounds of formula I where $G^1$ is —$OR^A$, $SR^A$, or $NR^AR^B$ and is synthesized from compounds where $G^1$ is =O.
Scheme IV:
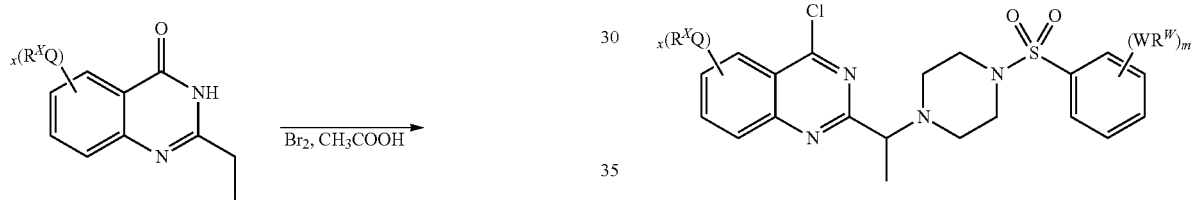
Scheme V:
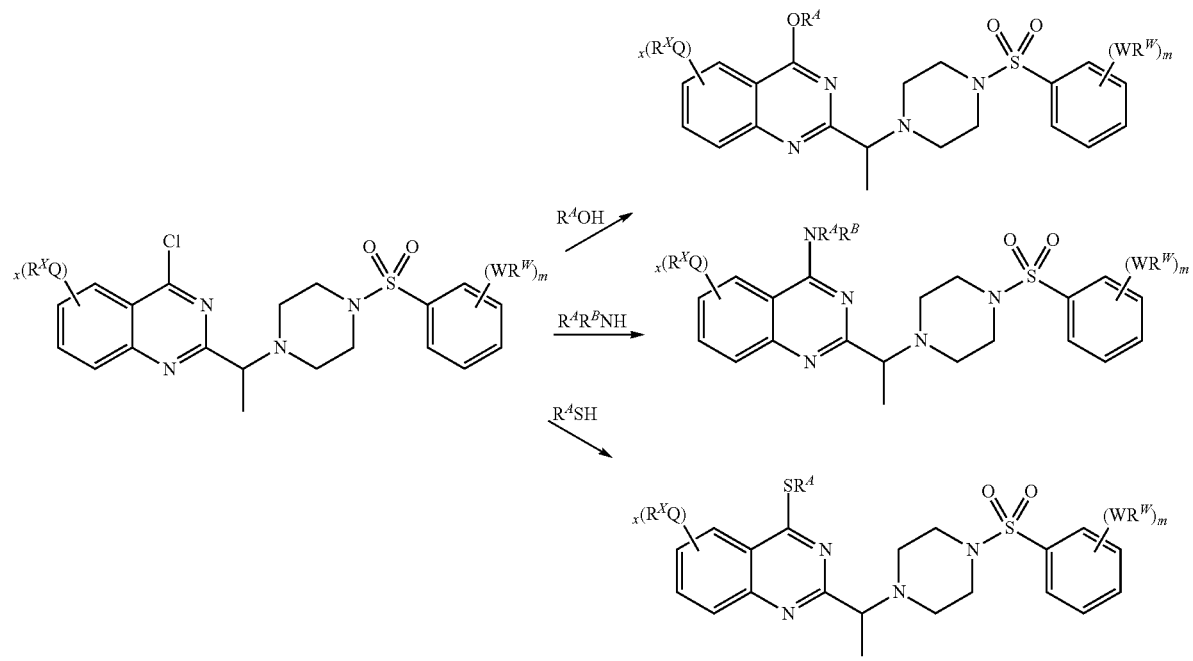
324
-continued
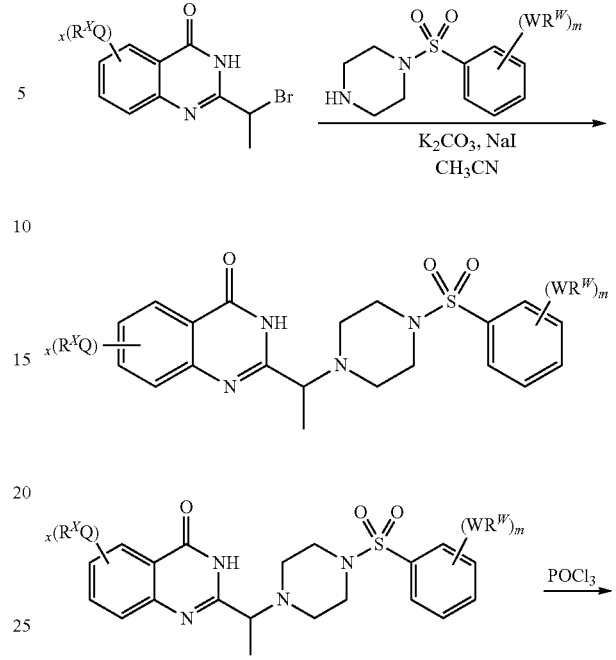

Scheme VI below depicts conditions for the preparation of quinazolinone analogs.
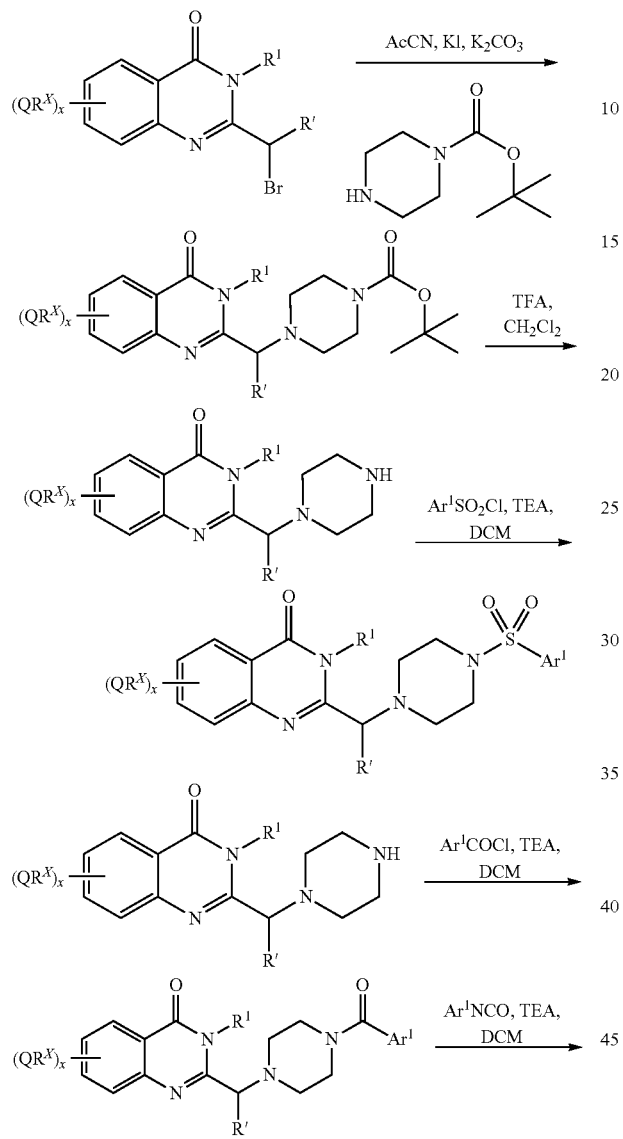
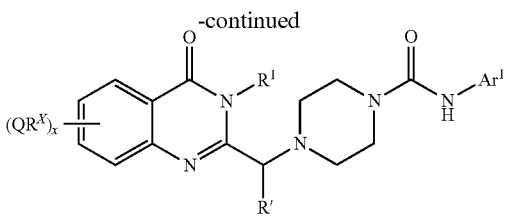
Scheme VII below depicts conditions for the conversion of bromine to cyano derivatives.
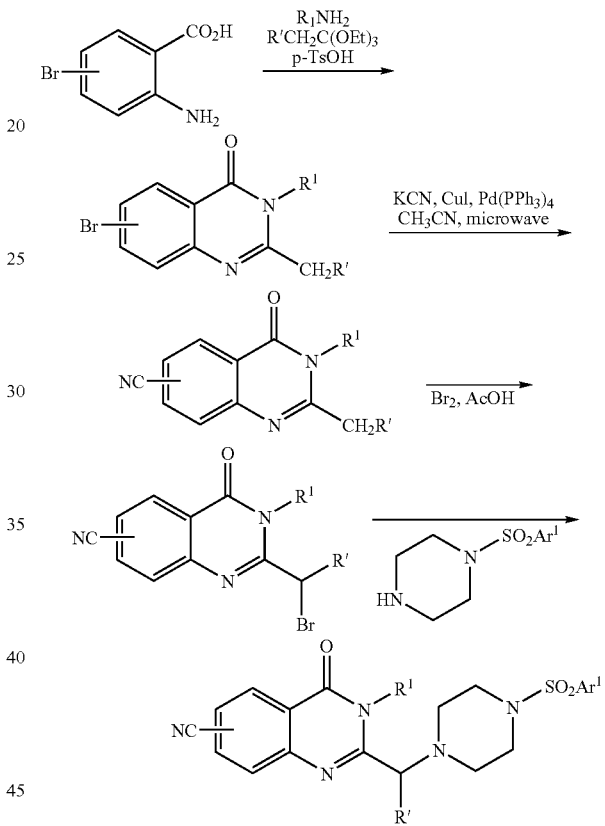
Scheme VIII below depicts conditions for the conversion of cyano to amide and tetrazole derivatives.
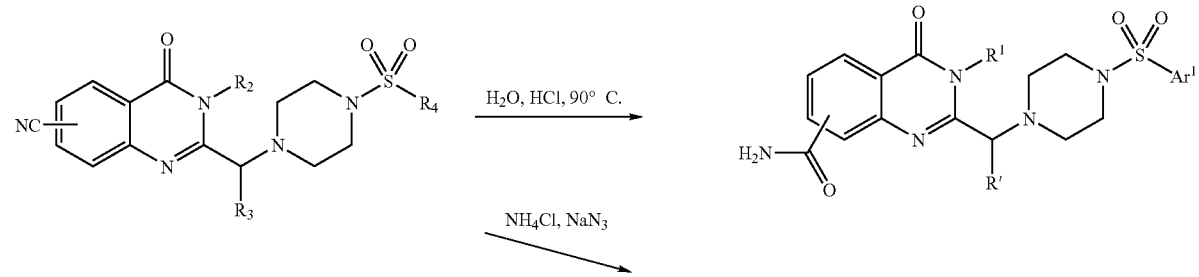

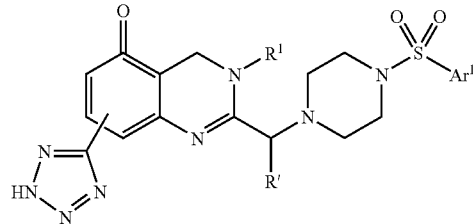

Scheme IX below depicts conditions for the conversion of bromo to methylsulfone derivatives.

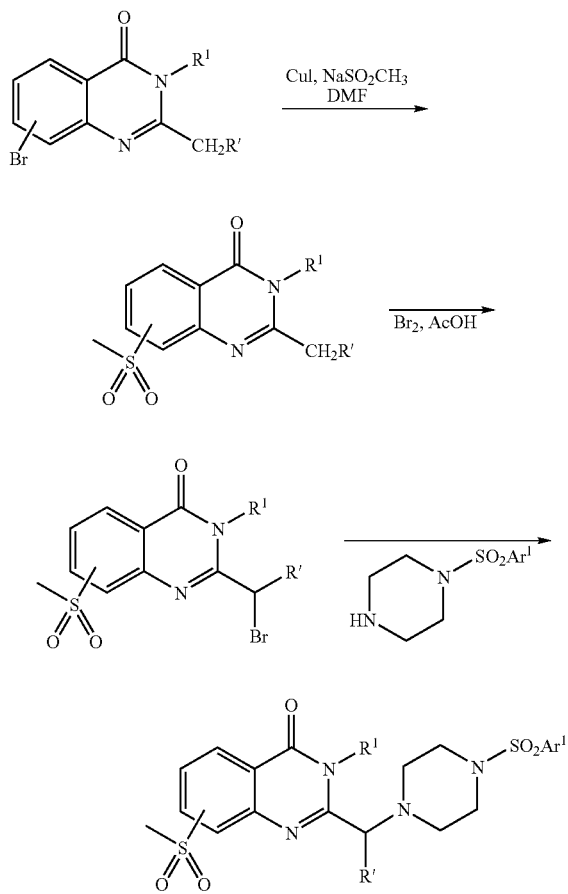

Scheme X below depicts conditions for converting a nitro derivative to the amino or NHC(O)CH$_3$ derivative.

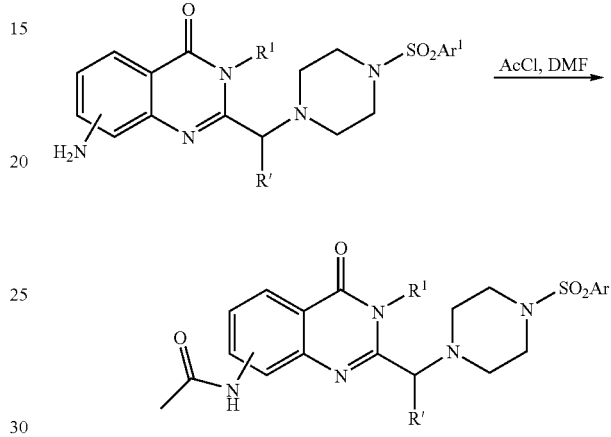

Scheme XI below depicts conditions for the synthesis of one exemplary embodiment of compounds of formula I, wherein G$^1$ is =O, R$^1$ is Me, G$^2$ is isopropyl, B is piperazinyl, G$^3$ is SO$_2$, and Ar$^1$ is 4-methoxyphenyl.

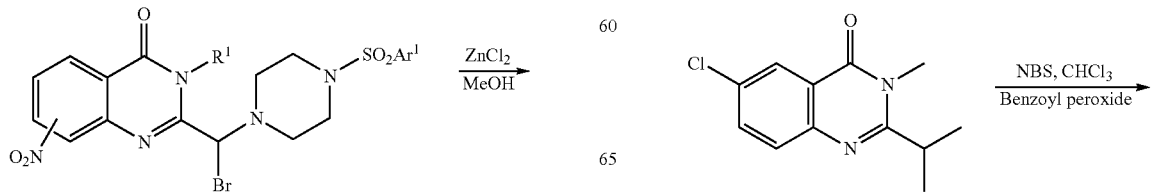

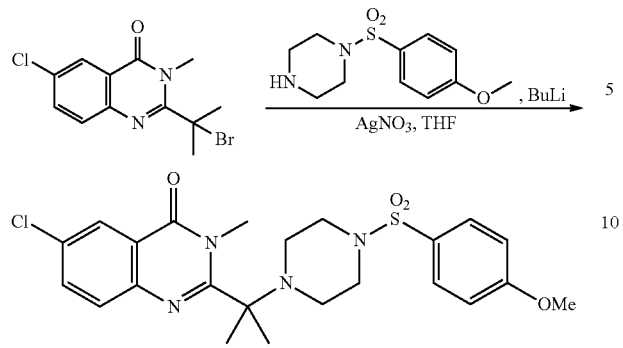

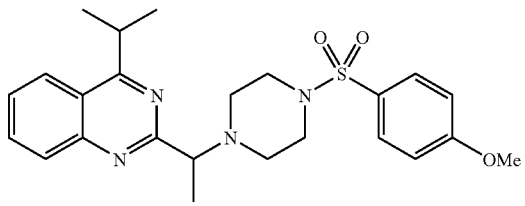

Scheme XIV below depicts the conditions for the synthesis of an exemplary embodiment of formula I, wherein $R^2$ and $R^3$ together form a pyrazine ring, $G^1$ is $OR^A$, B is a piperazine ring, $G^3$ is $SO_2$.

Scheme XII below depicts the conditions for synthesis of compounds of formula I, wherein $G^1$ is $R^A$.

Scheme XII:

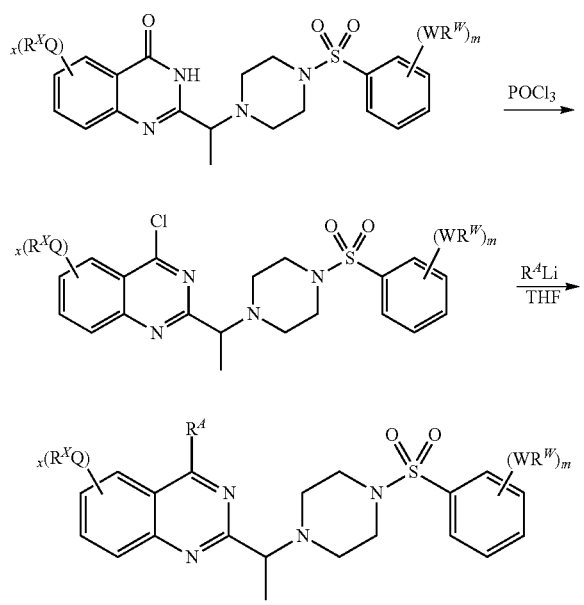

Scheme XIII below depicts an exemplary synthesis based on Scheme XII.

Scheme XIII:

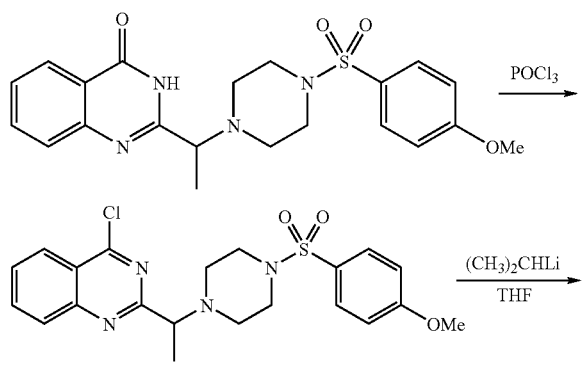

Scheme XIV:

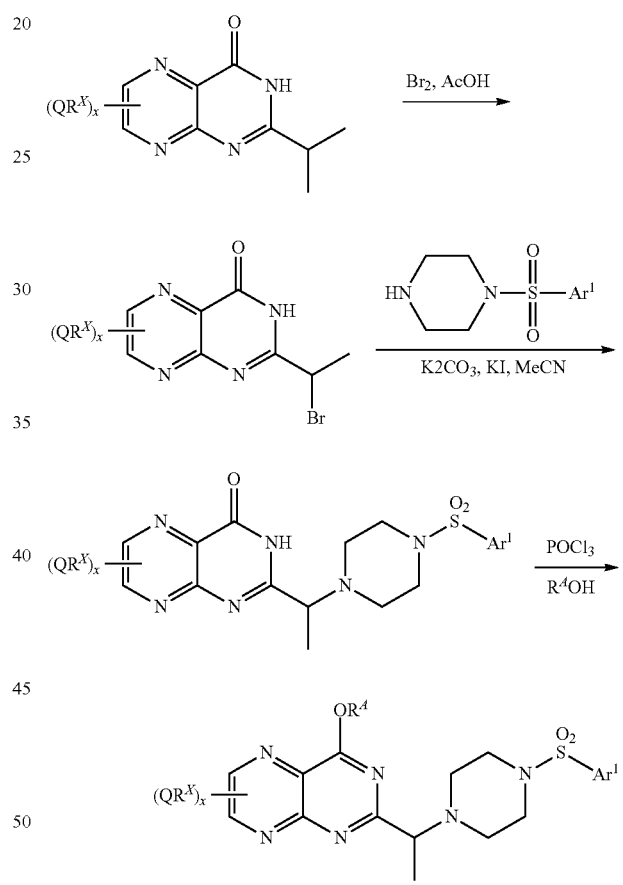

Scheme XV below depicts the conditions for the synthesis of compounds of formula I, wherein $G^1$ is hydrogen, $G^2$ is $CH(CH_3)$, B is piperazine, $G^2$ is $SO_2$.

Scheme XV:

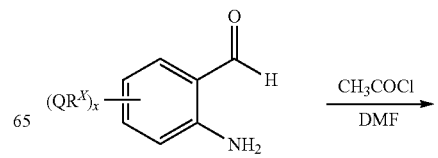

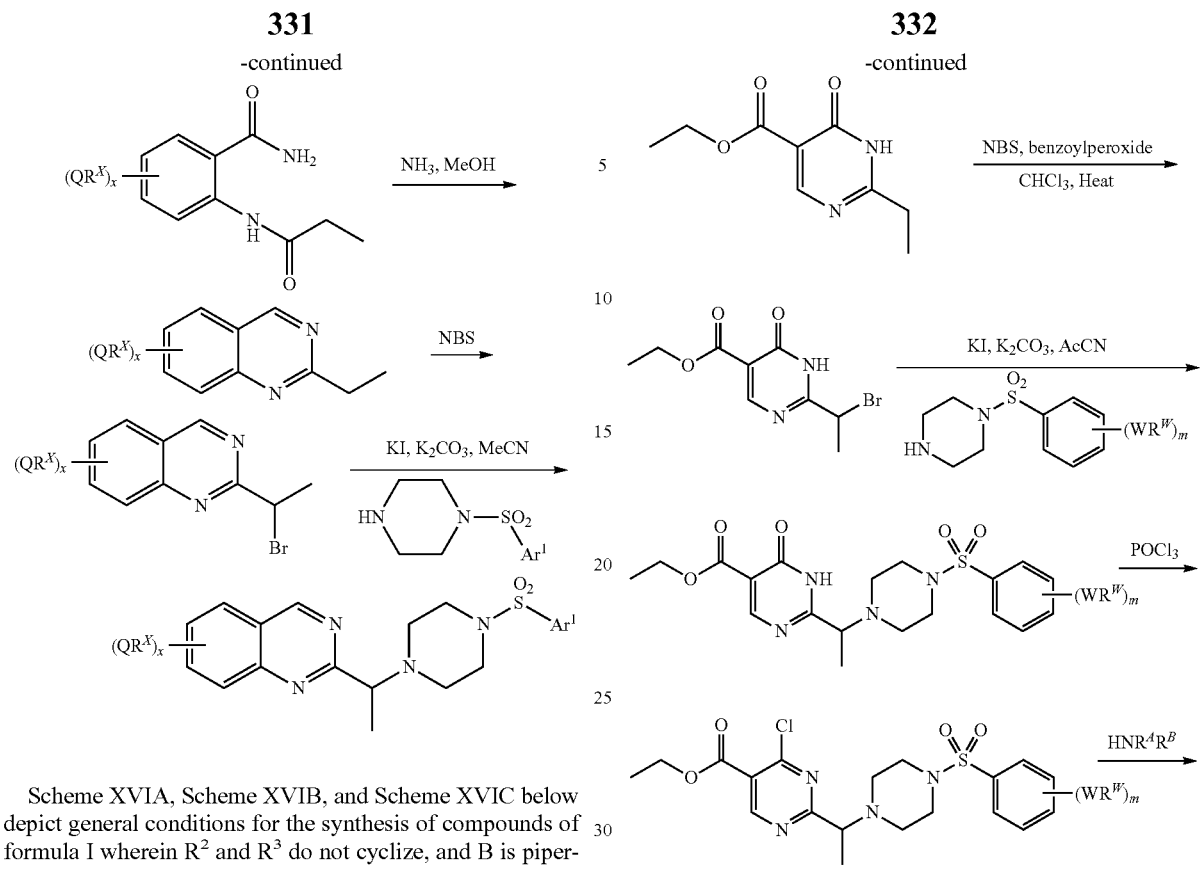
Scheme XVIA, Scheme XVIB, and Scheme XVIC below depict general conditions for the synthesis of compounds of formula I wherein $R^2$ and $R^3$ do not cyclize, and B is piperazinyl.
Scheme XVIA:
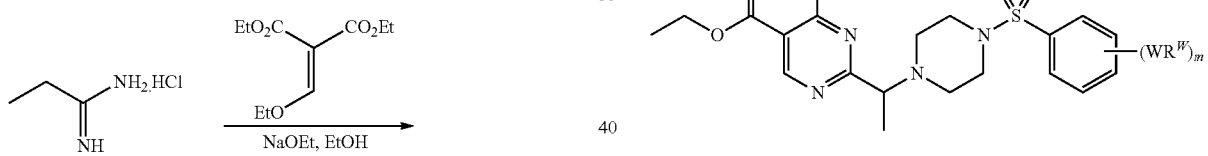
Scheme XVIB:
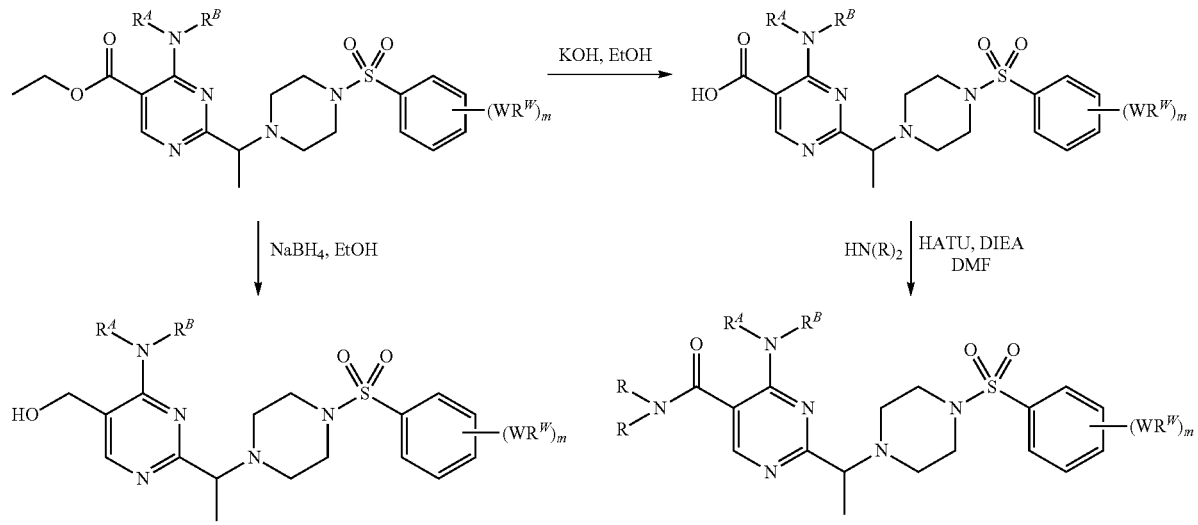

Scheme XVIC:

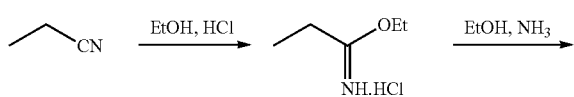

Scheme XVII below depicts the conditions for the synthesis of one exemplary embodiment of formula I, wherein $R^A$ and $R^B$ together form piperidyl, $G^2$ is —CH(CH$_3$)—, $G^3$ is SO$_2$, and Ar$^1$ is 4-methoxyphenyl.

Scheme XVII:

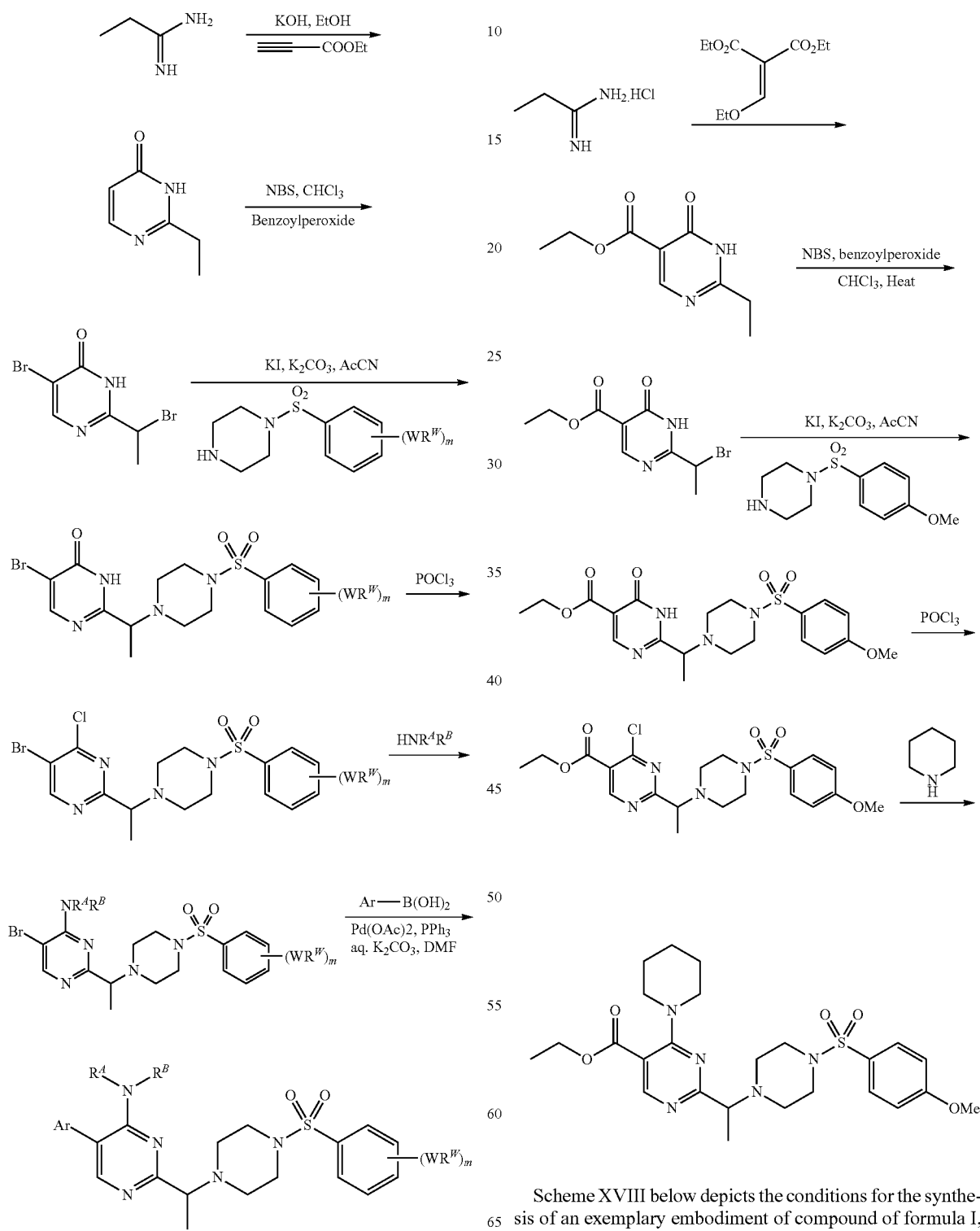

Scheme XVIII below depicts the conditions for the synthesis of an exemplary embodiment of compound of formula I, wherein $R^A$ and $R^B$ together form piperidyl, $G^2$ is —CH(CH$_3$)—, $G^3$ is SO$_2$, and Ar$^1$ is 4-methoxyphenyl.

Scheme XVIII

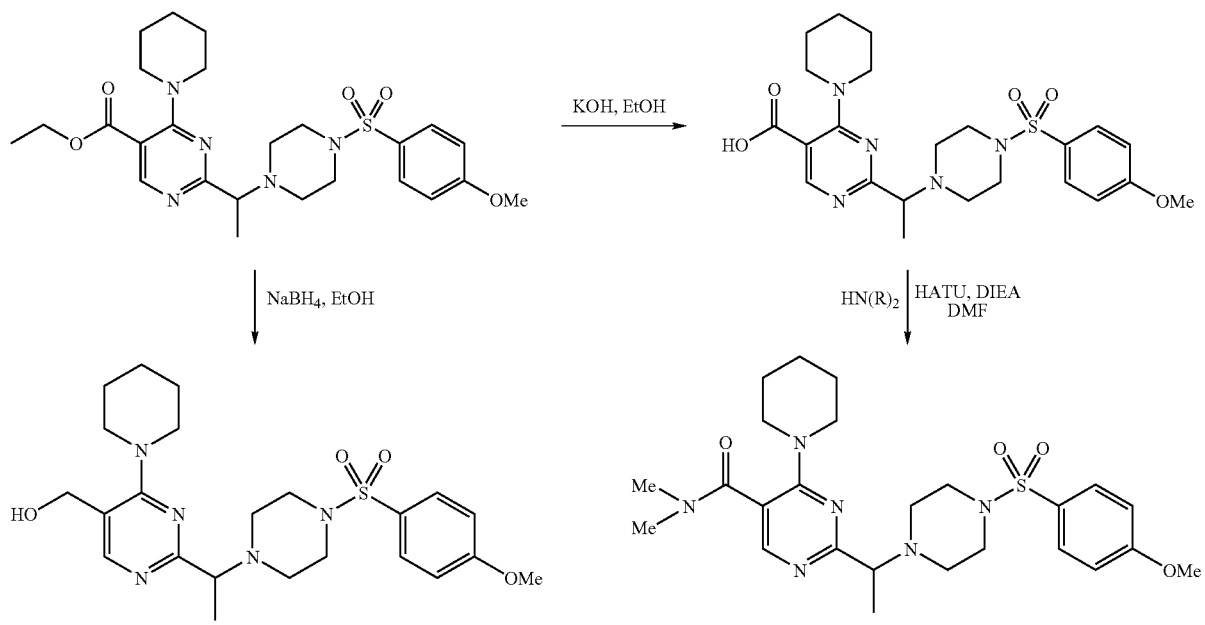

Scheme XIX below depicts the conditions for the synthesis of compounds of formula I, wherein $G^1$ is alkoxy, and $R^2$ and $R^3$ do not cyclize to form a ring.

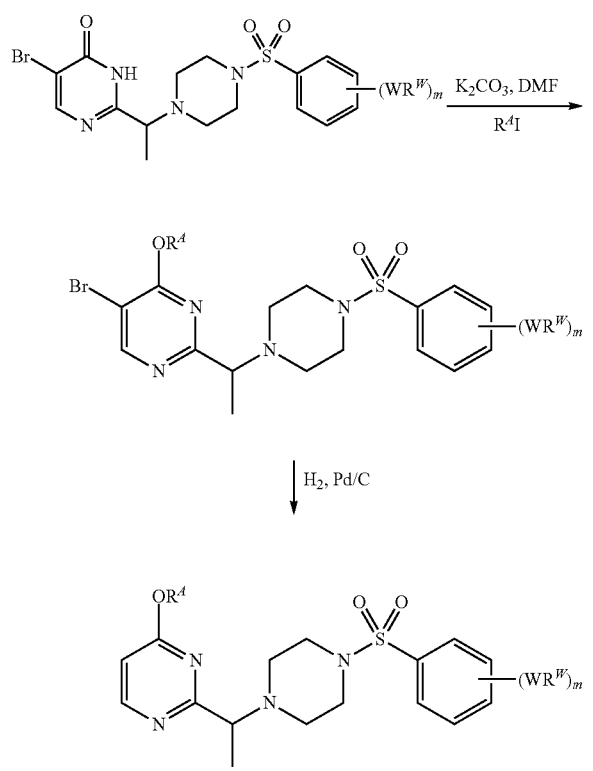

Scheme XX:

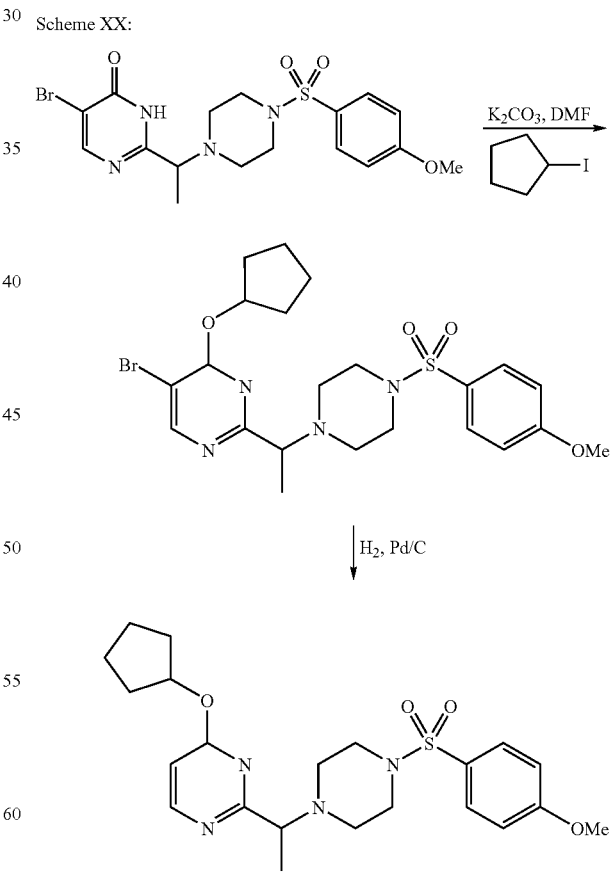

Scheme XX below depicts the conditions for the synthesis of an exemplary compound of formula I, wherein $G^1$ is cyclopentyloxy, and $R^2$ and $R^3$ both are hydrogen.

Scheme XXI below depicts the conditions for the general synthesis of compounds of formula I, wherein $R^2$ is carboethoxy, and $G^1$ is alkoxy.

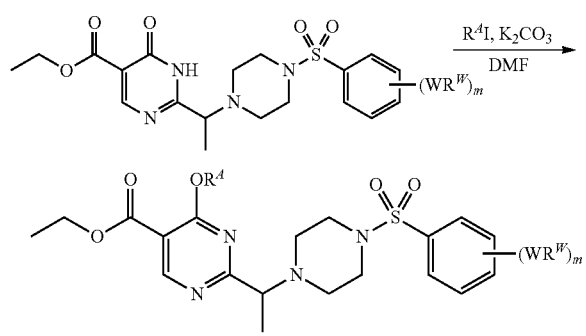

Scheme XXII below depicts the conditions for the synthesis of an exemplary embodiment of formula I, wherein $R^2$ is carboethoxy, $G^1$ is cyclopentyloxy, $G^2$ is —CH(CH$_3$)—, $G^3$ is SO$_2$, B is piperidyl, and Ar$^1$ is 4-methoxyphenyl.

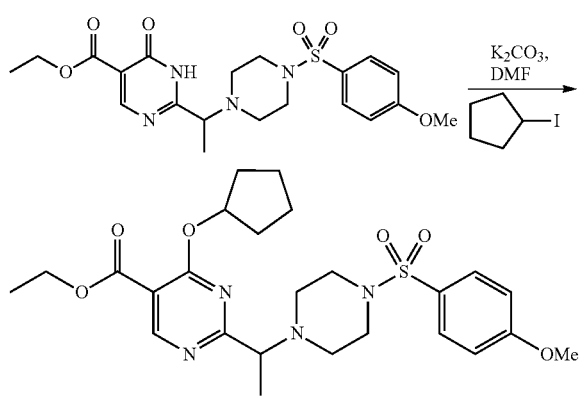

Scheme XXIII below depicts the conditions for the general synthesis of compounds of formula I, wherein $R^2$ and $R^3$ cyclize to form a phenyl ring, $G^1$ is an alkoxy and B is a piperidyl ring.

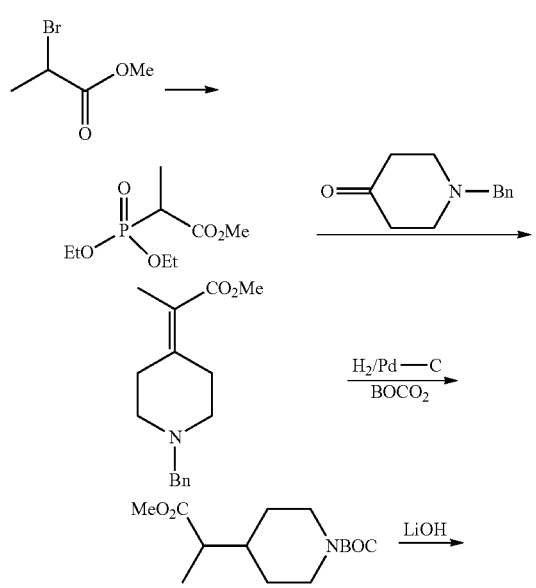

-continued

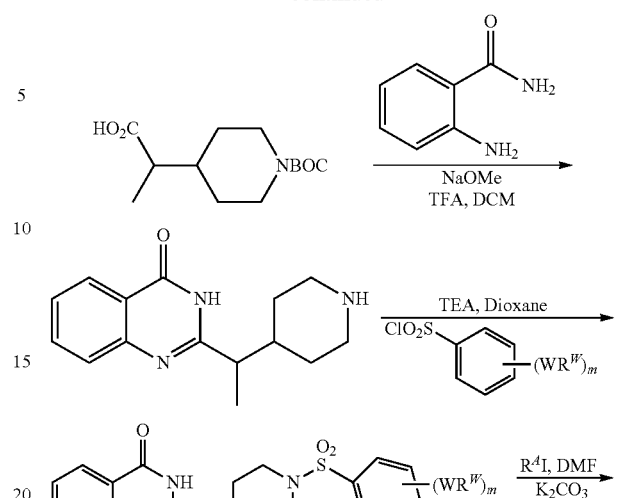

Scheme XXIV below depicts an exemplary embodiment of compound of formula I, wherein $R^A$ is cyclopentyloxy, B is piperidinyl, $G^1$ is —CH(CH$_3$)—, $G^3$ is SO$_2$, and Ar$^1$ is 4-methoxyphenyl.

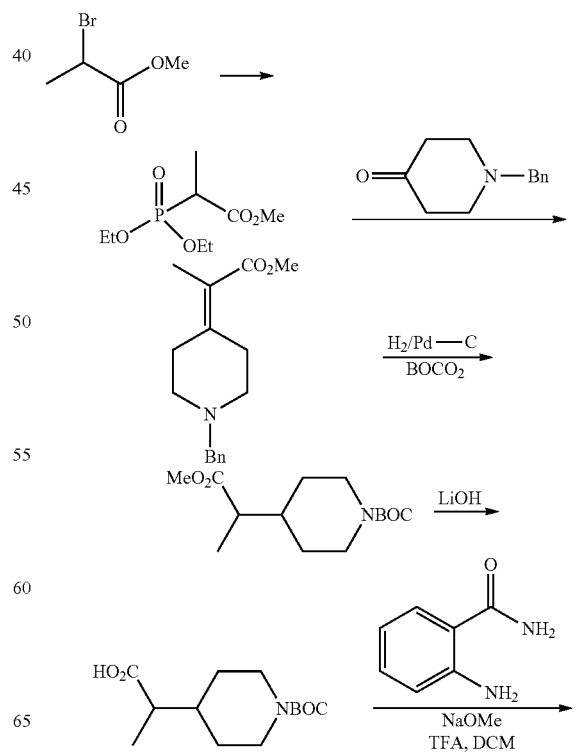

-continued

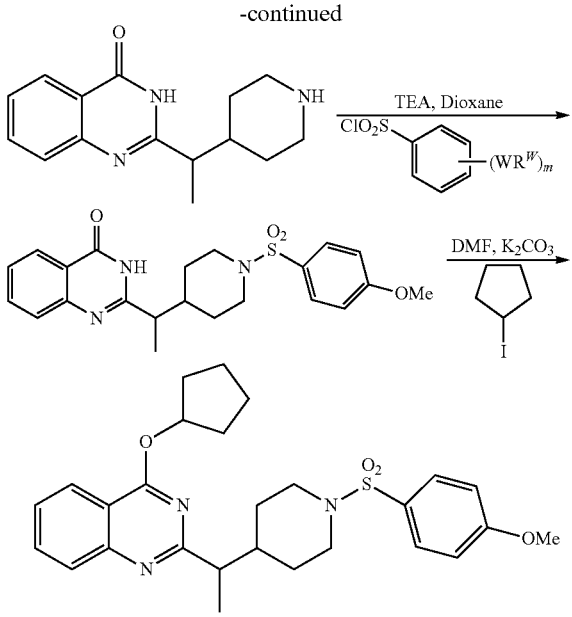

Although certain exemplary embodiments are depicted and described above and herein, it will be appreciated that compounds of the invention can be prepared according to the methods described generally above using appropriate starting materials by methods generally available to one of ordinary skill in the art.

5. Uses, Formulation and Administration

Pharmaceutically Acceptable Compositions

As discussed above, the present invention provides compounds that are useful as modulators of ABC transporters and thus are useful in the treatment of disease, disorders or conditions such as Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease and Straussler-Scheinker syndrome.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium ion channel.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating a condition, disease, or disorder implicated by ABC transporter activity. In certain embodiments, the present invention provides a method of treating a condition, disease, or disorder implicated by a deficiency of ABC transporter activity, the method comprising administering a composition comprising a compound of formula (I) to a subject, preferably a mammal, in need thereof.

In certain preferred embodiments, the present invention provides a method of treating Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease, Straussler-Scheinker disease, secretory diarrhea, and polycystic kidney disease, comprising the step of administering to said mammal an effective amount of a composition comprising a compound of formula (I), or a preferred embodiment thereof as set forth above.

According to an alternative preferred embodiment, the present invention provides a method of treating cystic fibrosis comprising the step of administering to said mammal a composition comprising the step of administering to said mammal an effective amount of a composition comprising a compound of formula (I), or a preferred embodiment thereof as set forth above.

According to the invention an "effective amount" of the compound or pharmaceutically acceptable composition is that amount effective for treating or lessening the severity of one or more of Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker disease, secretory diarrhea, and polycystic kidney disease.

The compounds and compositions, according to the method of the present invention, may be administered using any amount and any route of administration effective for treating or lessening the severity of one or more of Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker disease, secretory diarrhea, and polycystic kidney disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as modulators of ABC transporters. Thus, without wishing to be bound by any particular theory, the compounds and compositions are particularly useful for treating or lessening the severity of a disease, condition, or disorder where hyperactivity or inactivity of ABC transporters is implicated in the disease, condition, or disorder. When hyperactivity or inactivity of an ABC transporter is implicated in a particular disease, condition, or disorder, the disease, condition, or disorder may also be referred to as a "ABC transporter-mediated disease, condition or disorder". Accordingly, in another aspect, the present invention provides a method for treating or lessening the severity of a disease, condition, or disorder where hyperactivity or inactivity of an ABC transporter is implicated in the disease state.

The activity of a compound utilized in this invention as a modulator of an ABC transporter may be assayed according to methods described generally in the art and in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating ABC transporter activity in a biological sample or a patient (e.g., in vitro or in vivo), which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of ABC transporter activity in a biological sample is useful for a variety of purposes that are known to one of skill in the art. Examples of such purposes include, but are not limited to, the study of ABC transporters in biological and pathological phenomena; and the comparative evaluation of new modulators of ABC transporters.

In yet another embodiment, a method of modulating activity of an anion channel in vitro or in vivo, is provided comprising the step of contacting said channel with a compound of formula (I). In preferred embodiments, the anion channel is a chloride channel or a bicarbonate channel. In other preferred embodiments, the anion channel is a chloride channel.

According to an alternative embodiment, the present invention provides a method of increasing the number of functional ABC transporters in a membrane of a cell, comprising the step of contacting said cell with a compound of formula (I). The term "functional ABC transporter" as used herein means an ABC transporter that is capable of transport activity. In preferred embodiments, said functional ABC transporter is CFTR.

According to another preferred embodiment, the activity of the ABC transporter is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, $DiSBAC_2(3)$, and a fluorescent phospholipid, CC2-DMPE, which is attached to the outer leaflet of the plasma membrane and acts as a FRET donor. Changes in membrane potential ($V_m$) cause the negatively charged $DiSBAC_2(3)$ to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of a ABC transporter or a fragment thereof in a biological sample in vitro or in vivo comprising (i) a composition comprising a compound of formula (I); and (ii) instructions for a) contacting the composition with the biological sample and b) measuring activity of said ABC transporter or a fragment thereof. In one embodiment, the kit further comprises instructions for a) contacting an additional composition with the biological sample; b) measuring the activity of said ABC transporter or a fragment thereof in the presence of said additional compound, and c) comparing the activity of the ABC transporter in the presence of the additional compound with the density of the ABC transporter in the presence of a composition of formula (1). In preferred embodiments, the kit is used to measure the density of CFTR.

In order that the invention described herein may be more fully understood, the following examples are set forth. It should be understood that these examples are for illustrative purposes only and are not to be construed as limiting this invention in any manner.

EXAMPLES

2-Propionylamino-benzoic acid

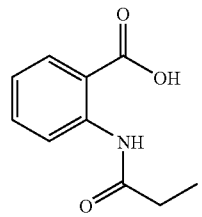

To a solution of anthranilic acid (2.96 g, 21.6 mmol) in DMF (10 mL) cooled in an ice-water bath was added propionyl chloride. The reaction was stirred for 2 hours while warming to room temperature. Water (20 mL) was added and the mixture was stirred vigorously for 1 hour. The precipitate was then collected by vacuum filtration to give the product as a white solid (3.11 g, 75%). $^1$H NMR (CDCl$_3$) δ 1.32 (t, 3H, J=7.6 Hz), 2.53 (q, 2H, J=7.6 Hz), 7.14 (t, 1H, J=8.2 Hz), 7.62 (t, 1H, J=8.7 Hz), 8.15 (dd, 1H, J=1.5, 8.1 Hz), 8.79 (dd, 1H, J=0.9, 8.5 Hz), 10.97 (s, 1H).

2-Ethyl-benzo[d][1,3]oxazin-4-one

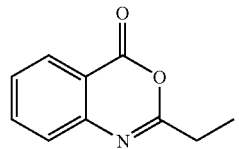

A mixture of 2-Propionylamino-benzoic acid (1.0 g, 5 mmol) and acetic anhydride (10 mL) were heated to reflux for 3 hours until TLC indicated that no more starting material remained. The remaining acetic anhydride was removed in vacuo. Toluene (2 mL) was added and then removed in vacuo. This was repeated 2 more times to try and remove final traces of acetic anhydride. The product was obtained as a pale yellow solid (820 mg, 90%). $^1$H NMR (CDCl$_3$) δ 1.37 (t, 3H, J=7.6 Hz), 2.73 (q, 2H, J=7.6 Hz), 7.50 (t, 1H, J=7.6 Hz), 7.57 (d, 1H, J=80 Hz), 7.79 (t, 1H, J=7.7 Hz), 8.19 (d, 1H, J=8.1 Hz).

2-Ethyl-3-propyl-3H-quinazolin-4-one

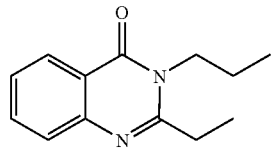 [SMILES: CCCn1c(CC)nc2ccccc2c1=O]

A mixture of 2-ethyl-benzo[d][1,3]oxazin-4-one (541 mg, 3.1 mmol) and propylamine (254 µL, 3.1 mmol) were heated to 110° C. for 1 hour. The crude product was purified by column chromatography (10-40% ethyl acetate-hexanes) to yield the product as a white solid (195 mg, 29%). $^1$H NMR (CDCl$_3$) δ 1.03 (t, 3H, J=7.4 Hz), 1.41 (t, 3H, J=7.3 Hz), 1.76 (sex, 2H, J=7.7 Hz), 2.86 (q, 2H, J=7.4 Hz), 4.05 (t, 2H, J=7.9 Hz), 7.42 (t, 1H, J=8.1 Hz), 7.63 (d, 1H, J=7.7 Hz), 7.70 (t, 1H, J=7.7 Hz), 8.24 (d, 1H, J=8.1 Hz).

2-(1-Bromo-ethyl)-3-propyl-3H-quinazolin-4-one

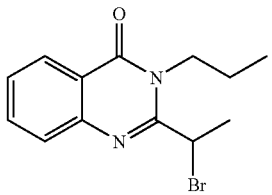 [SMILES: CCCn1c(C(C)Br)nc2ccccc2c1=O]

To a solution of 2-ethyl-3-propyl-3H-quinazolin-4-one (125 mg, 0.58 mmol) and sodium acetate (48 mg, 0.58 mmol) in glacial acetic acid (1 mL) cooled in an ice bath was added dropwise a solution of bromine (29.8 µL, 0.58 mmol) in glacial acetic acid (0.5 mL). After addition was complete the reaction was heated to reflux for 2 hours. Water was then added to the solution and the mixture extracted with dichloromethane. The organic layer was then washed with 10% sodium bisulfite solution, water and then dried over magnesium sulfate, filtered and concentrated to yield the product as a brown oil (158 mg, 92%). $^1$H NMR (CDCl$_3$) δ 1.05 (t, 3H, J=7.3 Hz), 1.66 (m, 1H), 1.91 (m, 1H), 2.19 (d, 3H, J=6.3 Hz), 3.89 (m, 1H,), 4.53 (m, 1H,), 5.04 (q, 1H, J=6.6 Hz), 7.49 (t, 1H, J=7.3 Hz), 7.73 (m, 2H), 8.27 (d, 1H, J=8.4 Hz).

4-(4-Bromo-benzenesulfonyl)-piperazine-1-carboxylic acid tert-butyl ester

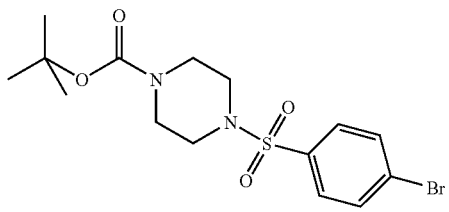 [SMILES: CC(C)(C)OC(=O)N1CCN(S(=O)(=O)c2ccc(Br)cc2)CC1]

To a solution of tert-butyl 1-piperazine-carboxylate (932 mg, 5 mmol) and triethyl amine (836 µL, 6 mmol) in dioxane (10 mL) was added 4-bromo-benzenesulfonyl chloride (1.28 g, 5 mmol). A white precipitate begins to form almost immediately. The reaction mixture was stirred for 1 hour at room temperature and the filtered. The filtrate was concentrated in vacuo to yield the product as a shiny white solid (1.85 g, 91%). $^1$H NMR (CDCl$_3$) δ 1.44 (s, 9H), 3.01 (t, 4H, J=5.1 Hz), 3.53 (t, 4H, J=5.1 Hz), 7.64 (dt, 2H, J=2.1, 8.7 Hz), 7.70 (dt, 2H, J=2.1, 8.7).

1-(4-Bromo-benzenesulfonyl)-piperazine

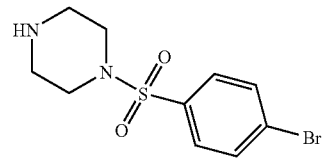 [SMILES: O=S(=O)(c1ccc(Br)cc1)N1CCNCC1]

4-(4-Bromo-benzenesulfonyl)-piperazine-1-carboxylic acid tert-butyl ester (500 mg, 1.23 mmol) was dissolved in a mixture of dichloromethane (5 mL) and trifluoroacetic acid (5 mL) and stirred at room temperature overnight. The reaction mixture was then concentrated in vacuo and then dissolved in dichloromethane and washed with saturated sodium bicarbonate solution and then water. The organic layer was then dried over magnesium sulfate and concentrated in vacuo to yield the product as a white solid (329 mg, 88%). $^1$H NMR (CDCl$_3$) δ 1.77 (s, 1H), 2.96 (m, 4H), 3.01 (m, 4H), 7.64 (dt, 2H, J=2.1, 8.7 Hz), 7.69 (dt, 2H, J=2.1, 8.7 Hz).

2-{1-[4-(4-Bromo-benzenesulfonyl)-piperazin-1-yl]-ethyl}-3-propyl-3H-quinazolin-4-one

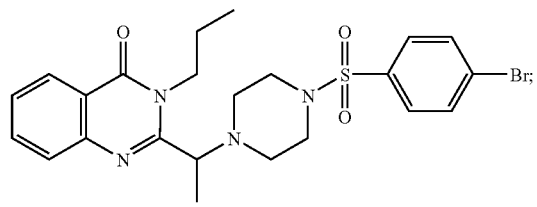 [SMILES: CCCn1c(C(C)N2CCN(S(=O)(=O)c3ccc(Br)cc3)CC2)nc2ccccc2c1=O]

A mixture of 2-(1-bromo-ethyl)-3-propyl-3H-quinazolin-4-one (30 mg, 0.1 mmol) and 1-(4-bromo-benzenesulfonyl)-piperazine (47 mg, 0.15 mmol) in ethanol (1 mL) was refluxed overnight. The reaction mixture was then concentrated in vacuo and purified by reverse phase HPLC to yield the product as a white powder (7 mg, 9%). $^1$H NMR (CDCl$_3$) δ 1.03 (t, 3H, J=5.8 Hz), 1.72 (sex, 2H, J=6.0), 1.80 (d, 3H, J=5.2), 3.48 (m, 6H), 3.90 (m, 3H), 4.23 (m, 1H), 4.77 (q, 1H, J=5.2 Hz), 7.58 (m, 3H), 7.68 (d, 1H, J=6.5 Hz), 7.72 (d, 2H, J=7.1 Hz), 7.81 (t, 1H, J=6.2 Hz), 8.28 (d, 1H, J=6.5 Hz).

2-Ethyl-3-methyl-3H-quinazolin-4-one

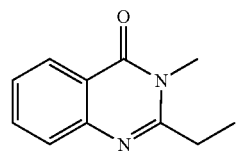

A mixture of anthranilic acid (13.7 g, 100 mmol), methylamine (2M solution in methanol, 100 mL, 200 mmol), triethylorthopropionate (40 mL, 200 mmol), pTSA (catalytic amount) was heated at 70° C. with stirring for 3 days. The reaction mixture was cooled to room temperature, 1N NaOH solution (160 mL) was added and the mixture stirred vigourously. The resulting precipitate was filtered, washed with water and dried under high vacuum to yield the product as a fluffy white solid (13.67 g, 73%). $^1$H NMR (400 MHz, CDCl$_3$) δ 1.41 (t, 3H, J=7.4 Hz), 2.87 (q, 2H, J=7.4 Hz), 3.64 (s, 3H), 7.44 (t, 1H, J=8.1 Hz), 7.65 (dd, 1H, J=8.8, 0.7 Hz), 7.72 (t, 1H, J=8.4 Hz), 8.27 (dd, 1H, J=9.2, 1.8 Hz); ESI-MS m/z 189.0 (M+1)+.

2-(1-Bromo-ethyl)-3-methyl-3H-quinazolin-4-one

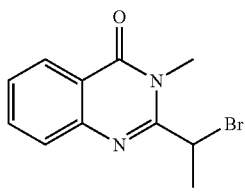

To a solution of 2-ethyl-3-methyl-3H-quinazolin-4-one (11.28 g, 60 mmol) and sodium acetate (4.92 g, 60 mmol) in glacial acetic acid (130 mL) heated to 50° C. was added dropwise a solution of bromine (3.70 mL, 72 mmol) in glacial acetic acid (50 mL). After addition was complete the reaction was heated to reflux for 2 hours. The reaction was then cooled to room temperature and concentrated in vacuo. The residue was dissolved in ethyl acetate and washed with 10% sodium bisulfite solution, water and dried over magnesium sulfate, filtered and concentrated in vacuo. The crude product was purified by column chromatography (0-25% ethyl acetate-hexanes) to yield the product as a white solid (12.68 g, 79%). $^1$H NMR (400 MHz, CDCl$_3$) δ 2.19 (d, 3H, J=6.6 Hz), 3.77 (s, 3H), 5.08 (q, 1H, J=6.6 Hz), 7.50 (t, 1H, J=8.1 Hz), 7.74 (m, 2H), 8.29 (d, 1H, J=8.9 Hz); ESI-MS m/z 267.0 (M+1)$^+$.

6-Bromo-2-ethyl-3-methyl-3H-quinazolin-4-one

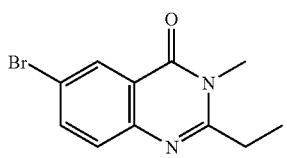

To a stirred solution of 2-amino-5-bromo-benzoic acid (10.00 g, 46.38 mmol) in methanol (25 mL) was added methylamine (100 ml of 2 M solution in methanol), p-toluenesulfonic acid monohydrate (8.82 g, 46.38 mmol), and triethyl orthopropionate (40.87 g, 231.9 mmol). The reaction was refluxed for 18 hours, at which time it was allowed to cool to room temperature. The solution was concentrated under reduced pressure. The residue was partitioned between sodium carbonate aqueous (50 ml) and dichloromethane (50 ml). The organic layer was then washed with saturated brine (2×30 ml). The combined organic phase was dried over magnesium sulfate and filtered. The solvent was removed under vacuum. The resulting residue was purified by silica gel chromatography with 100% dichloromethane. The product was collected and was dried under reduced pressure to give 6-Bromo-2-ethyl-3-methyl-3H-quinazolin-4-one (Yield 4.92 g, 39.9%). $^1$H NMR (400 MHz, CDCl$_3$): □ 1.42 (t, 3H, J=7.33 Hz), 2.86 (dd, 2H, J=14.65, 7.58 Hz), 7.45 (d, 1H, J=8.5 Hz), 7.80 (dd, 1H, J=8.50, 2.02 Hz), 8.40 (d, 1H, J=2.05 Hz). MS m/z calc. 266.01, found (ESI); 267.0 (M+1)$^+$. Retention time 2.44 minutes.

6-Bromo-2-(1-bromo-ethyl)-3-methyl-3H-quinazolin-4-one

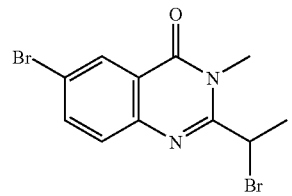 [SMILES: CC(Br)c1nc2ccc(Br)cc2c(=O)n1C]

To a solution of 6-bromo-2-ethyl-3-methyl-3H-quinazolin-4-one (2.6 g, 9.73 mmol) in glacial acetic acid (2 ml) cooled in an ice bath was added dropwise a solution of bromine (3.1 g, 19.46 mmol) in glacial acetic acid (5 ml). After addition was complete, the reaction was heated to reflux for 18 hours. At which time it was allowed to cool to room temperature. Water was then added to the solution and the mixture was extracted with dichloromethane. The organic layer was then washed with 10% sodium bisulfite solution, and then washed with saturated brine (2×30 ml). The combined organic phase was collected and dried over magnesium sulfate, filtered and concentrated under reduced pressure to yield a brown crude product. The resulting residue was purified by silica gel chromatography with 50% dichloromethane in hexane. The product was collected and was dried under reduced pressure to give 6-Bromo-2-(1-bromo-ethyl)-3-methyl-3H-quinazolin-4-one (Yield 2.78 g, 82.5%). $^1$H NMR (400 MHz, CDCl$_3$): δ 2.23 (d, 3H, J=6.82 Hz), 3.80 (s, 3H), 5.11 (q, 1H, J=13.14, 6.82 Hz), 7.64 (d, 1H, J=8.84 Hz), 7.87 (dd, 1H, J=8.59, 2.26 Hz), 8.46 (d, 1H, J=2.26 Hz). MS m/z calc. 345.9, found (ESI); 347.0 (M+1)$^+$. Retention time 3.43 minutes.

6-Bromo-2-{1-[4-(4-methoxy-benzenesulfonyl)-piperazin-1-yl]-ethyl}-3-methyl-3H-quinazolin-4-one

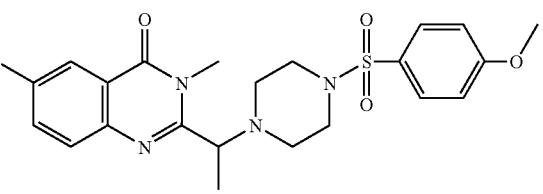

In a test tube containing of 6-bromo-2-(1-bromo-ethyl)-3-methyl-3H-quinazolin-4-one (50.0 mg, 0.14 mmol) in acetonitrile (2 ml) was added KI (34.0 mg, 0.21 mmol), and 4-methoxy-1-benzenesulfonyl-piperazine (40.0 mg, 0.17 mmol). The reaction was heated for 18 hours. The solution was concentrated under reduced pressure. The residue was partitioned between water (2 ml) and dichloromethane (5 ml). The organic layer was dried over magnesium sulfate, filtered and concentrated under reduced pressure. The solvent was removed under vacuum. The resulting residue was purified by HPLC (Gilson-215, 0.035% TFA in acetonitrile and 0.05% water as mobile phase). The product was collected and dried under reduced pressure to give 6-Bromo-2-{1-[4-(4-methoxy-benzenesulfonyl)-piperazin-1-yl]-ethyl}-3-methyl-3H-quinazolin-4-one (Yield 30.1 mg, 39.9%). $^1$H NMR (400 MHz, CDCl$_3$): δ 1.86 (d, 3H, J=6.82 Hz), 3.63-3.39 (m, 6H), 3.79-3.68 (m, 2H), 3.80 (s, 3H), 4.03 (s, 3H), 4.82-4.74 (m, 1H), 7.18-7.12 (m, 2H), 7.70 (d, 1H, J=8.55 Hz), 7.84-7.79 (m, 2H), 8.01 (dd, 2H, J=8.84, 2.27 Hz), 8.58 (d, 1H, J=2.5 Hz). MS m/z calc. 521.4, found (ESI); 523.2 (M+1)$^+$. Retention time 2.80 minutes.

2-[1-(4-Benzenesulfonyl-piperazin-1-yl)-ethyl]-6-bromo-3-methyl-3H-quinazolin-4-one

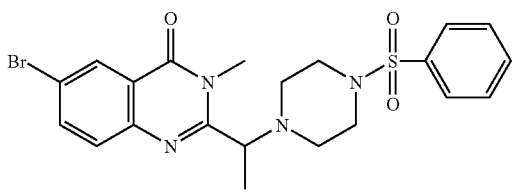 [SMILES: CC(c1nc2ccc(Br)cc2c(=O)n1C)N1CCN(S(=O)(=O)c2ccccc2)CC1]

2-[1-(4-Benzenesulfonyl-piperazin-1-yl)-ethyl]-6-bromo-3-methyl-3H-quinazolin-4-one compound was synthesized by using the same method as described as Scheme IA or Scheme IB above. (Yield 27.35 mg, 38.4%). $^1$H NMR (400 MHz, CDCl$_3$): δ 1.86 (d, 3H, J=7.07 Hz), 3.30-3.17 (m, 4H), 3.49-3.33 (m, 4H), 3.61 (s, 3H), 4.61-4.51 (m, 1H), 7.54-7.42 (m, 3H), 7.62-7.57 (m, 1H), 7.72-7.67 (m, 2H), 7.82 (dd, 1H, J=8.50, 2.51 Hz), 8.36 (d, 1H, J=2.5 Hz). MS m/z calc. 490.1, found (ESI); 491.2 (M+1)$^+$. Retention time 2.64 minutes.

6-Bromo-3-methyl-2-{1-[4-(toluene-4-sulfonyl)-piperazin-1-yl]-ethyl}-3H-quinazolin-4-one

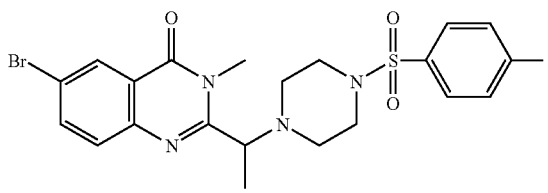 [SMILES: Cc1ccc(S(=O)(=O)N2CCN(C(C)c3nc4ccc(Br)cc4c(=O)n3C)CC2)cc1]

6-Bromo-3-methyl-2-{1-[4-(toluene-4-sulfonyl)-piperazin-1-yl]-ethyl}-3H-quinazolin-4-one compound was synthesized by using the same method as described as Scheme IA or Scheme IB. (Yield 8.17 mg, 11.16%). $^1$H NMR (400 MHz, CDCl$_3$): δ 1.79 (d, 3H, J=6.32 Hz), 2.47 (s, 3H), 3.61-3.41 (m, 6H), 3.68 (s, 1H), 3.93-3.81 (m, 2H), 4.86-4.77 (m, 1H), 7.37 (d, 2H, J=7.83), 7.58 (d, 1H, J=8.5 Hz), 7.64 (d, 2H, J=8.5 Hz), 7.89 (dd, 1H, J=8.5, 2.5 Hz), 8.43 (d, 1H, J=2.5 Hz). MS m/z calc. 505.4, found (ESI); 507.2 (M+1)$^+$. Retention time 2.80 minutes.

6-Bromo-2-{1-[4-(4-chloro-benzenesulfonyl)-piperazin-1-yl]-ethyl}-3-methyl-3H-quinazolin-4-one

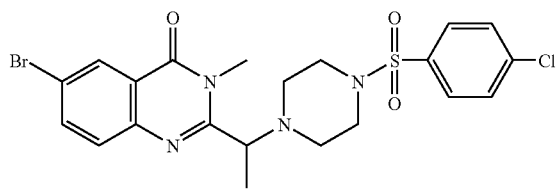 [SMILES: CC(c1nc2ccc(Br)cc2c(=O)n1C)N1CCN(S(=O)(=O)c2ccc(Cl)cc2)CC1]

6-Bromo-2-{1-[4-(4-chloro-benzenesulfonyl)-piperazin-1-yl]-ethyl}-3-methyl-3H-quinazolin-4-one compound was synthesized by using the same method described in Scheme IA or Scheme IB. (Yield 30.1 mg, 23.1%). $^1$H NMR (400 MHz, CDCl$_3$): δ 1.79 (d, 3H, J=6.82 Hz), 3.47-3.38 (m, 2H), 3.62-3.48 (m, 4H), 3.68 (s, 3H), 3.85-3.76 (m, 2H), 4.79 (q, 1H, J=13.80, 7.07 Hz), 7.60-7.54 (m, 3H), 7.73-7.68 (m, 2H), 7.90 (dd, 1H, J=8.59, 2.27 Hz), 8.44 (d, 1H, J=2.5 Hz). MS ml/z calc. 525.8, found (ESI); 527.2 (M+1)$^+$. Retention time 2.94 minutes.

6-Bromo-2-{1-[4-(4-bromo-benzenesulfonyl)-piperazin-1-yl]-ethyl}-3-methyl-3H-quinazolin-4-one

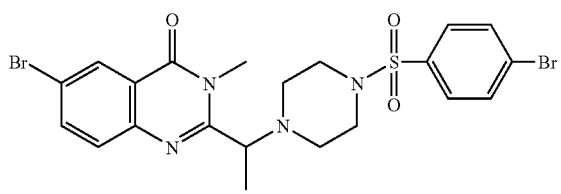 [SMILES: CC(c1nc2ccc(Br)cc2c(=O)n1C)N1CCN(S(=O)(=O)c2ccc(Br)cc2)CC1]

6-Bromo-2-{1-[4-(4-bromo-benzenesulfonyl)-piperazin-1-yl]-ethyl}-3-methyl-3H-quinazolin-4-one compound was synthesized by using the same method as described in Scheme IA or Scheme IB. (Yield 13.5 mg, 16.3%). $^1$H NMR (400 MHz, CDCl$_3$): δ 1.89 (d, 3H, J=7.07 Hz), 3.47-3.38 (m, 2H), 3.64-3.49 (m, 4H), 3.69 (s, 3H), 3.83-3.74 (m, 2H), 4.71 (q, 1H, J=13.64, 6.57, Hz), 7.65-7.59 (m, 3H), 7.75-7.70 (m, 2H), 7.90 (dd, 1H, J=8.59, 2.27 Hz), 8.44 (d, 1H, J=2.27 Hz). MS m/z calc. 570.3, found (ESI); 571.0 (M+1)$^+$. Retention time 2.98 minutes.

2-{1-[4-(4-Bromo-benzenesulfonyl)-piperazin-1-yl]-ethyl}-5-chloro-3-methyl-3H-quinazolin-4-one

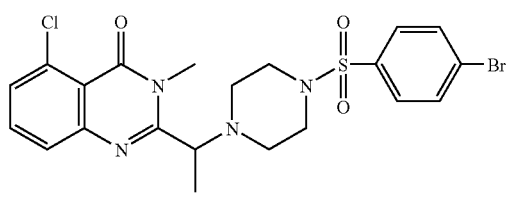 [SMILES: CC(c1nc2cccc(Cl)c2c(=O)n1C)N1CCN(S(=O)(=O)c2ccc(Br)cc2)CC1]

2-{1-[4-(4-Bromo-benzenesulfonyl)-piperazin-1-yl]-ethyl}-5-chloro-3-methyl-3H-quinazolin-4-one compound was synthesized by using the same method as described in Scheme IA or Scheme IB (Yield 25.39 mg, 32.2%). MS m/z calc. 525.8, found (ESI); 527.1 (M+1)⁺. Retention time 2.69 minutes.

2-Ethyl-3-methyl-4-oxo-3,4-dihydro-quinazoline-6-carbonitrile

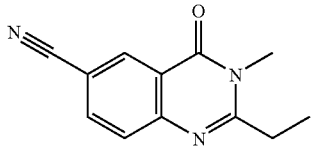 [SMILES: CCc1nc2ccc(C#N)cc2c(=O)n1C]

The substrate of 6-bromo-2-ethyl-3-methyl-3H-quinazolin-4-one (50.0 mg, 0.189 mmol), KCN (23.1 mg, 0.37 mmol), Pd(PPh$_3$)$_4$ (10.0 mg, 0.0094 mmol), and CuI (3.6 mg, 0.019 mmol) was added to a flask, which was flushed with N$_2$. The solvent acetonitrile (2 ml) was added via syringe. The resulting mixture was irradiated at 170° C. for 2 hours in the SmithSynthesizer Microwave Reactor (Personal Chemistry) with vigorous agitation by a magnetic stirrer. The mixture was cooled to room temperature, diluted with ethyl acetate (5 ml), and then filtered through Celite. The filtrate was washed with water and brine, dried over anhydrous MgSO$_4$, and concentrated by rotary evaporation. Purification was accomplished by HPLC (Gilson-215, 0.035% TFA in acetonitrile and 0.05% water as mobile phase). The product was collected and dried under reduced pressure to give 2-Ethyl-3-methyl-4-oxo-3,4-dihydro-quinazoline-6-carbonitrile (Yield 16.8 mg, 46.2%). ¹H NMR (400 MHz, CDCl$_3$): δ 1.35 (t, 3H, J=7.30 Hz), 2.85 (q, 2H, J=14.62, 7.30 Hz), 3.54 (s, 3H), 7.68 (d, 1H, J=8.58 Hz), 7.83 (dd, 1H, J=8.58, 2.02 Hz), 8.51 (d, 1H, J=2.02 Hz). MS/M/Z calc. 213.2, Found (ESI); 214.0 (M+1)⁺. Retention time 2.13 minutes.

2-(1-Bromo-ethyl)-3-methyl-4-oxo-3,4-dihydro-quinazoline-6-carbonitrile

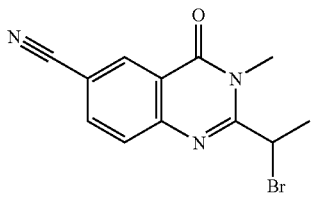 [SMILES: CC(Br)c1nc2ccc(C#N)cc2c(=O)n1C]

To a solution 2-isopropyl-3-methyl-4-oxo-3,4-dihydro-quinazoline-6-carbonitrile (0.35 g, 1.64 mmol) in glacial acetic acid (10 ml) cooled in an ice bath was added dropwise a solution of bromine (0.52 g, 3.28 mmol) in glacial acetic acid (5 ml). After addition was complete, the reaction was heated to reflux for 18 hours. At which time it was allowed to cool to room temperature. Water was then added to the solution and the mixture was extracted with dichloromethane. The organic layer was then washed with 10% sodium bisulfite solution, and then washed with saturated brine (2×10 ml). The combined organic phase was collected and dried over magnesium sulfate, filtered and concentrated under reduced pressure to yield a brown crude product. The resulting residue was purified by silica gel chromatography with 50% dichloromethane in hexane. The product was collected and was dried under reduced pressure to give 2-(1-Bromo-ethyl)-3-methyl-4-oxo-3,4-dihydro-quinazoline-6-carbonitrile (Yield 0.35 g, 73.1%). ¹H NMR (400 MHz, CDCl$_3$): δ 2.20 (d, 3H, J=6.54 Hz), 3.78 (s, 3H), 5.17 (q, 1H, J=12.88, 6.54 Hz), 7.81 (d, 1H, J=8.84 Hz), 7.94 (dd, 1H, J=8.34, 2.02 Hz), 8.61 (d, 1H, J=2.02 Hz). MS m/z calc. 291.0, found (ESI); 292.0 (M+1)⁺. Retention time 2.95 minutes.

2-{1-[4-(4-Methoxy-benzenesulfonyl)-piperazin-1-yl]-ethyl}-3-methyl-4-oxo-3,4-dihydro-quinazoline-6-carbonitrile

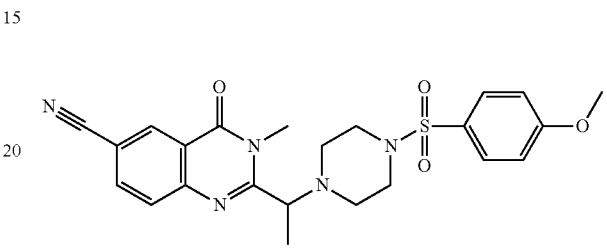

In a test tube containing of 2-(1-bromo-ethyl)-3-methyl-4-oxo-3,4-dihydro-quinazoline-6-carbonitrile (40.0 mg, 0.14 mmol) in acetonitrile (2 ml) was added KI (34.0 mg, 0.21 mmol), and (1-(4-Methoxy-benzenesulfonyl)-piperazine (46.4 mg, 0.21 mmol). The reaction was heated for 18 hours. The solution was concentrated under reduced pressure. The residue was partitioned between water (2 ml) and dichloromethane (5 ml). The organic layer was dried over magnesium sulfate, filtered and concentrated under reduced pressure. The solvent was removed under vacuum. The resulting residue was dissolvent in DMSO (2 ml) and purified by HPLC (Gilson-215, 0.035% TFA in acetonitrile and 0.05% water as mobile phase). The product was collected and dried under reduced pressure to give the 2-{1-[4-(4-Methoxy-benzenesulfonyl)-piperazin-1-yl]-ethyl}-3-methyl-4-oxo-3,4-dihydro-quinazoline-6-carbonitrile compound (Yield 5.52 mg, 8.2%). ¹H NMR (400 MHz, CDCl$_3$): δ 1.64 (d, 3H, J=6.57 Hz), 3.29-3.10 (m, 6H), 3.48-3.37 (m, 2H), 3.68 (s, 3H), 3.90 (s, 3H), 4.53 (q, 1H, J=13.14, 5.81 Hz), 6.97 (d, 2H, J=2.02 Hz), 7.66 (d, 2H, J=8.84, Hz), 7.76 (d, 1H, J=8.59 Hz), 7.94 (dd, 1H J=8.59, 2.02 Hz), 8.57 (d, 1H, J=2.02 Hz). MS m/z calc. 467.16, found (ESI); 468.4 (M+1)⁺. Retention time 2.75 minutes.

3-Methyl-4-oxo-2-{1-[4-(toluene-4-sulfonyl)-piperazin-1-yl]-ethyl}-3,4-dihydro-quinazoline-6-carbonitrile

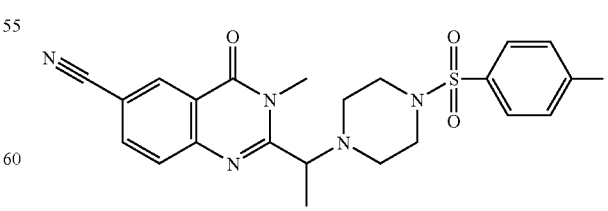

3-Methyl-4-oxo-2-{1-[4-(toluene-4-sulfonyl)-piperazin-1-yl]-ethyl}-3,4-dihydro-quinazoline-6-carbonitrile was synthesized by using the same method as described in Scheme IA or Scheme IB. (Yield 31.03 mg, 50.4%). ¹H NMR (400 MHz, CDCl$_3$): δ 1.67 (d, 3H, J=6.28 Hz), 2.46 (s, 3H), 3.34-3.17 (m, 6H), 3.56-3.47 (m, 2H), 3.67 (s, 3H), 4.60 (q, 1H, J=13.00, 6.57 Hz), 7.36 (d, 2H, J=8.08 Hz), 7.60 (d, 2H, J=8.08, Hz), 7.76 (d, 1H, J=8.59 Hz), 7.94 (dd, 1H J=8.59, 1.77 Hz), 8.56 (d, 1H, J=1.77 Hz). MS m/z calc. 451.17, found (ESI); 452.2 (M+1)[30]. Retention time 2.52 minutes.

2-{1-[4-(4-Chloro-benzenesulfonyl)-piperazin-1-yl]-ethyl}-3-methyl-4-oxo-3,4-dihydro-quinazoline-6-carbonitrile

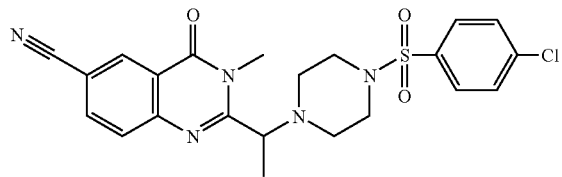 [SMILES: CC(c1nc2ccc(C#N)cc2c(=O)n1C)N1CCN(S(=O)(=O)c2ccc(Cl)cc2)CC1]

2-{1-[4-(4-Chloro-benzenesulfonyl)-piperazin-1-yl]-ethyl}-3-methyl-4-oxo-3,4-dihydro-quinazoline-6-carbonitrile was synthesized by using the same method as described in Scheme IA or Scheme IB. (Yield 28.30 mg, 44.0%). $^1$H NMR (400 MHz, CDCl$_3$): δ 1.54 (d, 3H, J=6.82 Hz), 3.23-2.96 (m, 6H), 3.35-3.25 (m, 2H), 3.59 (s, 3H), 4.41 (q, 1H, J=13.89, 6.82 Hz), 7.47-7.43 (m, 2H), 7.61-7.56 (m, 2H), 7.77-7.65 (m, 1H), 7.85 (dd, 1H J=8.59, 1.77 Hz), 8.47 (d, 1H, J=1.77 Hz). MS m/z calc. 471.1, found (ESI); 472.2 (M+1)$^+$. Retention time 2.65 minutes.

2-Ethyl-6-methanesulfonyl-3-methyl-3H-quinazolin-4-one

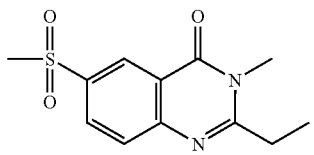 [SMILES: CCc1nc2ccc(S(C)(=O)=O)cc2c(=O)n1C]

The substrate of 6-bromo-2-ethyl-3-methyl-3H-quinazolin-4-one (50.0 mg, 0.189 mmol), sodium methanesulfinate (28.8 mg, 0.29 mmol) and copper (I) iodide (53.7 mg, 0.29 mmol) was placed in a flask, which was flushed with N$_2$. DMF (2 ml) was added via syringe. The resulting mixture was irradiated at 180° C. for 30 minutes in the SmithSynthesizer Microwave reactor (Personal Chemistry) with vigorous agitation by a magnetic stirrer. The mixture was cooled to room temperature, diluted with ethyl acetate (5 ml), and then filtered. The filtrate was washed with water and brine, dried over anhydrous MgSO$_4$, and concentrated by rotary evaporation. Purification was accomplished by HPLC (Gilson-215, 0.035% TFA in acetonitrile and 0.05% water as mobile phase). The product was collected and dried under reduced pressure to give 2-Ethyl-6-methanesulfonyl-3-methyl-3H-quinazolin-4-one (Yield 12.5 mg, 25.1%). $^1$H NMR (400 MHz, CDCl$_3$): δ 1.35 (t, 3H, J=7.58 Hz), 2.83 (dd, 2H, J=14.65, 7.58 Hz), 3.02 (s, 3H), 3.58 (s, 3H), 7.73 (d, 1H, J=8.84 Hz), 8.12 (dd, 1H, J=8.84 Hz), 8.77 (d, 1H, J=2.02 Hz). MS m/z calc. 265.1, found (ESI); 266.0 (M+1)$^+$. Retention time 2.41 minutes.

2-(1-Bromo-ethyl)-6-methanesulfonyl-3-methyl-3H-quinazolin-4-one

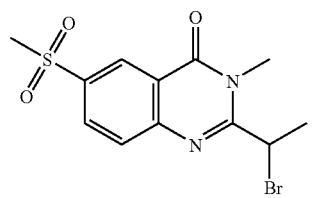 [SMILES: CC(Br)c1nc2ccc(S(C)(=O)=O)cc2c(=O)n1C]

To a solution 2-ethyl-6-methanesulfonyl-3-methyl-3H-quinazolin-4-one (300.0 mg, 1.13 mmol) in glacial acetic acid (10 ml) cooled in an ice bath was added dropwise a solution of bromine (0.39 g, 2.26 mmol) in glacial acetic acid (5 ml). After addition was complete, the reaction was heated to reflux for 18 hours. Evaporated acetic acid and then water was added to the solution and the mixture was extracted with dichloromethane. The organic layer was washed with 10% sodium bisulfite solution, and then washed with saturated brine (2×10 ml). The combined organic phase was collected and dried over magnesium sulfate, filtered and concentrated under reduced pressure to yield a brown crude product. The resulting residue was purified by silica gel chromatography with 50% ethyl acetate in hexane. The product was collected and was dried under reduced pressure to give 2-(1-Bromo-ethyl)-6-methanesulfonyl-3-methyl-3H-quinazolin-4-one (Yield 339 mg, 87.2%). $^1$H NMR (400 MHz, CDCl$_3$): δ 2.13 (d, 3H, J=5.31 Hz), 3.04 (s, 3H), 3.71 (s, 3H), 5.05 (m, 1H), 7.81 (d, 1H, J=7.58 Hz), 8.16 (d, 1H, J=7.58, Hz), 8.80 (s, 1H). MS m/z calc. 343.98, found (ESI); 344.8 (M+1)$^+$. Retention time 3.06 minutes.

6-Methanesulfonyl-2-{1-[4-(4-methoxy-benzenesulfonyl)-piperazin-1-yl]-ethyl}-3-methyl-3H-quinazolin-4-one

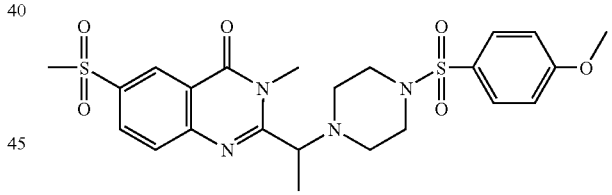

In a test tube containing of 2-(1-Bromo-ethyl)-6-methanesulfonyl-3-methyl-3H-quinazolin-4-one (40.0 mg, 0.12 mmol) in acetonitrile (2 ml) was added KI (28.0 mg, 0.18 mmol), and (1-(4-Methoxy-benzenesulfonyl)-piperazine (39.6 mg, 0.18 mmol). The reaction was heated at 80° C. for 18 hours. The solution was concentrated under reduced pressure. The residue was partitioned between water (2 ml) and dichloromethane (5 ml). The organic layer was dried over magnesium sulfate, filtered and concentrated under reduced pressure. The solvent was removed under vacuum. The resulting residue was dissolvent in DMSO (2 ml) and purified by HPLC (Gilson-215, 0.035% TFA in acetonitrile and 0.05% water as mobile phase). The product was collected and dried under reduced pressure to give 6-Methanesulfonyl-2-{1-[4-(4-methoxy-benzenesulfonyl)-piperazin-1-yl]-ethyl}-3-methyl-3H-quinazolin-4-one (Yield 32.4 mg, 55.2%). $^1$H NMR (400 MHz, CDCl$_3$): δ 1.82 (d, 3H, J=7.07 Hz), 3.12 (s, 3H), 3.64-3.40 (m, 4H), 3.70 (s, 3H), 4.00-3.86 (m, 7H), 4.89 (q, 1H, J=14.40, 6.03 Hz), 7.05 (d, 2H, J=9.09 Hz), 7.68 (d, 2H, J=9.09, Hz), 7.84 (d, 1H, J=8.84 Hz), 8.25 (dd, 1H J=8.84, 2.02 Hz), 8.82 (d, 1H, J=2.02 Hz). MS m/z calc. 490.1, found (ESI); 491.2 (M+1)⁺. Retention time 2.17 minutes.

6-Methanesulfonyl-3-methyl-2-{1-[4-(toluene-4-sulfonyl)-piperazin-1-yl]-ethyl}-3H-quinazolin-4-one

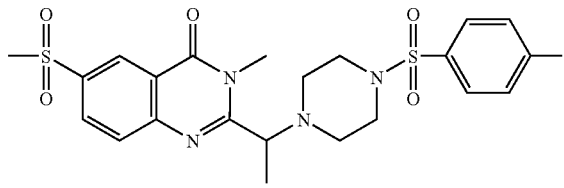

6-Methanesulfonyl-3-methyl-2-{1-[4-(toluene-4-sulfonyl)-piperazin-1-yl]-ethyl}-3H-quinazolin-4-one compound was synthesized by using the same method as described in Scheme IA or Scheme IB. (Yield 34.2 mg, 56.5%). ¹H NMR (400 MHz, CDCl₃): δ 1.85 (d, 3H, J=6.32 Hz), 2.47 (s, 3H), 3.13 (s, 3H), 3.66-3.45 (m, 4H), 3.71 (s, 3H), 4.05-3.92 (m, 4H), 4.89 (q, 1H, J=14.15, 6.32 Hz), 7.38 (d, 2H, J=8.08 Hz), 7.64 (d, 2H, J=8.34, Hz), 7.86 (d, 1H, J=8.59 Hz), 8.27 (dd, 2H J=8.84, 2.27 Hz), 8.84 (d, 1H, J=2.27 Hz). MS m/z calc. 520.2, found (ESI); 521.4 (M+1)⁺. Retention time 2.23 minutes.

2-{1-[4-(4-Chloro-benzenesulfonyl)-piperazin-1-yl]-ethyl}-6-methanesulfonyl-3-methyl-3H-quinazolin4-one

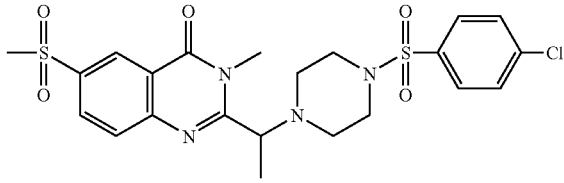 [SMILES: CC(c1nc2ccc(S(C)(=O)=O)cc2c(=O)n1C)N1CCN(S(=O)(=O)c2ccc(Cl)cc2)CC1]

2-{1-[4-(4-Chloro-benzenesulfonyl)-piperazin-1-yl]-ethyl}-6-methanesulfonyl-3-methyl-3H-quinazolin-4-one compound was synthesized by using the same method as described in Scheme IA or Scheme IB (Yield 16.8 mg, 27.6%). ¹H NMR (400 MHz, CDCl₃): δ 1.85 (d, 3H, J=7.07 Hz), 3.13 (s, 3H), 3.65-3.47 (m, 4H), 3.70 (s, 3H), 4.03-3.90 (m, 4H), 4.88 (q, 1H, J=14.89, 6.57 Hz), 7.58 (d, 2H, J=9.09 Hz), 7.71 (d, 2H, J=9.09, Hz), 7.84 (d, 1H, J=8.84 Hz), 8.26 (dd, 1H J=8.84, 2.27 Hz), 8.83 (d, 1H, J=2.27 Hz). MS m/z calc. 524.1 found (ESI); 525.2 (M+1)⁺. Retention time 2.46 minutes.

2-{1-[4-(4-Bromo-benzenesulfonyl)-piperazin-1-yl]-ethyl}-6-methanesulfonyl-3-methyl-3H-quinazolin-4-one

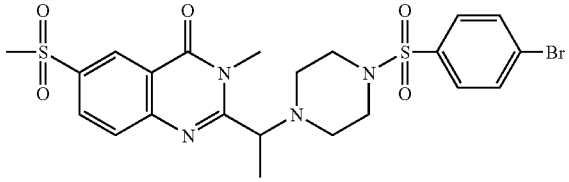 [SMILES: CC(c1nc2ccc(S(C)(=O)=O)cc2c(=O)n1C)N1CCN(S(=O)(=O)c2ccc(Br)cc2)CC1]

2-{1-[4-(4-Bromo-benzenesulfonyl)-piperazin-1-yl]-ethyl}-6-methanesulfonyl-3-methyl-3H-quinazolin-4-one compound was synthesized by using the same method as described in Scheme IA or Scheme IB (Yield 35.8 mg, 54.3%). ¹H NMR (400 MHz, CDCl₃): δ 1.86 (d, 3H, J=6.84 Hz), 3.13 (s, 3H), 3.65-3.43 (m, 4H), 3.71 (s, 3H), 4.05-3.93 (m, 4H), 4.85 (q, 1 h, J=13.64, 6.57 Hz), 7.63 (d, 2H, J=8.84 Hz), 7.74 (d, 2H, J=8.84, Hz), 7.87 (d, 1H, J=8.34 Hz), 8.28 (dd, 1H J=8.34, 2.27 Hz), 8.86 (d, 1H, J=2.27 Hz). MS m/z calc. 568.0 found (ESI); 571.2 (M+1)⁺. Retention time 2.51 minutes.

2-{1-[4-(4-Methoxy-benzenesulfonyl)-piperazin-1-yl]-ethyl}-3-methyl-6-(1H-tetrazol-5-yl)-3H-quinazolin-4-one

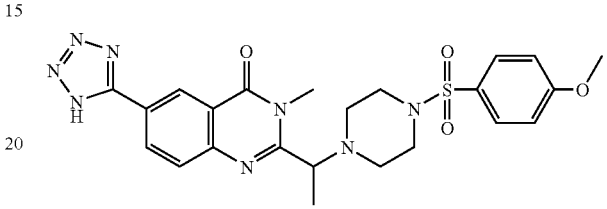

To the 1 ml DMF solution of 2-{1-[4-(4-Methoxy-benzenesulfonyl)-piperazin-1-yl]-ethyl}-3-methyl-4-oxo-3,4-dihydro-quinazoline-6-carbonitrile (10.0 mg, 0.02 mmol) was added sodium azide (16.7 mg, 0.24 mmol) and ammonium chloride (12.8 mg, 0.24 mmol). The reaction test tube was flushed with N₂ and was irradiated at 200° C. for 40 minutes in the SmithSynthesizer Microwave Reactor with vigorous agitation by a magnetic stirrer. The mixture was cooled to room temperature, the solvent was removed by reduce pressure and extracted with water and ethyl acetate, dried over anhydrous MgSO₄, and concentrated by rotary evaporation. Purification was accomplished by HPLC (Gilson-215, 0.035% TFA in acetonitrile and 0.05% water as mobile phase). The product was collected and dried under reduced pressure to give 2-{1-[4-(4-Methoxy-benzenesulfonyl)-piperazin-1-yl]-ethyl}-3-methyl-6-(1H-tetrazol-5-yl)-3H-quinazolin-4-one (Yield 3.09 mg, 9.8%). ¹H NMR (400 MHz, MeOD₋d₄): δ 1.79 (d, 3H, J=6.57 Hz), 3.39-3.12 (m, 8H), 3.70 (s, 3H), 3.92 (s, 3H), 4.70 (s, br, 1H), 7.17 (d, 2H, J=9.09 Hz), 7.76 (d, 2H, J=9.09 Hz), 7.87 (d, 1H, J=8.59 Hz), 8.47 (dd, 1H, J=8.59, 1.77 Hz), 8.89 (d, 1H, J=1.77 Hz). MS m/z calc. 510.18 found (ESI); 511.4 (M+1)⁺. Retention time 2.2 minutes.

2-{1-[4-(4-Chloro-benzenesulfonyl)-piperazin-1-yl]-ethyl}-3-methyl-6-(1H-tetrazol-5-yl)-3H-quinazolin-4-one

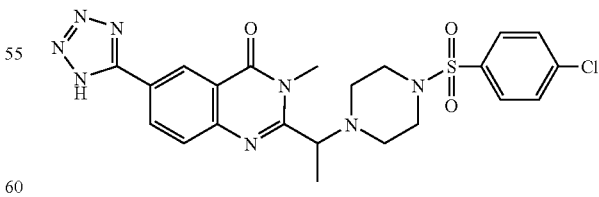

2-{1-[4-(4-Chloro-benzenesulfonyl)-piperazin-1-yl]-ethyl}-3-methyl-6-(1H-tetrazol-5-yl)-3H-quinazolin-4-one compound was synthesized by using the same method as described as above (Yield 40.0 mg, 38.9%). ¹H NMR (400 MHz, MeOD₋d₄): δ 1.64 (d, 3H, J=6.06 Hz), 3.12-3.04 (m, 4H), 3.16-3.54 (m, 4H), 3.70 (s, 3H), 4.64 (s, br, 3H), 7.71-

7.63 (m, 2H), 7.83-7.76 (m, 2H), 7.87 (d, 1H, J=8.84 Hz), 7.98 (s, 1H), 8.46 (dd, 1H, J=8.59, 2.02 Hz), 8.88 (d, 1H J=2.02 Hz). MS m/z calc. 514.1 found (ESI); 515.1 (M+1)⁺. Retention time 2.71 minutes.

2-{1-[4-(4-Methoxy-benzenesulfonyl)-piperazin-1-yl]-ethyl}-3-methyl-4-oxo-3,4-dihydro-quinazoline-6-carboxylic acid amide

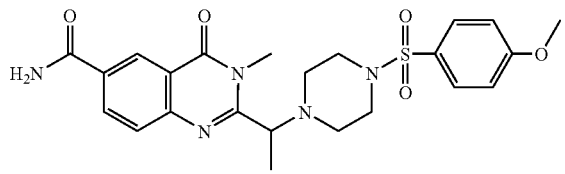 [SMILES: COc1ccc(S(=O)(=O)N2CCN(C(C)c3nc4ccc(C(N)=O)cc4c(=O)n3C)CC2)cc1]

To the 2 ml 6 N HCl solution of 2-{1-[4-(4-Methoxy-benzenesulfonyl)-piperazin-1-yl]-ethyl}-3-methyl-4-oxo-3,4-dihydro-quinazoline-6-carbonitrile (40.0 mg, 0.085 mmol) was heated at 90° C. for 18 hours. The mixture was cooled to room temperature, the solvent was removed by reduce pressure and extracted with water and ethyl acetate, dried over anhydrous MgSO₄, and concentrated by rotary evaporation. Purification was accomplished by HPLC (Gilson-215, 0.035% TFA in acetonitrile and 0.05% water as mobile phase). The product was collected and dried under reduced pressure to give the 2-{1-[4-(4-Methoxy-benzenesulfonyl)-piperazin-1-yl]-ethyl}-3-methyl-4-oxo-3,4-dihydro-quinazoline-6-carboxylic acid amide compound (Yield 20.9 mg, 50.69%). ¹H NMR (400 MHz, MeOD_d4): δ 1.64 (d, 3H, J=6.57 Hz), 3.35-3.29 (m, 8H), 3.67 (s, 3H), 3.92 (s, 3H), 4.70 (s, br, 1H), 7.17 (d, 2H, J=8.84 Hz), 7.78-7.76 (m, 3H), 8.38 (dd, 1H, J=8.59, 2.02 Hz), 8.88 (d, 1H J=2.02 Hz). MS m/z calc. 485.17 found (ESI); 487.2 (M+1)⁺. Retention time 2.18 minutes.

2-{1-[4-(4-Bromo-benzenesulfonyl)-piperazin-1-yl]-ethyl}-3-methyl-4-oxo-3,4-dihydro-quinazoline-6-carboxylic acid amide

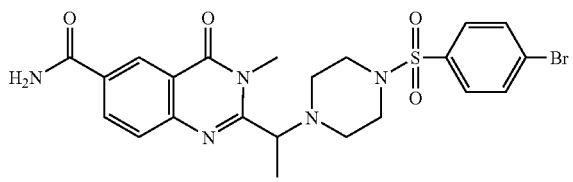 [SMILES: CC(c1nc2ccc(C(N)=O)cc2c(=O)n1C)N1CCN(S(=O)(=O)c2ccc(Br)cc2)CC1]

2-{1-[4-(4-Bromo-benzenesulfonyl)-piperazin-1-yl]-ethyl}-3-methyl-4-oxo-3,4-dihydro-quinazoline-6-carboxylic acid amide compound was synthesized by using the same method as described as above (Yield 13.9 mg, 45.0%). ¹H NMR (400 MHz, MeOD_d4): δ 1.64 (d, 3H, J=6.57 Hz), 3.39-3.20 (s, br, 8H), 3.68 (s, 3H), 4.67 (s, br, 1H), 7.77-7.72 (m, 3H), 7.88-7.84 (m, 2H), 8.38 (dd, 1H, J=8.34, 2.02 Hz), 7.87 (d, 1H, J=2.02 Hz). MS m/z calc. 533.06 found (ESI); 537.2 (M+1)⁺. Retention time 2.74 minutes.

2-{1-[4-(4-Chloro-benzenesulfonyl)-piperazin-1-yl]-ethyl}-3-methyl-4-oxo-3,4-dihydro-quinazoline-6-carboxylic acid amide

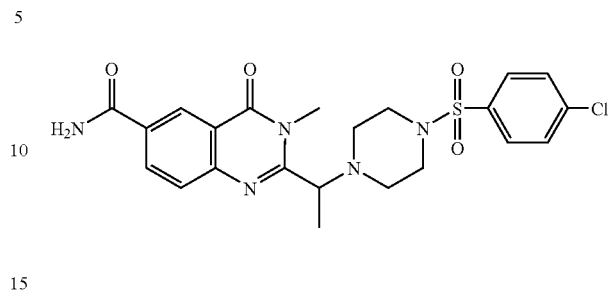

2-{1-[4-(4-Chloro-benzenesulfonyl)-piperazin-1-yl]-ethyl}-3-methyl-4-oxo-3,4-dihydro-quinazoline-6-carboxylic acid amide compound was synthesized by using the same method as described as above (Yield 12.7 mg, 40.8%). ¹H NMR (400 MHz, MeOD_d4): δ 1.65 (d, 3H, J=7.07 Hz), 3.34-3.33 (s, br, 8H), 3.67 (s, 3H), 4.67 (s, br, 1H), 7.70 (d, 2H, J=8.59 Hz), 7.75 (d, 1H, J=8.59 Hz), 7.82 (d, 2H, J=8.59 Hz), 8.38 (dd, 1H, J=8.59, 1.77 Hz), 8.89 (d, J=1.77 Hz). MS m/z calc. 489.11 found (ESI); 491.0 (M+1)⁺. Retention time 2.69 minutes.

6-Amino-2-{1-[4-(4-methoxy-benzenesulfonyl)-piperazin-1-yl]-ethyl}-3-methyl-3H-quinazolin-4-one

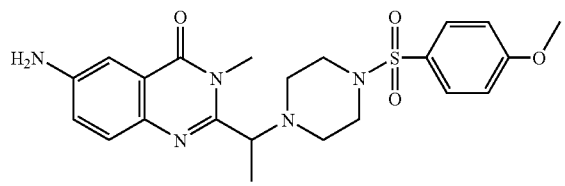 [SMILES: COc1ccc(S(=O)(=O)N2CCN(C(C)c3nc4ccc(N)cc4c(=O)n3C)CC2)cc1]

To the 15 ml ethanol solution of 2-{1-[4-(4-Methoxy-benzenesulfonyl)-piperazin-1-yl]-ethyl}-3-methyl-6-nitro-3H-quinazolin-4-one (560.0 mg, 1.14 mmol) was added ZnCl₂ (1.08 g, 5.7 mmol). The reaction was refluxed for 2 hours with vigorous agitation by a magnetic stirrer. The mixture was cooled to room temperature, the solvent was removed by reduce pressure and extracted with Na₂CO₃ aqueous and ethyl acetate, dried over anhydrous MgSO₄, and concentrated by rotary evaporation. Purification was accomplished by HPLC (Gilson-215, 0.035% TFA in acetonitrile and 0.05% water as mobile phase). The product was collected and dried under reduced pressure to give 6-Amino-2-{1-[4-(4-methoxy-benzenesulfonyl)-piperazin-1-yl]-ethyl}-3-methyl-3H-quinazolin-4-one (Yield 427.3 mg, 81.9%). ¹H NMR (400 MHz, DMSO_d6): δ 1.72 (d, 3H, J=6.57 Hz), 3.44-3.29 (m, 4H), 3.62-3.50 (m, 4H), 3.65 (s, 3H), 3.93 (s, 3H), 4.70 (q, 1H, J=12.88, 6.82 Hz), 7.19 (d, 2H, J=8.84 Hz), 7.49 (dd, 1H, J=8.84, 2.53 Hz), 7.65 (d, 1H, J=8.59 Hz), 7.81-7.77 (m, 3H). MS m/z calc. 457.2 found (ESI); 458.2 (M+1)⁺. Retention time 2.28 minutes.

6-Amino-2-{1-[4-(4-bromo-benzenesulfonyl)-piperazin-1-yl]-ethyl}-3-methyl-3H-quinazolin-4-one

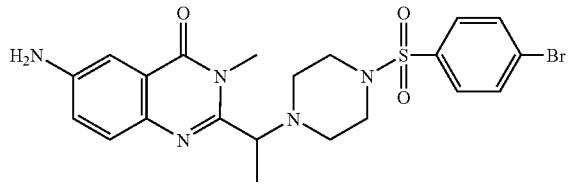 [SMILES: CC(c1nc2ccc(N)cc2c(=O)n1C)N1CCN(S(=O)(=O)c2ccc(Br)cc2)CC1]

6-Amino-2-{1-[4-(4-bromo-benzenesulfonyl)-piperazin-1-yl]-ethyl}-3-methyl-3H-quinazloin-4-one compound was synthesized by using the same method as described as above (Yield 448.3 mg, 85.0%). $^1$H NMR (400 MHz, MeOD$_{-d4}$): δ 1.55-1.32 (m, 3H), 3.35-2.85 (m, 8H), 3.52 (s, 3H), 4.53 (s, br, 1H), 7.10 (dd, 1H, J=8.59, 2.53 Hz), 7.23 (d, 1H, J=2.53 Hz), 7.39 (d, 1H, J=8.84 Hz), 7.58 (d, 2H, J=8.08 Hz). 7.91 (d, 2H, J=7.83 Hz), MS n/z calc. 507.2 found (ESI); 508.0 (M+1)$^+$. Retention time 2.52 minutes.

N-(2-{1-[4-(4-Methoxy-benzenesulfonyl)-piperazin-1-yl]-ethyl}-3-methyl-4-oxo-3,4-dihydro-quinazolin-6-yl)-acetamide

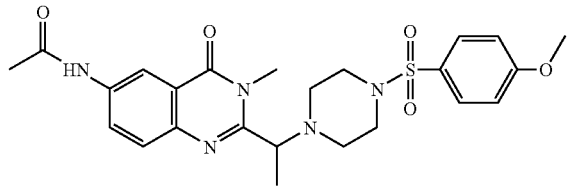 [SMILES: COc1ccc(S(=O)(=O)N2CCN(C(C)c3nc4ccc(NC(C)=O)cc4c(=O)n3C)CC2)cc1]

To the 1 ml DMF solution of 6-Amino-2-{1-[4-(4-methoxy-benzenesulfonyl)-piperazin-1-yl]-ethyl}-3-methyl-3H-quinazolin-4-one (50.0 mg, 0.11 mmol) was added acetyl chloride (9.44 mg, 0.12 mmol). The reaction was stirred for 2 hours. The solvent was removed by reduce pressure and extracted with Na$_2$CO$_3$ aqueous and ethyl acetate, dried over anhydrous MgSO$_4$, and concentrated by rotary evaporation. Purification was accomplished by HPLC (Gilson-215, 0.035% TFA in acetonitrile and 0.05% water as mobile phase). The product was collected and dried under reduced pressure to give the N-(2-{1-[4-(4-Methoxy-benzenesulfonyl)-piperazin-1-yl]-ethyl}-3-methyl-4-oxo-3,4-dihydro-quinazolin-6-yl)-acetamide (Yield 8.29 mg, 14.9%). $^1$H NMR (400 MHz, MeOD$_{-d4}$): δ 1.70 (d, 3H, J=6.57 Hz), 2.18 (s, 3H), 3.57-3.43 (m, 8H), 3.64 (s, 3H), 3.93 (s, 3H), 4.84 (q, 1H, J=6.57, 6.06 Hz), 7.19 (d, 2H, J=9.09 Hz), 7.64 (d, 1H, J=8.34 Hz), 7.79 (d, 2H, J=9.09 Hz), 7.98 (dd, 1H, J=8.59, 2.78 Hz), 8.46 (d, J=2.27 Hz). MS m/z calc. 499.2 found (ESI); 500.2 (M+1)$^+$. Retention time 2.42 minutes.

3-Isobutyl-2-{1-[4-(4-methoxy-benzenesulfonyl)-piperazin-1-yl]-ethyl}-3H-quinazolin-4-one

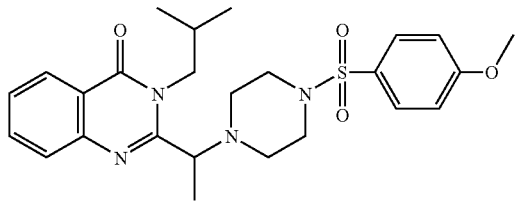 [SMILES: COc1ccc(S(=O)(=O)N2CCN(C(C)c3nc4ccccc4c(=O)n3CC(C)C)CC2)cc1]

In a flask containing of 2-{1-[4-(4-Methoxy-benzenesulfonyl)-piperazin-1-yl]-ethyl}-3H-quinazolin-4-one (50.0 mg, 0.12 mmol) in DMF was added I-Iodo-2-methylpropane (42.0 mg, 0.24 mmol), K$_2$CO$_3$ (80.0 mg, 0.6 mmol). The mixture was heated at 90° C. for 2 hours with stirring. After cooling down to room temperature, the excess K$_2$CO$_3$ was filtrated; the solution was treated with TFA (0.5 ml) and water (0.1 ml) with stirring at 90° C. for 2 hrs. Purification by HPLC (Gilson-215, 0.035% TFA in acetonitrile and 0.05% water as mobile phase) yielded 3-Isobutyl-2-{1-[4-(4-methoxy-benzenesulfonyl)-piperazin-1-yl]-ethyl}-3H-quinazolin-4-one (Yield 21.0 mg, 37.0%) that was dried under reduced pressure. $^1$H NMR (400 MHz, DMSO-$_6$): δ 0.98 (d, 3H, J=6.82 Hz), 1.01 (d, 3H, J=6.82 Hz), 1.76 (d, 3H, J=6.82 Hz), 2.08-1.99 (m, 1H), 3.51-3.19 (m, 6H), 3.86-3.75 (m, 2H), 3.93 (s. 3H), 4.16-3.93 (m, 2H), 4.84 (q, 1H, J=12.88, 7.07 Hz), 7.03 (dd, 2H, J=6.82, 2.27 Hz), 7.57 (dt, 1H, J=8.08, 1.01 Hz), 7.67 (dd, 2H, J=6.82, 2.27 Hz), 7.71 (d, 1H, J=8.08 Hz), 7.82 (dt, 1H, 8.59, 1.52 Hz), 8.39 (dd, 1H, J=8.08, 1.52 Hz). MS m/z calc. 484.21, found (ESI); 485.3 (M+1)$^+$. Retention time 2.83 minutes.

5-Chloro-2-isobutyrylamino-benzoic acid

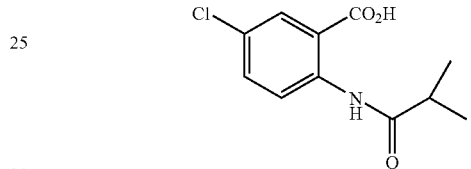

To a solution of 2-amino-5-chloro-benzoic acid (3.43 g, 20 mmol) in DMF (10 mL) cooled in an ice-water bath was added isobutyryl chloride (2.11 mL, 20 mmol). The reaction was stirred for 2 hours while warming to room temperature. Water (20 mL) was added and the mixture was stirred vigorously for 1 hour. The precipitate was then collected by vacuum filtration to give the product as a pale yellow solid (3.20 g, 66%). $^1$H NMR (400 MHz, DMSO-d6) δ 11.13 (s, 1H), 8.52 (d, J=9.0 Hz, 1H), 7.92 (d, J=2.6 Hz, 1H), 7.66 (dd, J=9.0, 2.7 Hz, 1H), 2.58 (septet, J=6.9 Hz, 1H), 1.16 (d, J=6.9 Hz, 6H).

6-Chloro-2-isopropyl-benzo[d][1,3]oxazin-4-one

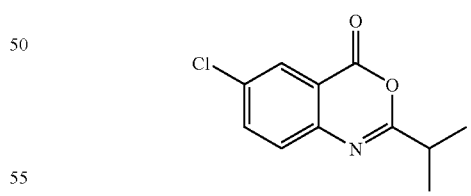

A mixture of 2-amino-5-chloro-benzoic acid (3.02 g, 12.5 mmol) and acetic anhydride (25 mL) were heated to reflux for 2 hours until TLC indicated that no more starting material remained. The remaining acetic anhydride was removed in vacuo. Toluene (2 mL) was added and then removed in vacuo. This was repeated 2 more times to try and remove final traces of acetic anhydride. The product was obtained as an orange solid (2.75 g, 98%). $^1$H NMR (400 MHz, DMSO-d6) δ 8.07 (d, J=2.5 Hz, 1H), 7.94 (dd, J=8.6, 2.5 Hz, 1H), 7.63 (d, J=8.6 Hz, 1H), 2.92 (septet, J=6.9 Hz, 1H), 1.28 (d, J=6.9 Hz, 6H).

6-Chloro-2-isopropyl-3-methyl-3H-quinazolin-4-one

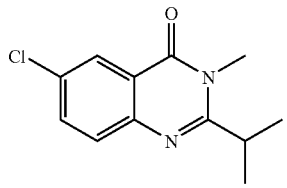 [SMILES: CC(C)c1nc2ccc(Cl)cc2c(=O)n1C]

A mixture of 6-chloro-2-isopropyl-benzo[d][1,3]oxazin-4-one (2.75 g, 12.3 mmol) and methylamine (7.4 mL, 14.8 mmol, 2M solution in MeOH) were heated to 90° C. for 24 hours. The solvent was removed in vacuo and the residue was heated under reduced pressure to 160° C. for 2 hours. The reaction mixture was purified by column chromatography (0-30% ethyl acetate-hexanes) to yield the product (960 mg, 33%). $^1$H NMR H NMR (400 MHz, CDCl3) δ 8.23 (d, J=2.4 Hz, 1H), 7.65 (dd, J=8.7, 2.4 Hz, 1H), 7.61 (d, J=8.8 Hz, 1H), 3.69 (s, 3H), 3.22 (septet, J=6.7 Hz, 1H), 1.39 (d, J=6.7 Hz, 6H).

2-(1-Bromo-1-methyl-ethyl)-6-chloro-3-methyl-3H-quinazolin-4-one

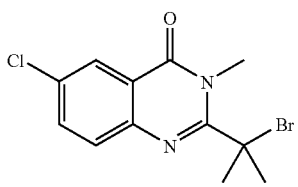 [SMILES: Cn1c(C(C)(C)Br)nc2ccc(Cl)cc2c1=O]

A solution of 6-chloro-2-isopropyl-3-methyl-3H-quinazolin-4-one (880 mg, 3.7 mmol), N-bromosuccinimide (662 mg, 3.7 mmol) and benzoyl peroxide (catalytic amount) in chloroform (20 mL) was heated to reflux for 2 hours. The reaction solution was concentrated in vacuo and purified by column chromatography (0-25% ethyl acetate-hexanes) to yield the product as a white solid (880 mg, 76%). $^1$H NMR (400 MHz, CDCl3) δ 8.26 (dd, J=2.3, 0.3 Hz, 1H), 7.69 (dd, J=8.7, 2.4 Hz, 1H), 7.64 (dd, J=8.6, 0.3 Hz, 1H), 3.98 (s, 3H), 2.30 (s, 3H); HPLC ret. time 3.75 min, 10-99% CH$_3$CN, 5 min run; ESI-MS m/z 317.0 (M+1)$^+$.

6-Chloro-2-{1-[4-(4-methoxy-benzenesulfonyl)-piperazin-1-yl]-1-methyl-ethyl}-3-methyl-3H-quinazolin-4-one

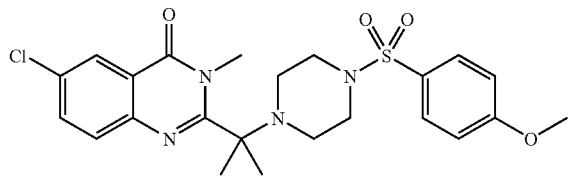 [SMILES: COc1ccc(S(=O)(=O)N2CCN(C(C)(C)c3nc4ccc(Cl)cc4c(=O)n3C)CC2)cc1]

To a solution of 1-(4-methoxy-benzenesulfonyl)-piperazine (51 mg, 0.2 mmol) in THF (0.5 mL) cooled to −78° C. was added butyl lithium (125 μL, 0.2 mmol, 1.6M solution in hexanes). This solution was allowed to stir for 10 minutes and then was transferred by syringe to a reaction tube containing a solution of 2-(1-Bromo-1-methyl-ethyl)-6-chloro-3-methyl-3H-quinazolin-4-one (32 mg, 0.1 mmol) in THF (0.5 mL) also cooled to −78° C. The reaction was allowed to slowly warm to room temperature while stirring overnight. The solution was then filtered and concentrated in vacuo. The residue was dissolved in DMSO and purified by LC-MS to yield the product (14 mg, 29%). $^1$H NMR (400 MHz, CDCl3) δ 8.21 (d, J=2.3 Hz, 1H), 7.69 (m, 3H), 7.62 (d, J=8.7 Hz, 1H), 7.04 (d, J=8.9 Hz, 2H), 3.92 (s, 3H), 3.89 (s, 3H), 2.86 (m, 8H), 1.62 (s, 6H); HPLC ret. time 3.61 min, 10-99% CH$_3$CN, 5 min run; ESI-MS m/z 491.2 (M+1)$^+$.

2-(1-Bromo-ethyl)-3H-quinazolin-4-one

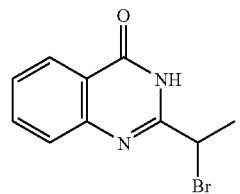

To a solution of 2-ethyl-3H-quinazolin-4-one (3.0 g, 17.22 mmol) in glacial acetic acid (50 ml) cooled in an ice bath was added dropwise a solution of bromine (2.75 g, 17.22 mmol) in glacial acetic acid (5 ml). After addition was complete, the reaction was heated to reflux for 18 hours. At which time it was allowed to cool to room temperature. Water was then added to the solution and the mixture was extracted with dichloromethane. The organic layer was then washed with 10% sodium bisulfite solution, and then washed with saturated brine (2×30 ml). The combined organic phase was collected and dried over magnesium sulfate, filtered and concentrated under reduced pressure to yield a brown crude product. The resulting residue was purified by silica gel chromatography with 50% dichloromethane in hexane. The product was collected and was dried under reduced pressure to give 2-(1-Bromo-ethyl)-3H-quinazolin-4-one (Yield 3.02 g, 69.74%). $^1$H NMR (400 MHz, DMSO-$d_6$): δ 2.22 (d, 3H, J=6.57 Hz), 5.09 (q, 1H, J=14.40, 6.57 Hz), 7.57 (m, 1H), 7.69 (d, 1H, J=8.08 Hz), 7.87-7.80 (m, 1H), 8.12 (d, 1H, J=6.82 Hz), 12.42 (s, 1H). MS m/z calc. 251.99, found (ESI); 253.0 (M+1)$^+$. Retention time 2.60 minutes.

Benzenesulfonic acid, 4-methoxy-, [[(4-methoxyphenyl)sulfonyl]imino]di-2,1-ethanediyl ester

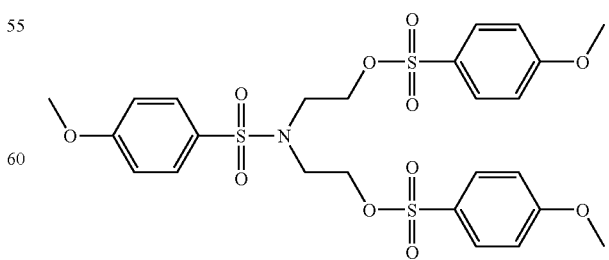

To a solution of 2-(2-hydroxy-ethylamino)-ethanol (7 g, 67 mmol) and 4-methoxybenzenesulfonyl chloride (40 g, 194 mmol) in THF (400 mL) KOH (100 mL, 40%) was added dropwise at 0° C., after stirring over 3 hr the mixture was filtrated and THF was evaporated in vacuo, then extracted with EtOAc (500 mL). The organic layer was washed with brine and dried over Na$_2$SO$_4$, filtered, and concentrated in vacuo. The residue was purified by silica gel column to afford Benzenesulfonic acid, 4-methoxy-, [[(4-methoxyphenyl)sulfonyl]imino]di-2,1-ethanediyl ester as a colorless gum (20 g, 49%). $^1$H NMR (DMSO-d$_6$) δ 7.81 (d, J=4.8 Hz, 4H), 7.79 (d, J=5.2 Hz, 2H), 7.01 (d, J=4.8 Hz, 4H), 6.93 (d, J=5.2 Hz, 2H), 4.08 (t, J=6 Hz, 4H), 3.88 (s, 6H), 3.86 (s, 3H), 3.35 (t, J=6 Hz, 4H). MS (ESI) m/z (M+1)$^+$: 615.7.

[4-(4-Methoxy-benzenesulfonyl)-piperazin-1-yl]-acetic acid tert-butyl ester

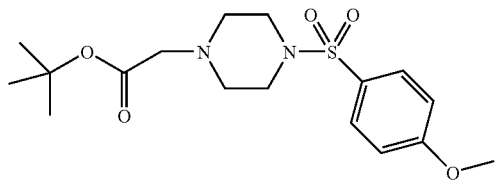 [SMILES: COc1ccc(S(=O)(=O)N2CCN(CC(=O)OC(C)(C)C)CC2)cc1]

A mixture of glycine tert-butyl ester hydrochloride (840 mg, 5 mmol) and benzenesulfonic acid, 4-methoxy-, [[(4-methoxyphenyl)sulfonyl]imino]di-2,1-ethanediyl ester (3.07 g, 5 mmol), potassium iodide (1.66 g, 10 mmol) and potassium carbonate (6.9 g, 50 mmol) in acetonitrile (50 mL) was heated at 65° C. for 3 days. The reaction mixture was then concentrated in vacuo. The residue was dissolved in dichloromethane and washed with water. The organic layer was dried over magnesium sulfate and concentrated in vacuo. The crude product was purified by column chromatography (25-50% ethyl acetate-hexanes) to yield the product as a clear oil (1.56 g, 84%). $^1$H NMR (400 MHz, CDCl3) δ 7.69 (d, J=8.8 Hz, 2H), 6.99 (d, J=8.9 Hz, 2H), 3.88 (s, 3H), 3.10 (s, 2H), 3.06 (m, 4H), 2.65 (m, 4H), 1.45 (s, 9H)

[4-(4-Methoxy-benzenesulfonyl)-piperazin-1-yl]-acetic acid

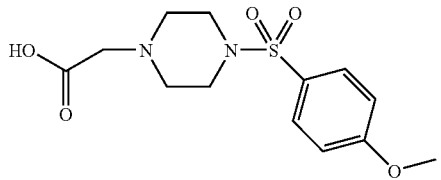 [SMILES: COc1ccc(S(=O)(=O)N2CCN(CC(=O)O)CC2)cc1]

Trifluoroacetic acid (2.5 mL) was added to a solution of [4-(4-methoxy-benzenesulfonyl)-piperazin-1-yl]-acetic acid tert-butyl ester (1.48 g, 4 mmol) in dichloromethane (10 mL). The reaction was stirred at room temperature for 3 days. The solvent was removed in vacuo and the residue was triturated with diethyl ether. Filtration yielded the product as a white solid (1.25 g, quant.). $^1$H NMR (400 MHz, DMSO-d6) δ 7.70 (dt, J=9.6, 2.4 Hz, 2H), 7.21 (dt, J=9.6, 2.4 Hz, 2H), 3.86 (m, 5H), 3.09 (m, 8H).

2-{2-[4-(4-Methoxy-benzenesulfonyl)-piperazin-1-yl]-acetylamino}-benzamide

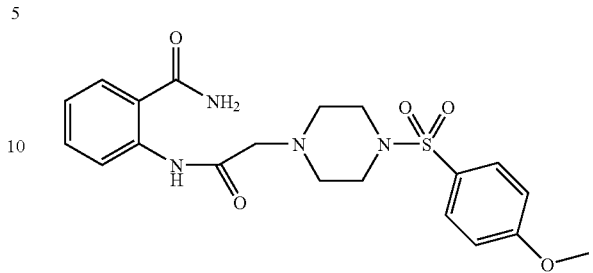

To a mixture of [4-(4-methoxy-benzenesulfonyl)-piperazin-1-yl]-acetic acid (1.10 g, 3.5 mmol), HATU (1.33 g, 3.5 mmol) and DIEA (1.22 mL, 7 mmol) in dichloromethane (40 mL) was added anthranilamide (714 mg, 5.25 mmol). The reaction was stirred at room temperature for 1 hour and then the reaction mixture was concentrated in vacuo. The residue was partitioned between ethyl acetate and saturated sodium bicarbonate solution. The organic layer was dried over magnesium sulfate and concentrated in vacuo. The crude product was purified by column chromatography (50-100% ethyl acetate-hexanes) to yield the pure product. (1.18 g, 78%). $^1$H NMR (400 MHz, CDCl3) δ 11.82 (s, 1H), 8.66 (d, J=8.0 Hz, 1H), 7.77 (d, J=7.0 Hz, 2H), 7.51 (m, 2H), 7.11 (t, J=7.6 Hz, 1H), 7.05 (d, J=7.1 Hz, 2H), 6.10 (br s, 1H), 5.51 (br s, 1H), 3.92 (s, 3H), 3.24 (m, 6H), 2.76 (t, J=4.7 Hz, 4H); HPLC ret. time 2.46 min, 10-99% CH$_3$CN, 5 min run; ESI-MS m/z 433.1 (M+1)$^+$.

2-[4-(4-Methoxy-benzenesulfonyl)-piperazin-1-ylmethyl]-3H-quinazolin-4-one

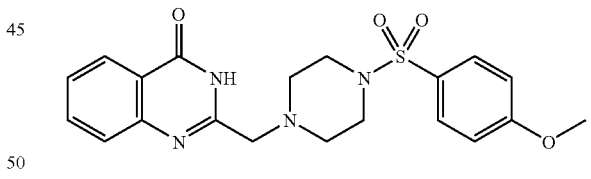

A mixture of 2-{2-[4-(4-methoxy-benzenesulfonyl)-piperazin-1-yl]-acetylamino}-benzamide (432 mg, 1 mmol), 1N sodium hydroxide solution (5 mL) and 1,4-dioxane (5 mL) was stirred a room temperature for 1 day. The reaction mixture was concentrated to approximately half the volume and then neutralized with 1N HCl solution. The product precipitated and was collected by filtration as a white solid (306 mg, 74%). $^1$H NMR (400 MHz, CDCl3) δ 8.26 (dd, J=8.0, 1.3 Hz, 1H), 7.79 (t, J=8.4 Hz, 1H), 7.73 (dt, J=9.5, 2.5 Hz, 2H), 7.68 (d, J=7.7 Hz, 1H), 7.51 (t, J=8.1 Hz, 1H), 7.08 (dt, J=9.5, 2.4 Hz, 2H), 3.94 (s, 3H), 3.65 (s, 2H), 3.11 (m, 4H), 2.75 (t, J=4.9 Hz, 4H); HPLC ret. time 2.59 min, 10-99% CH$_3$CN, 5 min run; ESI-MS m/z 415.3 (M+1)$^+$.

2-[4-(4-Methoxy-benzenesulfonyl)-piperazin-1-ylm-ethyl]-4-piperidin-1-yl-quinazoline

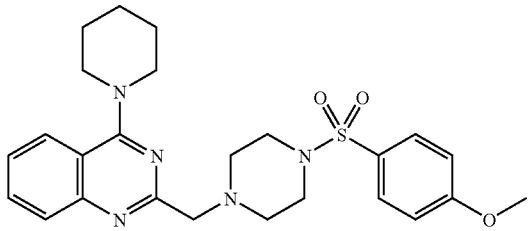 [SMILES: COc1ccc(S(=O)(=O)N2CCN(Cc3nc(N4CCCCC4)c4ccccc4n3)CC2)cc1]

2-[4-(4-Methoxy-benzenesulfonyl)-piperazin-1-ylm-ethyl]-3H-quinazolin-4-one (83 mg, 0.2 mmol) in POCl₃ (1 mL) was heated to 90° C. for 2 hours. Then the excess POCl₃ was removed in vacuo. The residue was dissolved in toluene (5 mL) and then the solvent was removed in vacuo. This step was repeated twice more. The residue was then dissolved in THF (1 mL) and piperidine (197 μL, 2 mmol) was added. The reaction was stirred at room temperature for 1 day. The reaction mixture was partitioned between dichloromethane and water. The organic layer was dried over magnesium sulfate and concentrated in vacuo. The crude product was purified by HPLC. $^1$H NMR (400 MHz, CDCl3) δ 7.92 (m, 3H), 7.67 (m, 3H), 7.03 (d, J=8.8 Hz, 2H), 4.70 (s, 2H), 4.12 (s, 4H), 3.90 (s, 3H), 3.45 (m, 8H), 1.88 (m, 6H); HPLC ret. time 2.61 min, 10-99% CH₃CN, 5 min run; ESI-MS m/z 482.0 (M+1)⁺.

4-Cyclohexyloxy-2-[4-(4-methoxy-benzenesulfo-nyl)-piperazin-1-ylmethyl]-quinazoline

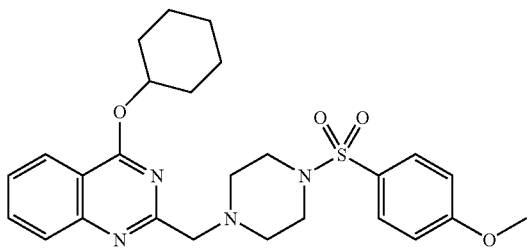 [SMILES: COc1ccc(S(=O)(=O)N2CCN(Cc3nc(OC4CCCCC4)c4ccccc4n3)CC2)cc1]

2-[4-(4-Methoxy-benzenesulfonyl)-piperazin-1-ylm-ethyl]-3H-quinazolin-4-one (83 mg, 0.2 mmol) in POCl₃ (1 mL) was heated to 90° C. for 2 hours. Then the excess POCl₃ was removed in vacuo. The residue was dissolved in toluene (5 mL) and then the solvent was removed in vacuo. This step was repeated twice more. The residue was then dissolved in THF (1 mL) and cyclohexanol (211 μL, 2 mmol) was added. The reaction was stirred at room temperature for 1 day. The reaction mixture was partitioned between dichloromethane and water. The organic layer was dried over magnesium sulfate and concentrated in vacuo. The crude product was purified by HPLC (in the absence of TFA). $^1$H NMR (400 MHz, CDCl3) δ 8.16 (d, J=7.5 Hz, 1H), 7.89 (d, J=8.3 Hz, 1H), 7.79 (t, J=7.3 Hz, 1H), 7.72 (dt, J=9.5, 2.4 Hz, 2H), 7.52 (t, J=7.4 Hz, 1H), 7.01 (dt, J=9.5, 2.4 Hz, 2H), 5.39 (quintet, J=4.2 Hz, 1H), 3.90 (m, 5H), 3.16 (m, 4H), 2.90 (m, 4H), 1.66 (m, 10H); HPLC ret. time 2.93 min, 10-99% CH₃CN, 5 min run; ESI-MS m/z 497.3 (M+1)⁺.

4-Cyclopentyloxy-2-[4-(4-methoxy-benzenesulfo-nyl)-piperazin-1-ylmethyl]-quinazoline

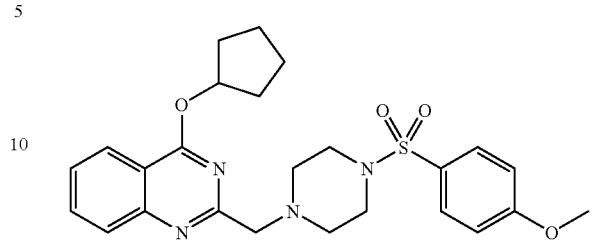

A mixture of 2-[4-(4-Methoxy-benzenesulfonyl)-piper-azin-1-ylmethyl]-3H-quinazolin-4-one (83 mg, 0.2 mmol), cyclopentyl iodide (46 μL, 0.4 mmol), and potassium carbonate (138 mg, 1 mmol) in DMF (1 mL) was heated to 90° C. for 1 day. The reaction mixture was partitioned between dichloromethane and water. The organic layer was concentrated in vacuo and the residue was purified by HPLC (in the absence of TFA) to yield the product. $^1$H NMR (400 MHz, CDCl3) δ 8.11 (d, J=8.1 Hz, 1H), 7.88 (d, J=8.4 Hz, 1H), 7.78 (t, J=7.6 Hz, 1H), 7.71 (d, J=8.8 Hz, 2H), 7.51 (t, J=7.5 Hz, 1H), 7.00 (d, J=8.8 Hz, 2H), 5.73 (quintet, J=3.0 Hz, 1H), 3.88 (m, 5H), 3.12 (m, 4H), 2.84 (m, 4H), 1.90 (m, 8H); HPLC ret. time 2.85 min, 10-99% CH₃CN, 5 min run; ESI-MS m/z 483.5 (M+1)⁺.

2-{1-[4-(4-Methoxy-benzenesulfonyl)-piperazin-1-yl]-ethyl}-3H-quinazolin-4-one

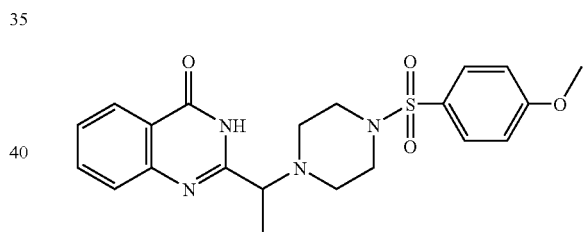

In a flask containing of 2-(1-bromo-ethyl)-3H-quinazolin-4-one (500.0 mg, 0.20 mmol) in acetonitrile (20 ml) was added KI (496.0 mg, 0.30 mmol), and 1-(4-methoxy-benze-nesulfonyl)-piperazine (509.6 mg, 0.20 mmol). The reaction was heated for 18 hours. The solution was concentrated under reduced pressure. The residue was partitioned between water (20 ml) and dichloromethane (20 ml). The organic layer was dried over magnesium sulfate, filtered and concentrated under reduced pressure. The solvent was removed under vacuum. The resulting residue was purified by silica gel chromatography with 50% dichloromethane in hexane. The product was collected and dried under reduced pressure to give 2-{1-[4-(4-Methoxy-benzenesulfonyl)-piperazin-1-yl]-ethyl}-3H-quinazolin-4-one (Yield 385.0 mg, 45.18%). $^1$H NMR (400 MHz, DMSO-₆): δ 1.25 (d, 3H, J=6.82 Hz), 2.67-2.56 (m, 4H), 2.88 (s, br, 4H), 3.85 (s, 3H), 3.53 (q, 1H, J=13.89, 6.82 Hz), 7.15 (d, 2H, J=8.84), 7.34 (t, 1H, J=7.33 Hz), 7.51 (d, 1H, J=8.34 Hz), 7.68-7.61 (m, 3H), 8.00 (d, 1H, J=7.83 Hz). MS m/z calc. 428.15, found (ESI); 429.4 (M+1)⁺. Retention time 2.68 minutes.

371

4-Chloro-2-{1-[4-(4-methoxy-benzenesulfonyl)-piperazin-1-yl]-ethyl}-quinazoline

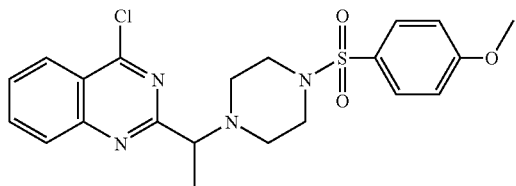 [SMILES: COc1ccc(S(=O)(=O)N2CCN(C(C)c3nc(Cl)c4ccccc4n3)CC2)cc1]

In a flask containing of 2-{1-[4-(4-methoxy-benzenesulfonyl)-piperazin-1-yl]-ethyl}-3H-quinazolin-4-one (380.0 mg, 0.89 mmol) in phosphorus oxychloride (20 ml) was heated to 90° C. for 2 hours, then the solvent was concentrated under reduced pressure to give 4-Chloro-2-{1-[4-(4-methoxy-benzenesulfonyl)-piperazin-1-yl]-ethyl}-quinazoline (Yield 394.2 mg, 100%) that was used directly without further purification. $^1$H NMR (400 MHz, CDCl$_3$): δ 1.93 (d, 3H, J=6.82 Hz), 3.23-3.04 (m, 3H), 3.54-3.34 (m, 1H), 3.87-3.65 (m, 4H), 3.90 (s, 3H), 4.77 (q, 1H, J=14.15, 6.82 Hz), 7.05 (d, 2H, J=8.84), 7.69 (d, 2H, J=8.84), 7.87 (t, H, J=7.84), 8.10 (t, 1H, J=8.34 Hz), 8.18 (d, 1H, 8.34 Hz), 8.35 (d, 1H, 8.34 Hz). MS m/z calc. 446.12, found (ESI); 447.4 (M+1)$^+$. Retention time 2.67 minutes.

4-Methoxy-2-{1-[4-(4-methoxy-benzenesulfonyl)-piperazin-1-yl]-ethyl}-quinazoline

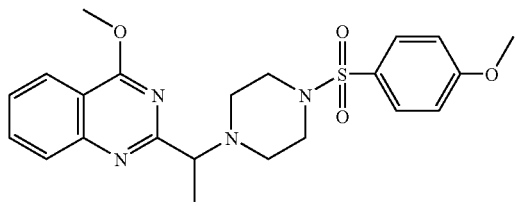 [SMILES: COc1ccc(S(=O)(=O)N2CCN(C(C)c3nc(OC)c4ccccc4n3)CC2)cc1]

In a test tube containing of 4-Chloro-2-{1-[4-(4-methoxy-benzenesulfonyl)-piperazin-1-yl]-ethyl}-quinazoline (38.0 mg, 0.089 mmol) in THF (2 ml) was added MeOH (280.0 mg, 8.9 mmol). The reaction was heated at 60° C. for 0.5 hour. The solution was concentrated under reduced pressure. The residue was partitioned between water (2 ml) and dichloromethane (5 ml). The organic layer was dried over magnesium sulfate, filtered and concentrated under reduced pressure. The solvent was removed under vacuum. The resulting residue was re-dissolvent in MeOH (2 ml) and purified by HPLC (Gilson-215, 0.035% TFA in acetonitrile and 0.05% water as mobile phase). The product was collected and dried under reduced pressure to give 4-Methoxy-2-{1-[4-(4-methoxy-benzenesulfonyl)-piperazin-1-yl]-ethyl}-quinazoline (Yield 4.43 mg, 11.13%). MS m/z calc. 442.17, found (ESI); 443.4 (M+1)$^+$. Retention time 2.40 minutes.

372

4-Ethoxy-2-{1-[4-(4-methoxy-benzenesulfonyl)-piperazin-1-yl]-ethyl}-quinazoline

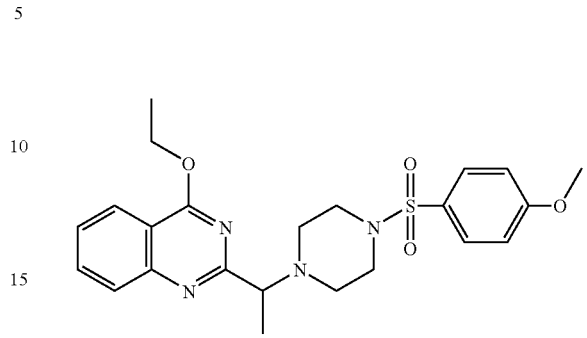

4-Ethoxy-2-{1-[4-(4-methoxy-benzenesulfonyl)-piperazin-1-yl]-ethyl}-quinazoline compound was synthesized by using the same method as described in Scheme V (Yield 4.59 mg, 11.30%). $^1$H NMR (400 MHz, CDCl$_3$): δ 1.54 (t, 3H, J=7.07 Hz), 1.87 (d, 3H, J=7.07 Hz), 3.61-3.31 (m, 6H), 3.76-3.61 (m, 2H), 3.89 (s, 3H), 4.73 (m, 1H), 7.02 (d, 2H, J=9.09 Hz), 7.71-7.62 (m, 3H), 7.96 (d, 1H, J=1.26 Hz), 7.96 (d, 2H J=1.26 Hz), 8.24 (d, 1H, J=8.08 Hz). MS m/z calc. 456.18, found (ESI); 457.4 (M+1)$^+$. Retention time 2.55 minutes.

2-{1-[4-(4-Methoxy-benzenesulfonyl)-piperazin-1-yl]-ethyl}-4-propoxy-quinazoline

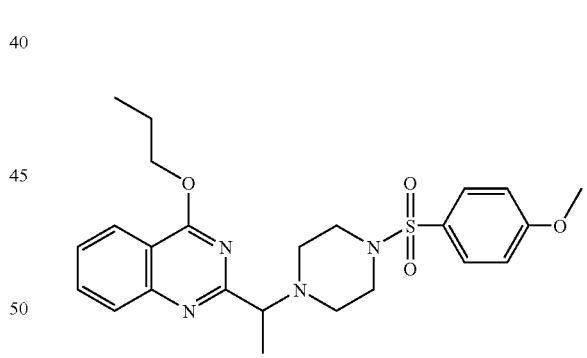

2-{1-[4-(4-Methoxy-benzenesulfonyl)-piperazin-1-yl]-ethyl}-4-propoxy-quinazoline compound was synthesized by using the same method as described in Scheme V (Yield 4.15 mg, 9.92%). $^1$H NMR (400 MHz, CDCl$_3$): δ 1.01-1.09 (m, 3H), 1.13 (t, 3H, J=7.33 Hz), 1.74-1.67 (m, 2H), 1.95-1.88 (m, 2H), 3.62-3.28 (m, 6H), 3.74-3.62 (m, 2H), 3.89 (s, 3H), 4.68 (q, 1H, J=13.64, 7.07 Hz), 7.04-7.00 (m, 2H), 7.70-7.64 (m, 3H), 7.98-7.92 (m, 2H), 8.24 (td, 1H, J=8.84, 1.01 Hz). MS m/z calc. 456.18, found (ESI); 457.4 (M+1)$^+$. Retention time 2.55 minutes.

4-Isopropoxy-2-{1-[4-(4-methoxy-benzenesulfonyl)-piperazin-1-yl]-ethyl}-quinazoline

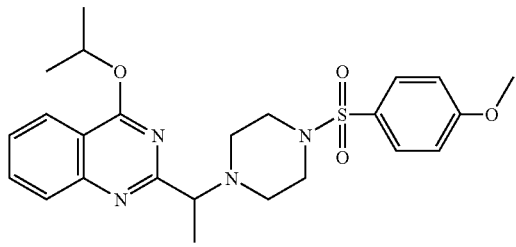 [SMILES: COc1ccc(S(=O)(=O)N2CCN(C(C)c3nc(OC(C)C)c4ccccc4n3)CC2)cc1]

4-Isopropoxy-2-{1-[4-(4-methoxy-benzenesulfonyl)-piperazin-1-yl]-ethyl}-quinazoline compound was synthesized by using the same method as described in Scheme V (Yield 1.89 mg, 4.51%). MS n/z calc. 470.20, found (ESI); 471.2 (M+1)$^+$. Retention time 2.84 minutes.

4-Cyclopentyloxy-2-{1-[4-(4-methoxy-benzene-sulfonyl)-piperazin-1-yl]-ethyl}-quinazoline

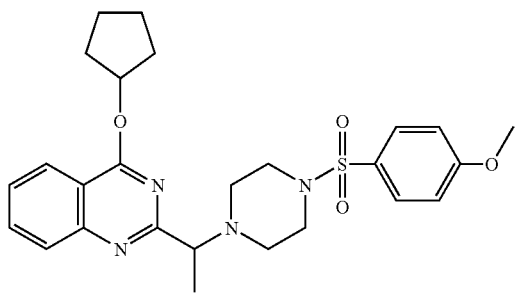 [SMILES: COc1ccc(S(=O)(=O)N2CCN(C(C)c3nc(OC4CCCC4)c4ccccc4n3)CC2)cc1]

4-Cyclopentyloxy-2-{1-[4-(4-methoxy-benzenesulfonyl)-piperazin-1-yl]-ethyl}-quinazolin was synthesized by using the same method as described in Scheme V (Yield 7.66 mg, 17.37%). $^1$H NMR (400 MHz, CDCl$_3$): δ 2.00-1.68 (m, 11H), 2.15-2.04 (m, 2H), 3.54-3.33 (m, 6H), 3.73-3.62 (m, 2H), 3.89 (s, 3H), 4.72 (q, 1H, J=13.39, 7.33 Hz), 7.02 (d, 2H, 9.09 Hz), 7.68-7.65 (m, 3H), 7.95 (td, 2H, J=8.08, 1.77 Hz), 8.19 (d, 1H, J=8.34 Hz). MS m/z calc. 496.21, found (ESI); 497.4 (M+1)$^+$. Retention time 2.84 minutes.

(2-{1-[4-(4-Methoxy-benzenesulfonyl)-piperazin-1-yl]-ethyl}-quinazolin-4-yl)-dimethyl-amine

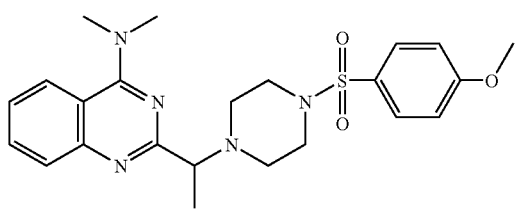 [SMILES: COc1ccc(S(=O)(=O)N2CCN(C(C)c3nc(N(C)C)c4ccccc4n3)CC2)cc1]

(2-{1-[4-(4-Methoxy-benzenesulfonyl)-piperazin-1-yl]-ethyl}-quinazolin-4-yl)-dimethyl was synthesized by using the same method as described in Scheme V. (Yield 26.25 mg, 66.86%). $^1$H NMR (400 MHz, CDCl$_3$): δ 1.74 (d, 3H, J=6.57 Hz), 3.33-3.31 (m, 6H), 3.58-3.43 (m, 2H), 3.87 (s, 3H), 5.00 (q, 1H, J=13.39, 6.82 Hz), 7.00 (d, 2H, 8.84 Hz), 7.61 (d, 2H, J=8.84), 7.65 (td, 1H, J=8.34, 1.26 Hz), 7.92 (td, 1H, J=8.34, 1.26 Hz), 8.22 (dd, 1H, J=8.59, 1.01 Hz), 8.13 (dd, 1H, J=8.59, 1.01 Hz). MS m/z calc. 455.20, found (ESI); 456.4 (M+1)$^+$. Retention time 2.15 minutes.

Ethyl-(2-{1-[4-(4-methoxy-benzenesulfonyl)-piperazin-1-yl]-ethyl}-quinazolin-4-yl)-amine

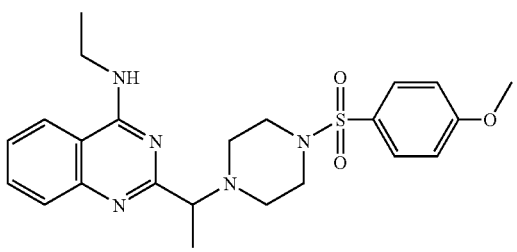 [SMILES: CCNc1nc(C(C)N2CCN(S(=O)(=O)c3ccc(OC)cc3)CC2)nc2ccccc12]

Ethyl-(2-{1-[4-(4-methoxy-benzenesulfonyl)-piperazin-1-yl]-ethyl}-quinazolin-4-yl)-amine was synthesized by using the same method as described as Scheme V. (Yield 9.53 mg, 23.53%). $^1$H NMR (400 MHz, MeOD-$_{d4}$): δ 1.38 (t, 3H, J=7.33 Hz), 1.54 (d, 3H, J=6.82 Hz), 2.84-2.77 (m, 2H), 2.93-2.86 (m, 2H), 3.16-3.10 (m, 4H), 3.85 (s, 3H), 3.97 (q, 1H, J=13.39, 6.82 Hz), 7.15 (d, 2H, J=8.84 Hz), 7.76-7.72 (m, 3H), 7.80 (d, 1H J=8.84 Hz), 7.98 (td, 1H, J=8.84, 1.26 Hz), 8.28 (d, 1H, J=8.34 Hz). MS m/z calc. 455.20, found (ESI); 456.4 (M+1)$^+$. Retention time 2.26 minutes.

Diethyl-(2-{1-[4-(4-methoxy-benzenesulfonyl)-piperazin-1-yl]-ethyl}-quinazolin-4-yl)-amine

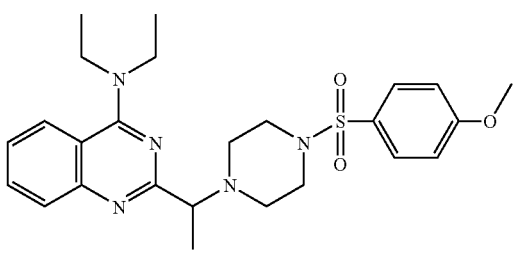 [SMILES: CCN(CC)c1nc(C(C)N2CCN(S(=O)(=O)c3ccc(OC)cc3)CC2)nc2ccccc12]

Diethyl-(2-{1-[4-(4-methoxy-benzenesulfonyl)-piperazin-1-yl]-ethyl}-quinazolin-4-yl)-amine was synthesized by using the same method as described in Scheme V (Yield 10.58 mg, 25.9%). $^1$H NMR (400 MHz, CDCl$_3$): δ 1.48 (t, 3H, J=6.82 Hz), 1.83 (d, 3H, J=6.82 Hz), 3.38-3.20 (m, 6H), 3.69-3.52 (m, 2H), 3.82-3.72 (m, 2H), 3.85 (s, 3H), 5.12 (q, 1H, J=14.15, 6.32 Hz), 7.00 (d, 2H, J=9.09 Hz), 7.63 (d, 2H, J=9.09 Hz), 7.95 (td, 1H J=8.59, 1.26 Hz), 7.95 (td, 1 H, J=8.59, 1.26 Hz), 8.00 (d, 2H, J=8.08 Hz), 8.06 (dd, 1H, J=8.34, 1.26 Hz). MS m/z calc. 483.23, found (ESI); 484.4 (M+1)$^+$. Retention time 2.48 minutes.

4-Methoxy-2-{1-[4-(4-methoxy-benzenesulfonyl)-piperazin-1-yl]-ethyl}-quinazoline

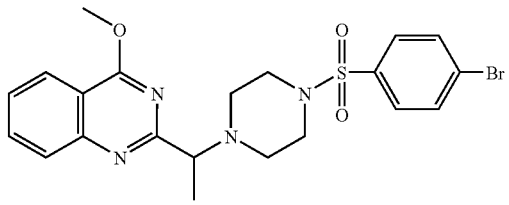 [SMILES: COc1nc(C(C)N2CCN(S(=O)(=O)c3ccc(Br)cc3)CC2)nc2ccccc12]

4-Methoxy-2-{1-[4-(4-methoxy-benzenesulfonyl)-piperazin-1-yl]-ethyl}-quinazoline was synthesized by using the same method as described in Scheme V (Yield 8.23 mg, 13.33%). $^1$H NMR (400 MHz, MeOD-$_4$): δ 1.60 (d, 3H, J=6.82 Hz), 3.15-3.05 (m, 2H), 3.27-3.18 (m, 6H), 3.32 (s, 3H), 3.99 (q, 1H, J=13.89, 6.32 Hz), 7.57 (t, 1H, J=8.08 Hz), 7.77-7.69 (m, 3H), 7.90-7.81 (m, 3H), 8.22 (dd, 1H, J=8.08, 1.26 Hz). MS m/z calc. 490.07, found (ESI); 493.2 (M+1)$^+$. Retention time 2.95 minutes.

2-{1-[4-(4-Bromo-benzenesulfonyl)-piperazin-1-yl]-ethyl}-4-ethoxy-quinazoline

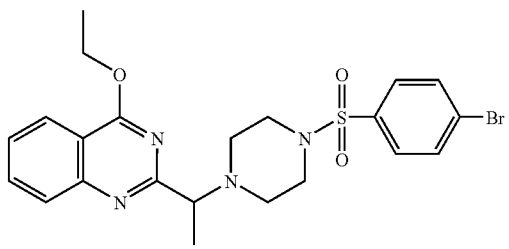 [SMILES: CCOc1nc(C(C)N2CCN(S(=O)(=O)c3ccc(Br)cc3)CC2)nc2ccccc12]

2-{1-[4-(4-Bromo-benzenesulfonyl)-piperazin-1-yl]-ethyl}-4-ethoxy-quinazoline was synthesized by using the same method as described in Scheme V (Yield 8.59 mg, 13.52%). $^1$H NMR (400 MHz, MeOD-$_4$): δ 1.55 (t, 3H, J=7.07 Hz), 1.79 (d, 3H, J=6.57 Hz), 3.60-3.30 (m, 6H), 3.76-3.63 (m, 2H), 4.74-4.61 (m, 3H), 7.72 (td, J=8.34, 2.02 Hz), 7.81-7.76 (m, 2H), 7.91-7.86 (m, 2H), 8.00-7.93 (m, 1H), 8.26 (d, 1H, J=7.58). MS m/z calc. 504.08, found (ESI); 507.2 (M+1)$^+$. Retention time 3.09 minutes.

2-{1-[4-(4-Bromo-benzenesulfonyl)-piperazin-1-yl]-ethyl}-4-propoxy-quinazoline

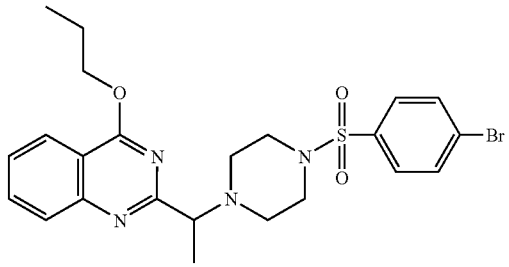 [SMILES: CCCOc1nc(C(C)N2CCN(S(=O)(=O)c3ccc(Br)cc3)CC2)nc2ccccc12]

2-{1-[4-(4-Bromo-benzenesulfonyl)-piperazin-1-yl]-ethyl}-4-propoxy-quinazoline was synthesized by using the same method as described in Scheme V (Yield 8.89 mg, 11.24%). MS m/z calc. 518.10, found (ESI); 521.0 (M+1)$^+$. Retention time 2.91 minutes.

2-{1-[4-(4-Bromo-benzenesulfonyl)-piperazin-1-yl]-ethyl}-4-isopropoxy-quinazoline

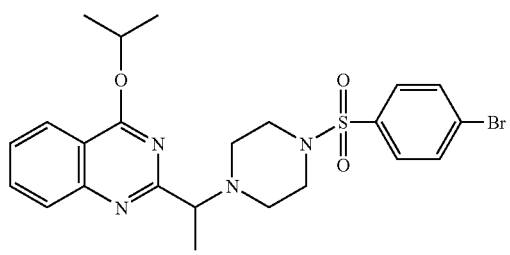 [SMILES: CC(C)Oc1nc(C(C)N2CCN(S(=O)(=O)c3ccc(Br)cc3)CC2)nc2ccccc12]

2-{1-[4-(4-Bromo-benzenesulfonyl)-piperazin-1-yl]-ethyl}-4-isopropoxy-quinazoline was synthesized by using the same method as described in Scheme V (Yield 9.29 mg, 14.23%). MS m/z calc. 518.10, found (ESI); 521.0 (M+1)$^+$. Retention time 2.91 minutes.

2-{1-[4-(4-Bromo-benzenesulfonyl)-piperazin-1-yl]-ethyl}-4-cyclopentyloxy-quinazoline

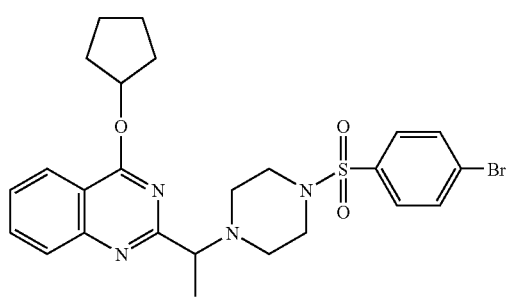 [SMILES: CC(c1nc(OC2CCCC2)c2ccccc2n1)N1CCN(S(=O)(=O)c2ccc(Br)cc2)CC1]

2-{1-[4-(4-Bromo-benzenesulfonyl)-piperazin-1-yl]-ethyl}-4-cyclopentyloxy-quinazoline synthesized by using the same method as described in Scheme V (Yield 9.36 mg, 13.65%). MS m/z calc. 544.11, found (ESI); 547.2 (M+1)$^+$. Retention time 2.91 minutes.

(2-{1-[4-(4-Bromo-benzenesulfonyl)-piperazin-1-yl]-ethyl}-quinazolin-4-yl)-methyl-amine

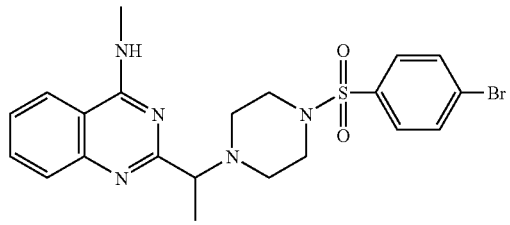 [SMILES: CNc1nc(C(C)N2CCN(S(=O)(=O)c3ccc(Br)cc3)CC2)nc2ccccc12]

(2-{1-[4-(4-Bromo-benzenesulfonyl)-piperazin-1-yl]-ethyl}-quinazolin-4-yl)-methyl-amine compound was synthesized by using the same method as described in Scheme V (Yield 11.09 mg, 18.00%). ¹H NMR (400 MHz, MeOD-$_4$): δ 1.58 (d, 3H, J=6.82 Hz), 2.91-2.84 (m, 2H), 3.02-2.94 (m, 2H), 3.32-3.14 (m, 4H), 4.07 (q, 1H, J=14.40, 6.82 Hz), 7.76-7.70 (m, 3H), 7.85-7.80 (m, 3H), 7.99 (td, 1H J=8.59, 1.26 Hz), 8.24 (dd, 1H, J=8.34, 0.76 Hz). MS m/z calc. 489.08, found (ESI); 492.2 (M+1)⁺. Retention time 2.34 minutes.

(2-{1-[4-(4-Bromo-benzenesulfonyl)-piperazin-1-yl]-ethyl}-quinazolin-4-yl)-dimethyl-amine

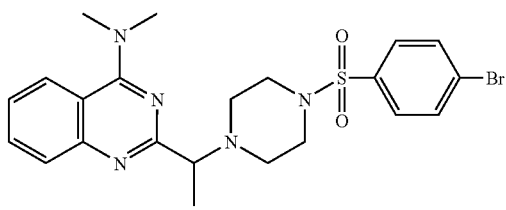 [SMILES: CC(c1nc(N(C)C)c2ccccc2n1)N1CCN(S(=O)(=O)c2ccc(Br)cc2)CC1]

(2-{1-[4-(4-Bromo-benzenesulfonyl)-piperazin-1-yl]-ethyl}-quinazolin-4-yl)-dimethyl-amine was synthesized by using the same method as described in Scheme V (Yield 16.78 mg, 26.47%). ¹H NMR (400 MHz, MeOD-$_4$): δ 1.56 (d, 3H, J=6.57 Hz), 3.01-2.80 (m, 4H), 3.23-3.08 (m, 4H), 4.14-3.96 (m, 1H), 7.75-7.63 (m, 3H), 7.87-7.75 (m, 3H), 8.01-7.90 (m, 1H), 8.39 (dd, 1H, J=8.08 Hz). MS m/z calc. 503.10, found (ESI); 506.0 (M+1)⁺. Retention time 2.39 minutes.

(2-{1-[4-(4-Bromo-benzenesulfonyl)-piperazin-1-yl]-ethyl}-quinazolin-4-yl)-ethyl-amine

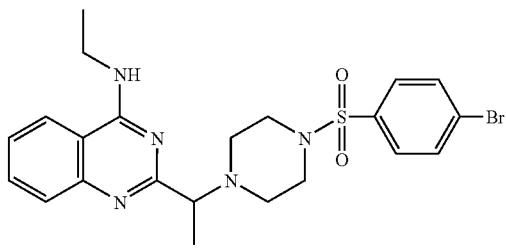

(2-{1-[4-(4-Bromo-benzenesulfonyl)-piperazin-1-yl]-ethyl}-quinazolin-4-yl)-ethyl-amine was synthesized by using the same method as described in Scheme V (Yield 20.60 mg, 32.49%). ¹H NMR (400 MHz, MeOD-$_4$): δ 1.38 (t, 3H, J=7.33 Hz), 1.54 (d, 3H, J=7.07 Hz), 2.83-2.74 (m, 2H), 2.93-2.85 (m, 2H), 3.20-3.08 (m, 4H), 3.85 (q, 1H, J=14.40, 7.33 Hz), 7.76-7.69 (m, 3H), 7.86-7.79 (m, 3H), 7.99 (td, 1H J=8.34, 1.26 Hz), 8.29 (d, 1H, J=8.34 Hz). MS m/z calc. 503.10, found (ESI); 506.0 (M+1)⁺. Retention time 2.39 minutes.

(2-{1-[4-(4-Bromo-benzenesulfonyl)-piperazin-1-yl]-ethyl}-quinazolin-4-yl)-diethyl-amine

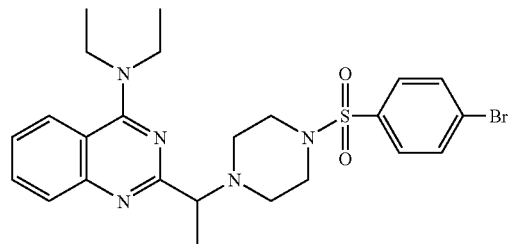 [SMILES: CCN(CC)c1nc(C(C)N2CCN(S(=O)(=O)c3ccc(Br)cc3)CC2)nc2ccccc12]

(2-{1-[4-(4-Bromo-benzenesulfonyl)-piperazin-1-yl]-ethyl}-quinazolin-4-yl)-diethyl-amine was synthesized by using the same method as described in Scheme V (Yield 18.66 mg, 27.88%). MS n/z calc. 531.13, found (ESI); 532.2 (M+1)⁺. Retention time 2.70 minutes.

2-{1-[4-(4-Bromo-benzenesulfonyl)-piperazin-1-yl]-ethyl}-4-morpholin-4-yl-quinazoline

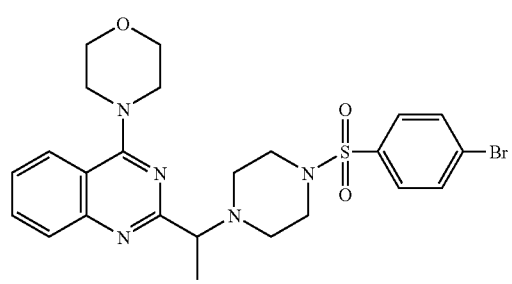 [SMILES: CC(c1nc(N2CCOCC2)c2ccccc2n1)N1CCN(S(=O)(=O)c2ccc(Br)cc2)CC1]

2-{1-[4-(4-Bromo-benzenesulfonyl)-piperazin-1-yl]-ethyl}-4-morpholin-4-yl-quinazolin was synthesized by using the same method as described in Scheme V (Yield 20.04 mg, 29.17%). ¹H NMR (400 MHz, MeOD-$_4$): δ 1.58 (t, 3H, J=6.82 Hz), 3.01-2.92 (m, 2H), 3.11-3.02 (m, 2H), 3.7-3.15 (m, 4H), 3.88 (t, 4H, 5.05 Hz), 4.14 (q, 1H, J=13.64, 7.07 Hz), 4.30-4.18 (m, 4H), 7.75-7.66 (m, 3H), 7.87-7.81 (m, 3H), 7.99 (td, 1H J=8.34, 1.77 Hz), 8.18 (d, 1H, J=8.59 Hz). MS m/z calc. 545.11, found (ESI); 548.4 (M+1)⁺. Retention time 2.43 minutes.

2-{1-[4-(4-Chloro-benzenesulfonyl)-piperazin-1-yl]-ethyl}-4-cyclopentyloxy-quinazoline

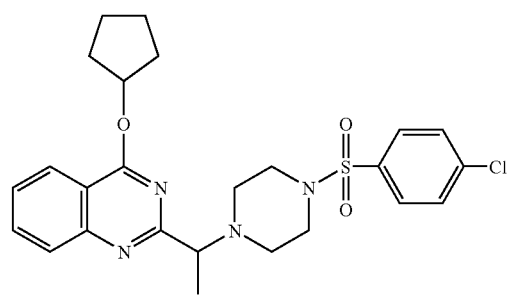 [SMILES: CC(c1nc(OC2CCCC2)c2ccccc2n1)N1CCN(S(=O)(=O)c2ccc(Cl)cc2)CC1]

2-{1-[4-(4-Chloro-benzenesulfonyl)-piperazin-1-yl]-ethyl}-4-cyclopentyloxy-quinazolin was synthesized by using the same method as described in Scheme V (Yield 6.27 mg, 13.6%). MS m/z calc. 500.16, found (ESI); 501.2 (M+1)⁺. Retention time 3.25 minutes.

(2-{1-[4-(4-Chloro-benzenesulfonyl)-piperazin-1-yl]-ethyl}-quinazolin-4-yl)-dimethyl-amine

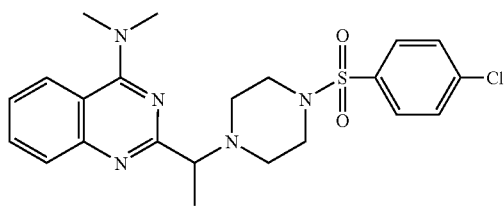 [SMILES: CC(c1nc(N(C)C)c2ccccc2n1)N1CCN(S(=O)(=O)c2ccc(Cl)cc2)CC1]

(2-{1-[4-(4-Chloro-benzenesulfonyl)-piperazin-1-yl]-ethyl}-quinazolin-4-yl)-dimethyl-amine was synthesized by using the same method as described in Scheme V (Yield 25.86 mg, 61.16%). ¹H NMR (400 MHz, MeOD-₄): δ 1.56 (t, 3H, J=6.82 Hz), 2.93-2.86 (m, 2H), 3.02-2.95 (m, 2H), 3.22-3.11 (m, 4H), 3.67 (s, 6H), 4.08 (q, 1H, J=13.64, 6.82 Hz), 7.73-7.64 (m, 3H), 7.83-7.76 (m, 3H), 7.97 (td, 1H, J=8.59, 1.26 Hz), 8.38 (dd, 1H, J=8.59, 0.76 Hz). MS m/z calc. 459.15, found (ESI); 460.2 (M+1)⁺. Retention time 2.66 minutes.

(2-{1-[4-(4-Chloro-benzenesulfonyl)-piperazin-1-yl]-ethyl}-quinazolin-4-yl)-ethyl-amine

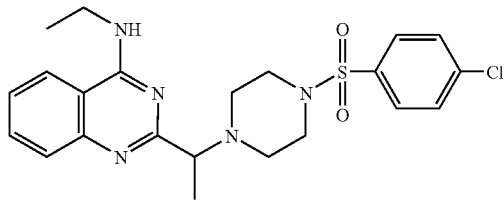 [SMILES: CCNc1nc(C(C)N2CCN(S(=O)(=O)c3ccc(Cl)cc3)CC2)nc2ccccc12]

(2-{1-[4-(4-Chloro-benzenesulfonyl)-piperazin-1-yl]-ethyl}-quinazolin-4-yl)-ethyl-amine was synthesized using the same method as described in Scheme V (Yield 20.27 mg, 47.9%). ¹H NMR (400 MHz, MeOD-₄): δ 1.38 (t, 3H, J=7.07 Hz), 1.54 (d, 3H, J=7.07 Hz), 2.83-2.75 (m, 2H), 2.92-2.85 (m, 2H), 3.19-3.11 (m, 4H), 3.85 (q, 2H J=14.65, 6.82 Hz), 3.98 (q, 1H, J=14.40, 6.82 Hz), 7.69-7.65 (m, 2H), 7.73 (dt, 1H, J=8.34, 1.26 Hz), 7.38-7.78 (m, 1H), 7.99 (td, 1H, J=8.34, 1.26 Hz), 8.29 (d, 1H, J=8.34 Hz). MS m/z calc. 459.15, found (ESI); 460.2 (M+1)⁺. Retention time 2.74 minutes.

(2-{1-[4-(4-Chloro-benzenesulfonyl)-piperazin-1-yl]-ethyl}-quinazolin-4-yl)-diethyl-amine

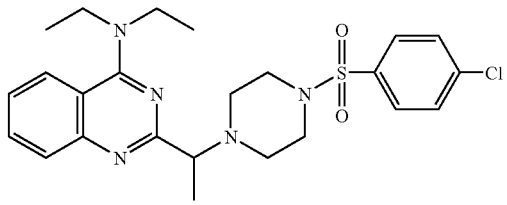 [SMILES: CCN(CC)c1nc(C(C)N2CCN(S(=O)(=O)c3ccc(Cl)cc3)CC2)nc2ccccc12]

(2-{1-[4-(4-Chloro-benzenesulfonyl)-piperazin-1-yl]-ethyl}-quinazolin-4-yl)-diethyl-amine was synthesized using the same method as described in Scheme V (Yield 22.89 mg, 50.9%). ¹H NMR (400 MHz, MeOD-₄): δ 1.51 (t, 9H, J=6.82 Hz), 2.81-2.71 (m, 2H), 2.89-2.81 (m, 2H), 3.20-3.05 (m, 4H), 4.03 (q, 5H J=14.65, 6.82 Hz), 7.68-7.65 (m, 2H), 7.70 (dt, 1H, J=8.34, 1.26 Hz), 7.83-7.77 (m, 3H), 7.97 (td, 1H, J=8.34, 1.26 Hz), 8.19 (d, 1H, J=8.34 Hz). MS m/z calc. 487.18, found (ESI); 488.4 (M+1)⁺. Retention time 2.93 minutes.

2-{1-[4-(4-Chloro-benzenesulfonyl)-piperazin-1-yl]-ethyl}-4-morpholin-4-yl-quinazoline

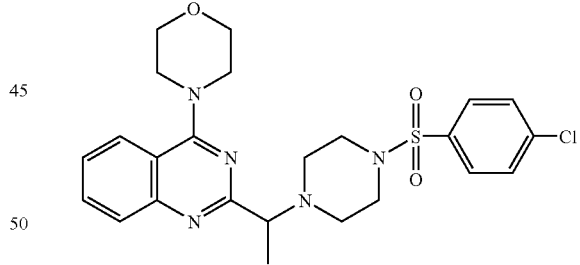

2-{1-[4-(4-Chloro-benzenesulfonyl)-piperazin-1-yl]-ethyl}-4-morpholin-4-yl-quinazoline was synthesized using the same method as described in Scheme V (Yield 31.71 mg, 68.67%). ¹H NMR (400 MHz, MeOD-₄): δ 1.58 (t, 3H, J=6.82 Hz), 3.02-2.92 (m, 2H), 3.12-3.03 (m, 2H), 3.28-3.16 (m, 4H), 3.87 (t, 4H, J=4.55 Hz), 4.14 (q, 1H J=13.89, 6.32 Hz), 4.30-4.19 (m, 4 M), 7.71-7.64 (m, 3H), 7.87-7.76 (m, 3H), 7.96 (dt, 1H, J=8.34, 1.26 Hz), 8.15 (d, 1H, J=8.59 Hz). MS m/z calc. 501.16, found (ESI); 502.21 (M+1)⁺. Retention time 2.66 minutes.

2-{1-[4-(4-Chloro-benzenesulfonyl)-piperazin-1-yl]-ethyl}-4-piperidin-1-yl-quinazoline

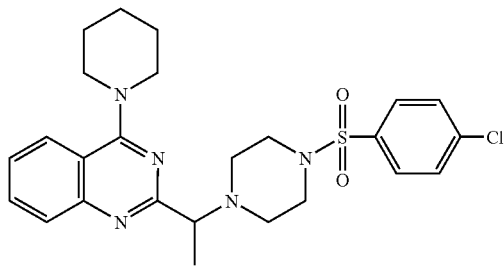 [SMILES: CC(c1nc(N2CCCCC2)c2ccccc2n1)N1CCN(S(=O)(=O)c2ccc(Cl)cc2)CC1]

2-{1-[4-(4-Chloro-benzenesulfonyl)-piperazin-1-yl]-ethyl}-4-piperidin-1-quinazoline was synthesized by using the same method as described in Scheme V (Yield 14.10 mg, 30.6%). $^1$H NMR (400 MHz, MeOD-$_4$): δ 1.42 (t, 3H, J=6.82 Hz), 1.78 (br, s, 6H), 2.74-2.66 (m, 2H), 2.85-2.75 (m, 2H), 3.05 (br, s, 4H), 3.89 (q, 1H, J=14.15, 6.82 Hz), 4.10 (br, s, 4H), 7.60-7.54 (m, 3H), 7.73-7.67 (m, 3H), 7.85 (dt, 1H, J=8.59, 1.26 Hz), 8.03 (d, 1H, J=8.59 Hz), $^{13}$C NMR (100 MHz, CD$_3$OD): δ 16.84, 24.78, 25.99, 46.55, 48.71, 50.88, 66.02, 115.22, 124.65, 124.99, 128.31, 128.88, 129.24, 129.25, 129.53, 132.11, 133.80, 139.27, 151.93, 164.42, 164.64. MS m/z calc. 499.18, found (ESI); 500.2 (M+1)$^+$. Retention time 2.95 minutes.

4-([1,3]Dioxolan-4-ylmethoxy)-2-{1-[4-(4-methoxy-benzenesulfonyl)-piperazin-1-yl]-ethyl}-quinazoline

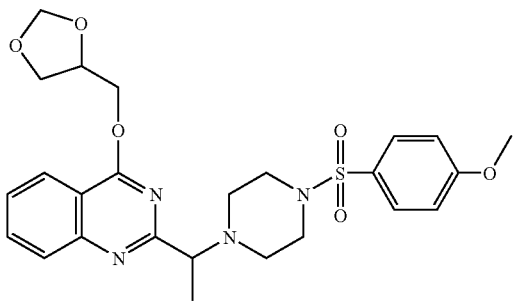 [SMILES: COc1ccc(S(=O)(=O)N2CCN(C(C)c3nc(OCC4COCO4)c4ccccc4n3)CC2)cc1]

4-([1,3]Dioxolan-4-ylmethoxy)-2-{1-[4-(4-methoxy-benzenesulfonyl)-piperazin-1-yl]-ethyl}-quinazoline was synthesized by using the same method as described in Scheme V (Yield 14.0 mg, 38.8%). MS n/z calc. 514.59, found (ESI); 515.4 (M+1)$^+$. Retention time 2.69 minutes.

2-{1-[4-(4-Methoxy-benzenesulfonyl)-piperazin-1-yl]-ethyl}-4-(5-methyl-[1,3]dioxan-5-ylmethoxy)-quinazoline

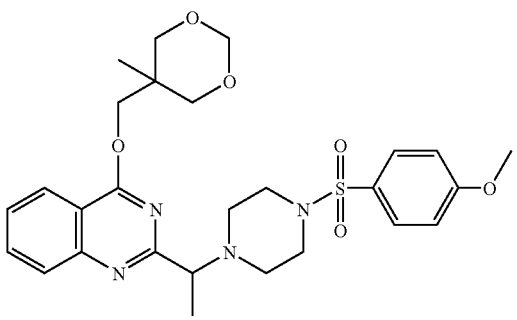 [SMILES: COc1ccc(S(=O)(=O)N2CCN(C(C)c3nc(OCC4(C)COCOC4)c4ccccc4n3)CC2)cc1]

2-{1-[4-(4-Methoxy-benzenesulfonyl)-piperazin-1-yl]-ethyl}-4-(5-methyl-[1,3]-dioxan-5-ylmethoxy)-quinazoline was synthesized by using the same method as described in Scheme V (Yield 8.9 mg, 23.4%). MS t/z calc. 542.65, found (ESI); 543.2 (M+1)$^+$. Retention time 2.76 minutes.

2-{1-[4-(4-Methoxy-benzenesulfonyl)-piperazin-1-yl]-ethyl}-4-(pyridin-4-yloxy)-quinazoline

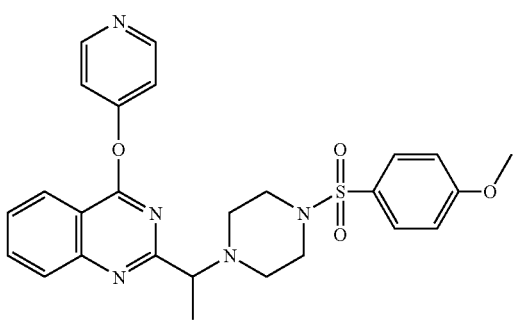 [SMILES: COc1ccc(S(=O)(=O)N2CCN(C(C)c3nc(Oc4ccncc4)c4ccccc4n3)CC2)cc1]

2-{1-[4-(4-Methoxy-benzenesulfonyl)-piperazin-1-yl]-ethyl}-4-(pyridin-4-yloxy)-quinazoline was synthesized by using the same method as described in Scheme V (Yield 2.7 mg, 7.6%). MS m/z calc. 505.59, found (ESI); 506.2 (M+1)$^+$. Retention time 2.28 minutes.

4-Cyclohexyloxy-2-{1-[4-(4-methoxy-benzenesulfonyl)-piperazin-1-yl]-ethyl}-quinazoline

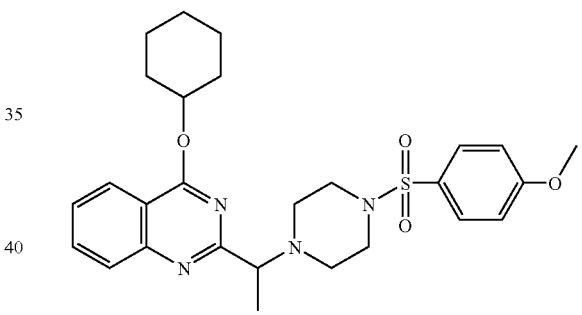

4-Cyclohexyloxy-2-{1-[4-(4-methoxy-benzenesulfonyl)-piperazin-1-yl]-ethyl}-quinazoline was synthesized by using the same method as described in Scheme V (Yield 2.8 mg, 7.8%). MS m/z calc. 510.65, found (ESI); 511.2 (M+1)$^+$. Retention time 3.17 minutes.

2-{1-[4-(4-Methoxy-benzenesulfonyl)-piperazin-1-yl]-ethyl}-4-(2-pyrrolidin-1-yl-ethoxy)-quinazoline

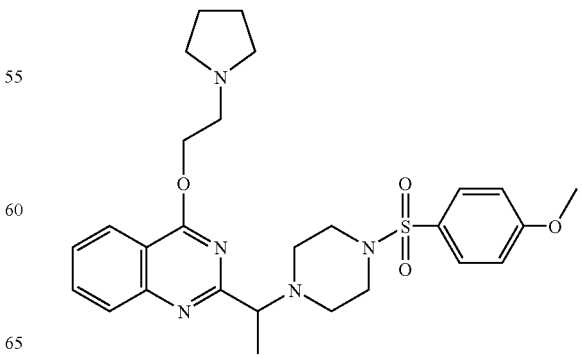

2-{1-[4-(4-Methoxy-benzenesulfonyl)-piperazin-1-yl]-ethyl}-4-(2-pyrrolidin-1-yl-ethoxy)-quinazoline was synthesized by using the same method as described in Scheme V (Yield 26.7 mg, 72.6%). MS m/z calc. 525.66, found (ESI); 526.2 (M+1)⁺. Retention time 2.20 minutes.

2-{1-[4-(4-Methoxy-benzenesulfonyl)-piperazin-1-yl]-ethyl}-4-(tetrahydro-pyran-4-yloxy)-quinazoline

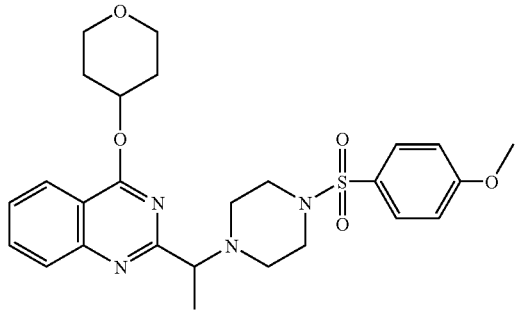 [SMILES: COc1ccc(S(=O)(=O)N2CCN(C(C)c3nc(OC4CCOCC4)c4ccccc4n3)CC2)cc1]

2-{1-[4-(4-Methoxy-benzenesulfonyl)-piperazin-1-yl]-ethyl}-4-(tetrahydro-pyran-4-yloxy)-quinazoline was synthesized by using the same method as described in Scheme V (Yield 7.8 mg, 21.7%). MS m/z calc. 512.62, found (ESI); 526.2 (M+1)⁺. Retention time 2.65 minutes.

2-{1-[4-(4-Methoxy-benzenesulfonyl)-piperazin-1-yl]-ethyl}-4-(3-methyl-butoxy)-quinazoline

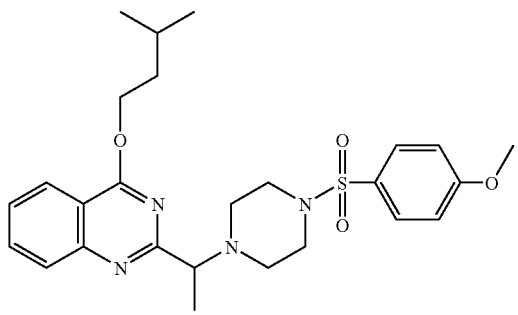 [SMILES: COc1ccc(S(=O)(=O)N2CCN(C(C)c3nc(OCCC(C)C)c4ccccc4n3)CC2)cc1]

2-{1-[4-(4-Methoxy-benzenesulfonyl)-piperazin-1-yl]-ethyl}-4-(3-methyl-butoxy)-quinazoline was synthesized by using the same method as described in Scheme V (Yield 29.6 mg, 84.6%). MS m/z calc. 499.63, found (ESI); 500.2 (M+1)⁺. Retention time 2.09 minutes.

2-{1-[4-(4-Methoxy-benzenesulfonyl)-piperazin-1-yl]-ethyl}-4-piperidin-1-yl-quinazoline

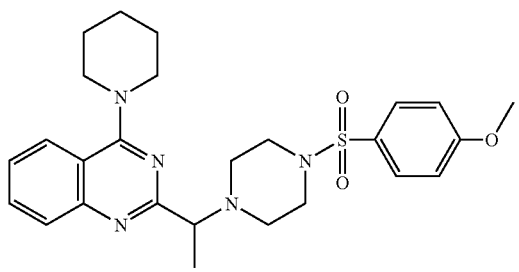 [SMILES: COc1ccc(S(=O)(=O)N2CCN(C(C)c3nc(N4CCCCC4)c4ccccc4n3)CC2)cc1]

2-{1-[4-(4-Methoxy-benzenesulfonyl)-piperazin-1-yl]-ethyl}-4-piperidin-1-yl-quinazoline was synthesized by using the same method as described in Scheme V (Yield 30.2 mg, 84.8%). MS m/z calc. 495.16, found (ESI); 496.4 (M+1)⁺. Retention time 2.76 minutes.

Cyclopentyl-(2-{1-[4-(4-methoxy-benzenesulfonyl)-piperazin-1-yl]-ethyl}-quinazolin-4-yl)-amine

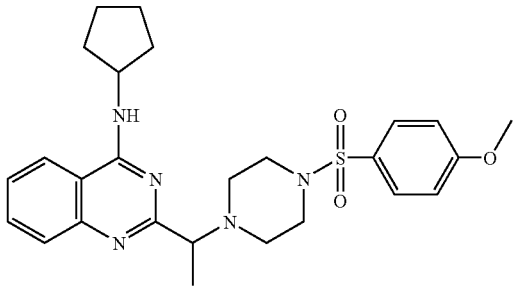 [SMILES: COc1ccc(S(=O)(=O)N2CCN(C(C)c3nc(NC4CCCC4)c4ccccc4n3)CC2)cc1]

Cyclopentyl-(2-{1-[4-(4-methoxy-benzenesulfonyl)-piperazin-1-yl]-ethyl}-quinazolin-4-yl)-amine was synthesized by using the same method as described in Scheme V (Yield 29.6 mg, 84.6%). MS m/z calc. 495.64, found (ESI); 496.4 (M+1)⁺. Retention time 2.86 minutes.

Cyclohexyl-(2-{1-[4-(4-methoxy-benzenesulfonyl)-piperazin-1-yl]-ethyl}-quinazolin-4-yl)-amine

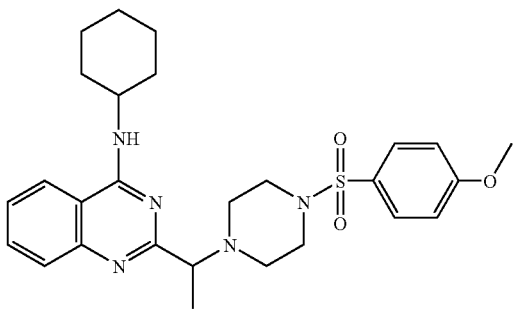 [SMILES: COc1ccc(S(=O)(=O)N2CCN(C(C)c3nc(NC4CCCCC4)c4ccccc4n3)CC2)cc1]

Cyclohexyl-(2-{1-[4-(4-methoxy-benzenesulfonyl)-piperazin-1-yl]-ethyl}-quinazolin-4-yl)-amine was synthesized by using the same method as described in Scheme V (Yield 24.4 mg, 69.7%). MS m/z calc. 509.66, found (ESI); 510.4 (M+1)⁺. Retention time 2.90 minutes.

2-{1-[4-(4-Methoxy-benzenesulfonyl)-piperazin-1-yl]-ethyl}-4-(3-methyl-piperidin-1-yl)-quinazoline

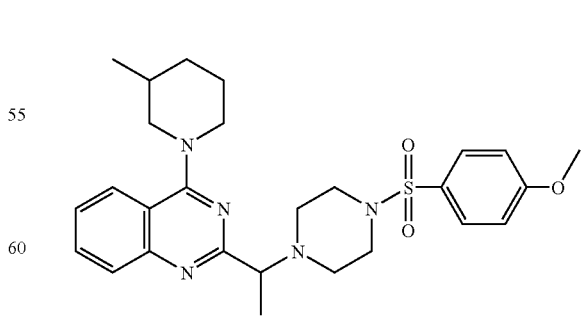

2-{1-[4-(4-Methoxy-benzenesulfonyl)-piperazin-1-yl]-ethyl}-4-(3-methyl-piperidin-1-yl)-quinazoline was synthesized by using the same method as described in Scheme V (Yield 27.7 mg, 77.4%). MS m/z calc. 509.66, found (ESI); 511.4 (M+1)$^+$. Retention time 2.14 minutes.

4-(3,5-Dimethyl-piperidin-1-yl)-2-{1-[4-(4-methoxy-benzenesulfonyl)-piperazin-1-yl]-ethyl}-quinazoline

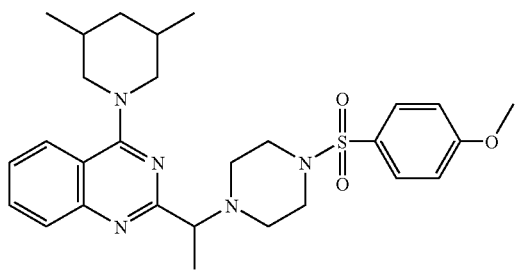 [SMILES: COc1ccc(S(=O)(=O)N2CCN(C(C)c3nc(N4CC(C)CC(C)C4)c4ccccc4n3)CC2)cc1]

4-(3,5-Dimethyl-piperidin-1-yl)-2-{1-[4-(4-methoxy-benzenesulfonyl)-piperazin-1-yl]-ethyl}-quinazoline was synthesized by using the same method as described in Scheme V (Yield 58.9 mg, 80.3%). MS m/z calc. 523.7, found (ESI); 524.4 (M+1)$^+$. Retention time 2.94 minutes.

4-Azepan-1-yl-2-{1-[4-(4-methoxy-benzenesulfonyl)-piperazin-1-yl]-ethyl}-quinazoline

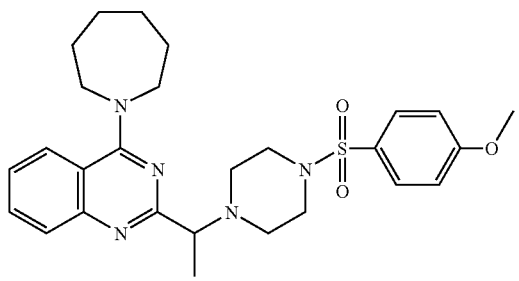 [SMILES: COc1ccc(S(=O)(=O)N2CCN(C(C)c3nc(N4CCCCCC4)c4ccccc4n3)CC2)cc1]

4-Azepan-1-yl-2-{1-[4-(4-methoxy-benzenesulfonyl)-piperazin-1-yl]-ethyl}-quinazoline was synthesized by using the same method as described in Scheme V (Yield 50.5 mg, 70.7%). MS m/z calc. 509.66, found (ESI); 510.4 (M+1)$^+$. Retention time 2.83 minutes.

2-{1-[4-(4-Methoxy-benzenesulfonyl)-piperazin-1-yl]-ethyl}-4-(4-methyl-piperidin-1-yl)-quinazoline

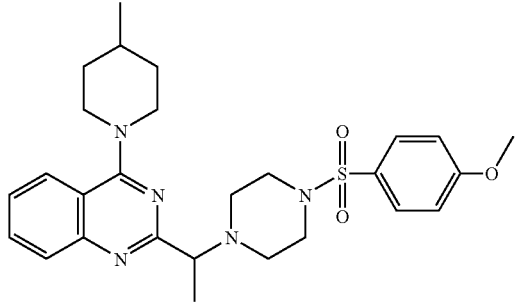

2-{1-[4-(4-Methoxy-benzenesulfonyl)-piperazin-1-yl]-ethyl}-4-(4-methyl-piperidin-1-yl)-quinazoline was synthesized by using the same method as described in Scheme V (Yield 55.9 mg, 78.3%). MS m/z calc. 509.66, found (ESI); 510.2 (M+1)$^+$. Retention time 2.83 minutes.

2-{1-[4-(4-Methoxy-benzenesulfonyl)-piperazin-1-yl]-ethyl}-4-thiomorpholin-4-yl-quinazoline

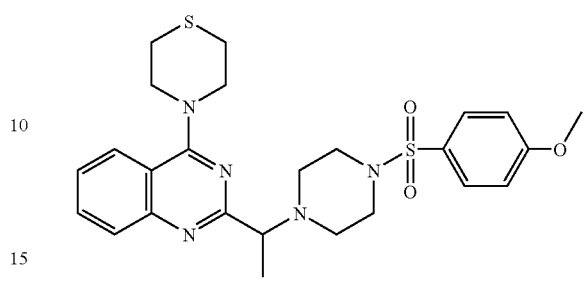

2-{1-[4-(4-Methoxy-benzenesulfonyl)-piperazin-1-yl]-ethyl}-4-thiomorpholin-4-yl-quinazoline was synthesized by using the same method as described in Scheme V. (Yield 52.0 mg, 72.3%). MS m/z calc. 513.67, found (ESI); 514.0 (M+1)$^+$. Retention time 2.65 minutes.

1-(2-{1-[4-(4-Methoxy-benzenesulfonyl)-piperazin-1-yl]-ethyl}-quinazolin-4-yl)-piperidine-4-carboxylic acid ethyl ester

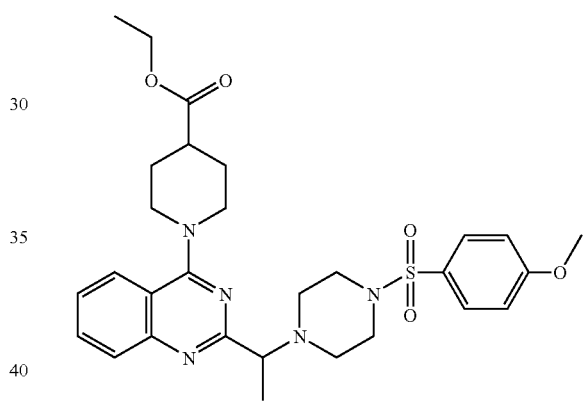

1-(2-{1-[4-(4-Methoxy-benzenesulfonyl)-piperazin-1-yl]-ethyl}-quinazolin-4-yl)-piperidine-4-carboxylic acid ethyl ester was synthesized by using the same method as described in Scheme V (Yield 57.6 mg, 72.4%). MS m/z calc. 567.7, found (ESI); 568.2 (M+1)$^+$. Retention time 2.76 minutes.

4-(1,4-Dioxa-8-aza-spiro[4.5]dec-8-yl)-2-{1-[4-(4-methoxy-benzenesulfonyl)-piperazin-1-yl]-ethyl}-quinazoline

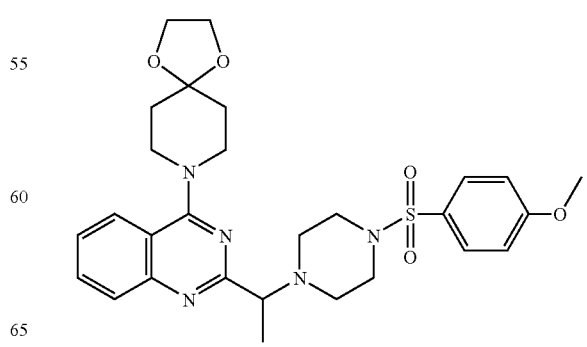

4-(1,4-Dioxa-8-aza-spiro[4.5]dec-8-yl)-2-{1-[4-(4-methoxy-benzenesulfonyl)-piperazin-1-yl]-ethyl}-quinazoline was synthesized by using the same method as described in Scheme V (Yield 45.8 mg, 59.1%). MS m/z calc. 553.67, found (ESI); 554.0 (M+1)$^+$. Retention time 2.61 minutes.

2-{1-[4-(4-Methoxy-benzenesulfonyl)-piperazin-1-yl]-ethyl}-4-(2-methyl-pyrrolidin-1-yl)-quinazoline

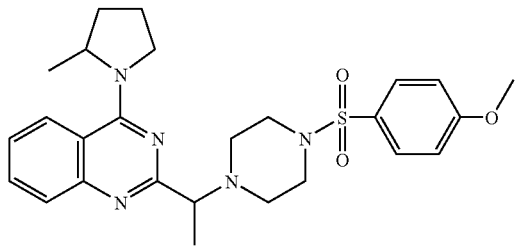 [SMILES: COc1ccc(S(=O)(=O)N2CCN(C(C)c3nc(N4CCCC4C)c4ccccc4n3)CC2)cc1]

2-{1-[4-(4-Methoxy-benzenesulfonyl)-piperazin-1-yl]-ethyl}-4-(2-methyl-pyrrolidin-1-yl)-quinazoline was synthesized by using the same method as described in Scheme V (Yield 44.6 mg, 64.4%). MS m/z calc. 595.63, found (ESI); 596.2 (M+1)$^+$. Retention time 2.73 minutes.

2-{1-[4-(4-Methoxy-benzenesulfonyl)-piperazin-1-yl]-ethyl}-4-(2-methyl-piperidin-1-yl)-quinazoline

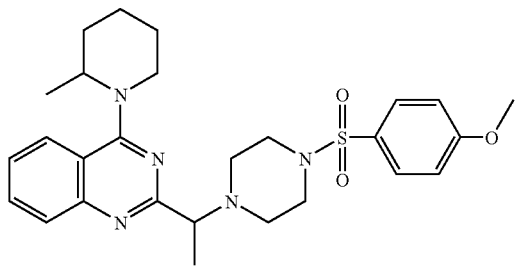 [SMILES: COc1ccc(S(=O)(=O)N2CCN(C(C)c3nc(N4CCCCC4C)c4ccccc4n3)CC2)cc1]

2-{1-[4-(4-Methoxy-benzenesulfonyl)-piperazin-1-yl]-ethyl}-4-(2-methyl-piperidin-1-yl)-quinazoline was synthesized by using the same method as described in Scheme V (Yield 11.5 mg, 15.8%). MS m/z calc. 509.66, found (ESI); 510.2 (M+1)$^+$. Retention time 2.79 minutes.

2-{1-[4-(4-Methoxy-benzenesulfonyl)-piperazin-1-yl]-ethyl}-4-(octahydro-isoquinolin-2-yl)-quinazoline

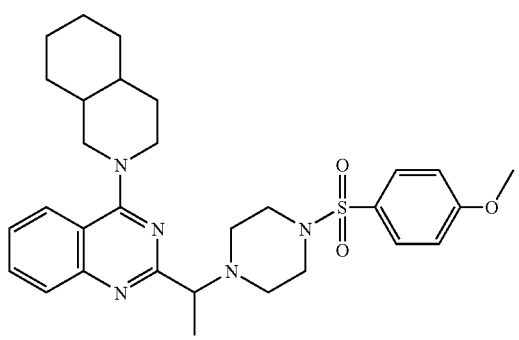 [SMILES: COc1ccc(S(=O)(=O)N2CCN(C(C)c3nc(N4CCC5CCCCC5C4)c4ccccc4n3)CC2)cc1]

2-{1-[4-(4-Methoxy-benzenesulfonyl)-piperazin-1-yl]-ethyl}-4-(octahydro-isoquinolin-2-yl-quinazoline was synthesized by using the same method as described in Scheme V (Yield 63.3 mg, 81.9%). MS m/z calc. 549.72, found (ESI); 550.2 (M+1)$^+$. Retention time 3.09 minutes.

9-(2-{1-[4-(4-Methoxy-benzenesulfonyl)-piperazin-1-yl]-ethyl}-quinazolin-4-yl)-1,5-dioxa-9-aza-spiro[5.5]undecane

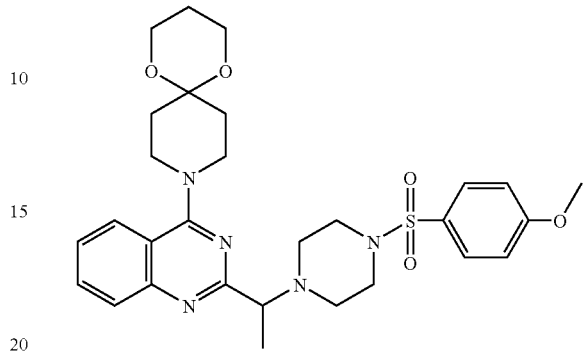

9-(2-{1-[4-(4-Methoxy-benzenesulfonyl)-piperazin-1-yl]-ethyl}-quinazolin-4-yl)-1,5-dioxa-9-aza-spiro[5.5]undecane was synthesized by using the same method as described in Scheme V (Yield 33.8 mg, 42.6%). MS m/z calc. 567.70, found (ESI); 568.2 (M+1)$^+$. Retention time 2.64 minutes.

4-tert-Butoxy-2-{1-[4-(4-methoxy-benzenesulfonyl)-piperazin-1-yl]-ethyl}-quinazoline

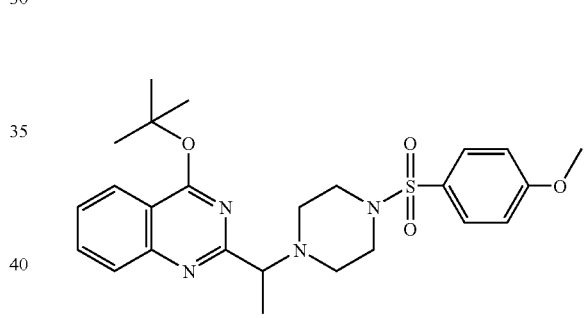

4-tert-Butoxy-2-{1-[4-(4-methoxy-benzenesulfonyl)-piperazin-1-yl]-ethyl}-quinazolin was synthesized by using the same method as described in Scheme V (Yield 24.0 mg, 42.5%). MS m/z calc. 484.22, found (ESI); 485.3 (M+1)$^+$. Retention time 2.97 minutes.

2-{1-[4-(4-Methoxy-benzenesulfonyl)-piperazin-1-yl]-ethyl}-4-pyrrolidin-1-yl-quinazoline

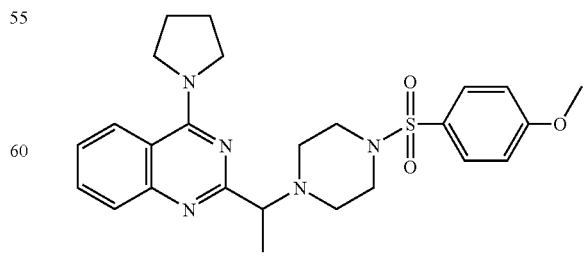

2-{1-[4-(4-Methoxy-benzenesulfonyl)-piperazin-1-yl]-ethyl}-4-pyrrolidin-1-yl-quinazoline was synthesized by using the same method as described in Scheme V (Yield 13.2 mg, 39.2%). MS m/z calc. 481.0, found (ESI); 482.2 (M+1)⁺. Retention time 2.61 minutes.

[1-(2-{1-[4-(4-Methoxy-benzenesulfonyl)-piperazin-1-yl]-ethyl}-quinazolin-4-yl)-piperidin-3-yl]-methanol

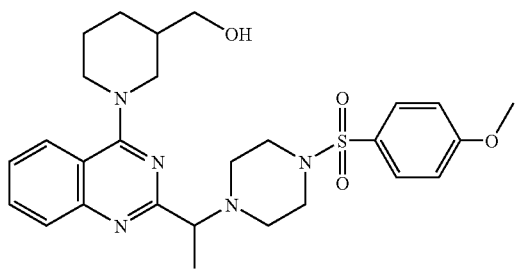 [SMILES: COc1ccc(S(=O)(=O)N2CCN(C(C)c3nc(N4CCCC(CO)C4)c4ccccc4n3)CC2)cc1]

[1-(2-{1-[4-(4-Methoxy-benzenesulfonyl)-piperazin-1-yl]-ethyl}-quinazolin-4-yl)-piperidin-3-yl]-methanol was prepared by using the same method as described in Scheme V (Yield 26.3 mg, 69.9%). MS m/z calc. 525.1, found (ESI); 526.2 (M+1)⁺. Retention time 2.46 minutes.

2-{1-[4-(4-Methoxy-benzenesulfonyl)-piperazin-1-yl]-ethyl}-4-(4-methyl-piperazin-1-yl)-quinazoline

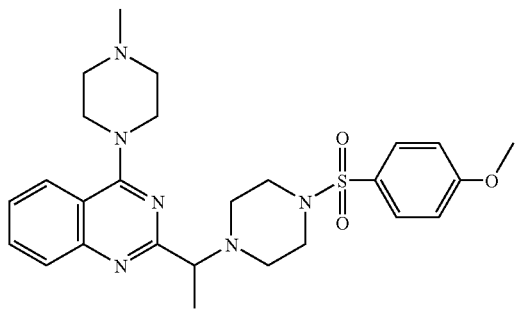 [SMILES: COc1ccc(S(=O)(=O)N2CCN(C(C)c3nc(N4CCN(C)CC4)c4ccccc4n3)CC2)cc1]

2-{1-[4-(4-Methoxy-benzenesulfonyl)-piperazin-1-yl]-ethyl}-4-(4-methyl-piperazin-1-yl)-quinazoline was prepared by using the same method as described in Scheme V (Yield 21.2 mg, 59.1%). MS m/z calc. 510.2, found (ESI); 511.4 (M+1)⁺. Retention time 2.14 minutes.

[1-(2-{1-[4-(4-Methoxy-benzenesulfonyl)-piperazin-1-yl]-ethyl}quinazolin-4-yl)-piperidin-4-yl]-methanol

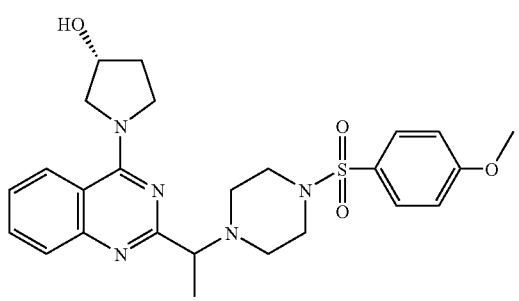 [SMILES: COc1ccc(S(=O)(=O)N2CCN(C(C)c3nc(N4CC[C@@H](O)C4)c4ccccc4n3)CC2)cc1]

[1-(2-{1-[4-(4-Methoxy-benzenesulfonyl)-piperazin-1-yl]-ethyl}-quinazolin-4-piperidin-4-yl]-methanol was prepared by using the same procedure as described in Scheme V (Yield 22.3 mg, 60.7%). MS m/z calc. 525.2, found (ESI); 526.2 (M+1)⁺. Retention time 2.39 minutes.

4-(3,4-Dimethyl-cyclohexyloxy)-2-{1-[4-(4-methoxy-benzenesulfonyl)-piperazin-1-yl]-ethyl}-quinazoline

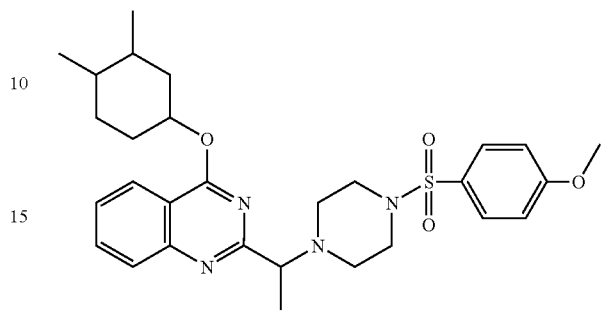

4-(3,4-Dimethyl-cyclohexyloxy)-2-{1-[4-(4-methoxy-benzenesulfonyl)-piperazin-1-yl]-ethyl}-quinazoline was prepared by using the same procedure as described in Scheme V (Yield 3.2 mg, 8.5%). MS m/z calc. 538.6, found (ESI); 539.4 (M+1)⁺. Retention time 3.45 minutes.

4-(2-Aza-bicyclo[2.2.1]hept-2-yl)-2-{1-[4-(4-methoxy-benzenesulfonyl)-piperazin-1-yl]-ethyl}-quinazoline

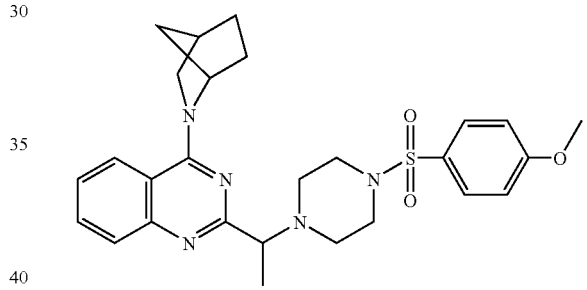

4-(2-Aza-bicyclo[2.2.1]hept-2-yl)-2-{1-[4-(4-methoxy-benzenesulfonyl)-piperazin-1-]ethyl}-quinazoline was prepared by using the same method as described in Scheme V (Yield 30.2 mg, 84.8%). MS m/z calc. 507.2, found (ESI); 508.4 (M+1)⁺. Retention time 2.71 minutes.

2-[1-(2-{1-[4-(4-Methoxy-benzenesulfonyl)-piperazin-1-yl]-ethyl}-quinazoline-4-yl)-piperidin-4-yl]-ethanol

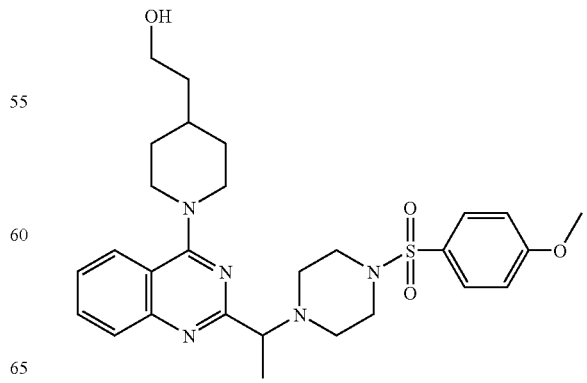

2-[1-(2-{1-[4-(4-Methoxy-benzenesulfonyl)-piperazin-1-yl]-ethyl}-quinazolin-4-yl)-piperidin-4-yl]-ethanol was prepared by using the same method as described in Scheme V (Yield 3.9 mg, 10.3%). MS m/z calc. 539.2, found (ESI); 540.2 (M+1)+. Retention time 2.45 minutes.

2-{1-[4-(4-Methoxy-benzenesulfonyl)-piperazin-1-yl]-ethyl}-4-(4-propyl-piperidin-1-yl)-quinazoline

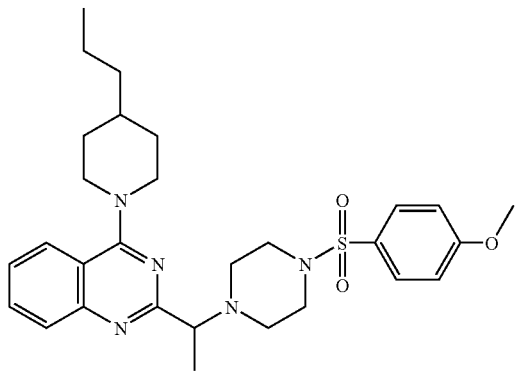 [SMILES: CCCC1CCN(c2nc(C(C)N3CCN(S(=O)(=O)c4ccc(OC)cc4)CC3)nc3ccccc23)CC1]

2-{1-[4-(4-Methoxy-benzenesulfonyl)-piperazin-1-yl]-ethyl}-4-(4-propyl-piperidin-1-yl)-quinazoline was prepared by using the same method as described in Scheme V (Yield 11.7 mg, 31.1%). MS m/z calc. 537.3, found (ESI); 538.2 (M+1)+. Retention time 3.16 minutes.

(2-{1-[4-(4-Methoxy-benzenesulfonyl)-piperazin-1-yl]-ethyl}-quinazolin-4-yl)-phenyl-amine

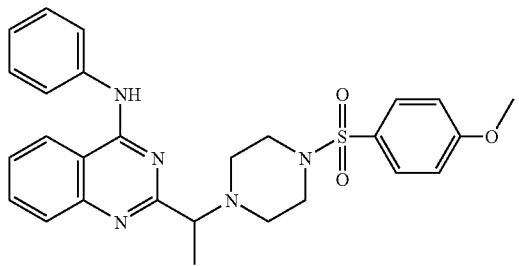 [SMILES: COc1ccc(S(=O)(=O)N2CCN(C(C)c3nc(Nc4ccccc4)c4ccccc4n3)CC2)cc1]

(2-{1-[4-(4-Methoxy-benzenesulfonyl)-piperazin-1-yl]-ethyl}-quinazolin-4-yl)-phenyl-amine was prepared by using the same procedure as described in Scheme V (Yield 27.8 mg, 78.9%). MS m/z calc. 503.6 found (ESI); 504.2 (M+1)+. Retention time 2.73 minutes.

Benzyl-(2-{1-[4-(4-methoxy-benzenesulfonyl)-piperazin-1-yl]-ethyl}-quinazolin-4-yl)-amine

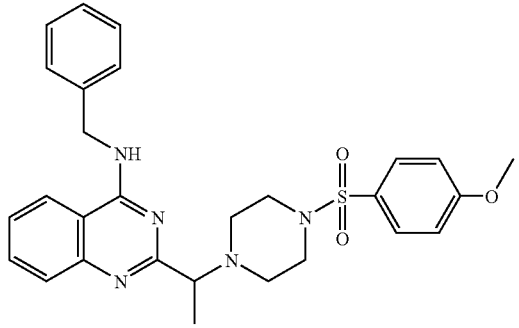 [SMILES: COc1ccc(S(=O)(=O)N2CCN(C(C)c3nc(NCc4ccccc4)c4ccccc4n3)CC2)cc1]

Benzyl-(2-{1-[4-(4-methoxy-benzenesulfonyl)-piperazin-1-yl]-ethyl}-quinazolin-4-yl)-amine was prepared by using the same procedure as described in Scheme V (Yield 25.2 mg, 55.2%). MS m/z calc. 517.6 found (ESI); 5518.2 (M+1)+. Retention time 2.78 minutes.

Benzyl-(2-{1-[4-(4-methoxy-benzenesulfonyl)-piperazin-1-yl]-ethyl}-quinazolin-4-yl)-methyl-amine

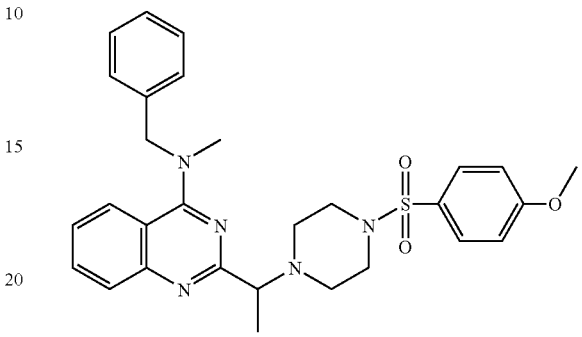

Benzyl-(2-{1-[4-(4-methoxy-benzenesulfonyl)-piperazin-1-yl]-ethyl}-quinazolin-4-yl)-methyl-amine amine was prepared by using the same procedure as described in Scheme V (Yield 30.1 mg, 80.9%). MS m/z calc. 531.7 found (ESI); 532.2 (M+1)+. Retention time 2.85 minutes.

1-[4-(2-{1-[4-(4-Methoxy-benzenesulfonyl)-piperazin-1-yl]-ethyl}-quinazolin-4-yl)-piperazin-1-yl]-ethanone

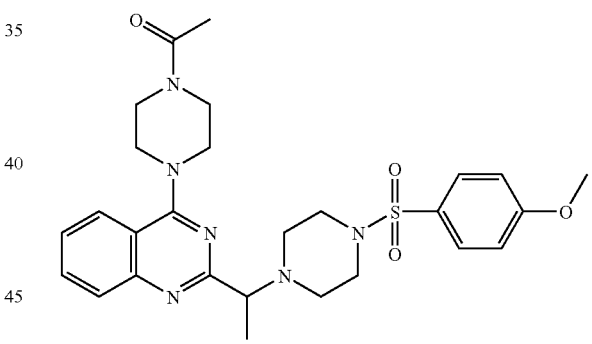

1-[4-(2-{1-[4-(4-Methoxy-benzenesulfonyl)-piperazin-1-yl]-ethyl}-quinazolin-4-yl)-piperazin-1-yl]-ethanone was prepared by using the same method as described in Scheme V (Yield 15.3 mg, 40.7%). MS m/z calc. 538.7 found (ESI); 539.2 (M+1)+. Retention time 2.36 minutes.

Preparation of 6-Fluoro-2-{1-[4-(4-methoxy-benzenesulfonyl)-piperazin-1-yl]-ethyl}-3H-quinazolin-4-one

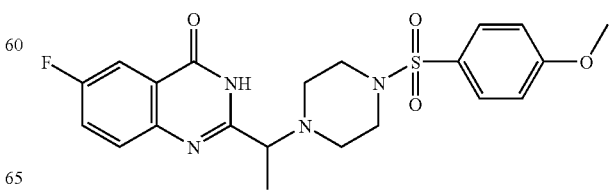

Step 1: Preparation of 2-Amino-5-fluoro-benzoic acid

A stirred solution of 5-fluoroisatin (39 g, 0.236 mol) in NaOH (5%, 500 mL) was treated dropwise over 10 min with 30% $H_2O_2$ (57 g, calculated to contain 17 g, 0.5 mol). After another 20 min of being stirred, during which became warm and effervesced, the solution was cooled in an ice-bath and acidified to pH=4 with 3 M HCl. The precipitated solid was collected and dried in air to obtain 2-amino-5-fluoro-benzoic acid 1 as a beige powder (29.6 g, 80%). $^1H$ NMR (DMSO-$d_6$) δ 7.3-8.2 (m, 2H), 7.08 (d, J=9 Hz, 1H), 6.63 (d, J=9 Hz, 2H), 2.13 (s, 3H).

Step 2: Preparation of 2-Ethyl-6-fluoro-benzo[d][1,3]oxazin-4-one

A mixture of 2-amino-5-fluorobenzoic acid (23.3 g, 0.15 mol) and propionic acid anhydride (150 mL) was heated to reflux for 3 hr, then the propionic acid anhydride was removed in vacuo to afford 2-ethyl-6-fluoro-benzo[d][1,3]oxazin-4-one 2 as a gray solid, which was used directly in the next step.

Step 3: Preparation of 2-Ethyl-6-fluoro-benzo[d][1,3]oxazin-4-one

A mixture of 2-ethyl-6-fluoro-benzo[d][1,3]oxazin-4-one (25 g) and ammonia (300 mL, 25-28%) was stirred overnight. The solid was filtered to give 2-ethyl-6-fluoro-benzo[d][1,3]oxazin-4-one 3 as a white solid (23 g, 80%).

Step 4: Preparation of 2-(1-Bromo-ethyl)-6-fluoro-3H-quinazolin-4-one

To a solution of 2-ethyl-6-fluoro-benzo[d][1,3]oxazin-4-one 3 (19.2 g, 0.1 mol) and sodium acetate (8.2 g, 0.1 mol) in acetic acid (500 mL) was added dropwise a solution of bromine (16.0 g, 0.1 mol) in acetic acid (40 mL) at 10° C. After stirred at r.t. for 2 days, the reaction mixture was gradually poured into cold water. The precipitated solid was filtered, washed with water, dried to give 2-(1-bromo-ethyl)-6-fluoro-3H-quinazolin-4-one (10 g, yield=37%). $^1H$ NMR (DMSO-$d_6$) δ 12.6 (b, 1H), 7.78-7.67 (m, 3H), 5.07 (q, J=6.8 Hz, 1H), 1.97 (d, J=6.8 Hz, 3H). MS (ESI) m/e (M+H$^{30}$): 253.0.

Step 5: Preparation of 6-Fluoro-2-{1-[4-(4-methoxy-benzenesulfonyl)-piperazin-1-yl]-ethyl}-3H-quinazolin-4-one 6-Fluoro-2-{1-[4-(4-methoxy-benzenesulfonyl)-piperazin-1-yl]-ethyl}-3H-quinazolin-4-one was prepared by using the same method as described in Scheme I. (Yield 431.0 mg, 13.1%). %). $^{1H}$ NMR (400 MHz, CDCl$_3$): δ 1.35 (d, J=6.82 Hz, 3H), 2.58-2.47 (m, 2H), 2.69-2.58 (m, 2H), 3.10-2.84 (m, 4H), 3.53 (q, J=13.39, 6.82 Hz, 1H), 3.85 (s, 3H), 6.98 (d, J=8.34, 2H), 7.48-7.34 (m, 1H), 7.65-7.58 (m, 3H), 7.78 (d, J=8.34, 3.03 Hz, 1H). MS m/z calc. 446.5 found (ESI); 447.0 (M+1)$^+$. Retention time 2.75 minutes.

6-Fluoro-2-{1-[4-(4-methoxy-benzenesulfonyl)-piperazin-1-yl]-ethyl}-4-piperidin-1-yl-quinazoline

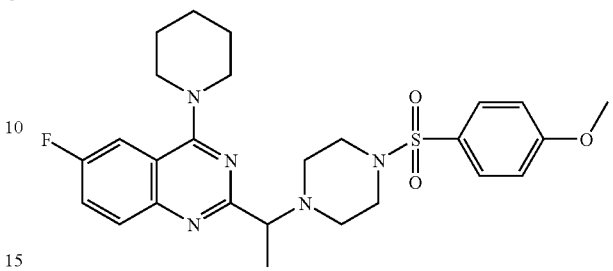

6-Fluoro-2-{1-[4-(4-methoxy-benzenesulfonyl)-piperazin-1-yl]-ethyl}-4-piperidin-1-yl-quinazoline was prepared using the same method as described in Scheme V (Yield 20.5 mg, 23.5%). MS m/z calc. 413.0 found (ESI); 514.4 (M+1)$^+$. Retention time 2.82 minutes.

6-Fluoro-2-{1-[4-(4-methoxy-benzenesulfonyl)-piperazin-1-yl]-ethyl}-4-(4-methyl-piperidin-1-yl)-quinazoline

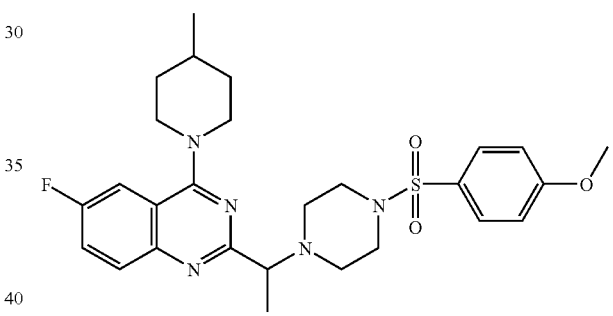

6-Fluoro-2-{1-[4-(4-methoxy-benzenesulfonyl)-piperazin-1-yl]-ethyl}-4-(4-methyl-piperidin-1-yl)-quinazoline was prepared by using the same method as described in Scheme V (Yield 50.2 mg, 57.3%). MS m/z calc. 527.0 found (ESI); 528.0 (M+1)$^+$. Retention time 2.96 minutes.

Cyclohexyl-(6-fluoro-2-{1-[4-(4-methoxy-benzenesulfonyl)-piperazin-1-yl]-ethyl}-quinazolin-4-yl)-amine

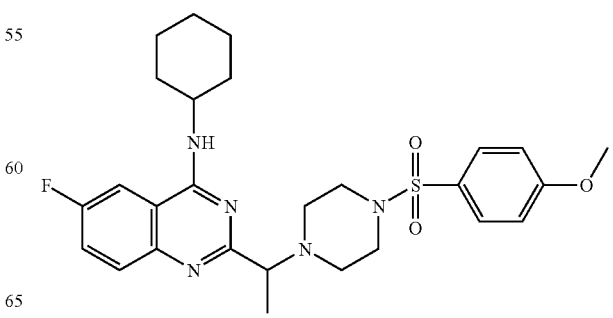

Cyclohexyl-(6-fluoro-2-{1-[4-(4-methoxy-benzenesulfonyl)-piperazin-1-yl]-ethyl}-quinazolin-4-yl)-amine was prepared using the same method as described in Scheme V (Yield 20.0 mg, 22.3%). MS m/z calc. 527.0 found (ESI); 528.2 (M+1)⁺. Retention time 2.96 minutes.

4-Cyclohexyloxy-6-fluoro-2-{1-[4-(4-methoxy-benzenesulfonyl)-piperazin-1-yl]-ethyl}-quinazoline

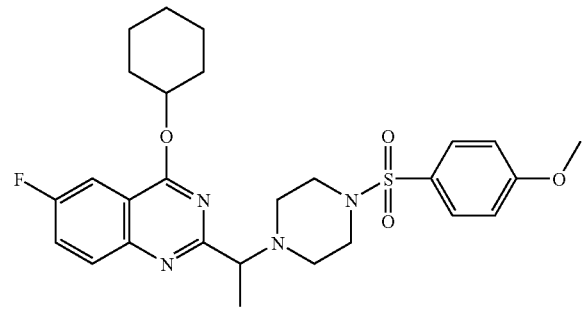 [SMILES: COc1ccc(S(=O)(=O)N2CCN(C(C)c3nc(OC4CCCCC4)c4cc(F)ccc4n3)CC2)cc1]

4-Cyclohexyloxy-6-fluoro-2-{1-[4-(4-methoxy-benzenesulfonyl)-piperazin-1-yl]-ethyl}-quinazoline was prepared using the same method as described in Scheme V (Yield 2.8 mg, 3.1%). MS m/z calc. 528.0 found (ESI); 529.2 (M+1)⁺. Retention time 3.29 minutes.

4-Cyclopentyloxy-6-fluoro-2-{1-[4-(4-methoxy-benzenesulfonyl)-piperazin-1-yl]-ethyl}-quinazoline

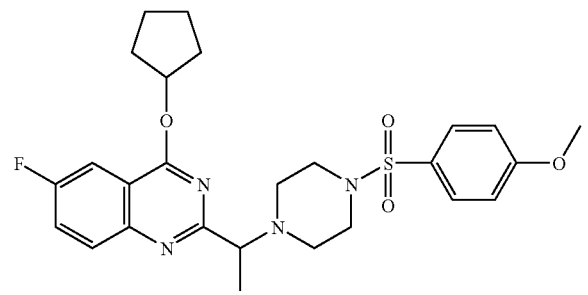 [SMILES: COc1ccc(S(=O)(=O)N2CCN(C(C)c3nc(OC4CCCC4)c4cc(F)ccc4n3)CC2)cc1]

4-Cyclopentyloxy-6-fluoro-2-{1-[4-(4-methoxy-benzenesulfonyl)-piperazin-1-yl]-ethyl}-quinazoline was prepared using the same procedure described in Scheme V. (Yield 5.2 mg, 5.9%). MS m/z calc. 514.2 found (ESI); 515.4 (M+1)⁺. Retention time 3.17 minutes.

4-(3,4-Dihydro-2H-quinolin-1-yl)-2-{1-[4-(4-methoxy-benzenesulfonyl)-piperazin-1-yl]-ethyl}-quinazoline

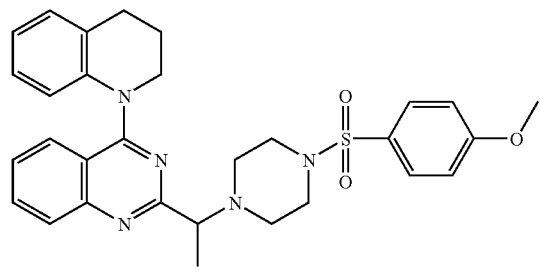 [SMILES: COc1ccc(S(=O)(=O)N2CCN(C(C)c3nc(N4CCCc5ccccc54)c4ccccc4n3)CC2)cc1]

4-(3,4-Dihydro-2H-quinolin-1-yl)-2-{1-[4-(4-methoxy-benzenesulfonyl)-piperazin-1-yl]-ethyl}-quinazoline was prepared using the same procedure described in Scheme V (Yield 16.0 mg, 41.5%). MS m/z calc. 543.6 found (ESI); 544.2 (M+1)⁺. Retention time 2.93 minutes.

4-(4-Benzyl-piperidin-1-yl)-2-{1-[4-(4-methoxy-benzenesulfonyl)-piperazin-1-yl]-ethyl}-quinazoline

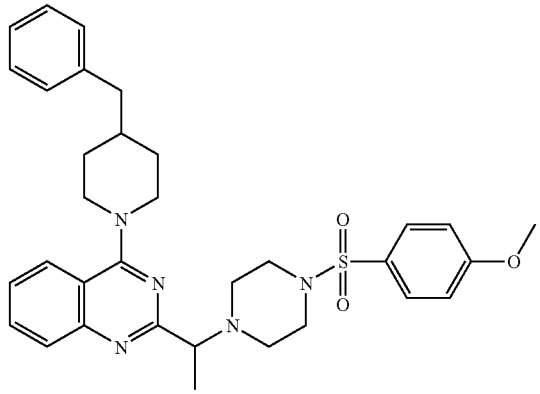 [SMILES: COc1ccc(S(=O)(=O)N2CCN(C(C)c3nc(N4CCC(Cc5ccccc5)CC4)c4ccccc4n3)CC2)cc1]

4-(4-Benzyl-piperidin-1-yl)-2-{1-[4-(4-methoxy-benzenesulfonyl)-piperazin-1-yl]-ethyl}-quinazoline was prepared using the same procedure described in Scheme V (Yield 18.7 mg, 45.7%). MS m/z calc. 585.7 found (ESI); 586.4 (M+1)⁺. Retention time 3.20 minutes.

2-{1-[4-(4-Methoxy-benzenesulfonyl)-piperazin-1-yl]-ethyl}-4-(4-phenyl-piperazin-1-yl)-quinazoline

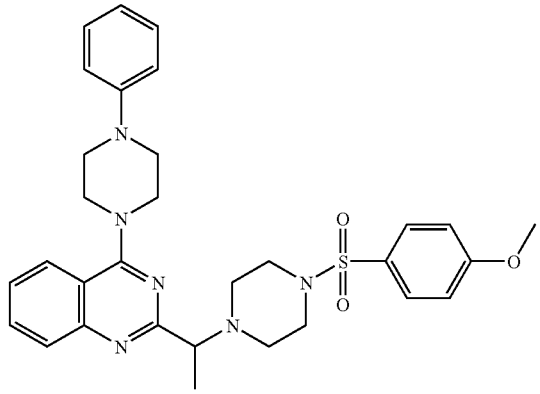 [SMILES: COc1ccc(S(=O)(=O)N2CCN(C(C)c3nc(N4CCN(c5ccccc5)CC4)c4ccccc4n3)CC2)cc1]

2-{1-[4-(4-Methoxy-benzenesulfonyl)-piperazin-1-yl]-ethyl}-4-(4-phenyl-piperazin-1-yl)-quinazoline was prepared using the same procedure described in Scheme V (Yield 32.2 mg, 80.4%). MS m/z calc. 572.3 found (ESI); 573.2 (M+1)⁺. Retention time 2.96 minutes.

4-(2,5-Dihydro-pyrrol-1-yl)-2-{1-[4-(4-methoxy-benzenesulfonyl)-piperazin-1-yl]-ethyl}-quinazoline

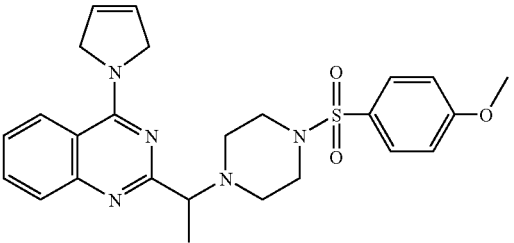 [SMILES: COc1ccc(S(=O)(=O)N2CCN(C(C)c3nc(N4CC=CC4)c4ccccc4n3)CC2)cc1]

4-(2,5-Dihydro-pyrrol-1-yl)-2-{1-[4-(4-methoxy-benzenesulfonyl)-piperazin-1-yl]-ethyl}-quinazoline was prepared using the same procedure described in Scheme V (Yield 28.7 mg, 85.6%). MS m/z calc. 479.3 found (ESI); 480.2 (M+1)⁺. Retention time 2.55 minutes.

4-(3,6-Dihydro-2H-pyridin-1-yl)-2-{1-[4-(4-methoxy-benzenesulfonyl)-piperazin-1-yl]-ethyl}-quinazoline

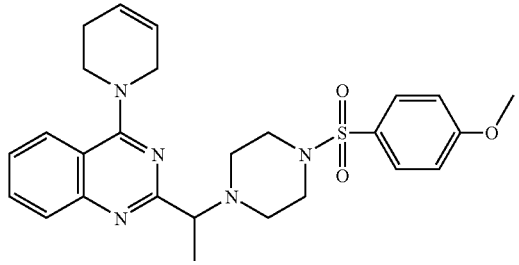 [SMILES: COc1ccc(S(=O)(=O)N2CCN(C(C)c3nc(N4CC=CCC4)c4ccccc4n3)CC2)cc1]

4-(3,6-Dihydro-2H-pyridin-1-yl)-2-{1-[4-(4-methoxy-benzenesulfonyl)-piperazin-1-yl]-ethyl}-quinazoline was prepared using the same procedure described in Scheme V (Yield 8.1 mg, 23.4%). MS m/z calc. 493.2 found (ESI); 494.4 (M+1)⁺. Retention time 2.68 minutes.

2-{1-[4-(4-Methoxy-benzenesulfonyl)-piperazin-1-yl]-ethyl}-4-thiazolidin-3-yl-quinazoline

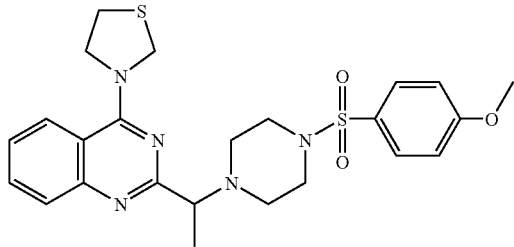 [SMILES: COc1ccc(S(=O)(=O)N2CCN(C(C)c3nc(N4CCSC4)c4ccccc4n3)CC2)cc1]

2-{1-[4-(4-Methoxy-benzenesulfonyl)-piperazin-1-yl]-ethyl}-4-thiazolidin-3-yl-quinazoline was prepared using the procedure described in Scheme V (Yield 23.8 mg, 68.1%). MS m/z calc. 499.2 found (ESI); 500.0 (M+1)⁺. Retention time 2.61 minutes.

[1,3]Dioxolan-2-ylmethyl-(2-{1-[4-(4-methoxy-benzenesulfonyl)-piperazin-1-yl]-ethyl}-quinazolin-4-yl)-methyl-amine

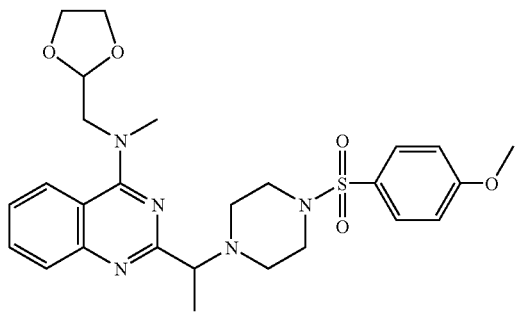 [SMILES: COc1ccc(S(=O)(=O)N2CCN(C(C)c3nc(N(C)CC4OCCO4)c4ccccc4n3)CC2)cc1]

[1,3]Dioxolan-2-ylmethyl-(2-{1-[4-(4-methoxy-benzenesulfonyl)-piperazin-1-yl]-ethyl}-quinazolin-4-yl)-methyl-amine was prepared using the same method as described in Scheme V (Yield 34.3 mg, 92.9%). MS m/z calc. 527.6 found (ESI); 528.2 (M+1)⁺. Retention time 2.52 minutes.

4-Cyclobutoxy-2-{1-[4-(4-methoxy-benzenesulfonyl)-piperazin-1-yl]-ethyl}-quinazoline

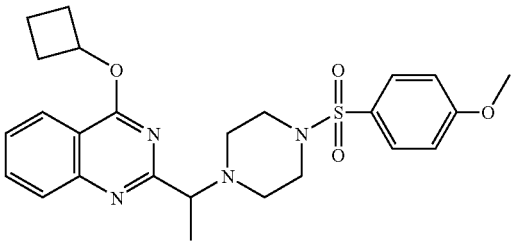 [SMILES: COc1ccc(S(=O)(=O)N2CCN(C(C)c3nc(OC4CCC4)c4ccccc4n3)CC2)cc1]

4-Cyclobutoxy-2-{1-[4-(4-methoxy-benzenesulfonyl)-piperazin-1-yl]-ethyl}-quinazoline was prepared by using the procedure described in Scheme V (Yield 10.0 mg, 22.3%). MS m/z calc. 482.2 found (ESI); 483.4 (M+1)⁺. Retention time 2.86 minutes.

2-{1-[4-(4-Methoxy-benzenesulfonyl)-piperazin-1-yl]-ethyl}-4-(4-methyl-cyclohexyloxy)-quinazoline

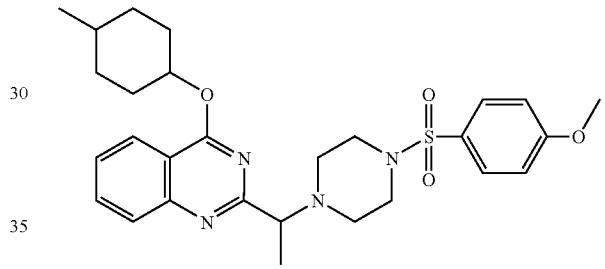

2-{1-[4-(4-Methoxy-benzenesulfonyl)-piperazin-1-yl]-ethyl}-4-(4-methyl-cyclohexyloxy)-quinazoline was prepared using the procedure described in Scheme V (Yield 10.0 mg, 20.5%). MS m/z calc. 4524.6 found (ESI); 525.2 (M+1)⁺. Retention time 3.31 minutes.

4-(Bicyclo[2.2.1]hept-2-yloxy)-2-{1-[4-(4-methoxy-benzenesulfonyl)-piperazin-1-yl]-ethyl}-quinazoline

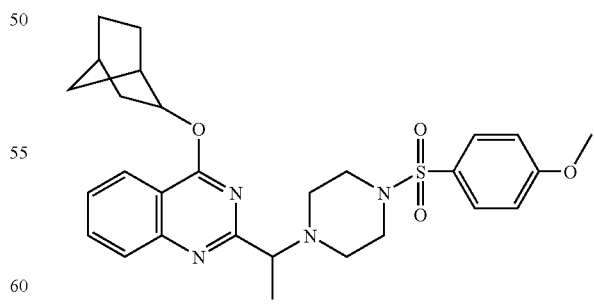

4-(Bicyclo[2.2.1]hept-2-yloxy)-2-{1-[4-(4-methoxy-benzenesulfonyl)-piperazin-1-yl]-ethyl}-quinazoline was prepared using the procedure described in Scheme V (Yield 10.0 mg, 20.6%). MS m/z calc. 4524.6 found (ESI); 525.2 (M+1)⁺. Retention time 3.32 minutes.

General Procedure for Formation of Diamine Spacer Analogs

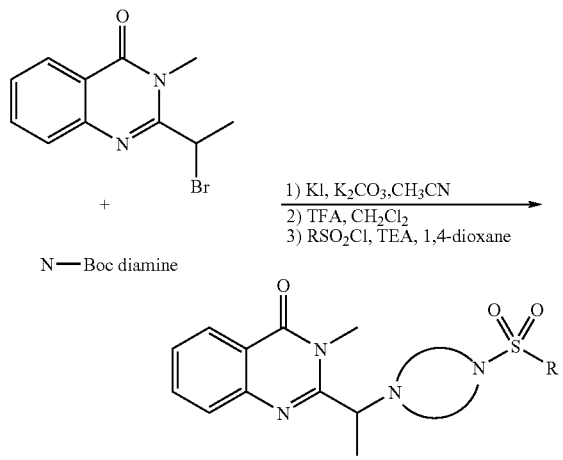

A mixture of 2-(1-bromo-ethyl)-3-methyl-3H-quinazolin-4-one (801 mg, 3 mmol), the N-Boc amine (3.3 mmol), potassium iodide (498 mg, 3 mmol) and potassium carbonate (622 mg, 4.5 mmol) in acetonitrile (12 mL) was heated at 65° C. for 3 days. The reaction mixture was then concentrated in vacuo. The residue was dissolved in dichloromethane and washed with saturated sodium thiosulphate solution and water. The organic layer was dried over magnesium sulfate and concentrated in vacuo. The residue was dissolved in dichloromethane (5 mL) and TFA (5 mL) was added. The reaction was stirred at RT until deprotection was complete (as detected by LC-MS). IN NaOH solution was added until the solution was basic (pH 11-12). The organic layer was extracted and washed with water, dried over magnesium sulfate and concentrated in vacuo to yield the product which was used with no further purification. The deprotected amine (0.2 mmol) and triethylamine (167 µL, 0.4 mmol) were dissolved in dioxane (1 mL) and to this was added the corresponding sulfonyl chloride (0.3 mmol). The reaction was shaken at room temperature overnight. Dichloromethane (2 mL) and water (2 mL) were added and the reaction tube was shaken. The top aqueous layer was aspirated off and the organic layer was concentrated in vacuo. The residue was dissolved in DMSO and purified by HPLC to yield the final product.

2-{1-[1-(4-Methoxy-benzenesulfonyl)-piperidin-4-ylamino]-ethyl}-3-methyl-3H-quinazolin-4-one

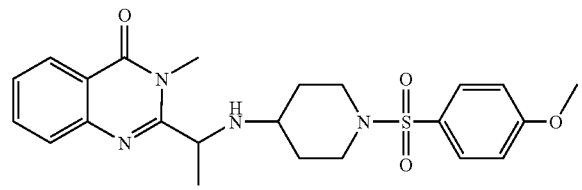 [SMILES: COc1ccc(S(=O)(=O)N2CCC(NC(C)c3nc4ccccc4c(=O)n3C)CC2)cc1]

Step 1:

A mixture of 2-(1-bromo-ethyl)-3-methyl-3H-quinazolin-4-one (801 mg, 3 mmol), 4-amino-1-N-Boc piperidine (661 mg, 3.3 mmol), potassium iodide (498 mg, 3 mmol) and potassium carbonate (622 mg, 4.5 mmol) in acetonitrile (12 mL) was heated at 65° C. for 3 days. The reaction mixture was then concentrated in vacuo. The residue was dissolved in dichloromethane and washed with saturated sodium thiosulphate solution and water. The organic layer was dried over magnesium sulfate and concentrated in vacuo to yield 4-[1-(3-Methyl-4-oxo-3,4-dihydro-quinazolin-2-yl)-ethylamino]-piperidine-1-carboxylic acid tert-butyl ester (HPLC ret. time 2.20, 10-99% $CH_3CN$, 5 min run, ESI-MS m/z 387.4 $(MH^+)$.

Step 2:

The product was dissolved in dichloromethane (5 mL) and TFA (5 mL) was added. The reaction was stirred at room temperature until deprotection was complete (as detected by LC-MS). 1N NaOH solution was added until the solution was basic (pH 11-12). The organic layer was extracted and washed with water, dried over magnesium sulfate and concentrated in vacuo to yield 3-Methyl-2-[1-(piperidin-4-ylamino)-ethyl]-3H-quinazolin-4-one, which was used with no further purification. (HPLC ret. time 1.19, 10-99% $CH_3CN$, 5 min run, ESI-MS m/z 287.2 (M+1)+.

Step 3:

3-Methyl-2-[1-(piperidin-4-ylamino)-ethyl]-3H-quinazolin-4-one (57.2 mg, 0.2 mmol) and triethylamine (167 µL, 0.4 mmol) were dissolved in dioxane (1 mL) and to this was added 4-methoxybenzenesulfonyl chloride (62 mg, 0.3 mmol). The reaction was shaken at room temperature overnight. Dichloromethane (2 mL) and water (2 mL) were added and the reaction tube was shaken. The top aqueous layer was aspirated off and the organic layer was concentrated in vacuo. The residue was dissolved in DMSO and purified by HPLC to yield the final product, 2-{1-[1-(4-Methoxy-benzenesulfonyl)-piperidin-4-ylamino]-ethyl}-3-methyl-3H-quinazolin-4-one. HPLC ret. time 2.23, 10-99% $CH_3CN$, 5 min run; $^1H$ NMR ($CDCl_3$) δ 1.55 (d, 3H, J=6.6 Hz), 1.66 (q, 2H, J=12.1 Hz), 2.16 (m, 4H), 3.19 (m, 1H), 3.53 (s, 3H), 3.68 (m, 2H), 3.80 (s, 3H), 4.86 (q, 1H, J=5.7 Hz), 7.12 (d, 2H, J=9.0 Hz), 7.57 (t, 1H, J=8.1 Hz), 7.63 (d, 2H, J=8.9 Hz), 7.69 (d, 1H, J=7.7 Hz), 7.86 (t, 1H, J=8.4 Hz), 8.15 (dd, 1H, J=8.0, 1.2 Hz); ESI-MS m/z 457.4 $(M+1)^+$.

2-(1-{[1-(4-Methoxy-benzenesulfonyl)-piperidin-4-yl]-methyl-amino}-ethyl)-3-methyl-3H-quinazolin-4-one

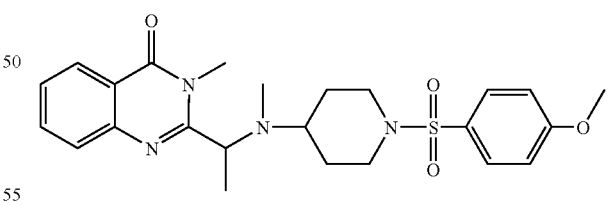

To a mixture of 2-{1-[1-(4-methoxy-benzenesulfonyl)-piperidin-4-ylamino]-ethyl}-3-methyl-3H-quinazolin-4-one (183 mg, 0.4 mmol), formaldehyde (39 µL, 0.48 mmol, 37% wt. solution in water) and DMF (1 mL) was added MP-Cyanoborohydride (300 mg, 2-3 mmol/g) and the reaction was stirred overnight at room temperature. The reaction mixture was then filtered and purified by HPLC to yield the product. HPLC ret. time 2.41 min, 10-99% $CH_3CN$, 5 min run; $^1H$ NMR (400 MHz, $CDCl_3$) δ 8.28 (d, J=8.0 Hz, 1H), 7.93 (t, J=7.2 Hz, 1H), 7.68 (m, 4H), 7.03 (d, J=8.6 Hz, 2H), 4.93 (m, 1H), 3.98 (s, 1H), 3.89 (s, 3H), 3.69 (s, 3H), 3.10 (s, 3H), 2.58 (m, 2H), 2.21 (m, 2H), 1.78 (d, J=6.6 Hz, 3H), 1.31 (m, 4H); ESI-MS m/z 471.3 (M+1)+.

2-{1-[4-(4-Bromo-benzenesulfonyl)-piperazin-1-yl]-ethyl}-quinazoline

Step 1: N-(2-Formyl-phenyl)-propionamide

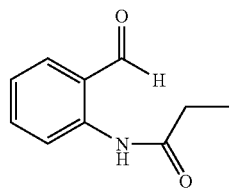

To a solution of 2-aminobenzaldehyde (1.21 g, 10 mmol), and triethylamine (1.39 mL, 10 mmol) in dichloromethane (50 mL) was added propionyl chloride (1.04 mL, 12 mol). The reaction was stirred at room temperature for 3 days. The reaction solution was washed with water and then dried over magnesium sulfate and concentrated in vacuo to yield the crude product (1.65 g, 93%). The product was used without further purification. $^1$H NMR (400 MHz, CDCl3) δ 11.16 (s, 1H), 9.93 (s, 1H), 8.77 (d, J=8.5 Hz, 1H), 7.67 (d, J=7.7 Hz, 1H), 7.62 (t, J=7.1 Hz, 1H), 7.22 (t, J=7.5 Hz, 1H), 2.51 (q, J=7.6 Hz, 2H), 1.29 (t, J=7.6 Hz, 3H); HPLC ret. time 1.34 min, 10-99% CH$_3$CN, 5 min run; ESI-MS m/z 177.2 (M+1)$^+$.

Step 2: 2-Ethyl-quinazoline

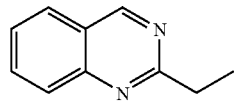

N-(2-Formyl-phenyl)-propionamide (1.65 g, 9.3 mmol) was combined with ammonia (24 mL, 2M solution in methanol) in a flask fitted with a condenser and stopper with a needle to vent. The reaction was heated to 100° C. for 1 day. The reaction mixture was concentrated in vacuo to yield the crude product as an orange oil (1.47 g, 100%). This product was used without further purification. $^1$H NMR (400 MHz, CDCl3) δ 9.36 (s, 1H), 7.99 (d, J=10.0 Hz, 1H), 7.89 (m, 2H), 7.60 (t, J=8.1 Hz, 1H), 3.16 (q, J=7.6 Hz, 2H), 1.47 (t, J=7.6 Hz, 3H); HPLC ret. time 0.61 min, 10-99% CH$_3$CN, 5 min run; ESI-MS m/z 159.0 (MH$^+$).

Step 3: 2-(1-Bromo-ethyl)-quinazoline

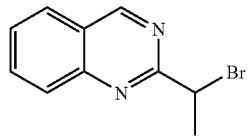

A solution of 2-ethyl-quinazoline (316 mg, 2 mmol), N-bromosuccinimide (356 mg, 2 mmol) and benzoyl peroxide (48 mg, 0.2 mmol) in chloroform (10 mL) was heated to reflux for 2 hours. The reaction solution was concentrated in vacuo and purified by column chromatography (0-25% ethyl acetate-hexanes) to yield the pure product (130 mg, 28%). $^1$H NMR (400 MHz, CDCl3) δ 9.45 (s, 1H), 8.04 (d, J=9.0 Hz, 1H), 7.94 (m, 2H), 7.68 (t, J=8.1 Hz, 1H), 5.47 (q, J=6.9 Hz, 1H), 2.23 (d, J=6.9 Hz, 3H); HPLC ret. time 2.79 min, 10-99% CH$_3$CN, 5 min run; ESI-MS m/z 236.9 (M+1)$^+$.

Step 4: 2-{1-[4-(4-Bromo-benzenesulfonyl)-piperazin-1-yl]-ethyl}-quinazoline

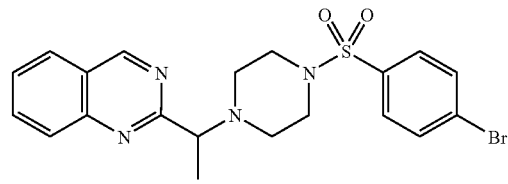 [SMILES: CC(c1ncc2ccccc2n1)N1CCN(S(=O)(=O)c2ccc(Br)cc2)CC1]

A mixture of 2-(1-Bromo-ethyl)-quinazoline (43 mg, 0.18 mmol) and 1-(4-Bromo-benzenesulfonyl)-piperazine (67 mg, 0.22 mmol), potassium iodide (30 g, 0.18 mmol) and potassium carbonate (37 mg, 0.27 mmol) in acetonitrile (1 mL) was heated at 65° C. for 1 day. The reaction mixture was then concentrated in vacuo. The residue was dissolved in dichloromethane and washed with saturated sodium thiosulphate solution, saturated sodium bicarbonate solution and then with water. The organic layer was dried over magnesium sulfate and concentrated in vacuo. The crude product was dissolved in DMSO and purified by HPLC. $^1$H NMR (400 MHz, CDCl3) δ 9.45 (s, 1H), 8.06 (m, 3H), 7.80 (t, J=7.9 Hz, 1H), 7.72 (d, J=8.5 Hz, 2H), 7.58 (d, J=8.5 Hz, 2H), 4.86 (q, J=7.0 Hz, 1H), 3.65 (m, 2H), 3.43 (m, 6H), 1.88 (d, J=7.0 Hz, 3H) HPLC ret. time 2.45 min, 10-99% CH$_3$CN, 5 min run; ESI-MS m/z 461.1 (M+1)$^+$.

Methyl 2-(diethoxyphosphoryl)-propionate

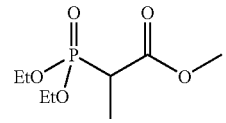

Methyl 2-bromo propionate (181 g, 1 mol) was preheated at 140° C. and then the triethyl phosphite was added dropwise over a period of 2 hours. Ethyl bromide was removed from the system and the temperature was raised to 160° C. After the addition was complete, the temperature was raised to 190° C. for 1 hr. The mixture was fractionated to give the product as a colorless liquid (185 g, 82.6%, Bp$_{16mmHg}$ 142-146° C.). $^1$HNMR (CDCl$_3$) δ 4.16-4.08 (m, 4H), 3.73 (s, 3H), 3.07-2.96 (dq, 1H, $J_{H-H}$=7.2 Hz, $J_{P-H}$=23.6 Hz), 1.44-1.38 (dd, 3H, $J_{H-H}$=7.2 Hz, $J_{P-H}$=16 Hz), 1.32-1.25 (m, 3H).

2-(1-benzylpiperidin-4-ylidene)-propionic acid methyl ester

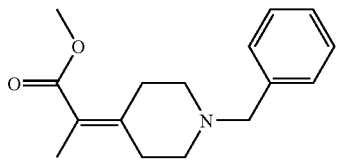 [SMILES: COC(=O)C(C)=C1CCN(Cc2ccccc2)CC1]

To a suspension of NaH (60% in mineral oil, 6 g, 0.15 mol) in dry THF (300 mL), under $N_2$ atmosphere, was added a solution of methyl 2-(diethoxyphosphoryl)-propionate (33.6 g, 0.15 mol) in dry THF (150 mL) at such a rate to keep the temperature below 30° C. After being stirred at r.t for 40 min, a solution of N-benzyl-4-piperidone (28.35 g, 0.15 mol) in dry THF (100 mL) was added dropwise keeping the temperature below 30° C. After the addition was completed, the mixture was stirred at r.t for 30 min. The reaction was quenched with $NH_4Cl$ (sat. aq., 400 mL). The mixture was extracted with $Et_2O$ (300 mL×2) and the combined extracts were washed with brine, dried and concentrated to give the crude product as a red oil, which was used directly in the next step.

4-(1-Methoxycarbonyl-ethyl)-piperidine-1-carboxylic acid tert-butyl ester

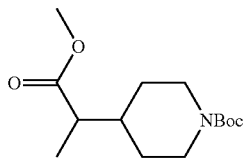 [SMILES: COC(=O)C(C)C1CCN(C(=O)OC(C)(C)C)CC1]

A mixture of 2-(1-benzylpiperidin-4-ylidene)-propionic acid methyl ester (45 g crude from last step, about 0.15 mol), $Boc_2O$ (32.7 g, 0.15 mol) and 10% Pd/C (4 g) in EtOH (600 mL) was stirred overnight at 55° C. under a $H_2$ atmosphere ($P_{H2}$=55 PSI). The catalyst was filtered off and the filtrate was concentrated in vacuo to give the crude product as light yellow oil, which was directly used in next step.

4-(1-Carboxy-ethyl)-piperidine-1-carboxylic acid tert-butyl ester

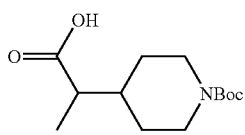

A mixture of 4-(1-methoxycarbonylethyl)-piperidine-1-carboxylic acid tert-butyl ester (40 g crude from last step, about 0.15 mol), LiOH (12.6 g, 0.3 mol) in water (200 mL) and THF (400 mL) was heated to reflux for 4 hours. The cooled mixture was diluted with water (200 mL) and washed with $Et_2O$ (200 mL×2). The aqueous layer was acidified with HCl (10%) at 0° C. to pH3-4. The mixture was extracted with $Et_2O$ (200 mL×3) and the combined extracts were washed with brine, dried and concentrated to give the product as a white solid (28 g, 73% from N-benzyl-4-piperidone). $^1$HNMR (CDCl$_3$) δ 4.11 (m, 2H), 2.69-2.63 (m, 2H), 2.30 (p, 1H, J=7.2 Hz), 1.72-1.62 (m, 3H), 1.44 (s, 9H), 1.27-1.18 (m, 2H), 1.16 (d, 3H, J=7.2 Hz).

Preparation of 4-[1-(2-carbamoylphenylcarbamoyl)-ethyl]-piperidine-1-carboxylic acid tert-butyl ester

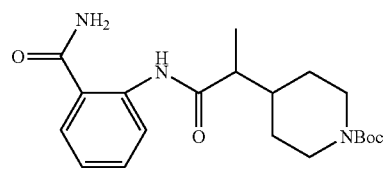 [SMILES: CC(C(=O)Nc1ccccc1C(N)=O)C1CCN(C(=O)OC(C)(C)C)CC1]

A mixture of 4-(1-carboxy-ethyl)-piperidine-1-carboxylic acid tert-butyl ester (28.6 g, 0.11 mol), 2-aminobenzamide (13.7 g, 0.1 mol), EDCI (21.3 g, 0.11 mol), HOBT (15 g, 0.11 mol) and $Et_3N$ (25 mL) in $CH_2Cl_2$ (500 mL) was stirred for 48 hr. The reaction mixture was diluted with $CH_2Cl_2$ (1000 mL) and washed with $NaHCO_3$ (aq), the organic layer was dried with $Na_2SO_4$ and concentrated in vacuo to give the product a yellow solid (20 g, 48%) which was used directly for the next step.

4-[1-(4-oxo-3,4-dihydro-quinazolin-2-yl)-ethyl]-piperidine-1-carboxylic acid tert-butyl ester

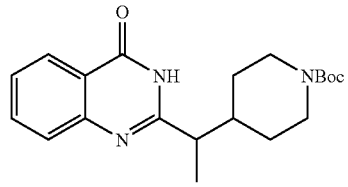 [SMILES: CC(c1nc2ccccc2c(=O)[nH]1)C1CCN(C(=O)OC(C)(C)C)CC1]

A solution of 4-[1-(2-carbamoyl-phenylcarbamoyl)-ethyl]-piperidine-1-carboxylic acid tert-butyl ester (20 g, 0.05 mmol, crude from the last step) and MeONa (10 g, 0.19 mol) in MeOH (500 mL) was heated to reflux for 6 hr and the solvent was removed in vacuo. The residue was diluted with water and extracted with EtOAc (300 mL×3), the organic layer was dried with $Na_2SO_4$, concentrated and purified by column chromatography to afford the product (2 g, 5%).

2-(1-piperidin-4-yl-ethyl)-3H-quinazolin-4-one

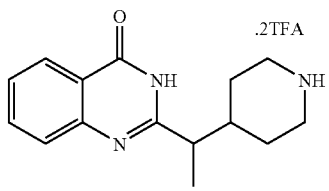 [SMILES: CC(c1nc2ccccc2c(=O)[nH]1)C1CCNCC1 ; ".2TFA"]

A solution of 4-[1-(4-oxo-3,4-dihydro-quinazolin-2-yl)-ethyl]-piperidine-1-carboxylic acid tert-butyl ester and TFA in $CH_2Cl_2$ was stirred at r.t. for 6 hr. The precipitated solid was filtered and dried to afford the product as a white solid. (2 g, 90%). $^1$H NMR (DMSO-d$_6$) δ 8.51 (br, s, 1H), 8.18 (br, s, 1H), 8.06 (d, 1H, J=7.6), 7.74 (t, 1H, J=8.0), 7.57 (d, 1H, J=8.0), 7.44 (t, 1H, J=8.0), 3.29-3.18 (m, 2H), 2.88-2.76 (m, 2H), 2.61-2.57 (m, 1H), 1.95-1.92 (m, 2H), 1.61-1.57 (m, 1H), 1.42-1.25 (m, 2H), 1.25 (d, 3H, J=6.8); ESI-MS m/z 258.1 (M+1)$^+$.

2-{1-[1-(4-Methoxy-benzenesulfonyl)-piperidin-4-yl]-ethyl}-3H-quinazolin-4-one

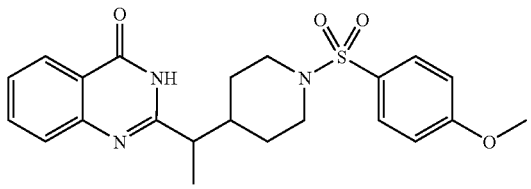 [SMILES: COc1ccc(S(=O)(=O)N2CCC(C(C)c3nc4ccccc4c(=O)[nH]3)CC2)cc1]

To a mixture of 2-(1-piperidin-4-yl-ethyl)-3H-quinazolin-4-one (971 mg, 2 mmol) and triethylamine (976 μL, 7 mmol) in 1,4-dioxane (10 mL) was added 4-methoxysulfonyl chloride (537 mg, 2.6 mmol). The reaction was stirred at room temperature for 3 hours, the filtered and the solute was concentrated in vacuo. The residue was dissolved in dichloromethane and extracted with water. The organic layer was concentrated in vacuo and purified by column chromatography (25-50% ethyl acetate-hexanes) to yield the product as a white solid (70 mg, 8%). $^1$H NMR (400 MHz, CDCl3) δ 11.11 (s, 1H), 8.24 (dd, J=7.9, 1.1 Hz, 1H), 7.79 (t, J=8.4 Hz, 1H), 7.68 (m, 3H), 7.48 (t, J=7.5 Hz, 1H), 6.98 (d, J=8.9 Hz, 2H), 3.89 (s, 3H), 3.75 (d, J=11.7 Hz, 1H), 2.62 (quintet, J=7.4 Hz, 1H), 2.24 (m, 2H), 1.71 (m, 4H), 1.50 (m, 2H), 1.39 (d, J=7.0 Hz, 3H); HPLC ret. time 2.89 min, 10-99% CH$_3$CN, 5 min run; ESI-MS m/z 428.1 (M+1)$^+$.

4-Cyclopentyloxy-2-{1-[1-(4-methoxy-benzenesulfonyl)-piperidin-4-yl]-ethyl}-quinazoline

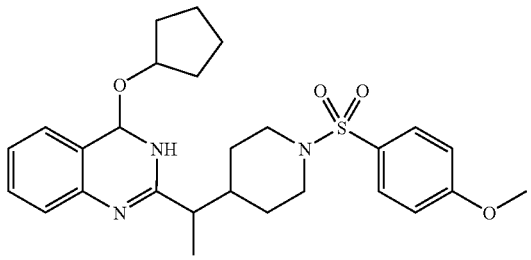 [SMILES: COc1ccc(S(=O)(=O)N2CCC(C(C)C3=Nc4ccccc4C(OC4CCCC4)N3)CC2)cc1]

A mixture of 2-{1-[1-(4-Methoxy-benzenesulfonyl)-piperidin-4-yl]-ethyl}-3H-quinazolin-4-one (34 mg, 0.08 mmol), cyclopentyl iodide (18 μL, 0.16 mmol), and potassium carbonate (55 mg, 0.4 mmol) in DMF (1 mL) was heated to 70° C. for 1 day. The reaction mixture was partitioned between dichloromethane and water. The organic layer was concentrated in vacuo and the residue was purified by HPLC (in the absence of TFA) to yield the product. $^1$H NMR (400 MHz, DMSO-d6) δ 8.07 (d, J=7.6 Hz, 1H), 7.81 (d, J=8.3 Hz, 1H), 7.75 (t, J=7.0 Hz, 1H), 7.67 (d, J=8.9 Hz, 2H), 7.46 (t, J=7.5 Hz, 1H), 6.97 (d, J=8.9 Hz, 2H), 5.63 (m, 1H), 3.68 (s, 3H), 3.80 (d, J=11.6 Hz, 1H), 3.67 (dd, J=11.2, 1.6 Hz, 1H), 2.81 (quintet, J=7.3 Hz, 1H), 2.28 (t, J=11.8 Hz, 1H), 2.17 (m, 1H), 1.93 (m, 10H), 1.44 (m, 3H), 1.29 (d, J=6.9 Hz, 3H); HPLC ret. time 3.24 min, 10-99% CH$_3$CN, 5 min run; ESI-MS m/z 496.3 (M+1)$^+$

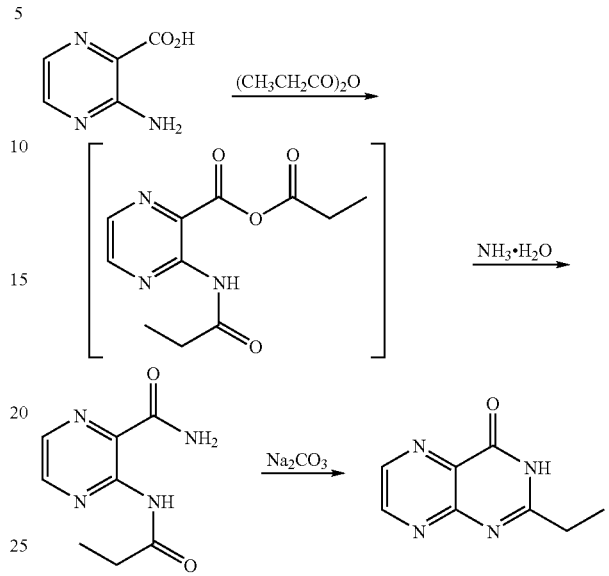

Preparation of 3-propionylamino-pyrazine-2-carboxylic acid amide

A mixture of 3-amino-pyrazine-2-carboxylic acid (20.9 g, 0.15 mol), pyridine (29.6 g, 0.375 mol) and DMAP (1.83 g, 15 mmol) in propionic acid anhydride (100 mL) was stirred at room temperature overnight. The reaction mixture was poured into NH$_3$.H$_2$O (500 mL) partially at 0° C. After stirred for 30 min at 0° C., the precipitated solid was filtered, washed with water, dried in air to give 3-propionylamino-pyrazine-2-carboxylic acid amide as a beige solid (12.4 g, 43%), which was used directly in the next step.

Preparation of 2-Ethyl-3H-pteridin-4-one

A mixture of 3-propionylamino-pyrazine-2-carboxylic acid amide (9.7 g, 50 mmol) and Na$_2$CO$_3$ (100 mL, 10%) was refluxed overnight. The water was removed in vacuo and the residue was treated with CH$_3$OH (200 mL). The insoluble salt was filtered and the filtrate was evaporated to give 2-Ethyl-3H-pteridin-4-one as a yellow solid (6.1 g, 69%). $^1$H NMR (DMSO-d$_6$) δ 8.64 (d, J=2 Hz, 1H), 8.36 (d, J=2 Hz, 1H), 2.52 (q, J=4.5 Hz, 2H), 1.18 (t, J=4.5 Hz, 3H). MS (ESI) m/e (M+1)$^{30}$: 177.3.

2-{1-[4-(4-Methoxy-benzenesulfonyl)-piperazin-1-yl]-ethyl}-3H-pteridin-4-one

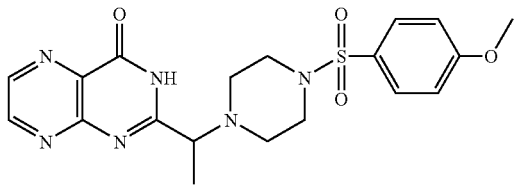 [SMILES: COc1ccc(S(=O)(=O)N2CCN(C(C)c3nc4nccnc4c(=O)[nH]3)CC2)cc1]

2-{1-[4-(4-Methoxy-benzenesulfonyl)-piperazin-1-yl]-ethyl}-3H-pteridin-4-one by using the same method as described in Scheme IA or Scheme IB. (Yield 249.0 mg, 24.4%). $^{1H}$ NMR (400 MHz, CDCl$_3$): δ 1.44 (d, J=7.33 Hz, 3H), 2.71-2.56 (m, 4H), 3.13-2.84 (m, 4H), 3.85 (s, 3H), 4.05 (q, 1H, J=14.15, 7.33 Hz), 6.99 (d, J=8.84, 1H), 7.63 (d, J=8.84, 2H), 8.74 (d, J=2.02, 1H), 8.88 (d, J=2.02, 1H). MS m/z calc. 430.4 found (ESI); 431.2 (M+1)$^+$. Retention time 2.30 minutes.

4-Cyclohexyloxy-2-{1-[4-(4-methoxy-benzenesulfonyl)-piperazin-1-yl]-ethyl}-pteridine

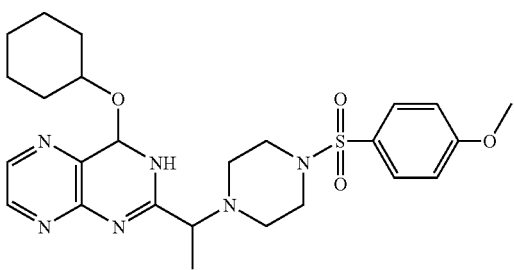 [SMILES: COc1ccc(S(=O)(=O)N2CCN(C(C)C3=Nc4nccnc4C(OC4CCCCC4)N3)CC2)cc1]

4-Cyclohexyloxy-2-{1-[4-(4-methoxy-benzenesulfonyl)-piperazin-1-yl]-ethyl}-pteridine by using the procedure described in Scheme V. (Yield 10.0 mg, 27.9%). MS m/z calc. 512.6 found (ESI); 513.2 (M+1)$^+$. Retention time 3.67 minutes.

4-Cyclopentyloxy-2-{1-[4-(4-methoxy-benzenesulfonyl)-piperazin-1-yl]-ethyl}-pteridine

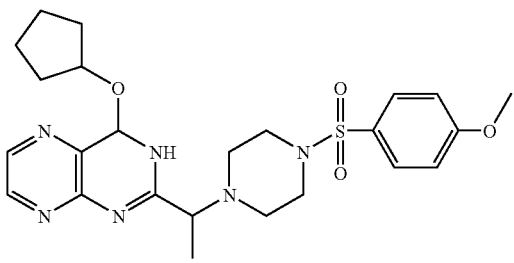 [SMILES: COc1ccc(S(=O)(=O)N2CCN(C(C)C3=Nc4nccnc4C(OC4CCCC4)N3)CC2)cc1]

4-Cyclopentyloxy-2-{1-[4-(4-methoxy-benzenesulfonyl)-piperazin-1-yl]-ethyl}-pteridine by using the procedure described in Scheme V (Yield 10.0 mg, 27.9%). MS m/z calc. 498.6 found (ESI); 499.2 (M+1)$^+$. Retention time 3.56 minutes.

Synthesis of Pyrimidines

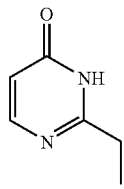

2-ethyl-3H-pyrimidin-4-one

Step 1:

Dry HCl (g) is passed into a cold solution (−20° C.) of dry propionitrile (406 g, 7.38 mol) in absolute alcohol (347 g, 7.56 mol) until an increase of 284 g (7.78 mol) in weight. It was stirred overnight and a solid mass of white crystals of propionimidic acid ethyl ester hydrochloride came out which were used directly in the next step without further purification.

Step 2:

The propionimidic acid ethyl ester hydrochloride from step 1 (171 g, 1.69 mol) was dissolved in a solution of ammonia in alcohol (350 g, 9.15%). The resulting mixture was allowed to stir overnight and the small amount of salt was filtered off. Removal of the solvent in vacuo gave 116 g (86%) of white solid, which can be used directly in the next step.

Step 3:

To a hot (60° C.) solution of propionamidine hydrochloride prepared in step 2 (54.3 g, 0.5 mol) and propynoic acid ethyl ester (53.9 g, 0.55 mol) in absolute alcohol (1 L) was added dropwise a solution of KOH (70 g, 80%, 1 mol) in absolute alcohol (300 mL) during 3 hours. The temperature was kept between 60° C. and 70° C. during the addition. The solvent was removed in vacuo and the residue was dissolved in water. The aqueous solution was acidified to pH 5 with HCl (6 M), extracted with ethyl acetate for at least 15 times. The organic layer was dried over Na$_2$SO$_4$ and then filtered. The filtrate was evaporated under reduced pressure and the residue was recrystallized with acetonitrile to afford 2-ethyl-3H-pyrimidin-4-one as light yellow crystals (14 g, 23%).

$^1$H-NMR(CDCl3) δ 8.00-7.98 (d, 1H, J=6.8 Hz), 6.34-6.33 (d, 1H, J=Hz), 2.77-2.71 (q, 2H), 1.37-1.33 (t, 3H). MS (ESI) m/e (M+1) 125.2.

5-Bromo-2-(1-bromo-ethyl)-3H-pyrimidin-4-one

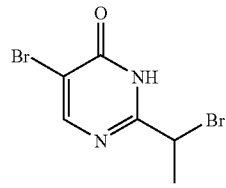

To a solution of 2-ethyl-3H-pyrimidin-4-one (3.0 g, 24.2 mmol) in chloroform (50 ml) were added NBS (4.3 g, 24.2 mmol) and benzoyl peroxide (5.8 g, 24.2 mmol) and the mixture was heated at 60° C. for 2 hours. The reaction was cooled to room temperature and the solvent was evaporated. The solid residue was washed with ether 3 times to give 5-Bromo-2-(1-bromo-ethyl)-3H-pyrimidin-4-one (Yield 3.6 g, 52.3%) that was used in next step without further purification. $^{1H}$ NMR (400 MHz, CDCl$_3$): δ 1.98 (d, J=7.1 Hz, 3H), 4.88 (q, J=7.1 Hz, 1H), 8.22 (s, 1H). MS m/z calc. 281.9 found (ESI); 283.0 (M+1)$^+$. Retention time 1.97 minutes.

5-Bromo-2-{1-[4-(4-methoxy-benzenesulfonyl)-piperazin-1-yl]-ethyl}-3H-pyrimidin-4-one

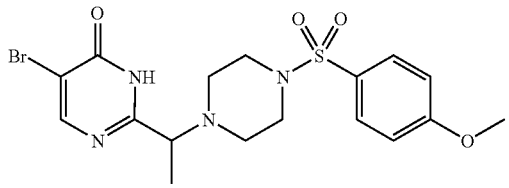 [SMILES: COc1ccc(S(=O)(=O)N2CCN(C(C)c3ncc(Br)c(=O)[nH]3)CC2)cc1]

In a round bottom flask containing 5-bromo-2-(1-bromo-ethyl)-3H-pyrimidin-4-one (1.0 g, 3.5 mmol) in acetonitrile (30 ml) was added KI (0.9 g, 5.3 mmol), $K_2CO_3$ (1.2 g, 5.3 mmol), and (1-(4-Methoxy-benzenesulfonyl)-piperazine (983 mg, 3.5 mmol). The reaction was heated at reflux for 12 hours. The solution was concentrated under reduced pressure. The residue was partitioned between water (10 ml) and dichloromethane (15 ml). The organic layer was dried over magnesium sulfate, filtered and concentrated under reduced pressure. The solvent was removed under vacuum. The resulting residue purified by column chromatography (ethyl acetate: hexanes 1:1) to give 5-bromo-2-{1-[4-(4-methoxy-benzenesulfonyl)-piperazin-1-yl]-ethyl}-3H-pyrimidin-4-one (Yield 854 mg, 53%). $^1$H NMR (400 MHz, $CDCl_3$): δ 1.28 (d, J=7.0 Hz, 3H), 2.62-2.49 (m, 4H), 3.00-2.94 (m, 4H), 3.84 (s, 3H), 4.05 (q, 1H, J=7.0 Hz), 6.97 (d, J=11.8 Hz, 2H), 7.62 (d, J=11.8 Hz, 2H), 8.11 (s, 1H). MS m/z calc. 457.3, found (ESI); 457.2 (M+1)$^+$. Retention time 2.50 minutes.

5-Bromo-4-cyclopentyloxy-2-{1-[4-(4-methoxy-benzenesulfonyl)-piperazin-1-yl]-ethyl}-pyrimidine

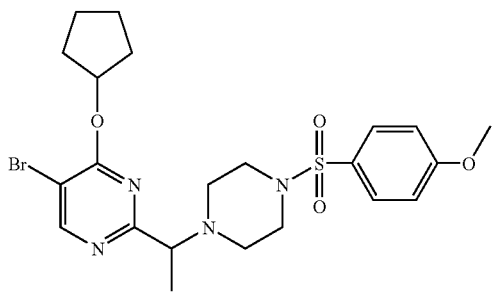 [SMILES: COc1ccc(S(=O)(=O)N2CCN(C(C)c3ncc(Br)c(OC4CCCC4)n3)CC2)cc1]

To a solution of 5-Bromo-2-{1-[4-(4-methoxy-benzene-sulfonyl)-piperazin-1-yl]-ethyl}-3H-pyrimidin-4-one(100 mg, 0.22 mmol) in 2 ml DMF was added iodo-cyclopentane (85.7 mg, 0.22 mmol) and potassium carbonate (152.0 mg, 1.1 mmol). This reaction was heated to 90° C. for 18 hours. After cooling down to room temperature, the $K_2CO_3$ was filtrated. Purification was accomplished by HPLC (Gilson-215, 0.035% TFA in acetonitrile and 0.05% water as mobile phase). The product was collected and dried under reduced pressure to give 5-bromo-4-cyclopentyloxy-2-{1-[4-(4-methoxy-benzenesulfonyl)-piperazin-1-yl]-ethyl}-pyrimidine. (Yield 11.5 mg, 9.9%). $^{1H}$ NMR (400 MHz, $CDCl_3$): δ 1.30 (d, J=6.82 Hz, 3H), 1.64-1.51 (m, 2H), 1.82-1.67 (m, 4H), 1.96-1.82 (m, 2H), 2.65-2.52 (m, 4H), 3.00-2.85 (m, 4H), 3.67 (q, J=6.82 Hz, 1H), 3.78 (s, 3H), 5.41 (m, 1H), 6.90 (d, J=9.09, 2H), 7.59 (d, J=9.09, 2H), 8.39 (s, 1H). MS m/z calc. 525.2 found (ESI); 526.2 (M+1)$^+$. Retention time 2.91 minutes.

4-Cyclopentyloxy-2-{1-[4-(4-methoxy-benzene-sulfonyl)-piperazin-1-yl]-ethyl}-pyrimidine

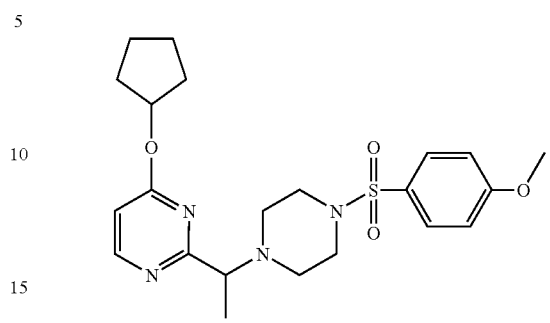

To a solution of 5-Bromo-4-cyclopentyloxy-2-{1-[4-(4-methoxy-benzenesulfonyl)-piperazin-1-yl]-ethyl}-pyrimidine (30.0 g, 0.06 mmol) in ethanol (10 ml) was added 10 mg platinum on carbon (0.5% wt). The solution was degassing three times and the hydrogen gas was introduced through a hydrogen balloon. The reaction was heated to reflux for 18 hours at room temperature. The solution was filtrated through a celite column and the solvent was evaporated. Water (5 ml) was then added to the solution and the mixture was extracted with dichloromethane (10 ml). The organic layer was then washed with 10% sodium bisulfite solution, and then washed with saturated brine (2×30 ml). The combined organic phase was collected and dried over magnesium sulfate, filtered and concentrated under reduced pressure to yield a brown crude product. The resulting residue was purified by silica gel chromatography with 50% dichloromethane in hexane. The product was collected and was dried under reduced pressure to give the 4-Cyclopentyloxy-2-{1-[4-(4-methoxy-benzene-sulfonyl)-piperazin-1-yl]-ethyl}-pyrimidine (Yield 15 mg, 60%. $^{1H}$NMR (400 MHz, $CDCl_3$): δ 1.60-1.54 (m, 2H), 1.64 (d, J=6.82 Hz, 3H), 1.76-1.67 (m, 4H), 1.96-1.84 (m, 2H), 3.35-3.12 (m, 4H), 3.50-3.35 (m, 2H), 3.05 (s, 3H), 4.41 (q, 1H, J=13.64, 7.33 Hz), 5.38 (m, 1H), 6.60 (d, J=5.81, 1H), 6.94 (d, J=8.84, 2H), 7.56 (d, J=8.84, 2H), 8.32 (d, J=5.81, 1H). MS m/z calc. 446.2 found (ESI); 447.2 (M+1)$^+$. Retention time 2.76 minutes.

5-Bromo-2-{1-[4-(4-methoxy-benzenesulfonyl)-piperazin-1-yl]-ethyl}-4-piperidin-1-yl-pyrimidin

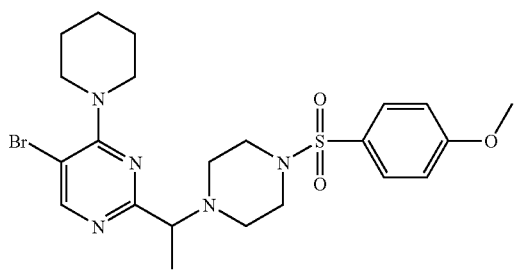 [SMILES: COc1ccc(S(=O)(=O)N2CCN(C(C)c3ncc(Br)c(N4CCCCC4)n3)CC2)cc1]

Step 1:
In a flask containing of 5-bromo-2-{1-[4-(4-methoxy-benzenesulfonyl)-piperazin-1-yl]-ethyl}-3H-pyrimidin-4-one (150.0 mg, 0.33 mmol) in phosphorus oxychloride (2 ml) was heated to 90° C. for 2 hours, then the solvent was concentrated under reduced pressure to give the 5-bromo-4-chloro-2-{1-

411

[4-(4-methoxy-benzenesulfonyl)-piperazin-1-yl]-ethyl}-pyrimidine that was used in the next step without any purification. MS m/z calc. 524.2 found (ESI); 526.2 (M+1)⁺. Retention time 2.91 minutes.

Step 2:

To the sample of step 1 dissolved in THF (5 ml) was added piperidine (278 mg, 3.28 mmol) and the reaction was heated at 60° C. for 0.5 hour. The solution was concentrated under reduced pressure. The residue was partitioned between water (2 ml) and dichloromethane (5 ml). The organic layer was dried over magnesium sulfate, filtered and concentrated under reduced pressure. The solvent was removed under vacuum. The resulting residue was re-dissolvent in MeOH (2 ml) and purified by HPLC (Gilson-215, 0.035% TFA in acetonitrile and 0.05% water as mobile phase). The product 5-Bromo-2-{1-[4-(4-methoxy-benzenesulfonyl)-piperazin-1-yl]-ethyl}-4-piperidin-1-yl-pyrimidine was collected and dried under reduced pressure (Yield 135 mg, 78.5%). $^{1}H$ NMR (400 MHz, CDCl$_3$): δ 1.29 (d, J=7.1 Hz, 3H), 1.61-1.52 (m, 9H), 2.6-2.5 (m, 4H), 3.00-2.90 (m, 4H), 3.11-3.04 (m, 2H), 3.82 (q, J=7.1 Hz, 1H), 6.89 (d, J=9.1, 2H), 7.62 (d, J=9.1, 2H), 8.26 (s, 1H). MS m/z calc. 524.4, found (ESI); 526.2 (M+1)⁺. Retention time 2.91 minutes.

2-{1-[4-(4-Methoxy-benzenesulfonyl)-piperazin-1-yl]-ethyl}-5-phenyl-4-piperidin-1-yl-pyrimidine

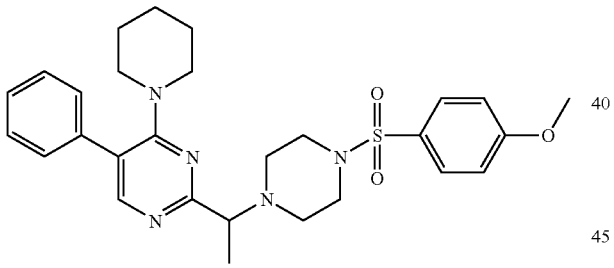

In a flask containing of 5-bromo-2-{1-[4-(4-methoxy-benzenesulfonyl)-piperazin-1-yl]-ethyl}-4-piperidin-1-yl-pyrimidine (100.0 mg, 0.19 mmol) in DMF (5 ml) was added phenylbroronic acid (23.2 mg, 0.19 mmol), triphenylphosphine polymer supported (63.0 mg, 3 mmol/g), palladium (II) acetate (42.6 mg, 0.19 mmol) and K$_2$CO$_3$ (52.5 mg, 0.38 mmol). The mixture was heated at 90° C. for 2 hours with stirring. After cooling down to room temperature, the excess K$_2$CO$_3$ was filtrated. Purification was accomplished by HPLC (Gilson-215, 0.035% TFA in acetonitrile and 0.05% water as mobile phase). The product was collected and dried under reduced pressure to give 2-{1-[4-(4-Methoxy-benzenesulfonyl)-piperazin-1-yl]-ethyl}-5-phenyl-4-piperidin-1-yl-pyrimidine (Yield 4.0 mg, 4.1%). MS m/z calc. 521.2 found (ESI); 522.4 (M+1)⁺. Retention time 3.06 minutes.

412

Preparation of 2-ethyl-6-oxo-1,6-dihydro-pyrimidine-5-carboxylic acid ethyl ester

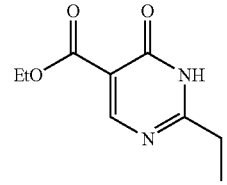

To a cold (0° C.) solution of NaOEt (0.2 mol) in absolute alcohol (150 mL) was added propionamidine hydrochloride (10.9 g, 0.1 mol) in one portion. A solution of 2-ethoxymethylene-malonic acid diethyl ester (21.6 g, 0.1 mol) in absolute alcohol (60 mL) was added dropwise to the above mixture during 20 minutes. After the addition was completed, the whole mixture was heated to reflux for 2.5 hours, then cooled and poured to ice water. The aqueous solution was acidified to pH 5 with HCl (6 M), extracted with ethyl acetate (4 100 mL). The organic layer was washed with brine and dried over Na$_2$SO$_4$. The solvent was removed under reduced pressure and the residue was re-crystallized with acetonitrile to afford 2-ethyl-6-oxo-1,6-dihydro-pyrimidine-5-carboxylic acid ethyl ester as white crystals (17 g, 86%). 1H NMR(CDCl$_3$) δ 8.71 (s, 1H), 4.37-4.32 (q, 2H), 2.84-2.78 (q, 2H), 1.38-1.34 (m, 6H). MS (ESI) m/e (M+1)⁺197.2.

2-(1-Bromo-ethyl)-6-oxo-1,6-dihydro-pyrimidine-5-carboxylic acid ethyl ester

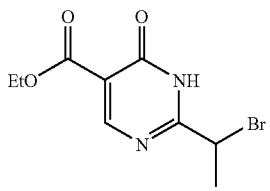

To a solution of 2-Ethyl-6-oxo-1,6-dihydro-pyrimidine-5-carboxylic acid ethyl ester (3.92 g, 20 mmol) and sodium acetate (1.64 g, 20 mmol) in glacial acetic acid (80 mL) heated to 50° C. was added dropwise a solution of bromine (1.03 mL, 20 mmol) in glacial acetic acid (40 mL). After addition was complete the reaction was heated to reflux for 1 hour. The reaction was then cooled to room temperature and then concentrated in vacuo. The residue was dissolved in ethyl acetate and washed with water then dried over magnesium sulfate, filtered and concentrated in vacuo. The crude product was then purified by column chromatography (35-75% ethyl acetate-hexanes) to yield the product as a white solid (2.29 g, 42%). $^1$H NMR (400 MHz, CDCl$_3$) δ 12.32 (br s, 1H), 8.87 (s, 1H), 5.08 (q, J=6.9 Hz, 1H), 4.44 (q, J=7.1 Hz, 2H), 2.08 (d, J=6.9 Hz, 3H), 1.43 (t, J=7.1 Hz, 3H); HPLC ret. time 2.13 min, 10-99% CH$_3$CN, 5 min run; ESI-MS m/z 276.9 (M+1)⁺.

2-{1-[4-(4-Methoxy-benzenesulfonyl)-piperazin-1-yl]-ethyl}-6-oxo-1,6-dihydro-pyrimidine-5-carboxylic acid ethyl ester

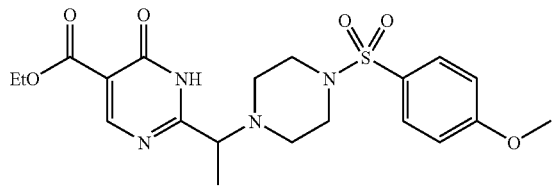 [SMILES: CCOC(=O)c1cnc(C(C)N2CCN(S(=O)(=O)c3ccc(OC)cc3)CC2)[nH]c1=O]

A mixture of 2-(1-Bromo-ethyl)-6-oxo-1,6-dihydro-pyrimidine-5-carboxylic acid ethyl ester (2.29 g, 8.3 mmol) and 1-(4-Methoxy-benzenesulfonyl)-piperazine (2.55 g, 10 mmol), potassium iodide (1.38 g, 8.3 mmol) and potassium carbonate (1.72 g, 12.5 mmol) in acetonitrile (35 mL) was heated at 65° C. for 1 day. The reaction mixture was then concentrated in vacuo. The residue was dissolved in dichloromethane and washed with saturated sodium thiosulphate solution, saturated sodium bicarbonate solution and then with water. The organic layer was dried over magnesium sulfate and concentrated in vacuo. The crude product was then purified by column chromatography (60-100% ethyl acetate-hexanes) to yield the product as a pale yellow solid (2.15 g, 57%). $^1$H NMR (400 MHz, CDCl$_3$) δ 10.34 (s, 1H), 8.63 (s, 1H), 7.71 (d, J=8.9 Hz, 2H), 7.06 (d, J=8.8 Hz, 2H), 4.38 (q, J=7.1 Hz, 2H), 3.93 (s, 3H), 3.63 (q, J=6.6 Hz, 1H), 3.06 (m, 4H), 2.65 (m, 4H), 1.38 (m, 6H); HPLC ret. time 2.46 min, 10-99% CH$_3$CN, 5 min run; ESI-MS m/z 451.5 (MH$^+$).

2-{1-[4-(4-Methoxy-benzenesulfonyl)-piperazin-1-yl]-ethyl}-4-piperidin-1-yl-pyrimidine-5-carboxylic acid ethyl ester

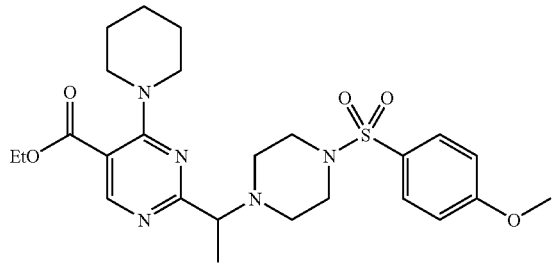 [SMILES: CCOC(=O)c1cnc(C(C)N2CCN(S(=O)(=O)c3ccc(OC)cc3)CC2)nc1N1CCCCC1]

2-{1-[4-(4-Methoxy-benzenesulfonyl)-piperazin-1-yl]-ethyl}-6-oxo-1,6-dihydro-pyrimidine-5-carboxylic acid ethyl ester (1.55 g, 3.4 mmol) in POCl$_3$ (10 mL) was heated to 90° C. for 2 hours. Then the excess POCl$_3$ was removed in vacuo. The residue was dissolved in toluene (5 mL) and then the solvent was removed in vacuo. This step was repeated twice more. The residue was then dissolved in THF (10 mL) and piperidine (3.36 mL, 34 mmol) was added. The reaction was stirred at room temperature for 1 day. The reaction mixture was partitioned between dichloromethane and water. The organic layer was dried over magnesium sulfate and concentrated in vacuo. The crude product was purified by column chromatography (30-80% ethyl acetate-hexanes) to yield the product as a pale yellow solid (1.61 g, 91%). $^1$H NMR (400 MHz, CDCl$_3$) δ 8.60 (s, 1H), 7.68 (d, J=8.8 Hz, 2H), 6.99 (d, J=8.9 Hz, 8.9 Hz, 2H), 4.35 (q, J=7.1 Hz, 2H), 3.88 (s, 3H), 3.69 (m, 1H), 3.54 (m, 4H), 3.02 (m, 4H), 2.69 (m, 4H), 1.68 (m, 6H), 1.38 (m, 6H); HPLC ret. time 2.66 min, 10-99% CH$_3$CN, 5 min run; ESI-MS m/z 518.1 (M+1)$^+$.

(2-{1-[4-(4-Methoxy-benzenesulfonyl)-piperazin-1-yl]-ethyl}-4-piperidin-1-yl-pyrimidin-5-yl)-methanol

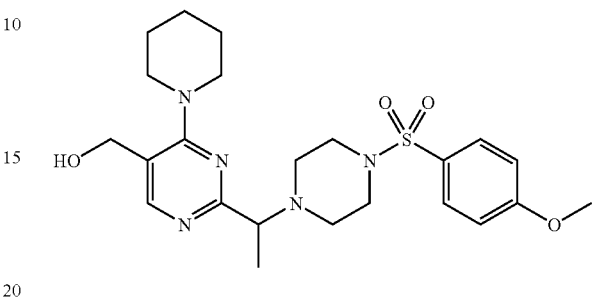

To a solution of 2-{1-[4-(4-methoxy-benzenesulfonyl)-piperazin-1-yl]-ethyl}-4-piperidin-1-yl-pyrimidine-5-carboxylic acid ethyl ester (104 mg, 0.2 mmol) in ethanol (1 mL) was added sodium borohydride (38 mg, 1.0 mmol) and the reaction mixture was heated to reflux for 1 day. The reaction was then partition between dichloromethane and saturated sodium bicarbonate solution. The organic layer was concentrated in vacuo and then the residue was dissolved in DMSO (1 mL) and purified by LC-MS to yield the product. $^1$H NMR (400 MHz, CDCl3) δ 8.26 (s, 1H), 7.65 (d, J=8.8 Hz, 2H), 7.03 (d, J=8.8 Hz, 2H), 4.62 (s, 2H), 4.53 (q, J=6.6 Hz, 1H), 3.93 (m, 7H), 3.25 (m, 8H), 1.77 (m, 6H), 1.67 (d, J=6.8 Hz, 3H); HPLC ret. time 2.49 min, 10-99% CH$_3$CN, 5 min run; ESI-MS m/z 476.1 (M+1)$^+$.

4-Cyclopentyloxy-2-{1-[4-(4-methoxy-benzenesulfonyl)-piperazin-1-yl]-ethyl}-pyrimidine-5-carboxylic acid ethyl ester

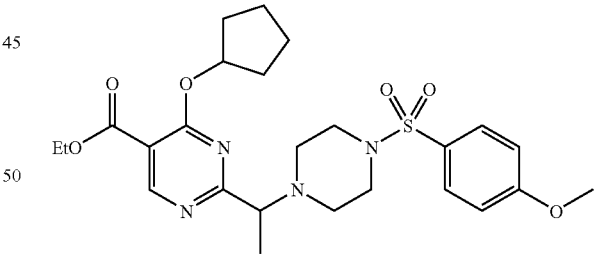

A mixture of 2-{1-[4-(4-methoxy-benzenesulfonyl)-piperazin-1-yl]-ethyl}-6-oxo-1,6-dihydro-pyrimidine-5-carboxylic acid ethyl ester (90 mg, 0.2 mmol), cyclopentyl iodide (46 μL, 0.4 mmol), and potassium carbonate (138 mg, 1 mmol) in DMF (1 mL) was heated to 90° C. for 1 day. The reaction mixture was then filtered and purified by HPLC (in the absence of TFA) to yield the product. $^1$H NMR (400 MHz, CDCl3) δ 8.91 (s, 1H), 7.68 (d, J=8.8 Hz, 2H), 6.99 (d, J=8.8 Hz, 2H), 5.58 (m, 1H), 4.36 (q, J=7.1 Hz, 2H), 3.89 (s, 3H), 3.84 (m, 1H), 3.04 (m, 4H), 2.73 (m, 4H), 1.83 (m, 8H), 1.40 (m, 6H); HPLC ret. time 2.80 min, 10-99% CH$_3$CN, 5 min run; ESI-MS m/z 519.5 (M+1)$^+$.

2-{1-[4-(4-Methoxy-benzenesulfonyl)-piperazin-1-yl]-ethyl}-4-piperidin-1-yl-pyrimidine-5-carboxylic acid

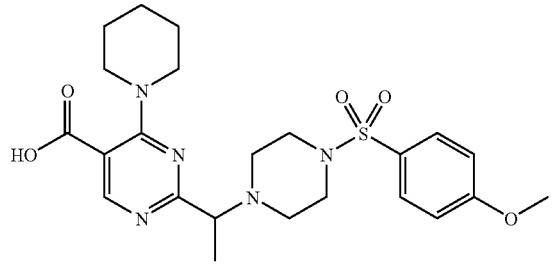 [SMILES: COc1ccc(S(=O)(=O)N2CCN(C(C)c3ncc(C(=O)O)c(N4CCCCC4)n3)CC2)cc1]

A mixture of 2-{1-[4-(4-methoxy-benzenesulfonyl)-piperazin-1-yl]-ethyl}-4-piperidin-1-yl-pyrimidine-5-carboxylic acid ethyl ester (518 mg, 1.0 mmol), ethanol (3.75 mL) and 2.5M aqueous potassium hydroxide solution (1.25 mL) was heated to 80° C. for 30 minutes. The reaction solution was neutralized with concentrated hydrochloric acid to pH 7 and extracted with dichloromethane. The aqueous solution was then made basic again with 1N NaOH solution at which time a precipitate formed. The solution was filtered to yield the product as a white solid (180 mg, 37%). $^1$H NMR (400 MHz, CDCl3) δ 7.99 (s, 1H), 7.63 (d, J=8.9 Hz, 2H), 7.15 (d, J=8.9 Hz, 2H), 3.86 (s, 3H), 3.53 (m, 5H), 2.78 (m, 4H), 2.56 (m, 4H), 1.58 (m, 4H), 1.22 (d, J=6.9 Hz, 3H); HPLC ret. time 2.41 min, 10-99% CH$_3$CN, 5 min run; ESI-MS m/z 490.1 (M+1)$^+$.

2-{1-[4-(4-Methoxy-benzenesulfonyl)-piperazin-1-yl]-ethyl}-4-piperidin-1-yl-pyrimidine-5-carboxylic acid dimethylamide

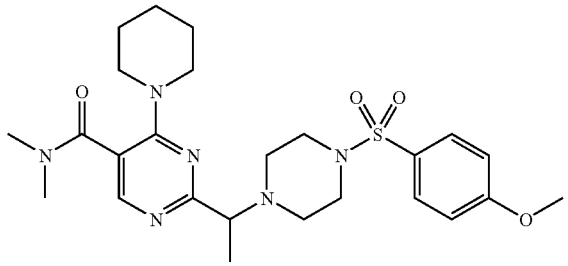

To a mixture of 2-{1-[4-(4-methoxy-benzenesulfonyl)-piperazin-1-yl]-ethyl}-4-piperidin-1-yl-pyrimidine-5-carboxylic acid (60 mg, 0.12 mmol), HATU (68 mg, 0.18 mmol), DIEA (42 µL, 0.24 mmol) in DMF (1 mL) was added dimethyl amine (120 µL, 0.24 mmol, 2M solution in THF). The reaction was stirred at room temperature for 3 hours. The solution was then filtered and purified by HPLC to yield the desired product. HPLC ret. time 2.41 min, 10-99% CH$_3$CN, 5 min run; ESI-MS m/z 517.3 (M+1)$^+$.

4-Cyclopentyloxy-2-{1-[4-(4-methoxy-benzenesulfonyl)-piperazin-1-yl]-ethyl}-pyrimidine-5-carboxylic acid ethyl ester

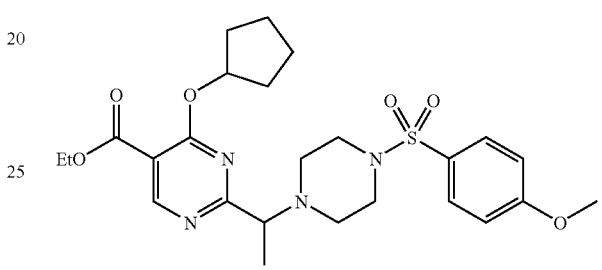

A mixture of 2-{1-[4-(4-methoxy-benzenesulfonyl)-piperazin-1-yl]-ethyl}-6-oxo-1,6-dihydro-pyrimidine-5-carboxylic acid ethyl ester (90 mg, 0.2 mmol), cyclopentyl iodide (46 µL, 0.4 mmol), and potassium carbonate (138 mg, 1 mmol) in DMF (1 mL) was heated to 90° C. for 1 day. The reaction mixture was then filtered and purified by HPLC (in the absence of TFA) to yield the product. $^1$H NMR (400 MHz, CDCl3) δ 8.91 (s, 1H), 7.68 (d, J=8.8 Hz, 2H), 6.99 (d, J=8.8 Hz, 2H), 5.58 (m, 1H), 4.36 (q, J=7.1 Hz, 2H), 3.89 (s, 3H), 3.84 (m, 1H), 3.04 (m, 4H), 2.73 (m, 4H), 1.83 (m, 8H), 1.40 (m, 6H); HPLC ret. time 2.80 min, 10-99% CH$_3$CN, 5 min run; ESI-MS m/z 519.5 (MH$^+$).

Other compounds of formula I have been prepared by methods substantially similar to those described above. Depicted below in Table 2 are LC Mass Retention Time, and LC Mass Plus values for compounds as depicted in Table 1, along with NMR data for selected compounds.

TABLE 2

| Cmpd No. | LC_MASS_PLUS (M+) | LC_MASS_RT (min) | $^1$H NMR (Unless otherwise indicated, solvent is CDCl$_3$) |
|---|---|---|---|
| 4 | 487.20 | 2.41 | |
| 5 | 537.00 | 2.91 | |
| 6 | 443.20 | 3.21 | |
| 9 | 447.00 | 3.48 | |
| 10 | 431.40 | 2.33 | |
| 11 | 427.20 | 3.30 | |
| 13 | 497.20 | 2.66 | |
| 15 | 425.00 | 3.20 | |
| 17 | 491.00 | 3.18 | |
| 18 | 460.00 | 3.33 | |
| 19 | 441.20 | 2.53 | |
| 22 | 471.20 | 2.57 | |

TABLE 2-continued

| Cmpd No. | LC_MASS_PLUS (M+) | LC_MASS_RT (min) | $^1$H NMR (Unless otherwise indicated, solvent is CDCl$_3$) |
|---|---|---|---|
| 27 | 521.40 | 4.49 | d 1.03(t, 3 H, J = 5.8 Hz), 1.72(sex, 2 H, J = 6.0), 1.80(d, 3 H, J = 5.2), 3.48(m, 6 H), 3.90(m, 3 H), 4.23(m, 1 H), 4.77(q, 1 H, J = 5.2 Hz), 7.58(m, 3 H), 7.68(d, 1 H, J = 6.5 Hz), 7.72(d, 2 H, J = 7.1 Hz), 7.81(t, 1 H, J = 6.2 Hz), 8.28(d, 1 H, J = 6.5 Hz). |
| 31 | 392.00 | 2.85 | |
| 32 | 391.40 | 2.97 | |
| 33 | 426.00 | 3.10 | |
| 38 | 411.20 | 3.11 | |
| 39 | 445.00 | 3.06 | |
| 40 | 445.20 | 3.39 | |
| 41 | 461.00 | 3.32 | |
| 42 | 526.80 | 3.86 | |
| 43 | 426.00 | 3.11 | |
| 44 | 481.20 | 3.82 | |
| 45 | 440.20 | 3.24 | |
| 48 | 427.20 | 3.32 | |
| 49 | 473.00 | 3.12 | |
| 50 | 497.20 | 3.64 | |
| 51 | 493.00 | 3.47 | |
| 52 | 377.20 | 2.81 | |
| 53 | 411.20 | 3.06 | |
| 54 | 445.20 | 3.24 | |
| 55 | 455.00 | 3.12 | |
| 56 | 406.20 | 2.99 | |
| 57 | 391.00 | 2.94 | |
| 58 | 425.20 | 3.25 | |
| 59 | 425.20 | 3.25 | |
| 60 | 349.20 | 2.63 | |
| 61 | 447.00 | 3.49 | |
| 62 | 447.00 | 3.56 | |
| 63 | 481.00 | 3.64 | |
| 64 | 481.00 | 3.82 | |
| 65 | 433.20 | 3.41 | |
| 66 | 447.00 | 3.56 | |
| 67 | 467.00 | 3.67 | |
| 68 | 413.00 | 3.01 | |
| 69 | 427.00 | 3.35 | |
| 70 | 481.00 | 3.33 | |
| 71 | 447.00 | 3.56 | |
| 72 | 507.00 | 3.19 | |
| 73 | 515.20 | 3.58 | |
| 74 | 391.00 | 2.89 | |
| 75 | 411.20 | 2.92 | |
| 76 | 437.20 | 3.04 | |
| 77 | 471.20 | 2.93 | |
| 78 | 479.20 | 3.24 | |
| 79 | 351.20 | 2.39 | |
| 80 | 461.20 | 3.37 | |
| 81 | 407.40 | 2.83 | |
| 82 | 411.20 | 2.86 | |
| 83 | 445.00 | 3.17 | |
| 84 | 513.00 | 3.41 | |
| 85 | 461.20 | 3.40 | |
| 86 | 461.20 | 2.76 | |
| 87 | 189.20 | 1.96 | |
| 88 | 225.00 | 2.70 | |
| 89 | 261.20 | 2.87 | |
| 90 | 307.12 | 2.86 | |
| 91 | 447.12 | 3.39 | |
| 92 | 461.13 | 3.48 | |
| 93 | 477.13 | 3.41 | |
| 94 | 481.08 | 3.58 | |
| 95 | 525.03 | 3.62 | |
| 96 | 461.13 | 2.85 | |
| 97 | 481.08 | 2.91 | |
| 98 | 515.11 | 2.98 | |
| 99 | 531.10 | 2.99 | |
| 100 | 507.14 | 2.77 | |
| 101 | 479.14 | 2.75 | |
| 102 | 223.00 | 2.87 | |
| 103 | 447.20 | 2.37 | |
| 104 | 481.20 | 2.65 | |
| 105 | 527.10 | 2.69 | |
| 106 | 477.20 | 2.41 | |
| 107 | 461.20 | 2.52 | |
| 108 | 385.10 | 1.92 | |

TABLE 2-continued

| Cmpd No. | LC_MASS_PLUS (M+) | LC_MASS_RT (min) | $^1$H NMR (Unless otherwise indicated, solvent is CDCl$_3$) |
|---|---|---|---|
| 109 | 461.13 | 2.47 | |
| 110 | 525.10 | 2.79 | |
| 111 | 504.14 | 2.67 | |
| 112 | 425.17 | 2.66 | |
| 113 | 425.17 | 2.24 | |
| 114 | 491.20 | 2.64 | 1.86(d, 3 H, J = 7.07 Hz), 3.30–3.17(m, 4 H), 3.49–3.33(m, 4 H), 3.61(s, 3 H), 4.61–4.51(m, 1 H), 7.54–7.42(m, 3 H), 7.62–7.57(m, 1 H), 7.72–7.67 (m, 2 H), 7.82(dd, 1 H, J = 8.50, 2.51 Hz), 8.36(d, 1 H, J = 2.5 Hz). |
| 115 | 507.20 | 2.80 | 1.79(d, 3 H, J = 6.32 Hz), 2.47(s, 3 H), 3.61–3.41 (m, 6 H), 3.68(s, 1 H), 3.93–3.81(m, 2 H), 4.86–4.77 (m, 1 H), 7.37(d, 2 H, J = 7.83), 7.58(d, 1 H, J = 8.5 Hz), 7.64(d, 2 H, J = 8.5 Hz), 7.89(dd, 1 H, J = 8.5, 2.5 Hz), 8.43(d, 1 H, J = 2.5 Hz). |
| 116 | 523.20 | 2.70 | 2.23(d, 3 H, J = 6.82 Hz), 3.80(s, 3 H), 5.11(q, 1 H, J = 13.14, 6.82 Hz), 7.64(d, 1 H, J = 8.84 Hz), 7.87(dd, 1 H, J = 8.59, 2.26 Hz), 8.46(d, 1 H, J = 2.26 Hz |
| 117 | 527.20 | 2.94 | CDC13, 1.79(d, 3 H, J = 6.82 Hz), 3.47–3.38(m, 2 H), 3.62–3.48(m, 4 H), 3.68(s, 3 H), 3.85–3.76(m, 2 H), 4.79(q, 1 H, J = 13.80, 7.07 Hz), 7.60–7.54(m, 3 H), 7.73–7.68(m, 2 H), 7.90(dd, 1 H, J = 8.59, 2.27 Hz), 8.44(d, 1 H, J = 2.5 Hz). |
| 118 | 571.00 | 2.98 | 1.89(d, 3 H, J = 7.07 Hz), 3.47–3.38(m, 2 H), 3.64–3.49(m, 4 H), 3.69(s, 3 H), 3.83–3.74(m, 2 H), 4.71 (q, 1 H, J = 13.64, 6.57 Hz), 7.65–7.59(m, 3 H), 7.75–7.70(m, 2 H), 7.90(dd, 1 H, J = 8.59, 2.27 Hz), 8.44(d, 1 H, J = 2.27 Hz). |
| 119 | 425.17 | 2.26 | |
| 120 | 425.17 | 2.28 | |
| 121 | 429.14 | 2.19 | |
| 122 | 441.16 | 2.14 | |
| 123 | 438.40 | 2.35 | |
| 124 | 468.40 | 2.40 | 1.64(d, 3 H, J = 6.57 Hz), 3.29–3.10(m, 6 H), 3.48–3.37(m, 2 H), 3.68(s, 3 H), 3.90(s, 3 H), 4.53(q, 1 H, J = 13.14, 5.81 Hz), 6.97(d, 2 H, J = 2.02 Hz), 7.66(d, 2 H, J = 8.84, Hz), 7.76(d, 1 H, J = 8.59 Hz), 7.94(dd, 1 H J = 8.59, 2.02 Hz), 8.57(d, 1 H, J = 2.02 Hz). |
| 125 | 452.00 | 2.52 | 1.67(d, 3 H, J = 6.28 Hz), 2.46(s, 3 H), 3.34–3.17 (m, 6 H), 3.56–3.47(m, 2 H), 3.67(s, 3 H), 4.60(q, 1 H, J = 13.99, 6.57 Hz), 7.36(d, 2 H, J = 8.08 Hz), 7.60(d, 2 H, J = 8.08, Hz), 7.76(d, 1 H, J = 8.59 Hz), 7.94(dd, 1 H J = 8.59, 1.77 Hz), 8.56(d, 1 H, J = 1.77 Hz) |
| 126 | 472.20 | 2.65 | 1.54(d, 3 H, J = 6.82 Hz), 3.23–2.96(m, 6 H), 3.35–3.25(m, 2 H), 3.59(s, 3 H), 4.41(q, 1 H, J = 13.89, 6.82 Hz), 7.47–7.43(m, 2 H), 7.61–7.56(m, 2 H), 7.77–7.65(m, 1 H), 7.85(dd, 1 H J = 8.59, 1.77 Hz), 8.47(d, 1 H, J = 1.77 Hz). |
| 127 | 477.00 | 2.66 | |
| 128 | 399.20 | 2.30 | |
| 129 | 413.20 | 2.47 | |
| 130 | 429.20 | 2.37 | |
| 131 | 433.20 | 2.61 | |
| 132 | 523.40 | 2.60 | |
| 133 | 443.40 | 2.27 | |
| 134 | 457.40 | 2.46 | |
| 135 | 473.20 | 2.34 | |
| 136 | 477.00 | 2.55 | |
| 137 | 463.20 | 2.49 | |
| 138 | 491.20 | 2.17 | |
| 139 | 505.20 | 2.34 | 1.82(d, 3 H, J = 7.07 Hz), 3.12(s, 3 H), 3.64–3.40 (m, 4 H), 3.70(s, 3 H), 4.00–3.86(m, 7 H), 4.89(q, 1 H, J = 14.40, 6.03 Hz), 7.05(d, 2 H, J = 9.09 Hz), 7.68(d, 2 H, J = 9.09, Hz), 7.84(d, 1 H, J = 8.84 Hz), 8.25(dd, 1 H J = 8.84, 2.02 Hz), 8.82(d, 1 H, J = 2.02 Hz). |
| 140 | 521.40 | 2.23 | 1.85(d, 3 H, J = 6.32 Hz), 2.47(s, 3 H), 3.13(s, 3 H), 3.66–3.45(m, 4 H), 3.71(s, 3 H), 4.05–3.92(m, 4 H), 4.89(q, 1 H, J = 14.15, 6.32 Hz), 7.38(d, 2 H, J = 8.08 Hz), 7.64(d, 2 H, J = 8.34 Hz), 7.86(d, 1 H, J = 8.59 Hz), 8.27(dd, 2 H, J = 8.84, 2.27 Hz), 8.84 (d, 1 H, J = 2.27 Hz). |
| 141 | 525.20 | 2.46 | 1.85(d, 3 H, J = 7.07 Hz), 3.13(s, 3 H), 3.65–3.47 (m, 4 H), 3.70(s, 3 H), 4.03–3.90(m, 4 H), 4.88(q, 1 |

TABLE 2-continued

| Cmpd No. | LC_MASS_PLUS (M+) | LC_MASS_RT (min) | $^1$H NMR (Unless otherwise indicated, solvent is CDCl$_3$) |
|---|---|---|---|
| | | | H, J = 14.89, 6.57 Hz), 7.58(d, 2 H, J = 9.09 Hz), 7.71(d, 2 H, J = 9.09, Hz), 7.84(d, 1 H, J = 8.84 Hz), 8.26(dd, 1 H J = 8.84, 2.27 Hz), 8.83(d, 1 H, J = 2.27 Hz). |
| 142 | 571.20 | 2.51 | 1.86(d, 3 H, J = 6.84 Hz), 3.13(s, 3 H), 3.65–3.43 (m, 4 H), 3.71(s, 3 H), 4.05–3.93(m, 4 H), 4.85(q, 1 H, J = 13.64, 6.57 Hz), 7.63(d, 2 H, J = 8.84 Hz), 7.74(d, 2 H, J = 8.84, Hz), 7.87(d, 1 H, J = 8.34 Hz), 8.28(dd, 1 H J = 8.34, 2.27 Hz), 8.86(d, 1 H, J = 2.27 Hz). |
| 143 | 487.20 | 2.16 | CD$_3$OD 1.64(d, 3 H, J = 6.57 Hz), 3.35–3.29(m, 8 H), 3.67 (s, 3 H), 3.92(s, 3 H), 4.70(s, br, 1 H), 7.17(d, 2 H, J = 8.84 Hz), 7.78–7.76(m, 3 H), 8.38(dd, 1 H, J = 8.59, 2.02 Hz), 8.88(d, 1 H J = 2.02 Hz). |
| 144 | 511.30 | 2.51 | 1.79(d, 3 H, J = 6.57 Hz), 3.29–3.12(m, 8 H), 3.70 (s, 3 H), 3.92(s, 3 H), 4.70(s, br, 1 H), 7.17(d, 2 H, J = 9.09 Hz), 7.76(d, 2 H, J = 9.09 Hz), 7.87(d, 1 H, J = 8.59 Hz), 8.47(dd, 1 H, J = 8.59, 1.77 Hz), 8.89 (d, 1 H, J = 1.77 Hz). |
| 145 | 458.20 | 2.28 | DMSO-d6 44–3.29(m, 4 H), 3.62–3.50(m, 4 H), 3.65(s, 3 H), 3.93(s, 3 H), 4.70(q, 1 H, J = 12.88, 6.82 Hz), 7.19 (d, 2 H, J = 8.84 Hz), 7.49(dd, 1 H, J = 8.84, 2.53 Hz), 7.65(d, 1 H, J = 8.59 Hz), 7.81–7.77(m, 3 H). |
| 146 | 508.00 | 2.52 | CD$_3$OD 1.55–1.32(m, 3 H), 3.35–2.85(m, 8 H), 3.52(s, 3 H), 4.53(s, br, 1 H), 7.10(dd, 1 H, J = 8.59, 2.53 Hz), 7.23(d, 1 H, J = 2.53 Hz), 7.39(d, 1 H, J = 8.84 Hz), 7.58(d, 2 H, J = 8.08 Hz). 7.91(d, 2 H, J = 7.83 Hz) |
| 147 | 521.20 | 19.50 | |
| 148 | 521.20 | 27.20 | |
| 149 | 491.20 | 3.61 | 8.21(d, J = 2.3 Hz, 1 H), 7.69(m, 3 H), 7.62(d, J = 8.7 Hz, 1 H), 7.04(d, J = 8.9 Hz, 2 H), 3.92(s, 3 H), 3.89(s, 3 H), 2.86(m, 8 H), 1.62(s, 6 H); |
| 150 | 457.40 | 2.48 | |
| 151 | 461.20 | 2.71 | 8.25(dd, J = 8.0, 1.2 Hz, 1 H), 7.77(t, J = 8.4 Hz, 1 H), 7.68(m, 3 H), 7.55(m, 3 H), 4.22(s, 2 H), 3.98 (t, J = 8.0 Hz, 2 H), 3.37(m, 8 H), 1.71(sextet, J = 7.8 Hz, 2 H), 0.98(t, J = 7.4 Hz, 3 H). |
| 152 | 507.20 | 2.76 | |
| 153 | 523.10 | 2.66 | |
| 154 | 515.10 | 2.71 | 1.64(d, 3 H, J = 6.06 Hz), 3.12–3.04(m, 4 H), 3.16–3.54(m, 4 H), 3.70(s, 3 H), 4.64(s, br, 3 H), 7.71–7.63(m, 2 H), 7.83–7.76(m, 2 H), 7.87(d, 1 H, J = 8.84 Hz), 7.98(s, 1 H), 8.46(dd, 1 H, J = 8.59, 2.02 Hz), 8.88(d, 1 H J = 2.02 Hz). |
| 155 | 500.20 | 2.42 | CD$_3$OD 1.70(d, 3 H, J = 6.57 Hz), 2.18(s, 3 H), 3.57–3.43 (m, 8 H), 3.64(s, 3 H), 3.93(s, 3 H), 4.84(q, 1 H, J = 6.57, 6.06 Hz), 7.19(d, 2 H, J = 9.09 Hz), 7.64(d, 1 H, J = 8.34 Hz), 7.79(d, 2 H, J = 9.09 Hz), 7.98 (dd, 1 H, J = 8.59, 2.78 Hz), 8.46(d, J = 2.27 Hz). |
| 156 | 537.20 | 2.74 | CD$_3$OD 1.64(d, 3 H, J = 6.57 Hz), 3.39–3.20(s, br, 8 H), 3.68(s, 3 H), 4.67(s, br, 1 H), 7.77–7.72(m, 3 H), 7.88–7.84(m, 2 H), 8.38(dd, 1 H, J = 8.34, 2.02 Hz), 7.87(d, 1 H, J = 2.02 Hz). |
| 157 | 489.10 | 2.69 | 1.65(d, 3 H, J = 7.07 Hz), 3.34–3.33(s, br, 8 H), 3.67(s, 3 H), 4.67(s, br, 1 H), 7.70(d, 2 H, J = 8.59 Hz), 7.75(d, 1 H, J = 8.59 Hz), 7.82(d, 2 H, J = 8.59 Hz), 8.38(dd, 1 H, J = 8.59, 1.77 Hz), 8.89(d, J = 1.77 Hz). |
| 158 | 217.20 | 2.50 | |
| 159 | 202.20 | 2.02 | |
| 160 | 418.20 | 2.18 | |
| 161 | 443.40 | 2.06 | |
| 162 | 447.20 | 2.23 | |
| 163 | 493.00, 491.20 | 2.28, 2.26 | |
| 164 | 457.40 | 2.08 | |
| 165 | 461.20 | 2.21 | |
| 166 | 507.20, 507.20 | 2.29, 2.28 | |
| 167 | 417.20 | 2.09 | |
| 168 | 421.00 | 2.23 | |
| 169 | 467.00 | 2.28 | |

TABLE 2-continued

| Cmpd No. | LC_MASS_PLUS (M+) | LC_MASS_RT (min) | $^1$H NMR (Unless otherwise indicated, solvent is CDCl$_3$) |
|---|---|---|---|
| 170 | 457.40 | 2.19 | |
| 171 | 461.20 | 2.34 | |
| 172 | 507.20 | 2.40 | |
| 173 | 435.20 | 2.26 | |
| 174 | 481.20 | 2.29 | |
| 175 | 455.40 | 2.13 | |
| 176 | 459.20 | 2.26 | |
| 177 | 505.20 | 2.31 | |
| 178 | 273.20 | 1.13 | |
| 179 | 287.20 | 1.19 | |
| 180 | 287.20 | 1.14 | |
| 181 | 247.00 | 1.22 | |
| 182 | 261.20 | 1.16 | |
| 183 | 301.40 | 1.31 | |
| 184 | 287.20 | 1.32 | |
| 185 | 261.20 | 1.11 | |
| 186 | 285.20 | 1.14 | |
| 187 | 443.40 | 2.40 | |
| 188 | 457.40 | 2.55 | 1.54(t, 3 H, J = 7.07 Hz), 1.87(d, 3 H, J = 7.07 Hz), 3.61–3.31(m, 6 H), 3.76–3.61(m, 2 H), 3.89(s, 3 H), 4.73(m, 1 H), 7.02(d, 2 H, J = 9.09 Hz), 7.71–7.62 (m, 3 H), 7.96(d, 1 H, J = 1.26 Hz), 7.96(d, 2 H J = 1.26 Hz), 8.24(d, 1 H, J = 8.08 Hz). |
| 189 | 471.20 | 2.69 | 1.01–1.09(m, 3 H), 1.13(t, 3 H, J = 7.33 Hz), 1.74–1.67(m, 2 H), 1.95–1.88(m, 2 H), 3.62–3.28(m, 6 H), 3.74–3.62(m, 2 H), 3.89(s, 3 H), 4.68(q, 1 H, J = 13.64, 7.07 Hz), 7.04–7.00(m, 2 H), 7.70–7.64(m, 3 H), 7.98–7.92(m, 2 H), 8.24(td, 1 H, J = 8.84, 1.01 Hz). |
| 190 | 471.20 | 2.85 | |
| 191 | 497.40 | 2.84 | 2.00–1.68(m, 11 H), 2.15–2.04(m, 2 H), 3.54–3.33 (m, 6 H), 3.73–3.62(m, 2 H), 3.89(s, 3 H), 4.72(q, 1 H, J = 13.39, 7.33 Hz), 7.02(d, 2 H, 9.09 Hz), 7.68–7.65(m, 3 H), 7.95(td, 2 H, J = 8.08, 1.77 Hz), 8.19 (d, 1 H, J = 8.34 Hz). |
| 192 | 442.40 | 2.11 | |
| 193 | 456.40 | 2.15 | 1.74(d, 3 H, J = 6.57 Hz), 3.33–3.31(m, 6 H), 3.58–3.43(m, 2 H), 3.87(s, 3 H), 5.00(q, 1 H, J = 13.39, 6.82 Hz), 7.00(d, 2 H, 8.84 Hz), 7.61(d, 2 H, J = 8.84), 7.65(td, 1 H, J = 8.34, 1.26 Hz), 7.92(td, 1 H, J = 8.34, 1.26 Hz), 8.22(dd, 1 H, J = 8.59, 1.01 Hz), 8.13(dd, 1 H, J = 8.59, 1.01 Hz). |
| 194 | 456.40 | 2.26 | CD$_3$OD<br>1.38(t, 3 H, J = 7.33 Hz), 1.54(d, 3 H, J = 6.82 Hz), 2.84–2.77(m, 2 H), 2.93–2.86(m, 2 H), 3.16–3.10 (m, 4 H), 3.85(s, 3 H), 3.97(q, 1 H, J = 13.39, 6.82 Hz), 7.15(d, 2 H, J = 8.84 Hz), 7.76–7.72(m, 3 H), 7.80(d, 1 H J = 8.84 Hz), 7.98(td, 1 H, J = 8.84, 1.26 Hz), 8.28(d, 1 H, J = 8.34 Hz). |
| 195 | 484.40 | 2.48 | 1.48(t, 3 H, J = 6.82 Hz), 1.83(d, 3 H, J = 6.82 Hz), 3.38–3.20(m, 6 H), 3.69–3.52(m, 2 H), 3.82–3.72 (m, 2 H), 3.85(s, 3 H), 5.12(q, 1 H, J = 14.15, 6.32 Hz), 7.00(d, 2 H, J = 9.09 Hz), 7.63(d, 2 H, J = 9.09 Hz), 7.95(td, 1 H J = 8.59, 1.26 Hz), 7.95(td, 1 H, J = 8.59, 1.26 Hz), 8.00(d, 2 H, J = 8.08 Hz), 8.06 (dd, 1 H, J = 8.34, 1.26 Hz). |
| 196 | 498.40 | 2.21 | |
| 197 | 587.20 | 3.30 | |
| 198 | 595.20 | 3.70 | |
| 199 | 685.00 | 3.77 | |
| 200 | 601.40 | 3.54 | |
| 201 | 609.20 | 3.95 | |
| 202 | 699.20 | 4.03 | |
| 203 | 641.40 | 3.76 | |
| 204 | 739.00 | 4.25 | |
| 205 | 601.40 | 3.36 | |
| 206 | 609.20 | 3.78 | |
| 207 | 699.20 | 3.86 | |
| 208 | 457.40 | 2.23 | 1.55(d, 3 H, J = 6.6 Hz), 1.66(q, 2 H, J = 12.1 Hz), 2.16(m, 4 H), 3.19(m, 1 H), 3.53(s, 3 H), 3.68(m, 2 H), 3.80(s, 3 H), 4.86(q, 1 H, J = 5.7 Hz), 7.12(d, 2 H, J = 9.0 Hz), 7.57(t, 1 H, J = 8.1 Hz), 7.63(d, 2 H, J = 8.9 Hz), 7.69(d, 1 H, J = 7.7 Hz), 7.86(t, 1 H, J = 8.4 Hz), 8.15(dd, 1 H, J = 8.0, 1.2 Hz); |
| 209 | 461.20 | 2.40 | |
| 210 | 507.20 | 2.41 | |
| 211 | 431.20 | 2.16 | |

TABLE 2-continued

| Cmpd No. | LC_MASS_PLUS (M+) | LC_MASS_RT (min) | $^1$H NMR (Unless otherwise indicated, solvent is CDCl$_3$) |
|---|---|---|---|
| 212 | 435.20 | 2.36 | |
| 213 | 481.20 | 2.40 | |
| 214 | 475.20 | 2.56 | |
| 215 | 521.20 | 2.58 | |
| 216 | 521.20 | 2.86 | |
| 217 | 521.20 | 2.88 | |
| 218 | 547.40 | 3.07 | |
| 219 | 492.20 | 2.31 | CD$_3$OD 1.58(d, 3 H, J = 6.82 Hz), 2.91–2.84(m, 2 H), 3.02–2.94(m, 2 H), 3.32–3.14(m, 4 H), 4.07(q, 1 H, J = 14.40, 6.82 Hz), 7.76–7.70(m, 3 H), 7.85–7.80(m, 3 H), 7.99(td, 1 H J = 8.59, 1.26 Hz), 8.24(dd, 1 H, J = 8.34, 0.76 Hz). |
| 220 | 506.20 | 2.36 | CD$_3$OD 1.56(d, 3 H, J = 6.57 Hz), 3.01–2.80(m, 4 H), 3.23–3.08(m, 4 H), 4.14–3.96(m, 1 H), 7.75–7.63(m, 3 H), 7.87–7.75(m, 3 H), 8.01–7.90(m, 1 H), 8.39(dd, 1 H, J = 8.08 Hz). |
| 221 | 506.20 | 2.46 | CD$_3$OD 1.38(t, 3 H, J = 7.33 Hz), 1.54(d, 3 H, J = 7.07 Hz), 2.83–2.74(m, 2 H), 2.93–2.85(m, 2 H), 3.20–3.08(m, 4 H), 3.85(q, 1 H, J = 14.40, 7.33 Hz), 7.76–7.69(m, 3 H), 7.86–7.79(m, 3 H), 7.99(td, 1 H J = 8.34, 1.26 Hz), 8.29(d, 1 H, J = 8.34 Hz). |
| 222 | 532.20 | 2.66 | |
| 223 | 548.40 | 2.41 | CD$_3$OD 1.58(t, 3 H, J = 6.82 Hz), 3.01–2.92(m, 2 H), 3.11–3.02(m, 2 H), 3.7–3.15(m, 4 H), 3.88(t, 4 H, 5.05 Hz), 4.14(q, 1 H, J = 13.64, 7.07 Hz), 4.30–4.18(m, 4 H), 7.75–7.66(m, 3 H), 7.87–7.81(m, 3 H), 7.99 (td, 1 H J = 8.34, 1.77 Hz), 8.18(d, 1 H, J = 8.59 Hz). |
| 224 | 443.40 | 2.21 | |
| 225 | 447.00 | 2.38 | |
| 226 | 493.00 | 2.40 | |
| 227 | 493.20 | 2.95 | CD$_3$OD 1.60(d, 3 H, J = 6.82 Hz), 3.15–3.05(m, 2 H), 3.27–3.18(m, 6 H), 3.32(s, 3 H), 3.99(q, 1 H, J = 13.89, 6.32 Hz), 7.57(t, 1 H, J = 8.08 Hz), 7.77–7.69(m, 3 H), 7.90–7.81(m, 3 H), 8.22(dd, 1 H, J = 8.08, 1.26 Hz). |
| 228 | 507.20 | 3.09 | 1.55(t, 3 H, J = 7.07 Hz), 1.79(d, 3 H, J = 6.57 Hz), 3.60–3.30(m, 6 H), 3.76–3.63(m, 2 H), 4.74–4.61(m, 3 H), 7.72(td, J = 8.34, 2.02 Hz), 7.81–7.76(m, 2 H), 7.91–7.86(m, 2 H), 8.00–7.93(m, 1 H), 8.26 (d, 1 H, J = 7.58). |
| 229 | 447.00 | 2.31 | |
| 230 | 470.40 | 2.04 | |
| 231 | 501.20 | 3.23 | |
| 232 | 446.20 | 2.61 | |
| 233 | 460.20 | 2.66 | CD$_3$OD 1.56(t, 3 H, J = 6.82 Hz), 2.93–2.86(m, 2 H), 3.02–2.95(m, 2 H), 3.22–3.11(m, 4 H), 3.67(s, 6 H), 4.08(q, 1 H, J = 13.64, 6.82 Hz), 7.73–7.64(m, 3 H), 7.83–7.76(m, 3 H), 7.97(td, 1 H, J = 8.59, 1.26 Hz), 8.38(dd, 1 H, J = 8.59, 0.76 Hz). |
| 234 | 460.20 | 2.74 | CD$_3$OD 1.38(t, 3 H, J = 7.07 Hz), 1.54(d, 3 H, J = 7.07 Hz), 2.83–2.75(m, 2 H), 2.92–2.85(m, 2 H), 3.19–3.11(m, 4 H), 3.85(q, 2 H J = 14.65, 6.82 Hz), 3.98(q, 1 H, J = 14.40, 6.82 Hz), 7.69–7.65(m, 2 H), 7.73(dt, 1 H, J = 8.34, 1.26 Hz), 7.38–7.78(m, 1 H), 7.99(td, 1 H, J = 8.34, 1.26 Hz), 8.29(d, 1 H, J = 8.34 Hz). |
| 235 | 488.40 | 2.93 | CD$_3$OD 1.51(t, 9 H, J = 6.82 Hz), 2.81–2.71(m, 2 H), 2.89–2.81(m, 2 H), 3.20–3.05(m, 4 H), 4.03(q, 5 H J = 14.65, 6.82 Hz), 7.68–7.65(m, 2 H), 7.70(dt, 1 H, J = 8.34, 1.26 Hz), 7.83–7.77(m, 3 H), 7.97(td, 1 H, J = 8.34, 1.26 Hz), 8.19(d, 1 H, J = 8.34 Hz). |
| 236 | 502.20 | 2.66 | CD$_3$OD d 1.58(t, 3 H, J = 6.82 Hz), 3.02–2.92(m, 2 H), 3.12–3.03(m, 2 H), 3.28–3.16(m, 4 H), 3.87(t, 4 H, J = 4.55 Hz), 4.14(q, 1 H J = 13.89, 6.32 Hz), 4.30–4.19(m, 4 H), 7.71–7.64(m, 3 H), 7.87–7.76(m, 3 H), 7.96(dt, 1 H, J = 8.34, 1.26 Hz), 8.15(d, 1 H, J = 8.59 Hz). |

TABLE 2-continued

| Cmpd No. | LC_MASS_PLUS (M+) | LC_MASS_RT (min) | ¹H NMR (Unless otherwise indicated, solvent is CDCl₃) |
|---|---|---|---|
| 237 | 500.20 | 2.95 | 1.42(t, 3 H, J = 6.82 Hz), 1.78(br, s, 6 H), 2.74–2.66 (m, 2 H), 2.85–2.75(m, 2 H), 3.05(br, s, 4 H), 3.89(q, 1 H, J = 14.15, 6.82 Hz), 4.10(br, s, 4 H), 7.60–7.54 (m, 3 H), 7.73–7.67(m, 3 H), 7.85(dt, 1 H, J = 8.59, 1.26 Hz), 8.03(d, 1 H, J = 8.59 Hz). HCl salt(CDC13): 1.53(d, J = 6.82 Hz, 3 H), 1.75(s, br, 6 H), 3.18(s, br, 8 H), 4.02(s, br, 4 H), 4.42(s, br, 1 H), 7.65(dt, J = 8.59, 1.26, 1 H), 7.82–7.75(m, 2 H), 7.98–7.88(m, 2 H), 8.08(d, J = 8.08, 1 H). |
| 238 | 435.20 | 2.21 | |
| 239 | 455.40 | 2.28 | |
| 240 | 457.40 | 2.13 | |
| 241 | 481.20 | 2.80 | |
| 242 | 489.40 | 2.83 | |
| 243 | 491.20 | 2.16 | |
| 244 | 439.20 | 2.51 | |
| 245 | 471.20 | 2.26 | |
| 246 | 457.40 | 2.11 | |
| 247 | 497.20 | 2.66 | |
| 248 | 431.20 | 2.38 | |
| 249 | 443.40 | 2.34 | |
| 250 | 438.40 | 2.34 | |
| 251 | 464.20 | 1.98 | |
| 252 | 481.20 | 2.24 | |
| 253 | 431.20 | 2.29 | |
| 254 | 489.40 | 2.46 | |
| 255 | 505.20 | 2.85 | |
| 256 | 477.00 | 2.19 | |
| 257 | 465.20 | 2.16 | |
| 258 | 567.40 | 2.95 | |
| 259 | 438.40 | 2.28 | |
| 260 | 453.20 | 2.63 | |
| 261 | 554.20 | 3.07 | |
| 262 | 491.20 | 2.19 | |
| 263 | 559.00 | 2.75 | |
| 264 | 455.20 | 2.35 | |
| 265 | 559.00 | 2.88 | |
| 266 | 432.20 | 2.28 | |
| 267 | 506.20 | 2.70 | |
| 268 | 493.00 | 2.38 | |
| 269 | 486.20 | 2.43 | |
| 270 | 517.20 | 3.07 | |
| 271 | 489.20 | 2.64 | |
| 272 | 469.40 | 2.60 | |
| 273 | 455.40 | 2.73 | |
| 274 | 419.00 | 2.23 | |
| 275 | 567.40 | 2.95 | |
| 276 | 464.20 | 2.09 | |
| 277 | 543.20 | 2.81 | |
| 278 | 427.20 | 2.21 | |
| 279 | 438.40 | 2.33 | |
| 280 | 503.00 | 2.51 | |
| 281 | 496.40 | 2.55 | |
| 282 | 471.20 | 2.21 | |
| 283 | 507.20 | 2.78 | |
| 284 | 553.20 | 2.81 | |
| 285 | 503.20 | 2.58 | |
| 286 | 487.40 | 2.52 | |
| 287 | 564.20 | 2.78 | |
| 288 | 514.40 | 2.51 | |
| 289 | 518.20 | 2.69 | |
| 290 | 501.00 | 3.18 | |
| 291 | 456.20 | 2.22 | |
| 292 | 380.00 | 1.79 | |
| 293 | 479.20 | 2.87 | |
| 294 | 283.20 | 2.66 | |
| 295 | 283.20 | 2.65 | |
| 296 | 543.20 | 2.76 | |
| 297 | 506.20 | 2.28 | |
| 298 | 511.40, 511.40, 511.40 | 3.15, 3.22, 3.16 | |
| 299 | 526.20 | 2.14 | |
| 300 | 513.20 | 2.65 | |
| 301 | 283.20 | 2.09 | |
| 302 | 496.40 | 2.76 | |
| 303 | 496.40 | 2.86 | |

TABLE 2-continued

| Cmpd No. | LC_MASS_PLUS (M+) | LC_MASS_RT (min) | ¹H NMR (Unless otherwise indicated, solvent is CDCl₃) |
|---|---|---|---|
| 304 | 510.40 | 2.90 | |
| 305 | 511.40 | 2.14 | |
| 306 | 521.30 | 2.57 | |
| 307 | 465.20 | 3.13 | |
| 308 | 469.20 | 3.37 | |
| 309 | 513.20 | 3.42 | |
| 310 | 455.30 | 2.75 | DMSO-d6 1.35(d, 6 H, J = 6.82 Hz), 1.78(d, 3 H, J = 7.07 Hz), 3.47–2.82(m, 6 H), 3.65–3.43(m, 2 H), 3.80(s, 3 H), 3.91–3.82(m, 1 H), 4.75(q, 1 H, J = 13.89, 7.07 Hz), 6.93(d, 2 H, J = 9.35 Hz), 7.56(d, 2 H, J = 8.84 Hz), 7.65(dt, 1 H, J = 8.34, 1.77 Hz), 7.88(dt, 1 H, J = 8.59, 1.77 Hz), 7.96(d, 1 H, 8.08 Hz), 8.14(d, 1 H, J = 8.59 Hz). |
| 311 | 485.30 | 2.92 | |
| 312 | 413.10 | 2.28 | |
| 313 | 461.10 | 2.45 | 9.45(s, 1 H), 8.06(m, 3 H), 7.80(t, J = 7.9 Hz, 1 H), 7.72(d, J = 8.5 Hz, 2 H), 7.58(d, J = 8.5 Hz, 2 H), 4.86(q, J = 7.0 Hz, 1 H), 3.65(m, 2 H), 3.43(m, 6 H), 1.88(d, J = 7.0 Hz, 3 H) |
| 314 | 471.30 | 2.41 | 8.28(d, J = 8.0 Hz, 1 H), 7.93(t, J = 7.2 Hz, 1 H), 7.68(m, 4 H), 7.03(d, J = 8.6 Hz, 2 H), 4.93(m, 1 H), 3.98(s, 1 H), 3.89(s, 3 H), 3.69(s, 3 H), 3.10(s, 3 H), 2.58(m, 2 H), 2.21(m, 2 H), 1.78(d, J = 6.6 Hz, 3 H), 1.31(m, 4 H); |
| 315 | 475.10 | 2.53 | |
| 316 | 524.40 | 2.94 | |
| 317 | 579.40 | 2.21 | |
| 318 | 498.00 | 2.27 | |
| 319 | 510.40 | 2.83 | |
| 320 | 510.20 | 2.83 | |
| 321 | 514.00 | 2.65 | |
| 322 | 568.20 | 2.76 | |
| 323 | 554.00 | 2.61 | |
| 324 | 526.20 | 2.43 | |
| 325 | 496.20 | 2.73 | |
| 326 | 510.20 | 2.79 | |
| 327 | 550.20 | 3.09 | |
| 328 | 568.20 | 2.64 | |
| 329 | 441.30 | 2.78 | |
| 330 | 452.10 | 2.46 | |
| 331 | 485.30 | 2.83 | DMSO-d6 0.98(d, 3 H, J = 6.82 Hz), 1.01(d, 3 H, J = 6.82 Hz), 1.76(d, 3 H, J = 6.82 Hz), 2.08-1.99(m, 1 H), 3.51–3.19(m, 6 H), 3.86–3.75(m, 2 H), 3.93(s. 3 H), 4.16–3.93(m, 2 H), 4.84(q, 1 H, J = 12.88, 7.07 Hz), 7.03(dd, 2 H, J = 6.82, 2.27 Hz), 7.57(dt, 1 H, J = 8.08, 1.01 Hz), 7.67(dd, 2 H, J = 6.82, 2.27 Hz), 7.71(d, 1 H, J = 8.08, Hz), 7.82(dt, 1 H, 8.59, 1.52 Hz), 8.39(dd, 1 H, J = 8.08, 1.52 Hz). |
| 332 | 499.30 | 2.99 | |
| 333 | 482.10 | 2.61 | |
| 334 | 443.50 | 2.61 | |
| 335 | 457.30 | 2.80 | |
| 336 | 510.30 | 2.68 | 8.07(d, J = 8.2 Hz, 1 H), 7.94(m, 2 H), 7.66(m, 3 H), 7.01(d, J = 8.9 Hz, 2 H), 4.91(t, J = 7.5 Hz, 1 H), 4.14(m, 4 H), 3.88(s, 3 H), 3.59(m, 2 H), 3.23(m, 6 H), 2.24(m, 2 H), 1.89(m, 6 H), 0.87(t, J = 7.4 Hz, 3 H). |
| 337 | 457.30 | 2.73 | |
| 338 | 471.30 | 2.88 | |
| 339 | 524.30 | 2.85 | 8.05(d, J = 7.9 Hz, 1 H), 7.92(m, 2 H), 7.63(m, 3 H), 7.00(dt, J = 9.6, 2.4 Hz, 2 H), 4.92(dd, J = 10.4, 4.5 Hz, 1 H), 4.13(m, 4 H), 3.88(s, 3 H), 3.55(m, 2 H), 3.21(m, 6 H), 2.13(m, 2 H), 1.88(m, 6 H), 1.29(m, 1 H), 1.06(m, 1 H), 0.91(t, J = 7.3 Hz, 3 H). |
| 340 | 471.30 | 2.95 | 8.29(dd, J = 8.0, 1.2 Hz, 1 H), 7.80(td, J = 7.6, 1.4 Hz, 1 H), 7.70(d, J = 7.7 Hz, 1 H), 7.65(dt, J = 9.5, 2.4 Hz, 2 H), 7.54(t, J = 8.1 Hz, 1 H), 7.01(dt, J = 9.6, 2.4 Hz, 2 H), 4.60(m, 1 H), 3.89(s, 3 H), 3.70(s, 3 H), 3.52(m, 2 H), 3.13(m, 6 H), 2.25(m, 1 H), 1.92(m, 1 H), 1.30(m, 2 H), 0.96(t, J = 7.3 Hz, 3 H). |
| 341 | 485.50 | 3.10 | |
| 342 | 485.50 | 3.05 | |
| 343 | 527.20 | 2.59 | |
| 344 | 526.20 | 2.46 | |
| 345 | 511.40 | 2.14 | |

TABLE 2-continued

| Cmpd No. | LC_MASS_PLUS (M+) | LC_MASS_RT (min) | ¹H NMR (Unless otherwise indicated, solvent is CDCl₃) |
|---|---|---|---|
| 346 | 512.40 | 2.34 | |
| 347 | 526.20 | 2.39 | |
| 348 | 539.40 | 3.45 | |
| 349 | 451.10 | 2.46 | |
| 350 | 459.30 | 2.68 | |
| 351 | 473.30 | 2.83 | |
| 352 | 513.30 | 3.02 | |
| 353 | 518.10 | 2.66 | 8.60(s, 1 H), 7.68(d, J = 8.8 Hz, 2 H), 6.99(d, J = 8.9 Hz, 2 H), 4.35(q, J = 7.1 Hz, 2 H), 3.88(s, 3 H), 3.69(m, 1 H), 3.54(m, 4 H), 3.02(m, 4 H), 2.69(m, 4 H), 1.68(m, 6 H), 1.38(m, 6 H) |
| 354 | 437.30 | 2.67 | |
| 355 | 490.10 | 2.41 | |
| 356 | 489.30 | 2.33 | |
| 357 | 503.30 | 2.36 | |
| 358 | 517.30 | 2.41 | |
| 359 | 476.10 | 2.49 | 8.26(s, 1 H), 7.65(d, J = 8.8 Hz, 2 H), 7.03(d, J = 8.8 Hz, 2 H), 4.62(s, 2 H), 4.53(q, J = 6.6 Hz, 1 H), 3.93(m, 7 H), 3.25(m, 8 H), 1.77(m, 6 H), 1.67(d, J = 6.8 Hz, 3 H) |
| 360 | 446.20 | 2.63 | |
| 361 | 508.40 | 2.71 | |
| 362 | 519.50 | 2.80 | 8.91(s, 1 H), 7.68(d, J = 8.8 Hz, 2 H), 6.99(d, J = 8.8 Hz, 2 H), 5.58(m, 1 H), 4.36(q, J = 7.1 Hz, 2 H), 3.89(s, 3 H), 3.84(m, 1 H), 3.04(m, 4 H), 2.73(m, 4 H), 1.83(m, 8 H), 1.40(m, 6 H) |
| 363 | 540.20 | 2.45 | |
| 364 | 539.02 | 2.28 | |
| 365 | 538.20 | 3.16 | |
| 366 | 504.20 | 2.73 | |
| 367 | 518.20 | 2.78 | |
| 368 | 532.20 | 2.85 | |
| 369 | 539.20 | 2.36 | |
| 370 | 540.40 | 2.46 | |
| 371 | 514.40 | 2.82 | |
| 372 | 528.00 | 2.96 | |
| 373 | 528.20 | 2.96 | |
| 374 | 529.20 | 2.96 | |
| 375 | 515.40 | 3.07 | |
| 376 | 522.40 | 3.06 | |
| 377 | 447.00 | 2.75 | 1.35(d, J = 6.82 Hz, 3 H), 2.58–2.47(m, 2 H), 2.69–2.58(m, 2 H), 3.10–2.84(m, 4 H), 3.53(q, J = 13.39, 6.82 Hz, 1 H), 3.85(s, 3 H), 6.98(d, J = 8.34 Hz, 2 H), 7.48–7.34(m, 1 H), 7.65–7.58(m, 3 H), 7.78(d, J = 8.34, 3.03 Hz, 1 H). |
| 378 | 457.20 | 2.50 | |
| 379 | 500.20 | 2.89 | |
| 380 | 500.20 | 2.89 | |
| 381 | 527.00 | 3.09 | 1.30(d, J = 6.82 Hz, 3 H), 1.64–1.51(m, 2 H), 1.82–1.67(m, 4 H), 1.96–1.82(m, 2 H), 2.65–2.52(m, 4 H), 3.00–2.85(m, 4 H), 3.67(q, J = 13.89, 6.82 Hz, 1 H), 3.78(s, 3 H), 5.41(m, 1 H), 6.90(d, J = 9.09, 2 H), 7.59(d, J = 9.09, 2 H), 8.39(s, 1 H). |
| 382 | 447.20 | 2.76 | 1.60–1.54(m, 2 H), 1.64(d, J = 6.82 Hz, 3 H), 1.76–1.67(m, 4 H), 1.96–1.84(m, 2 H), 3.35–3.12(m, 4 H), 3.50–3.35(m, 2 H), 3.05(s, 3 H), 4.41(q, 1 H, J = 13.64, 7.33 Hz), 5.38(m, 1 H), 6.60(d, J = 5.81, 1 H), 6.94(d, J = 8.84, 2 H), 7.56(d, J = 8.84, 2 H), 8.32(d, J = 5.81, 1 H). |
| 383 | 415.30 | 2.59 | |
| 384 | 482.00 | 2.61 | 7.92(m, 3 H), 7.67(m, 3 H), 7.03(d, J = 8.8 Hz, 2 H), 4.70(s, 2 H), 4.12(s, 4 H), 3.90(s, 3 H), 3.45(m, 8 H), 1.88(m, 6 H) |
| 385 | 497.30 | 2.93 | 8.16(d, J = 7.5 Hz, 1 H), 7.89(d, J = 8.3 Hz, 1 H), 7.79(t, J = 7.3 Hz, 1 H), 7.72(dt, J = 9.5, 2.4 Hz, 2 H), 7.52(t, J = 7.4 Hz, 1 H), 7.01(dt, J = 9.5, 2.4 Hz, 2 H), 5.39(quintet, J = 4.2 Hz, 1 H), 3.90(m, 5 H), 3.16(m, 4 H), 2.90(m, 4 H), 1.66(m, 10 H) |
| 386 | 483.50 | 2.85 | 8.11(d, J = 8.1 Hz, 1 H), 7.88(d, J = 8.4 Hz, 1 H), 7.78(t, J = 7.6 Hz, 1 H), 7.71(d, J = 8.8 Hz, 2 H), 7.51(t, J = 7.5 Hz, 1 H), 7.00(d, J = 8.8 Hz, 2 H), 5.73(quintet, J = 3.0 Hz, 1 H), 3.88(m, 5 H), 3.12 (m, 4 H), 2.84(m, 4 H), 1.90(m, 8 H) |
| 387 | 508.00 | 3.02 | DMSO-d6<br>8.14(d, J = 8.3 Hz, 1 H), 8.07(d, J = 8.3 Hz, 1 H), 7.95(t, J = 7.7 Hz, 1 H), 7.70(d, J = 8.7 Hz, 2 H), 7.64(t, J = 7.6 Hz, 1 H), 7.19(d, J = 8.7 Hz, 2 H), |

TABLE 2-continued

| Cmpd No. | LC_MASS_PLUS (M+) | LC_MASS_RT (min) | $^1$H NMR (Unless otherwise indicated, solvent is CDCl$_3$) |
|---|---|---|---|
|  |  |  | 4.06(m, 4 H), 3.87(s, 3 H), 2.95(m, 8 H), 1.75(m, 6 H), 1.43(s, 4 H). |
| 388 | 544.20 | 2.93 |  |
| 389 | 586.42 | 3.20 |  |
| 390 | 573.20 | 2.96 |  |
| 391 | 480.00 | 2.55 |  |
| 392 | 494.40 | 2.68 |  |
| 393 | 500.00 | 2.61 |  |
| 394 | 539.40 | 2.33 |  |
| 395 | 528.00 | 2.52 |  |
| 396 | 513.20 | 3.67 |  |
| 397 | 499.20 | 3.56 |  |
| 398 | 483.40 | 2.86 |  |
| 399 | 525.20 | 3.31 |  |
| 400 | 523.40 | 3.30 |  |
| 401 | 431.20 | 2.31 |  |
| 402 | 496.30 | 2.76 |  |
| 403 | 496.30 | 3.24 | 8.07(d, J = 7.6 Hz, 1 H), 7.81(d, J = 8.3 Hz, 1 H), 7.75(t, J = 7.0 Hz, 1 H), 7.67(d, J = 8.9 Hz, 2 H), 7.46(t, J = 7.5 Hz, 1 H), 6.97(d, J = 8.9 Hz, 2 H), 5.63(m, 1 H), 3.86(s, 3 H), 3.80(d, J = 11.6 Hz, 1 H), 3.67(dd, J = 11.2, 1.6 Hz, 1 H), 2.81(quintet, J = 7.3 Hz, 1 H), 2.28(t, J = 11.8 Hz, 1 H), 2.17(m, 1 H), 1.93(m, 10 H), 1.44(m, 3 H), 1.29(d, J = 6.9 Hz, 3 H) |
| 404 | 510.50 | 3.51 |  |
| 405 | 428.10 | 2.89 |  |

B) Assays for Detecting and Measuring ΔF508-CFTR Correction Properties of Compounds I) Membrane Potential Optical Methods for Assaying ΔF508-CFTR Modulation Properties of Compounds The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential (V$_m$) cause the negatively charged DiSBAC$_2$(3) to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

Identification of Correction Compounds

To identify small molecules that correct the trafficking defect associated with ΔF508-CFTR; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" ΔF508-CFTR. The cells were subsequently rinsed 3× with Krebs Ringers solution and loaded with the voltage-sensitive dyes. To activate ΔF508-CFTR, 10 μM forskolin and the CFTR potentiator, genistein (20 μM), were added along with Cl$^-$-free medium to each well. The addition of Cl$^-$-free medium promoted Cl$^-$ efflux in response to ΔF508-CFTR activation and the resulting membrane depolarization was optically monitored using the FRET-based voltage-sensor dyes.

Identification of Potentiator Compounds

To identify potentiators of ΔF508-CFTR, a double-addition HTS assay format was developed. During the first addition, a Cl$^-$-free medium with or without test compound was added to each well. After 22 sec, a second addition of Cl$^-$-free medium containing 2-10 μM forskolin was added to activate ΔF508-CFTR. The extracellular Cl$^-$ concentration following both additions was 28 mM, which promoted Cl$^-$ efflux in response to ΔF508-CFTR activation and the resulting membrane depolarization was optically monitored using the FRET-based voltage-sensor dyes.

| Solutions | |
|---|---|
| Bath Solution #1: (in mM) | NaCl 160, KCl 4.5, CaCl$_2$ 2, MgCl$_2$ 1, HEPES 10, pH 7.4 with NaOH. |
| Chloride-free bath solution: | Chloride salts in Bath Solution #1 are substituted with gluconate salts. |
| CC2-DMPE: | Prepared as a 10 mM stock solution in DMSO and stored at −20° C. |
| DiSBAC$_2$(3): | Prepared as a 10 mM stock in DMSO and stored at −20° C. |

Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For all optical assays, the cells were seeded at 30,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hours B) Electrophysiological Assays for assaying ΔF508-CFTR modulation properties of compounds Ussing Chamber Assay Ussing chamber experiments were performed on polarized epithelial cells expressing ΔF508-CFTR to further characterize the ΔF508-CFTR modulators identified in the optical assays. FRT$^{\Delta F508\text{-}CFTR}$ epithelial cells grown on Costar Snapwell cell culture inserts were mounted in an Ussing chamber (Physiologic Instruments, Inc., San Diego, Calif.), and the monolayers were continuously short-circuited using a Voltage-clamp System (Department of Bioengineering, University of Iowa, IA, and, Physiologic Instruments, Inc., San Diego, Calif.). Transepithelial resistance was measured by applying a 2-mV pulse. Under these conditions, the FRT epithelia demonstrated resistances of 4 KΩ/cm² or more. The solutions were maintained at 27° C. and bubbled with air. The electrode offset potential and fluid resistance were corrected using a cell-free insert. Under these conditions, the current reflects the flow of Cl⁻ through ΔF508-CFTR expressed in the apical membrane. The $I_{SC}$ was digitally acquired using an MP100A-CE interface and AcqKnowledge software (v3.2.6; BIOPAC Systems, Santa Barbara, Calif.).

Identification of Correction Compounds

Typical protocol utilized a basolateral to apical membrane Cl⁻ concentration gradient. To set up this gradient, normal ringer was used on the basolateral membrane, whereas apical NaCl was replaced by equimolar sodium gluconate (titrated to pH 7.4 with NaOH) to give a large Cl⁻ concentration gradient across the epithelium. All experiments were performed with intact monolayers. To fully activate ΔF508-CFTR, forskolin (10 μM) and the PDE inhibitor, IBMX (100 μM), were applied followed by the addition of the CFR potentiator, genistein (50 μM).

As observed in other cell types, incubation at low temperatures of FRT cells stably expressing ΔF508-CFTR increases the functional density of CFTR in the plasma membrane. To determine the activity of correction compounds, the cells were incubated with 10 μM of the test compound for 24 hours at 37° C. and were subsequently washed 3× prior to recording. The cAMP- and genistein-mediated $I_{SC}$ in compound-treated cells was normalized to the 27° C. and 37° C. controls and expressed as percentage activity. Preincubation of the cells with the correction compound significantly increased the cAMP- and genistein-mediated $I_{SC}$ compared to the 37° C. controls.

Identification of Potentiator Compounds

Typical protocol utilized a basolateral to apical membrane Cl⁻ concentration gradient. To set up this gradient, normal ringers was used on the basolateral membrane and was permeabilized with nystatin (360 μg/ml), whereas apical NaCl was replaced by equimolar sodium gluconate (titrated to pH 7.4 with NaOH) to give a large Cl⁻ concentration gradient across the epithelium. All experiments were performed 30 min after nystatin permeabilization. Forskolin (10 μM) and all test compounds were added to both sides of the cell culture inserts. The efficacy of the putative ΔF508-CFTR potentiators was compared to that of the known potentiator, genistein.

| Solutions | |
|---|---|
| Basolateral solution (in mM): | NaCl (135), CaCl₂ (1.2), MgCl₂ (1.2), K₂HPO₄ (2.4), KHPO₄ (0.6), N-2-hydroxyethyl-piperazine-N'-2-ethanesulfonic acid (HEPES) (10), and dextrose (10). The solution was titrated to pH 7.4 with NaOH. |
| Apical solution (in mM): | Same as basolateral solution with NaCl replaced with Na Gluconate (135). |

Cell Culture

Fisher rat epithelial (FRT) cells expressing ΔF508-CFTR (FRT$^{\Delta F508\text{-}CFTR}$) were used for Ussing chamber experiments for the putative ΔF508-CFTR modulators identified from our optical assays. The cells were cultured on Costar Snapwell cell culture inserts and cultured for five days at 37° C. and 5% CO₂ in Coon's modified Ham's F-12 medium supplemented with 5% fetal calf serum, 100 U/ml penicillin, and 100 μg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

2. Whole-Cell Recordings

The macroscopic ΔF508-CFTR current ($I_{\Delta F508}$) in temperature- and test compound-corrected NIH3T3 cells stably expressing ΔF508-CFTR were monitored using the perforated-patch, whole-cell recording. Briefly, voltage-clamp recordings of $I_{\Delta F508}$ were performed at room temperature using an Axopatch 200B patch-clamp amplifier (Axon Instruments Inc., Foster City, Calif,). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl⁻ ($E_{Cl}$) at room temperature was −28 mV. All recordings had a seal resistance >20 GΩ and a series resistance <15 MΩ. Pulse generation, data acquisition, and analysis were performed using a PC equipped with a Digidata 1320 A/D interface in conjunction with Clampex 8 (Axon Instruments Inc.). The bath contained <250 μl of saline and was continuously perifused at a rate of 2 ml/min using a gravity-driven perfusion system.

Identification of Correction Compounds

To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 μM forskolin and 20 μM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 μM of the test compound for 24 hours at 37° C. and the current density was compared to the 27° C. and 37° C. controls (% activity). Prior to recording, the cells were washed 3× with extracellular recording medium to remove any remaining test compound. Preincubation with 10

μM of correction compounds significantly increased the cAMP- and genistein-dependent current compared to the 37° C. controls.

Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$(−28 mV).

| Solutions | |
|---|---|
| Intracellular solution (in mM): | Cs-aspartate (90), CsCl (50), $MgCl_2$ (1), HEPES (10), and 240 μg/ml amphotericin-B (pH adjusted to 7.35 with CsOH). |
| Extracellular solution (in mM): | N-methyl-D-glucamine (NMDG)-Cl (150), $MgCl_2$ (2), $CaCl_2$ (2), HEPES (10) (pH adjusted to 7.35 with HCl). |

Cell Culture

NIH3T3 mouse fibroblasts stably expressing ΔF508-CFTR are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

3. Single-Channel Recordings

The single-channel activities of temperature-corrected ΔF508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 MΩ when filled with the extracellular solution. The ΔF508-CFTR was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system. The inflow was placed adjacent to the patch, resulting in complete solution exchange within 1-2 sec. To maintain ΔF508-CFTR activity during the rapid perifusion, the non-specific phosphatase inhibitor F⁻ (10 mM NaF) was added to the bath solution. Under these recording conditions, channel activity remained constant throughout the duration of the patch recording (up to 60 min). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing ≤2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

| Solutions | |
|---|---|
| Extracellular solution (in mM): | NMDG (150), aspartic acid (150), $CaCl_2$ (5), $MgCl_2$ (2), and HEPES (10) (pH adjusted to 7.35 with Tris base). |
| Intracellular solution (in mM): | NMDG-Cl (150), $MgCl_2$ (2), EGTA (5), TES (10), and Trisbase (14) (pH adjusted to 7.35 with HCl). |

Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For single channel recordings, 2,500-5,000 cells were seeded on poly-L-lysine-coated glass coverslips and cultured for 24-48 hrs at 27° C. before use.

Compound of the invention are useful as modulators of ATP binding cassette transporters. Table 3 illustrates the EC50 and relative efficacy of certain embodiments in Table 1.

In Table 3 below, the following meanings apply:

TABLE 3

| Cmpd No. | EC50 | % Efficacy |
|---|---|---|
| 1 | + | ++ |
| 2 | + | ++ |
| 3 | + | + |
| 4 | ++ | ++ |
| 5 | +++ | +++ |
| 6 | ++ | ++ |
| 7 | ++ | ++ |
| 8 | + | + |
| 9 | ++ | +++ |
| 10 | + | ++ |
| 11 | ++ | ++ |
| 12 | ++ | ++ |
| 13 | + | + |
| 14 | + | + |
| 15 | ++ | ++ |
| 16 | + | + |
| 17 | ++ | ++ |
| 18 | ++ | ++ |
| 19 | ++ | ++ |
| 20 | + | + |
| 21 | + | ++ |
| 22 | +++ | +++ |
| 23 | + | ++ |
| 24 | + | ++ |
| 25 | + | + |
| 26 | +++ | +++ |
| 27 | +++ | +++ |
| 28 | ++ | ++ |
| 29 | ++ | +++ |

TABLE 3-continued

| Cmpd No. | EC50 | % Efficacy |
|---|---|---|
| 30 | + | ++ |
| 31 | ++ | + |
| 32 | +++ | + |
| 33 | + | ++ |
| 34 | + | + |
| 35 | +++ | ++ |
| 36 | + | ++ |
| 37 | ++ | ++ |
| 38 | + | + |
| 39 | + | ++ |
| 40 | ++ | ++ |
| 41 | + | + |
| 42 | +++ | ++ |
| 43 | + | + |
| 44 | +++ | ++ |
| 45 | + | ++ |
| 46 | + | ++ |
| 47 | +++ | ++ |
| 48 | + | ++ |
| 49 | + | + |
| 50 | ++ | ++ |
| 51 | ++ | +++ |
| 52 | ++ | + |
| 53 | + | ++ |
| 54 | + | ++ |
| 55 | ++ | + |
| 56 | ++ | + |
| 57 | + | + |
| 58 | ++ | + |
| 59 | + | ++ |
| 60 | + | + |
| 61 | ++ | ++ |
| 62 | +++ | ++ |
| 63 | ++ | + |
| 64 | ++ | ++ |
| 65 | ++ | + |
| 66 | + | + |
| 67 | ++ | ++ |
| 68 | + | ++ |
| 69 | + | ++ |
| 70 | +++ | ++ |
| 71 | ++ | ++ |
| 72 | ++ | ++ |
| 73 | +++ | ++ |
| 74 | ++ | + |
| 75 | + | + |
| 76 | ++ | + |
| 77 | + | + |
| 78 | ++ | + |
| 79 | + | + |
| 80 | ++ | ++ |
| 81 | + | + |
| 82 | + | + |
| 83 | ++ | + |
| 84 | + | + |
| 85 | ++ | ++ |
| 86 | ++ | + |
| 87 | + | + |
| 88 | + | + |
| 89 | + | + |
| 90 | + | + |
| 91 | ++ | ++ |
| 92 | +++ | +++ |
| 93 | +++ | ++ |
| 94 | +++ | ++ |
| 95 | +++ | ++ |
| 96 | +++ | ++ |
| 97 | +++ | ++ |
| 98 | +++ | ++ |
| 99 | +++ | ++ |
| 100 | ++ | ++ |
| 101 | ++ | ++ |
| 102 | + | + |
| 103 | ++ | + |
| 104 | ++ | + |
| 105 | ++ | ++ |
| 106 | ++ | + |
| 107 | ++ | + |
| 108 | ++ | + |
| 109 | ++ | ++ |
| 110 | ++ | + |
| 111 | ++ | ++ |
| 112 | ++ | + |
| 113 | ++ | + |
| 114 | ++ | ++ |
| 115 | ++ | + |
| 116 | +++ | ++ |
| 117 | ++ | ++ |
| 118 | +++ | ++ |
| 119 | ++ | ++ |
| 120 | ++ | + |
| 121 | ++ | + |
| 122 | ++ | + |
| 123 | ++ | + |
| 124 | ++ | ++ |
| 125 | ++ | ++ |
| 126 | ++ | ++ |
| 127 | ++ | ++ |
| 128 | ++ | + |
| 129 | ++ | + |
| 130 | ++ | + |
| 131 | ++ | + |
| 132 | +++ | +++ |
| 133 | ++ | ++ |
| 134 | ++ | ++ |
| 135 | ++ | ++ |
| 136 | +++ | +++ |
| 137 | ++ | ++ |
| 138 | ++ | + |
| 139 | ++ | ++ |
| 140 | ++ | ++ |
| 141 | ++ | ++ |
| 142 | ++ | ++ |
| 143 | + | ++ |
| 144 | + | ++ |
| 145 | ++ | ++ |
| 146 | +++ | +++ |
| 147 | +++ | +++ |
| 148 | +++ | +++ |
| 149 | +++ | ++ |
| 150 | ++ | ++ |
| 151 | ++ | +++ |
| 152 | +++ | +++ |
| 153 | ++ | ++ |
| 154 | + | +++ |
| 155 | +++ | ++ |
| 156 | ++ | ++ |
| 157 | + | ++ |
| 158 | + | + |
| 159 | + | + |
| 160 | + | ++ |
| 161 | + | + |
| 162 | + | + |
| 163 | + | + |
| 164 | + | ++ |
| 165 | +++ | ++ |
| 166 | +++ | ++ |
| 167 | + | + |
| 168 | + | + |
| 169 | + | ++ |
| 170 | + | ++ |
| 171 | ++ | ++ |
| 172 | +++ | ++ |
| 173 | + | ++ |
| 174 | + | ++ |
| 175 | + | + |
| 176 | + | ++ |
| 177 | + | ++ |
| 178 | + | + |
| 179 | + | + |
| 180 | + | + |
| 181 | + | + |
| 182 | + | + |
| 183 | + | + |

TABLE 3-continued

| Cmpd No. | EC50 | % Efficacy |
|---|---|---|
| 184 | + | + |
| 185 | + | + |
| 186 | + | + |
| 187 | + | ++ |
| 188 | ++ | +++ |
| 189 | ++ | +++ |
| 190 | +++ | +++ |
| 191 | +++ | +++ |
| 192 | + | ++ |
| 193 | + | ++ |
| 194 | + | ++ |
| 195 | ++ | ++ |
| 196 | + | ++ |
| 197 | + | ++ |
| 198 | + | + |
| 199 | + | + |
| 200 | + | + |
| 201 | + | + |
| 202 | + | + |
| 203 | + | + |
| 204 | + | + |
| 205 | + | + |
| 206 | + | + |
| 207 | +++ | ++ |
| 208 | + | ++ |
| 209 | ++ | ++ |
| 210 | +++ | +++ |
| 211 | + | + |
| 212 | + | + |
| 213 | + | + |
| 214 | + | + |
| 215 | + | + |
| 216 | +++ | +++ |
| 217 | +++ | +++ |
| 218 | +++ | +++ |
| 219 | + | ++ |
| 220 | + | +++ |
| 221 | + | ++ |
| 222 | +++ | ++ |
| 223 | ++ | +++ |
| 224 | + | + |
| 225 | + | + |
| 226 | + | ++ |
| 227 | + | ++ |
| 228 | +++ | +++ |
| 229 | + | ++ |
| 230 | + | + |
| 231 | +++ | +++ |
| 232 | + | ++ |
| 233 | + | ++ |
| 234 | ++ | ++ |
| 235 | +++ | ++ |
| 236 | + | ++ |
| 237 | +++ | +++ |
| 238 | + | + |
| 239 | + | + |
| 240 | + | + |
| 241 | +++ | +++ |
| 242 | + | + |
| 243 | + | ++ |
| 244 | + | ++ |
| 245 | + | + |
| 246 | + | + |
| 247 | ++ | ++ |
| 248 | + | + |
| 249 | + | ++ |
| 250 | + | ++ |
| 251 | + | + |
| 252 | + | ++ |
| 253 | + | ++ |
| 254 | +++ | ++ |
| 255 | + | + |
| 256 | + | + |
| 257 | + | + |
| 258 | + | + |
| 259 | + | + |
| 260 | ++ | ++ |

TABLE 3-continued

| Cmpd No. | EC50 | % Efficacy |
|---|---|---|
| 261 | + | ++ |
| 262 | + | + |
| 263 | + | + |
| 264 | + | + |
| 265 | + | + |
| 266 | + | + |
| 267 | + | + |
| 268 | + | + |
| 269 | + | + |
| 270 | + | + |
| 271 | + | + |
| 272 | +++ | ++ |
| 273 | + | + |
| 274 | + | + |
| 275 | + | + |
| 276 | + | + |
| 277 | + | + |
| 278 | + | + |
| 279 | + | + |
| 280 | ++ | + |
| 281 | + | + |
| 282 | + | + |
| 283 | + | ++ |
| 284 | + | ++ |
| 285 | + | ++ |
| 286 | + | ++ |
| 287 | + | ++ |
| 288 | + | + |
| 289 | + | ++ |
| 290 | + | ++ |
| 291 | + | + |
| 292 | + | + |
| 293 | + | +++ |
| 294 | + | ++ |
| 295 | + | ++ |
| 296 | ++ | +++ |
| 297 | +++ | ++ |
| 298 | +++ | +++ |
| 299 | ++ | ++ |
| 300 | + | +++ |
| 301 | + | ++ |
| 302 | +++ | +++ |
| 303 | +++ | +++ |
| 304 | +++ | ++ |
| 305 | +++ | ++ |
| 306 | + | ++ |
| 307 | + | ++ |
| 308 | +++ | ++ |
| 309 | +++ | ++ |
| 310 | +++ | ++ |
| 311 | +++ | +++ |
| 312 | + | ++ |
| 313 | + | ++ |
| 314 | + | ++ |
| 315 | + | ++ |
| 316 | + | ++ |
| 317 | + | + |
| 318 | + | ++ |
| 319 | +++ | ++ |
| 320 | +++ | +++ |
| 321 | +++ | +++ |
| 322 | +++ | +++ |
| 323 | ++ | ++ |
| 324 | + | + |
| 325 | +++ | +++ |
| 326 | +++ | ++ |
| 327 | +++ | +++ |
| 328 | ++ | +++ |
| 329 | +++ | ++ |
| 330 | + | ++ |
| 331 | +++ | +++ |
| 332 | + | ++ |
| 333 | ++ | ++ |
| 334 | + | ++ |
| 335 | ++ | ++ |
| 336 | +++ | +++ |
| 337 | ++ | +++ |

TABLE 3-continued

| Cmpd No. | EC50 | % Efficacy |
|---|---|---|
| 338 | +++ | +++ |
| 339 | +++ | +++ |
| 340 | +++ | +++ |
| 341 | +++ | +++ |
| 342 | +++ | ++ |
| 343 | + | ++ |
| 344 | ++ | ++ |
| 345 | + | ++ |
| 346 | + | ++ |
| 347 | + | ++ |
| 348 | +++ | +++ |
| 349 | + | ++ |
| 350 | + | + |
| 351 | + | + |
| 352 | +++ | ++ |
| 353 | +++ | ++ |
| 354 | ++ | ++ |
| 355 | + | + |
| 356 | + | ++ |
| 357 | + | ++ |
| 358 | + | ++ |
| 359 | + | ++ |
| 360 | + | ++ |
| 361 | +++ | +++ |
| 362 | +++ | +++ |
| 363 | ++ | +++ |
| 364 | + | ++ |
| 365 | +++ | +++ |
| 366 | +++ | ++ |
| 367 | +++ | ++ |
| 368 | +++ | +++ |
| 369 | + | ++ |
| 370 | + | + |
| 371 | +++ | +++ |
| 372 | ++ | +++ |
| 373 | ++ | ++ |
| 374 | +++ | ++ |
| 375 | +++ | +++ |
| 376 | +++ | ++ |
| 377 | + | ++ |
| 378 | + | + |
| 379 | +++ | +++ |
| 380 | +++ | +++ |
| 381 | +++ | +++ |
| 382 | ++ | ++ |
| 383 | + | + |
| 384 | ++ | +++ |
| 385 | +++ | +++ |
| 386 | +++ | +++ |
| 387 | +++ | +++ |
| 388 | +++ | +++ |
| 389 | +++ | +++ |
| 390 | +++ | +++ |
| 391 | ++ | +++ |
| 392 | +++ | +++ |
| 393 | ++ | ++ |
| 394 | + | ++ |
| 395 | ++ | ++ |
| 396 | ++ | +++ |
| 397 | ++ | ++ |
| 398 | +++ | +++ |
| 399 | +++ | ++ |
| 400 | +++ | +++ |
| 401 | + | + |
| 402 | + | + |
| 403 | +++ | +++ |
| 404 | +++ | +++ |
| 405 | ++ | ++ |

EC50: "+++" means <10 uM; "++" means between 10 uM to 25 uM; "+" means between 25 uM to 60 uM.
% Efficacy: "+" means <25%; "++" means between 25% to 100%; "+++" means >100%.

The invention claimed is:
1. A compound of formula I:

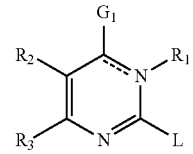

or a pharmaceutically acceptable salt thereof, wherein:
$G_1$ is =O, $OR^A$, $SR^A$, or $NR^A R^B$, wherein $R^A$ and $R^B$ are each independently V—$R^V$, or $R^A$ and $R^B$, taken together with the nitrogen atom, form an optionally substituted 3-12 membered saturated, partially unsaturated, or fully unsaturated monocyclic or bicyclic ring having 0-4 heteroatoms independently selected from nitrogen, oxygen, or sulfur, wherein V is a bond or is an optionally substituted $C_1$-$C_6$ alkylidene chain wherein up to two methylene units of V are optionally and independently replaced by —CO—, —CS—, —COCO—, —CONR'—, —CONR'NR'—, —CO$_2$—, —OCO—, —NR'CO$_2$—, —O—, —NR'CONR'—, —OCONR'—, —NR'NR', —NR'NR'CO—, —NR'CO—, —S—, —SO, —SO$_2$—, —NR'—, —SO$_2$NR'—, NR'SO$_2$—, —NR'SO$_2$NR'—, and each occurrence of $R^V$ is independently R', halogen, NO$_2$, or CN, and wherein $R^A$ and $R^B$, or any ring formed by $R^A$ and $R^B$ taken together with the nitrogen atom, are optionally and independently substituted by q occurrences of U—$R^U$, wherein q is 0-5, U is a bond or is an optionally substituted $C_1$-$C_6$ alkylidene chain wherein up to two methylene units of U are optionally and independently replaced by —CO—, —CS—, —COCO—, —CONR'—, —CONR'NR'—, —CO$_2$—, —OCO—, —NR'CO$_2$—, —O—, —NR'CONR'—, —OCONR'—, —NR'NR', —NR'NR'CO—, —NR'CO—, —S—, —SO, —SO$_2$—, —NR'—, —SO$_2$NR'—, —NR'SO$_2$—, —NR'SO$_2$NR'—, and each occurrence of $R^U$ is independently R', halogen, NO$_2$, or CN;

$R^1$ is absent or is Y—$R^Y$; wherein Y is a bond or is an optionally substituted $C_1$-$C_6$ alkylidene chain wherein up to two methylene units of Y are optionally and independently replaced by —CO—, —CONR—, —O—, —NRCO—, —S—, —SO$_2$—, —NR—, —SO$_2$NR—, or —NRSO$_2$—, and each occurrence of $R^Y$ is independently R', OR', SR', N(R')$_2$, halogen, NO$_2$, or CN, provided that when $R^1$ is present, it is always bonded to the nitrogen atom through a carbon atom;

each occurrence of R is independently selected from hydrogen or an optionally substituted $C_{1-8}$ aliphatic group; and each occurrence of R' is independently selected from hydrogen or an optionally substituted group selected from a $C_1$-$C_8$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R', or two occurrences of R, are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;

$R^2$ and $R^3$, taken together, form a ring selected from:

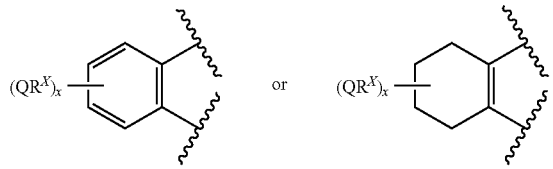

with x independent occurrences of Q-$R^X$, wherein x is 0-5;
Q is a bond or is an optionally substituted $C_1$-$C_6$ alkylidene chain wherein up to two methylene units of Q are optionally and independently replaced by —CO—, —CS—, —COCO—, —CONR—, —CONRNR—, —$CO_2$—, —OCO—, —$NRCO_2$—, —O—, —NRCONR—, —OCONR—, —NRNR, —NRNRCO—, —NRCO—, —S—, —SO—, —$SO_2$—, —NR—, —$SO_2$NR—, —$NRSO_2$—, —$NRSO_2$NR—, and each occurrence of $R^X$ is independently R', halogen, $NO_2$, or CN;

L is $G^2$-B-$G^3$-$Ar^1$,
wherein $G^2$ is absent, an optionally substituted $C_1$-$C_6$ alkylidene chain, or a $C_3$-$C_6$ spirocycloalkylidene ring, wherein one or two methylene units in said alkylidene are optionally and independently replaced with —CO—, —CS—, —SO—, —$SO_2$—, —NR'—, N($SO_2$R')—, N(COR')—, —O—, or —S—, and wherein one or two hydrogen atoms of one or more methylene units are optionally substituted with R';

$G^3$ is —NR'—, —CO—, or —$SO_2$—;

B is an optionally substituted 5-, 6- or 7-membered saturated, partially unsaturated or fully unsaturated ring having the structure

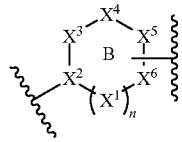

wherein n is 0, 1, or 2; $X^2$ and $X^5$ are each N; and each occurrence of $X^1$, when present, and $X^3$, $X^4$ and $X^6$ are each independently, as valency and stability permit, C(R')$_2$, —O—, —NR—, S, C=O, or C=S; and $Ar^1$ is a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein $Ar^1$ is optionally substituted with m independent occurrences of W$R^W$, wherein m is 0-5 and W is a bond or is an optionally substituted $C_1$-$C_6$ alkylidene chain wherein up to two methylene units of W are optionally and independently replaced by —CO—, —CS—, —COCO—, —CONR—, —CONRNR—, —$CO_2$—, —OCO—, —$NRCO_2$—, —O—, —NR-CONR—, —OCONR—, —NRNR, —NRNRCO—, —NRCO—, —S—, —SO—, —$SO_2$—, —NR—, —$SO_2$NR—, —$NRSO_2$—, —$NRSO_2$NR—, and each occurrence of $R^W$ is independently R', halogen, $NO_2$, or CN.

2. The compound of claim 1, wherein compounds have one of the following general structures I-A, I-B, I-D and I-E, as depicted below

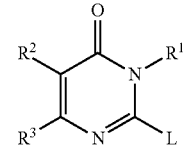

I-A

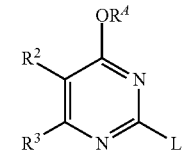

I-B

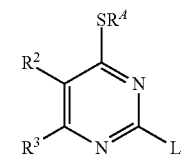

I-D

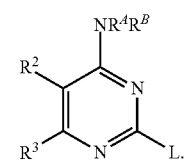

I-E

3. The compound of claim 1, wherein $R^A$ and $R^B$ are each independently hydrogen, an optionally substituted $C_1$-$C_8$alkyl group, or V—$R^V$, where V is as defined generally above, and $R^V$ is an optionally substituted 3-12 membered saturated, partially unsaturated, or fully unsaturated monocyclic or bicyclic ring having 0-4 heteroatoms independently selected from nitrogen, oxygen, or sulfur.

4. The compound of claim 1, wherein $R^A$ and $R^B$ are each independently hydrogen; an optionally substituted group selected from methyl, ethyl, propyl, isopropyl, butyl, tert-butyl, or pentyl; an optionally substituted ring selected from:

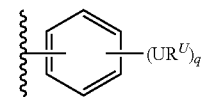

i

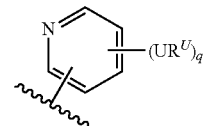

ii

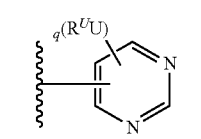

iii

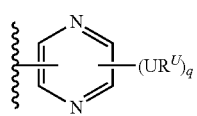 iv
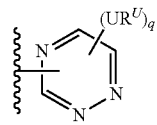 v
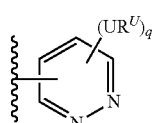 vi
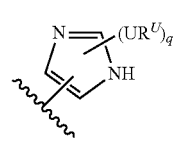 vii
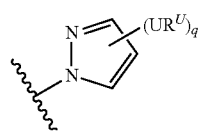 viii
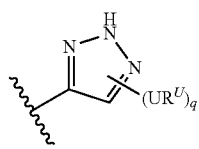 ix
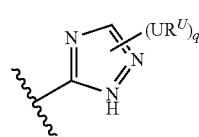 x
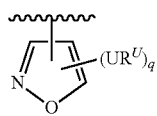 xi
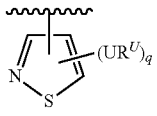 xii
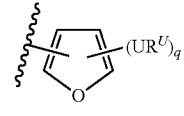 xiii
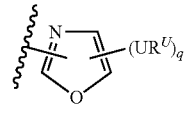 xiv
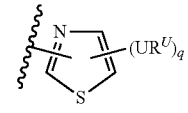 xv
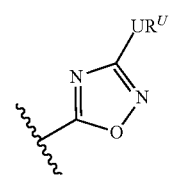 xvi
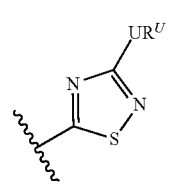 xvii
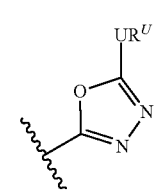 xviii
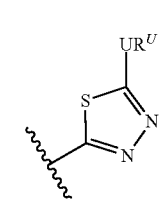 xix
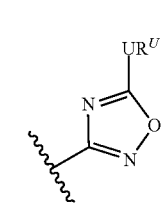 xx
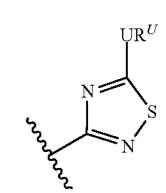 xxi
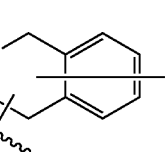 xxii
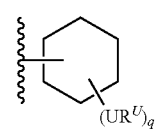 xxiii
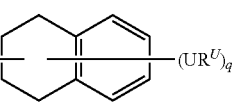 xxiv -continued
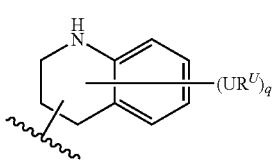
xxv
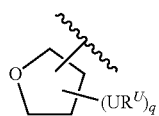
xxvi
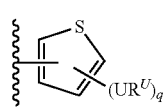
xxvii
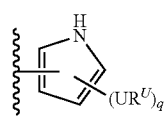
xxviii
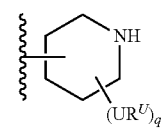
xxix
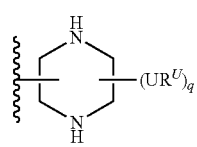
xxx
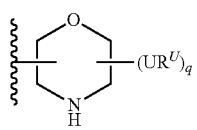
xxxi
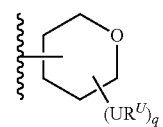
xxxii
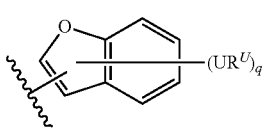
xxxiii
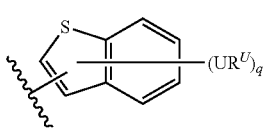
xxxiv
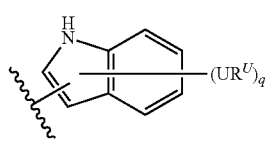
xxxv
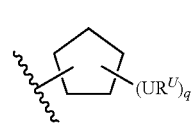
xxxvi
-continued
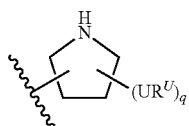
xxxvii
xxxviii
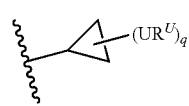
xxxix
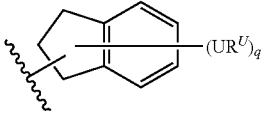
xL
xLi
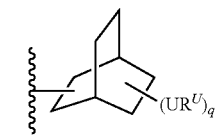
xLii
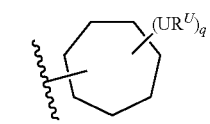
xLiii
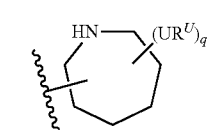
xLiv
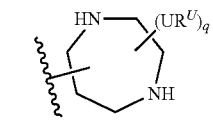
xLv
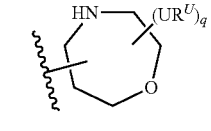
xLvi
or $R^A$ and $R^B$, taken together are optionally substituted group selected from:
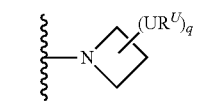
a

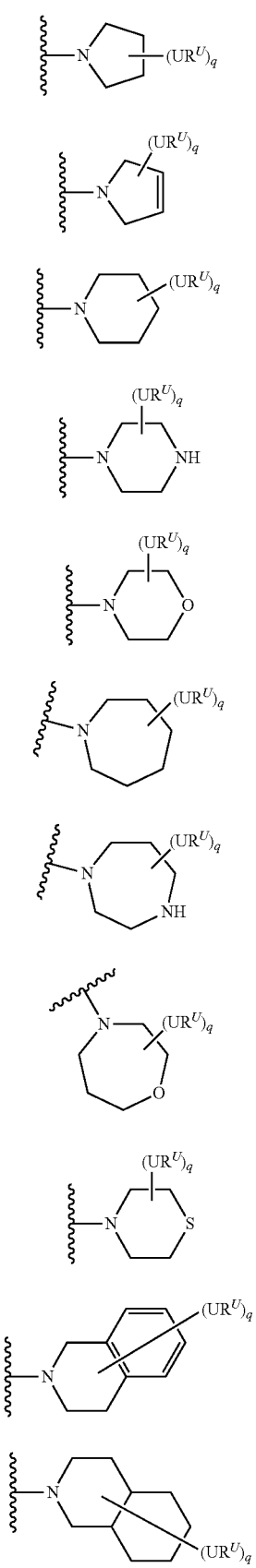
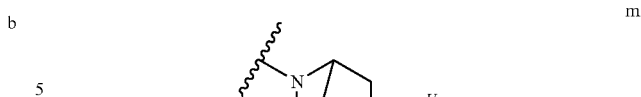
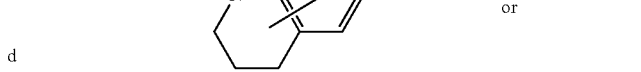
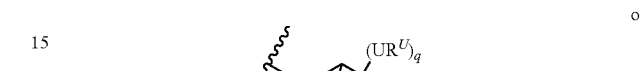
5. The compound of claim 1, wherein $R^2$ and $R^3$, taken together form an optionally substituted phenyl group and compounds have the formula II:
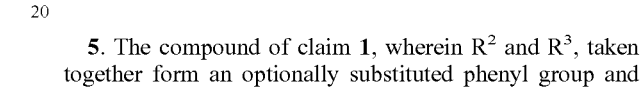
II
6. The compound of claim 1, wherein compounds have one of formulas II-A, II-B, II-D, or II-E:
II-A
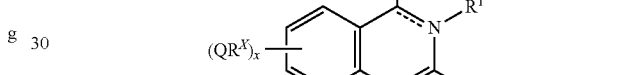
II-B
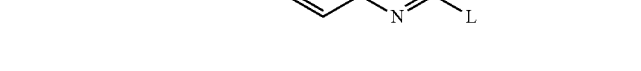
II-D
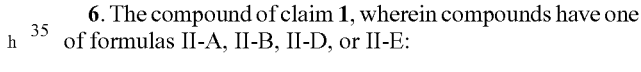
II-E
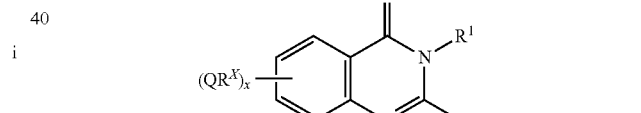
7. The compound of claim 6, wherein x is 0-4, and each occurrence of $Q\text{-}R^X$, when present, is independently halogen, CN, NO₂, or an optionally substituted group selected from $C_{1-4}$-alkyl, aryl, aralkyl, heteroaryl, a cycloalkyl or heterocycloalkyl group having 3-10 atoms.

8. The compound of claim 1, wherein $G^2$ is a $C_1$-$C_3$alkylidene chain or a $C_3$-$C_6$ spiroalkylidene ring, wherein one or two methylene units are optionally replaced by —NR'—, —N(SO₂R')—, N(COR')—, —O—, —S—, —CO—, —CS, or —SO₂—, and wherein any hydrogen atom in the $C_1$-$C_3$alkylidene chain is optionally and independently substituted with R', and $G^3$ is a $C_1$-$C_3$alkylidene chain wherein one or two methylene units are optionally replaced by —NR'—, —N(SO₂R')—, N(COR')—, —O—, —S—, —CO—, —CS, or —SO₂—, and wherein any hydrogen atom in the $C_1$-$C_3$alkylidene chain is optionally and independently substituted with R'.

9. The compound of claim 8, wherein $G^2$ is —CHR'—, wherein R' is hydrogen, or optionally substituted $C_1$-$C_4$alkyl and $G^3$ is —(C(R')₂)₁₋₃—, —NR'—, —CO—, —SO₂—, or —CONR—.

10. The compound of claim 1, wherein $X^1$, when present, $X^3$, $X^4$, and $X^6$ are each C(R')₂.

11. The compound of claim 1, wherein compounds have one of the structures IV-A, IV-B, IV-D, or IV-E:

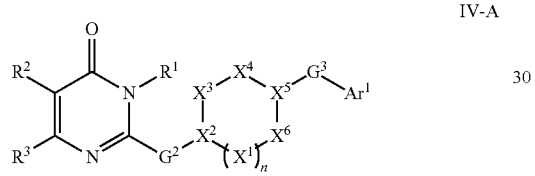
IV-A

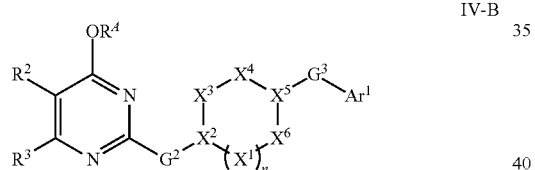
IV-B

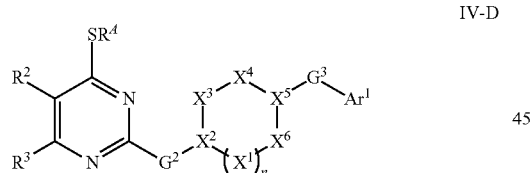
IV-D

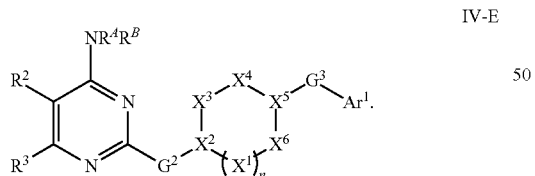
IV-E

12. The compound of claim 11 wherein compounds have one of the structures V-A, V-B, V-D, or V-E:

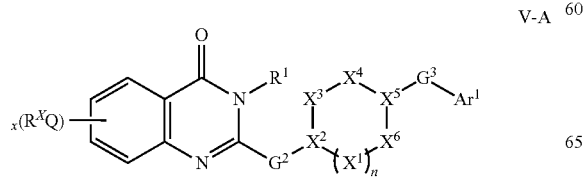
V-A

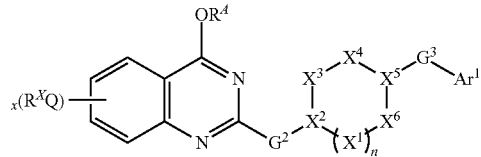
V-B

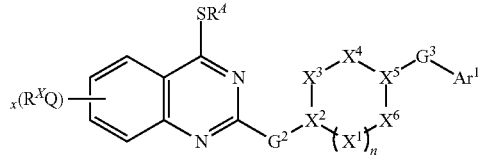
V-D

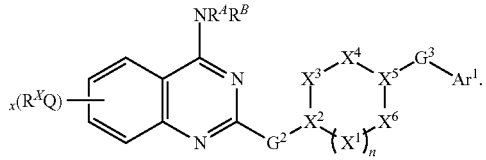
V-E

13. The compound of claim 1, wherein Ar¹ is selected from:

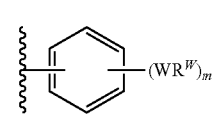
i

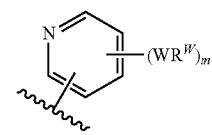
ii

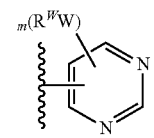
iii

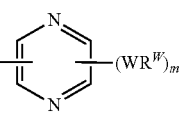
iv

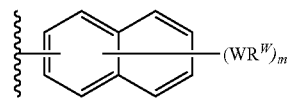
v

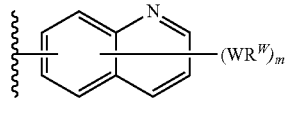
vi

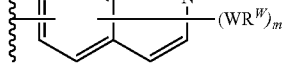
vii

-continued
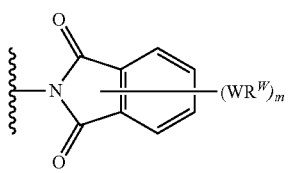
viii
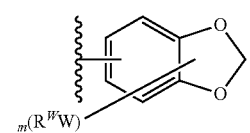
ix
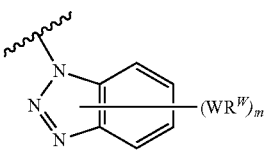
x
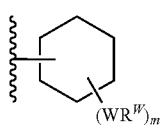
xi
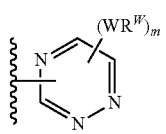
xii
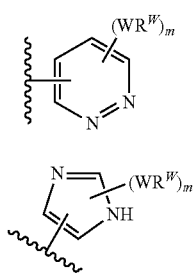
xiii
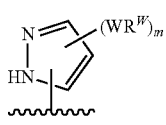
xiv
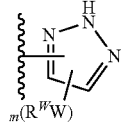
xv
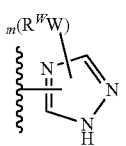
xvi
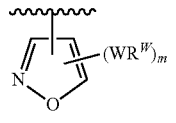
xvii
xviii
-continued
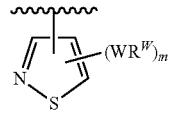
xix
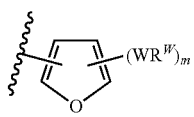
xx
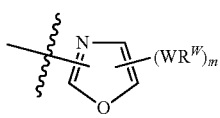
xxi
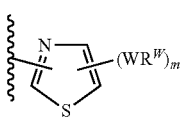
xxii
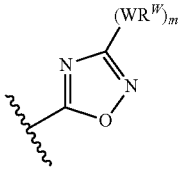
xxiii
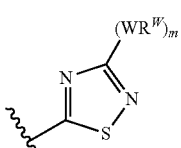
xxiv
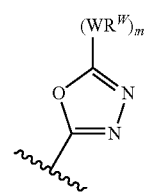
xxv
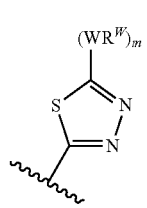
xxvi
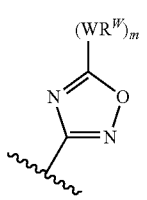
xxvii

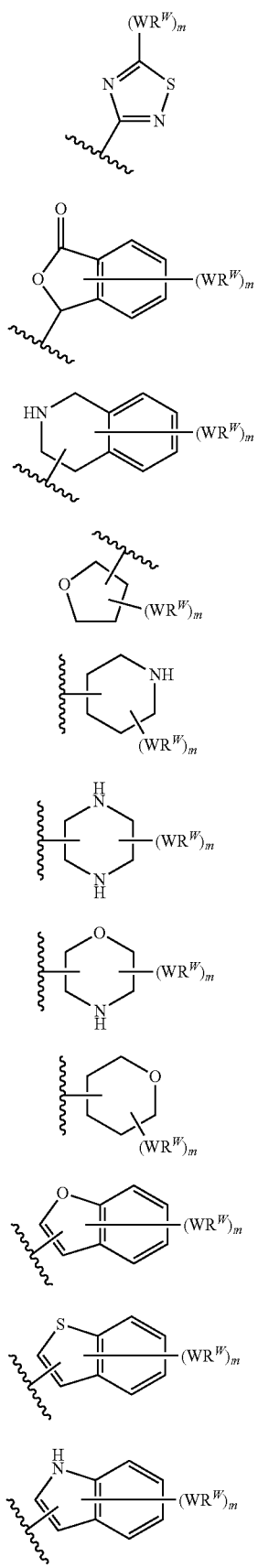
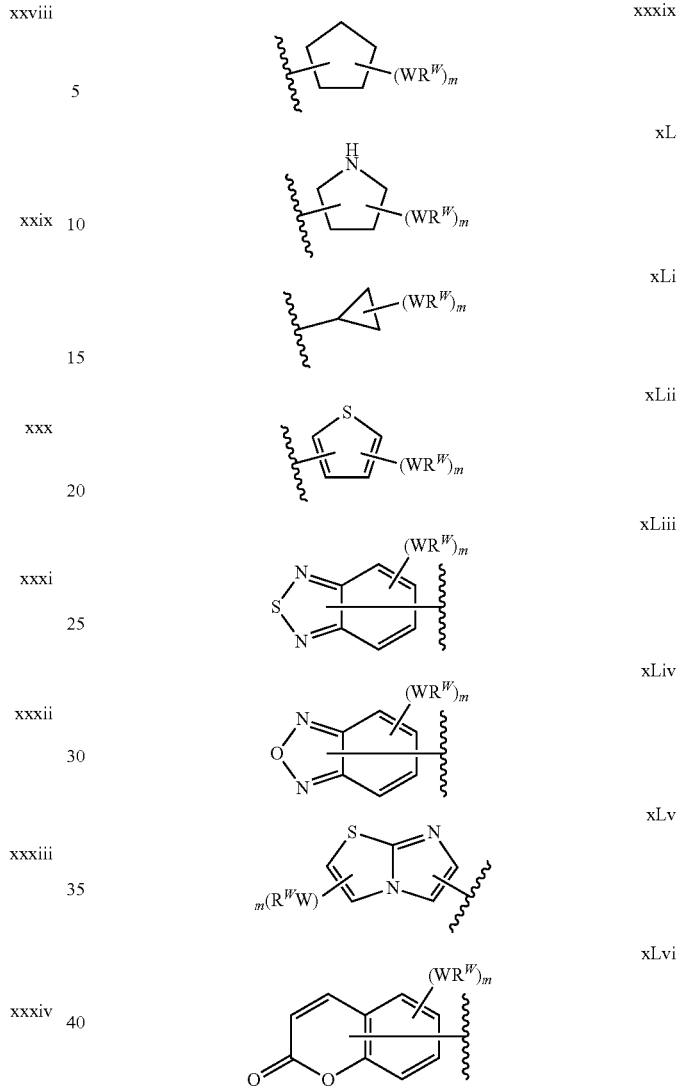

wherein m is 0, 1, 2, 3, 4 or 5, and wherein any $Ar^1$ is bonded to $G^3$ through any substitutable nitrogen or carbon atom, and wherein one or more hydrogen atoms on any substitutable nitrogen or carbon atom is substituted with one or more independent occurrences of W—$R^W$.

14. The compound of claim 13, wherein $Ar^1$ is an optionally substituted group selected from i, ii, v, vi, vii, x, xLii, xLiii, xLv, xLv, or xLvi.

15. The compound of claim 13, wherein $Ar^1$ is an optionally substituted phenyl group (i).

16. The compound of claim 13, wherein W is a bond or is an optionally substituted $C_{1-6}$ alkylidene chain wherein one or two non-adjacent methylene units are optionally and independently replaced by O, NR, S, $SO_2$, or COO, CO, and $R^W$ is R' or halogen.

17. The compound of claim 16, wherein each occurrence of $WR^W$ is independently —$C_{1-3}$alkyl, —O($C_{1-3}$alkyl), —$CF_3$, —$OCF_3$, —$SCF_3$, —F, —Cl, —Br, or —COOR', —COR', —O(CH$_2$)$_2$N(R)(R'), —O(CH$_2$)N(R)(R'), —CON(R)(R'), —(CH$_2$)$_2$OR', —(CH$_2$)OR', optionally substituted phenyl, —N(R)(R'), —(CH$_2$)$_2$N(R)(R'), or —(CH$_2$)N(R)(R').

18. The compound of claim 12 wherein:
$R^A$ and $R^B$ are each independently hydrogen, an optionally substituted group selected from $C_1$-$C_7$alkyl, $C_3$-$C_7$ cycloalkyl, or $C_3$-$C_7$ heterocyclyl, or $R^A$ and $R^B$, taken together, form an optionally substituted 5-, 6-, or 7-membered heterocyclyl ring;

$R^1$ is —$CH_3$, —$CH_2CH_3$, —$CH_2CH_2CH_3$, —$CH_2CH_2CH_2CH_3$, —$(CH_2)_2OR'$, —$(CH_2)_3OR'$, —$(CH_2)_2N(R')_2$, —$(CH_2)_3N(R')_2$, —$(CH_2)_2NRCOR'$, or —$(CH_2)_3NRCOR'$, x is 0, 1, or 2, and each occurrence of -Q-$R^X$ when present, is Cl, Br, F, $CF_3$, methyl, ethyl, propyl, butyl, CN, —COOH, —$N(CH_3)_2$, —$N(Et)_2$, —$N(iPr)_2$, —$O(CH_2)_2OCH_3$, —$CONH_2$, —$COOCH_3$, —OH, —$OCH_3$, —$OCH_2CH_3$, —$OCH_2CH_2CH_3$, —$OCH_2CH_2CH_2CH_3$, —$CH_2OH$, —$NHCOCH_3$, —$SO_2NH_2$, or an optionally substituted group selected from piperidinyl, piperizinyl, morpholino, phenyl, phenyloxy, benzyl, benzyloxy, pyridyl, pyrimidinyl, pyridazinyl, thiophene, furan, thiazole, oxazole, thiadiazole, oxadiazole, pyrazole, or pyrrole;

n is 1 and $X^1$, $X^3$, $X^4$, and $X^6$ are each CHR;

$G^2$ is —$(C(R)_2)_{1-3}$—, —NR'—, —$C(R')_2NR'$—, or —$NR'C(R')_2$—;

$Ar^1$ is selected from one of rings a-i through a-xLVi; and each occurrence of $WR^W$ is independently —$C_{1-3}$alkyl, —$O(C_{1-3}$alkyl), —$CF_3$, —$OCF_3$, —$SCF_3$, —F, —Cl, —Br, or —COOR', —COR', —$O(CH_2)_2N(R)(R')$, —$O(CH_2)N(R)(R')$, —C(O)N(R)(R'), —$(CH_2)_2OR'$, —$(CH_2)OR'$, optionally substituted phenyl, —N(R)(R'), —$(CH_2)_2N(R)(R')$, or —$(CH_2)N(R)(R')$.

19. The compound of claim 18, wherein $G^2$ is $CH(C_{1-3}$alkyl) or spirocyclopropyl; $G^3$ is —CO—, or —$SO_2$— and $Ar^1$ is phenyl optionally substituted with —$WR^W$.

20. A pharmaceutical composition comprising:
(i) a compound according to claim 1; and
(ii) a pharmaceutically acceptable carrier.

21. The composition of claim 20, optionally further comprising an additional agent selected from a mucolytic agent, bronchodialator, an anti-biotic, an anti-infective agent, an anti-inflammatory agent, CFTR modulator, or a nutritional agent.

\* \* \* \* \*